US011660136B2

(12) United States Patent
Brustad et al.

(10) Patent No.: US 11,660,136 B2
(45) Date of Patent: May 30, 2023

(54) ELECTROSURGICAL SYSTEM

(71) Applicant: Applied Medical Resources Corporation, Rancho Santa Margarita, CA (US)

(72) Inventors: John R. Brustad, Rancho Santa Margarita, CA (US); Zoran Falkenstein, Rancho Santa Margarita, CA (US); Christopher J. Cappello, Broomfield, CO (US); Gary M. Johnson, Rancho Santa Margarita, CA (US); Benjamin A. Gianneschi, Orange, CA (US); Olivia J. Tran, San Diego, CA (US); Matthew A. Wixey, San Jose, CA (US); Kennii Pravongviengkham, Rancho Santa Margarita, CA (US); Boun Pravong, Rancho Santa Margarita, CA (US); Haruyasu Yawata, Huntington Beach, CA (US); Matthew M. Becerra, Lake Forest, CA (US); Adam J. Cohen, Shirley, MA (US); Nabil Hilal, Rancho Santa Margarita, CA (US); Edward D. Pingleton, San Juan Capistrano, CA (US); Said S. Hilal, Rancho Santa Margarita, CA (US); Charles C. Hart, Rancho Santa Margarita, CA (US); Chris R. Wikoff, Avon, CT (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 331 days.

(21) Appl. No.: 17/144,587

(22) Filed: Jan. 8, 2021

(65) Prior Publication Data
US 2021/0186599 A1    Jun. 24, 2021

Related U.S. Application Data

(63) Continuation of application No. 16/448,492, filed on Jun. 21, 2019, now Pat. No. 10,888,371, which is a
(Continued)

(51) Int. Cl.
*A61B 18/14* (2006.01)
*A61B 18/16* (2006.01)
(Continued)

(52) U.S. Cl.
CPC .... *A61B 18/1445* (2013.01); *A61B 17/07207* (2013.01); *A61B 18/1206* (2013.01);
(Continued)

(58) Field of Classification Search
CPC ............ A61B 18/1442; A61B 18/1445; A61B 18/16; A61B 2017/2945;
(Continued)

(56) References Cited

U.S. PATENT DOCUMENTS 371,664 A    10/1887   Brannan et al.
702,472 A     6/1902   Pignolet
(Continued)

FOREIGN PATENT DOCUMENTS

DE    4024636 A1    2/1992
DE    4024636 C2   12/1992
(Continued)

OTHER PUBLICATIONS

International Preliminary Examining Authority/US, International Preliminary Report on Patentability for International Application No. PCT/US2019/049768, titled "Electrosurgical Generator Verification System," dated Mar. 18, 2021, 13 pgs.
(Continued)

*Primary Examiner* — Jason E Flick
(74) *Attorney, Agent, or Firm* — Patrick Ikehara

(57) ABSTRACT

An electrosurgical system can include an electrosurgical generator, a feedback circuit or controller, and an electrosurgical tool. The feedback circuit can provide an electrosurgery endpoint by determining the phase end point of a tissue to be treated. The electrosurgical system can include more than one electrosurgical tool for different electrosurgical operations and can include a variety of user interface features and audio/visual performance indicators. The elec-
(Continued)

trosurgical system can also power conventional bipolar electrosurgical tools and direct current surgical appliances.

20 Claims, 109 Drawing Sheets

Related U.S. Application Data continuation of application No. 15/431,595, filed on Feb. 13, 2017, now Pat. No. 10,342,604, which is a continuation of application No. 14/076,469, filed on Nov. 11, 2013, now Pat. No. 9,566,108, which is a continuation of application No. 12/416,751, filed on Apr. 1, 2009, now Pat. No. 8,579,894, which is a continuation of application No. 12/416,128, filed on Mar. 31, 2009, now Pat. No. 8,568,411.

(60) Provisional application No. 61/115,756, filed on Nov. 18, 2008, provisional application No. 61/041,012, filed on Mar. 31, 2008, provisional application No. 61/040,980, filed on Mar. 31, 2008, provisional application No. 61/040,828, filed on Mar. 31, 2008, provisional application No. 61/040,957, filed on Mar. 31, 2008, provisional application No. 61/040,994, filed on Mar. 31, 2008, provisional application No. 61/040,890, filed on Mar. 31, 2008, provisional application No. 61/041,045, filed on Mar. 31, 2008.

(51) Int. Cl.
*A61B 90/90* (2016.01)
*A61B 17/072* (2006.01)
*A61B 18/12* (2006.01)
*A61B 17/29* (2006.01)
*A61B 18/00* (2006.01)
*A61B 17/00* (2006.01)

(52) U.S. Cl.
CPC .......... *A61B 18/1442* (2013.01); *A61B 18/16* (2013.01); *A61B 90/90* (2016.02); *A61B 2017/00199* (2013.01); *A61B 2017/2945* (2013.01); *A61B 2018/00041* (2013.01); *A61B 2018/00077* (2013.01); *A61B 2018/00178* (2013.01); *A61B 2018/00208* (2013.01); *A61B 2018/00345* (2013.01); *A61B 2018/00404* (2013.01); *A61B 2018/00494* (2013.01); *A61B 2018/00511* (2013.01); *A61B 2018/00589* (2013.01); *A61B 2018/00601* (2013.01); *A61B 2018/00607* (2013.01); *A61B 2018/00619* (2013.01); *A61B 2018/00642* (2013.01); *A61B 2018/00666* (2013.01); *A61B 2018/00702* (2013.01); *A61B 2018/00869* (2013.01); *A61B 2018/00875* (2013.01); *A61B 2018/00892* (2013.01); *A61B 2018/00898* (2013.01); *A61B 2018/00916* (2013.01); *A61B 2018/00922* (2013.01); *A61B 2018/00988* (2013.01); *A61B 2018/124* (2013.01); *A61B 2018/126* (2013.01); *A61B 2018/1266* (2013.01); *A61B 2018/144* (2013.01); *A61B 2018/1412* (2013.01); *A61B 2018/1432* (2013.01); *A61B 2018/1455* (2013.01); *A61B 2018/1467* (2013.01); *A61B 2018/162* (2013.01)

(58) Field of Classification Search
CPC .......... A61B 2018/00345; A61B 2018/00404; A61B 2018/00589; A61B 2018/00601; A61B 2018/00619; A61B 2018/00869; A61B 2018/00875; A61B 2018/00916; A61B 2018/00988; A61B 2018/124; A61B 2018/1412; A61B 2018/1432; A61B 2018/1455; A61B 90/90

See application file for complete search history.

(56) References Cited

U.S. PATENT DOCUMENTS

| | | |
|---|---|---|
| 728,883 A | 5/1903 | Downes |
| 1,586,645 A | 6/1926 | Bierman |
| 1,935,289 A | 4/1933 | Evans |
| 2,002,594 A | 5/1935 | Wappler et al. |
| 2,031,682 A | 2/1936 | Wappler et al. |
| 2,113,246 A | 4/1938 | Wappler |
| 2,176,479 A | 10/1939 | Willis |
| 2,305,156 A | 4/1941 | Grubel |
| 2,632,661 A | 3/1953 | Cristofv |
| 2,827,056 A | 3/1958 | Degelman |
| 3,085,566 A | 4/1963 | Tolles |
| 3,459,187 A | 8/1969 | Pallotta |
| 3,494,363 A | 2/1970 | Jackson |
| 3,588,710 A | 6/1971 | Masters |
| 3,651,811 A | 3/1972 | Hildebrandt et al. |
| 3,685,518 A | 8/1972 | Beuerle et al. |
| 3,780,416 A | 12/1973 | Rider |
| 3,826,263 A | 7/1974 | Cage |
| 3,911,766 A | 10/1975 | Fridolph |
| 3,920,021 A | 11/1975 | Hiltebrandt |
| 3,938,527 A | 2/1976 | Rioux |
| 3,963,030 A | 6/1976 | Newton |
| 3,970,088 A | 7/1976 | Morrison |
| 3,980,085 A | 9/1976 | Ikuno |
| 3,987,795 A | 10/1976 | Morrison |
| 4,030,501 A | 6/1977 | Archibald |
| 4,041,952 A | 8/1977 | Morrison, Jr. et al. |
| 4,043,342 A | 8/1977 | Morrison |
| 4,060,088 A | 11/1977 | Morrison, Jr. et al. |
| 4,074,718 A | 2/1978 | Morrison, Jr. |
| 4,089,336 A | 5/1978 | Cage |
| 4,092,986 A | 6/1978 | Schneiderman |
| 4,094,320 A | 6/1978 | Newton et al. |
| 4,114,623 A | 9/1978 | Meinke |
| 4,126,137 A | 11/1978 | Archibald |
| 4,154,240 A | 5/1979 | Ikuno |
| 4,171,700 A | 10/1979 | Farin |
| 4,181,131 A | 1/1980 | Ogui |
| 4,188,927 A | 2/1980 | Harris |
| 4,196,734 A | 4/1980 | Harris |
| 4,198,957 A | 4/1980 | Cage et al. |
| 4,198,960 A | 4/1980 | Utsugi |
| 4,200,104 A | 4/1980 | Harris |
| 4,231,372 A | 11/1980 | Newton |
| 4,237,887 A | 12/1980 | Gonser |
| 4,244,371 A | 1/1981 | Farin |
| 4,325,374 A | 4/1982 | Komiya |
| 4,331,149 A | 5/1982 | Gonser |
| 4,338,940 A | 7/1982 | Ikuno |
| 4,352,156 A | 9/1982 | Gyugyi |
| 4,370,980 A | 2/1983 | Lottick |
| 4,416,276 A | 11/1983 | Newton |
| 4,416,277 A | 11/1983 | Newton et al. |
| 4,427,014 A | 1/1984 | Bel |
| 4,429,694 A | 2/1984 | McGreevy |
| 4,463,759 A | 8/1984 | Garito et al. |
| 4,487,489 A | 12/1984 | Takamatsu |
| 4,514,619 A | 4/1985 | Kugelman |
| 4,522,206 A | 6/1985 | Whipple et al. |
| 4,552,143 A | 11/1985 | Lottick |
| 4,569,131 A | 2/1986 | Faulk et al. |
| 4,569,345 A | 2/1986 | Manes et al. |
| 4,590,934 A | 5/1986 | Malis et al. |
| 4,599,553 A | 7/1986 | Brennen et al. |
| 4,630,218 A | 12/1986 | Hurley |
| 4,632,109 A | 12/1986 | Paterson |
| 4,644,950 A | 2/1987 | Valli |
| 4,651,280 A | 3/1987 | Chang et al. |
| 4,655,216 A | 4/1987 | Tischer |

(56) References Cited

U.S. PATENT DOCUMENTS

| | | |
|---|---|---|
| 4,657,018 A | 4/1987 | Hakky |
| 4,658,815 A | 4/1987 | Farin et al. |
| 4,658,819 A | 4/1987 | Harris et al. |
| 4,658,820 A | 4/1987 | Klicek |
| 4,674,498 A | 6/1987 | Stasz |
| 4,685,459 A | 8/1987 | Koch et al. |
| 4,699,146 A | 10/1987 | Sieverding |
| 4,712,545 A | 12/1987 | Honkanen |
| 4,716,897 A | 1/1988 | Noguchi et al. |
| 4,727,874 A | 3/1988 | Bowers |
| 4,739,759 A | 4/1988 | Rexroth et al. |
| 4,741,334 A | 5/1988 | Irnich |
| 4,752,864 A | 6/1988 | Clappier |
| 4,754,757 A | 7/1988 | Feucht |
| 4,788,977 A | 12/1988 | Farin et al. |
| 4,802,476 A | 2/1989 | Noerenberg et al. |
| 4,818,954 A | 4/1989 | Flachenecker |
| 4,827,927 A | 5/1989 | Newton |
| 4,848,335 A | 7/1989 | Manes |
| 4,850,353 A | 7/1989 | Stasz et al. |
| 4,860,745 A | 8/1989 | Farin et al. |
| 4,862,889 A | 9/1989 | Feucht |
| 4,862,890 A | 9/1989 | Stasz et al. |
| 4,872,456 A | 10/1989 | Hasson |
| 4,887,612 A | 12/1989 | Esser et al. |
| 4,889,722 A | 12/1989 | Sheffield et al. |
| 4,903,696 A | 2/1990 | Stasz et al. |
| 4,905,691 A | 3/1990 | Rydell |
| 4,922,903 A | 5/1990 | Welch et al. |
| 4,936,281 A | 6/1990 | Stasz |
| 4,937,254 A | 6/1990 | Sheffield et al. |
| 4,938,761 A | 7/1990 | Ensslin |
| 4,942,313 A | 7/1990 | Kinzel |
| 4,958,539 A | 9/1990 | Stasz et al. |
| 4,969,885 A | 11/1990 | Farin |
| 4,976,711 A | 12/1990 | Parins et al. |
| 5,007,908 A | 4/1991 | Rydell |
| 5,013,312 A | 5/1991 | Parins et al. |
| 5,015,227 A | 5/1991 | Broadwin et al. |
| 5,016,521 A | 5/1991 | Haka |
| 5,026,370 A | 6/1991 | Lottick |
| 5,026,371 A | 6/1991 | Rydell et al. |
| 5,035,696 A | 7/1991 | Rydell |
| 5,038,109 A | 8/1991 | Goble et al. |
| 5,047,026 A | 9/1991 | Rydell |
| 5,047,027 A | 9/1991 | Rydell |
| 5,052,402 A | 10/1991 | Bencini et al. |
| 5,057,107 A | 10/1991 | Parins et al. |
| 5,061,269 A | 10/1991 | Muller |
| 5,062,031 A | 10/1991 | Flachenecker et al. |
| 5,071,419 A | 12/1991 | Rydell et al. |
| 5,078,717 A | 1/1992 | Parins et al. |
| 5,083,565 A | 1/1992 | Parins |
| 5,085,659 A | 2/1992 | Rydell |
| 5,087,257 A | 2/1992 | Farin et al. |
| 5,098,431 A | 3/1992 | Rydell |
| 5,116,332 A | 5/1992 | Lottick |
| 5,122,137 A | 6/1992 | Lennox |
| 5,125,928 A | 6/1992 | Parins et al. |
| 5,127,412 A | 7/1992 | Cosmetto et al. |
| 5,151,102 A | 9/1992 | Kamiyama et al. |
| 5,158,561 A | 10/1992 | Rydell et al. |
| 5,160,343 A | 11/1992 | Brancel et al. |
| 5,167,658 A | 12/1992 | Ensslin |
| 5,171,255 A | 12/1992 | Rydell |
| 5,171,311 A | 12/1992 | Rydell |
| 5,190,517 A | 3/1993 | Klicek et al. |
| 5,190,541 A | 3/1993 | Abele et al. |
| 5,192,280 A | 3/1993 | Parins |
| 5,197,963 A | 3/1993 | Parins |
| 5,197,964 A | 3/1993 | Parins |
| 5,201,732 A | 4/1993 | Parins et al. |
| 5,217,457 A | 6/1993 | Delahuerga et al. |
| 5,217,458 A | 6/1993 | Parins |
| 5,234,427 A | 8/1993 | Ohtomo et al. |
| 5,244,462 A | 9/1993 | Delahuerga et al. |
| 5,246,440 A | 9/1993 | Van Noord |
| 5,250,047 A | 10/1993 | Rydell |
| 5,250,056 A | 10/1993 | Hasson |
| 5,254,126 A | 10/1993 | Filipi et al. |
| 5,256,149 A | 10/1993 | Banik et al. |
| 5,258,006 A | 11/1993 | Rydell et al. |
| 5,267,997 A | 12/1993 | Farin et al. |
| 5,269,780 A | 12/1993 | Roos |
| 5,273,524 A | 12/1993 | Fox et al. |
| 5,281,216 A | 1/1994 | Klicek |
| 5,282,799 A | 2/1994 | Rydell |
| 5,286,255 A | 2/1994 | Weber |
| 5,290,286 A | 3/1994 | Parins |
| 5,300,070 A | 4/1994 | Gentelia et al. |
| 5,304,190 A | 4/1994 | Reckelhoff et al. |
| 5,312,329 A | 5/1994 | Beaty et al. |
| 5,314,424 A | 5/1994 | Nicholas |
| 5,318,563 A | 6/1994 | Malis et al. |
| 5,322,055 A | 6/1994 | Davison et al. |
| 5,324,289 A | 6/1994 | Eggers |
| 5,330,471 A | 7/1994 | Eggers |
| 5,334,183 A | 8/1994 | Wuchinich |
| 5,338,317 A | 8/1994 | Hasson et al. |
| 5,341,807 A | 8/1994 | Nardella |
| 5,341,815 A | 8/1994 | Cofone et al. |
| 5,342,359 A | 8/1994 | Rydell |
| 5,342,381 A | 8/1994 | Tidemand |
| 5,352,222 A | 10/1994 | Rydell |
| 5,352,223 A | 10/1994 | McBrayer et al. |
| 5,354,313 A | 10/1994 | Boebel |
| 5,356,408 A | 10/1994 | Rydell |
| 5,370,645 A | 12/1994 | Klicek et al. |
| 5,372,124 A | 12/1994 | Takayama et al. |
| 5,372,596 A | 12/1994 | Klicek et al. |
| 5,374,277 A | 12/1994 | Hassler |
| 5,382,247 A | 1/1995 | Cimino et al. |
| 5,383,880 A | 1/1995 | Hovven |
| 5,383,922 A | 1/1995 | Zipes et al. |
| 5,387,196 A | 2/1995 | Green et al. |
| 5,387,197 A | 2/1995 | Smith et al. |
| 5,389,104 A | 2/1995 | Hahnen et al. |
| 5,389,849 A | 2/1995 | Asano et al. |
| 5,391,166 A | 2/1995 | Eggers |
| 5,392,917 A | 2/1995 | Alpern et al. |
| 5,400,267 A | 3/1995 | Denen |
| 5,403,312 A | 4/1995 | Yates et al. |
| 5,403,342 A | 4/1995 | Tovey et al. |
| 5,405,344 A | 4/1995 | Williamson et al. |
| 5,409,498 A | 4/1995 | Braddock et al. |
| 5,417,687 A | 5/1995 | Nardella et al. |
| 5,422,567 A | 6/1995 | Matsunaga |
| 5,423,808 A | 6/1995 | Edwards et al. |
| 5,423,810 A | 6/1995 | Goble et al. |
| 5,431,638 A | 7/1995 | Hennig et al. |
| 5,431,649 A | 7/1995 | Mulier et al. |
| 5,431,674 A | 7/1995 | Basile et al. |
| 5,432,459 A | 7/1995 | Thompson et al. |
| 5,436,566 A | 7/1995 | Thompson et al. |
| 5,437,664 A | 8/1995 | Cohen et al. |
| 5,438,302 A | 8/1995 | Goble |
| 5,443,463 A | 8/1995 | Stern et al. |
| 5,445,142 A | 8/1995 | Hassler, Jr. |
| 5,445,638 A * | 8/1995 | Rydell ............... A61B 18/1482 606/171 |
| 5,447,513 A | 9/1995 | Davison et al. |
| 5,449,355 A | 9/1995 | Rhum et al. |
| 5,456,684 A | 10/1995 | Schmidt et al. |
| 5,458,598 A | 10/1995 | Feinberg et al. |
| 5,460,182 A | 10/1995 | Goodman et al. |
| 5,462,546 A | 10/1995 | Rydell |
| 5,464,144 A | 11/1995 | Guy et al. |
| 5,472,439 A | 12/1995 | Hurd |
| 5,472,442 A | 12/1995 | Klicek |
| 5,472,443 A | 12/1995 | Cordis et al. |
| 5,472,451 A | 12/1995 | Freitas et al. |
| 5,474,057 A | 12/1995 | Makower et al. |
| 5,476,479 A | 12/1995 | Green et al. |
| 5,478,351 A | 12/1995 | Meade et al. |

(56) References Cited

U.S. PATENT DOCUMENTS

| | | |
|---|---|---|
| 5,484,400 A | 1/1996 | Edwards et al. |
| 5,486,185 A | 1/1996 | Freitas et al. |
| 5,496,312 A | 3/1996 | Klicek |
| 5,496,317 A | 3/1996 | Goble et al. |
| 5,499,992 A | 3/1996 | Meade et al. |
| 5,499,998 A | 3/1996 | Meade et al. |
| 5,503,320 A | 4/1996 | Webster et al. |
| 5,507,773 A | 4/1996 | Hutema et al. |
| 5,509,916 A | 4/1996 | Taylor et al. |
| 5,514,129 A | 5/1996 | Smith |
| 5,514,134 A | 5/1996 | Rydell et al. |
| 5,518,163 A | 5/1996 | Hooven |
| 5,518,164 A | 5/1996 | Hooven |
| 5,527,313 A | 6/1996 | Scott et al. |
| 5,527,330 A | 6/1996 | Tovey |
| 5,531,744 A | 7/1996 | Nardella et al. |
| 5,540,681 A | 7/1996 | Strul et al. |
| 5,540,684 A | 7/1996 | Hassler et al. |
| 5,540,685 A | 7/1996 | Parins et al. |
| 5,541,376 A | 7/1996 | Ladtkow et al. |
| 5,551,945 A | 9/1996 | Yabe et al. |
| 5,558,429 A | 9/1996 | Cain |
| 5,558,671 A | 9/1996 | Yates |
| 5,562,699 A | 10/1996 | Heimberger et al. |
| 5,562,700 A | 10/1996 | Huitema et al. |
| 5,571,100 A | 11/1996 | Goble et al. |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,573,535 A | 11/1996 | Viklund |
| 5,575,789 A | 11/1996 | Bell et al. |
| 5,575,805 A | 11/1996 | Li |
| 5,584,830 A | 12/1996 | Ladd et al. |
| 5,599,344 A | 2/1997 | Paterson |
| 5,599,350 A | 2/1997 | Schulze et al. |
| 5,603,711 A | 2/1997 | Parins et al. |
| D378,611 S | 3/1997 | Croley |
| 5,607,391 A | 3/1997 | Klinger et al. |
| 5,609,151 A | 3/1997 | Mulier et al. |
| 5,609,560 A | 3/1997 | Ichikawa et al. |
| 5,609,573 A | 3/1997 | Sandock |
| 5,611,709 A | 3/1997 | McAnulty |
| 5,613,966 A | 3/1997 | Makower et al. |
| 5,620,415 A | 4/1997 | Lucey et al. |
| 5,620,447 A | 4/1997 | Smith et al. |
| 5,624,452 A | 4/1997 | Yates |
| 5,626,575 A | 5/1997 | Crenner |
| 5,626,607 A | 5/1997 | Malecki et al. |
| 5,626,608 A | 5/1997 | Cuny et al. |
| 5,627,584 A | 5/1997 | Nishikori et al. |
| 5,633,578 A | 5/1997 | Eggers et al. |
| 5,645,540 A | 7/1997 | Henniges et al. |
| 5,647,869 A | 7/1997 | Goble et al. |
| 5,651,780 A | 7/1997 | Jackson et al. |
| 5,658,279 A | 8/1997 | Nardella et al. |
| 5,658,281 A | 8/1997 | Heard |
| 5,665,100 A | 9/1997 | Yoon |
| 5,665,105 A | 9/1997 | Furnish et al. |
| 5,667,517 A | 9/1997 | Hooven |
| 5,669,907 A | 9/1997 | Platt, Jr. et al. |
| 5,674,184 A | 10/1997 | Hassler, Jr. |
| 5,674,220 A | 10/1997 | Fox et al. |
| 5,683,349 A | 11/1997 | Makower et al. |
| 5,688,270 A | 11/1997 | Yates et al. |
| 5,693,045 A | 12/1997 | Eggers |
| 5,693,051 A | 12/1997 | Schulze et al. |
| 5,695,494 A | 12/1997 | Becker |
| 5,697,281 A | 12/1997 | Eggers et al. |
| 5,697,909 A | 12/1997 | Eggers et al. |
| 5,700,261 A | 12/1997 | Brinkerhoff |
| 5,702,386 A | 12/1997 | Stern et al. |
| 5,702,387 A | 12/1997 | Arts et al. |
| 5,702,390 A | 12/1997 | Austin et al. |
| 5,707,369 A | 1/1998 | Vaitekunas et al. |
| 5,709,680 A | 1/1998 | Yates et al. |
| 5,713,128 A | 2/1998 | Schrenk et al. |
| 5,713,895 A | 2/1998 | Lontine et al. |
| 5,713,896 A | 2/1998 | Nardella |
| 5,720,293 A | 2/1998 | Quinn et al. |
| 5,720,742 A | 2/1998 | Zacharias |
| 5,720,744 A | 2/1998 | Eggleston et al. |
| 5,720,745 A | 2/1998 | Farin et al. |
| 5,722,975 A | 3/1998 | Edwards et al. |
| 5,725,524 A | 3/1998 | Mulier et al. |
| 5,735,848 A | 4/1998 | Yates et al. |
| 5,735,849 A | 4/1998 | Baden et al. |
| 5,743,456 A | 4/1998 | Jones et al. |
| 5,743,906 A | 4/1998 | Parins et al. |
| 5,746,210 A | 5/1998 | Benaron et al. |
| 5,746,740 A | 5/1998 | Nicholas |
| 5,746,759 A | 5/1998 | Meade et al. |
| 5,752,519 A | 5/1998 | Benaron et al. |
| 5,755,717 A | 5/1998 | Yates et al. |
| 5,759,185 A | 6/1998 | Grinberg |
| 5,762,609 A | 6/1998 | Benaron et al. |
| 5,766,167 A | 6/1998 | Eggers et al. |
| 5,769,791 A | 6/1998 | Benaron et al. |
| 5,769,841 A | 6/1998 | Odell et al. |
| 5,772,597 A | 6/1998 | Goldberger et al. |
| 5,772,659 A | 6/1998 | Becker et al. |
| 5,772,660 A | 6/1998 | Young et al. |
| 5,776,092 A | 7/1998 | Farin et al. |
| 5,776,129 A | 7/1998 | Mersch |
| 5,776,130 A | 7/1998 | Buysse et al. |
| 5,776,155 A | 7/1998 | Beaupre et al. |
| 5,782,397 A | 7/1998 | Koukline |
| 5,785,658 A | 7/1998 | Benaron et al. |
| 5,792,139 A | 8/1998 | Chambers et al. |
| 5,792,178 A | 8/1998 | Welch et al. |
| 5,797,906 A | 8/1998 | Rhum et al. |
| 5,797,938 A | 8/1998 | Paraschac et al. |
| 5,797,941 A | 8/1998 | Schulze |
| 5,800,449 A | 9/1998 | Wales |
| 5,807,261 A | 9/1998 | Benaron et al. |
| 5,807,393 A | 9/1998 | Williamson, IV et al. |
| 5,807,395 A | 9/1998 | Mulier et al. |
| 5,810,806 A | 9/1998 | Ritchart et al. |
| 5,810,811 A | 9/1998 | Yates et al. |
| 5,810,859 A | 9/1998 | Dimatteo et al. |
| 5,817,091 A | 10/1998 | Nardella et al. |
| 5,817,093 A | 10/1998 | Williamson, IV et al. |
| 5,817,119 A | 10/1998 | Klieman et al. |
| 5,827,271 A | 10/1998 | Buysse et al. |
| 5,827,279 A | 10/1998 | Hughett et al. |
| 5,827,299 A | 10/1998 | Thomason et al. |
| 5,830,231 A | 11/1998 | Geiges, Jr. |
| 5,833,690 A | 11/1998 | Yates et al. |
| 5,836,942 A | 11/1998 | Netherly et al. |
| 5,836,943 A | 11/1998 | Miller, III |
| 5,846,194 A | 12/1998 | Wasson et al. |
| 5,849,020 A | 12/1998 | Long et al. |
| 5,853,412 A | 12/1998 | Mayenbergr |
| 5,860,975 A | 1/1999 | Goble et al. |
| 5,873,873 A | 2/1999 | Smith et al. |
| 5,876,398 A | 3/1999 | Mulier et al. |
| 5,876,401 A | 3/1999 | Schulze et al. |
| 5,885,277 A | 3/1999 | Korth |
| 5,891,095 A | 4/1999 | Eggers et al. |
| 5,891,141 A | 4/1999 | Rydell |
| 5,891,142 A | 4/1999 | Eggers et al. |
| 5,893,835 A | 4/1999 | Witt et al. |
| 5,893,873 A | 4/1999 | Rader et al. |
| 5,897,490 A | 4/1999 | Fox et al. |
| 5,897,523 A | 4/1999 | Wright et al. |
| 5,897,553 A | 4/1999 | Mulier et al. |
| 5,897,569 A | 4/1999 | Kellogg et al. |
| 5,902,264 A | 5/1999 | Toso et al. |
| 5,902,301 A | 5/1999 | Olig |
| 5,904,709 A | 5/1999 | Arndt et al. |
| 5,906,613 A | 5/1999 | Mulier et al. |
| 5,908,402 A | 6/1999 | Blythe |
| 5,908,420 A | 6/1999 | Parins et al. |
| 5,910,152 A | 6/1999 | Bays |

(56) References Cited

U.S. PATENT DOCUMENTS

| | | |
|---|---|---|
| 5,928,137 A | 7/1999 | Green |
| 5,928,255 A | 7/1999 | Meade et al. |
| 5,928,256 A | 7/1999 | Riza |
| 5,931,836 A | 8/1999 | Hatta et al. |
| 5,935,126 A | 8/1999 | Riza |
| 5,938,633 A | 8/1999 | Beaupre |
| 5,944,715 A | 8/1999 | Goble et al. |
| 5,944,718 A | 8/1999 | Austin et al. |
| 5,944,737 A | 8/1999 | Tsonton et al. |
| 5,947,284 A | 9/1999 | Foster |
| 5,947,984 A | 9/1999 | Whipple |
| 5,951,552 A | 9/1999 | Long et al. |
| 5,954,736 A | 9/1999 | Bishop et al. |
| 5,954,746 A | 9/1999 | Holthaus et al. |
| 5,957,943 A | 9/1999 | Vaitekunas |
| 5,961,514 A | 10/1999 | Long et al. |
| 5,968,062 A | 10/1999 | Thomas et al. |
| 5,968,074 A | 10/1999 | Prestel |
| 5,976,077 A | 11/1999 | Wittens et al. |
| 5,976,128 A | 11/1999 | Schilling et al. |
| 5,980,510 A | 11/1999 | Tsonton et al. |
| 5,980,516 A | 11/1999 | Mulier et al. |
| 5,984,921 A | 11/1999 | Long et al. |
| 5,987,346 A | 11/1999 | Benaron et al. |
| 5,993,380 A | 11/1999 | Yabe et al. |
| 5,993,447 A | 11/1999 | Blewett et al. |
| 5,995,875 A | 11/1999 | Blewett et al. |
| 5,997,533 A | 12/1999 | Kuhns |
| 6,003,517 A | 12/1999 | Sheffield et al. |
| 6,004,319 A | 12/1999 | Goble et al. |
| 6,004,335 A | 12/1999 | Vaitekunas et al. |
| 6,010,499 A | 1/2000 | Cobb |
| 6,010,516 A | 1/2000 | Hulka |
| 6,013,076 A | 1/2000 | Goble et al. |
| 6,015,406 A | 1/2000 | Goble et al. |
| 6,016,809 A | 1/2000 | Mulier et al. |
| D420,741 S | 2/2000 | Croley |
| 6,024,741 A | 2/2000 | Williamson, IV et al. |
| 6,024,744 A | 2/2000 | Kese et al. |
| 6,027,501 A | 2/2000 | Goble et al. |
| 6,027,522 A | 2/2000 | Palmer |
| 6,030,384 A | 2/2000 | Nezhat |
| 6,030,402 A | 2/2000 | Thompson et al. |
| 6,033,399 A | 3/2000 | Gines |
| 6,033,404 A | 3/2000 | Melzer et al. |
| 6,036,657 A | 3/2000 | Milliman et al. |
| 6,039,733 A | 3/2000 | Buysse et al. |
| 6,039,734 A | 3/2000 | Goble et al. |
| 6,039,736 A | 3/2000 | Platt, Jr. |
| 6,050,996 A | 4/2000 | Schmaltz et al. |
| 6,051,010 A | 4/2000 | Dimatteo et al. |
| 6,053,172 A | 4/2000 | Hovda et al. |
| 6,053,914 A | 4/2000 | Eggers et al. |
| 6,056,746 A | 5/2000 | Goble et al. |
| 6,063,050 A | 5/2000 | Manna et al. |
| 6,063,075 A | 5/2000 | Mohori |
| 6,063,081 A | 5/2000 | Mulier et al. |
| 6,063,086 A | 5/2000 | Benecke et al. |
| 6,066,139 A | 5/2000 | Ryan et al. |
| 6,068,627 A | 5/2000 | Orszulak et al. |
| 6,068,647 A | 5/2000 | Witt et al. |
| 6,070,444 A | 6/2000 | Lontine et al. |
| 6,074,386 A | 6/2000 | Goble et al. |
| RE36,795 E | 7/2000 | Rydell |
| 6,083,191 A | 7/2000 | Rose |
| 6,086,586 A | 7/2000 | Hooven |
| 6,090,106 A | 7/2000 | Goble et al. |
| 6,090,120 A | 7/2000 | Wright et al. |
| 6,092,722 A | 7/2000 | Heinrichs et al. |
| 6,093,186 A | 7/2000 | Goble |
| 6,096,037 A | 8/2000 | Mulier et al. |
| 6,102,909 A | 8/2000 | Chen et al. |
| 6,106,521 A | 8/2000 | Blewett et al. |
| 6,109,268 A | 8/2000 | Thapliyal et al. |
| 6,110,171 A | 8/2000 | Rydell |
| 6,113,591 A | 9/2000 | Whayne et al. |
| 6,113,594 A | 9/2000 | Savage |
| 6,113,596 A | 9/2000 | Hooven et al. |
| 6,113,598 A | 9/2000 | Baker |
| 6,117,152 A | 9/2000 | Huitema |
| 6,120,501 A | 9/2000 | Long et al. |
| H1904 H | 10/2000 | Yates |
| 6,132,429 A | 10/2000 | Baker |
| 6,135,998 A | 10/2000 | Palanker |
| 6,139,519 A | 10/2000 | Blythe |
| 6,139,547 A | 10/2000 | Lontine et al. |
| 6,142,992 A | 11/2000 | Cheng et al. |
| 6,152,923 A | 11/2000 | Ryan |
| 6,159,146 A | 12/2000 | El Gazayerli |
| 6,162,235 A | 12/2000 | Vaitekunas |
| 6,165,175 A | 12/2000 | Wampler et al. |
| 6,168,605 B1 | 1/2001 | Measamer et al. |
| 6,171,304 B1 | 1/2001 | Netherly et al. |
| 6,174,308 B1 | 1/2001 | Goble et al. |
| 6,174,309 B1 | 1/2001 | Wrublewski et al. |
| 6,179,834 B1 | 1/2001 | Buysse et al. |
| 6,186,147 B1 | 2/2001 | Cobb |
| 6,187,003 B1 | 2/2001 | Buysse et al. |
| 6,187,026 B1 | 2/2001 | Devlin et al. |
| 6,190,383 B1 | 2/2001 | Schmaltz et al. |
| 6,190,385 B1 | 2/2001 | Tom et al. |
| 6,190,386 B1 | 2/2001 | Rydell |
| 6,193,129 B1 | 2/2001 | Bittner et al. |
| 6,193,653 B1 | 2/2001 | Evans et al. |
| 6,193,713 B1 | 2/2001 | Geistert et al. |
| 6,197,026 B1 | 3/2001 | Farin et al. |
| 6,203,541 B1 | 3/2001 | Keppel |
| 6,206,823 B1 | 3/2001 | Kolata et al. |
| 6,206,844 B1 | 3/2001 | Reichel et al. |
| 6,206,875 B1 | 3/2001 | Long et al. |
| 6,206,877 B1 | 3/2001 | Kese et al. |
| 6,210,403 B1 | 4/2001 | Klicek |
| 6,210,405 B1 | 4/2001 | Goble et al. |
| 6,214,003 B1 | 4/2001 | Morgan et al. |
| 6,214,023 B1 | 4/2001 | Whipple et al. |
| 6,228,023 B1 | 5/2001 | Zaslavsky et al. |
| 6,228,055 B1 | 5/2001 | Foerster et al. |
| 6,228,080 B1 | 5/2001 | Gines |
| 6,228,081 B1 | 5/2001 | Goble |
| 6,228,083 B1 | 5/2001 | Lands et al. |
| 6,234,178 B1 | 5/2001 | Goble et al. |
| 6,237,604 B1 | 5/2001 | Burnside et al. |
| 6,238,366 B1 | 5/2001 | Savage et al. |
| 6,238,392 B1 | 5/2001 | Long |
| 6,238,393 B1 | 5/2001 | Mulier et al. |
| 6,242,741 B1 | 6/2001 | Miller et al. |
| 6,246,912 B1 | 6/2001 | Sluijter et al. |
| 6,251,106 B1 | 6/2001 | Becker et al. |
| 6,251,110 B1 | 6/2001 | Wampler |
| 6,254,623 B1 | 7/2001 | Haibel et al. |
| 6,257,241 B1 | 7/2001 | Wampler |
| 6,258,085 B1 | 7/2001 | Eggleston |
| 6,261,286 B1 | 7/2001 | Goble et al. |
| 6,267,761 B1 | 7/2001 | Ryan |
| 6,270,497 B1 | 8/2001 | Sekino et al. |
| 6,273,862 B1 | 8/2001 | Privitera et al. |
| 6,277,114 B1 | 8/2001 | Bullivant et al. |
| 6,277,115 B1 | 8/2001 | Saadat |
| 6,277,117 B1 | 8/2001 | Tetzlaff et al. |
| 6,280,398 B1 | 8/2001 | Ritchart et al. |
| 6,280,407 B1 | 8/2001 | Manna et al. |
| 6,280,441 B1 | 8/2001 | Ryan |
| 6,283,963 B1 | 9/2001 | Regula |
| 6,287,344 B1 | 9/2001 | Wampler |
| 6,293,942 B1 | 9/2001 | Goble et al. |
| 6,293,945 B1 | 9/2001 | Parins et al. |
| 6,296,637 B1 | 10/2001 | Thorne et al. |
| 6,296,640 B1 | 10/2001 | Wampler et al. |
| 6,298,550 B1 | 10/2001 | Kirwan, Jr. |
| 6,302,903 B1 | 10/2001 | Mulier et al. |
| 6,306,131 B1 | 10/2001 | Hareyama et al. |
| 6,306,134 B1 | 10/2001 | Goble et al. |
| 6,308,089 B1 | 10/2001 | von der Ruhr et al. |
| 6,309,400 B2 | 10/2001 | Beaupre |

(56) References Cited

U.S. PATENT DOCUMENTS

| | | |
|---|---|---|
| 6,312,426 B1 | 11/2001 | Goldberg et al. |
| 6,315,777 B1 | 11/2001 | Comben |
| 6,319,221 B1 | 11/2001 | Savage et al. |
| 6,322,494 B1 | 11/2001 | Bullivant et al. |
| 6,322,549 B1 | 11/2001 | Eggers et al. |
| 6,322,561 B1 | 11/2001 | Eggers et al. |
| 6,325,795 B1 | 12/2001 | Lindemann et al. |
| 6,325,799 B1 | 12/2001 | Goble |
| 6,325,811 B1 | 12/2001 | Messerly |
| 6,328,736 B1 | 12/2001 | Mulier et al. |
| 6,328,751 B1 | 12/2001 | Beaupre |
| 6,331,181 B1 | 12/2001 | Tierney et al. |
| 6,334,068 B1 | 12/2001 | Hacker |
| 6,334,861 B1 | 1/2002 | Chandler et al. |
| 6,336,926 B1 | 1/2002 | Goble et al. |
| 6,348,051 B1 | 2/2002 | Farin et al. |
| 6,352,532 B1 | 3/2002 | Kramer et al. |
| 6,352,536 B1 | 3/2002 | Buysse et al. |
| 6,358,248 B1 | 3/2002 | Mulier et al. |
| 6,358,249 B1 | 3/2002 | Chen et al. |
| 6,358,267 B1 | 3/2002 | Murakami |
| 6,361,534 B1 | 3/2002 | Chen et al. |
| 6,364,877 B1 | 4/2002 | Goble et al. |
| 6,364,879 B1 | 4/2002 | Chen et al. |
| 6,371,967 B1 | 4/2002 | Long et al. |
| D457,958 S | 5/2002 | Dycus |
| 6,383,183 B1 | 5/2002 | Sekino et al. |
| 6,387,092 B1 | 5/2002 | Burnside et al. |
| 6,387,109 B1 | 5/2002 | Davison et al. |
| 6,391,024 B1 | 5/2002 | Sun et al. |
| 6,391,025 B1 | 5/2002 | Weinstein et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,747 B1 | 6/2002 | Lindemann et al. |
| 6,402,748 B1 | 6/2002 | Schoenman et al. |
| 6,406,475 B1 | 6/2002 | Wenzler et al. |
| 6,409,722 B1 | 6/2002 | Hoey et al. |
| 6,409,724 B1 | 6/2002 | Penny et al. |
| 6,409,728 B1 | 6/2002 | Ehr et al. |
| 6,416,486 B1 | 7/2002 | Wampler |
| 6,416,509 B1 | 7/2002 | Goble et al. |
| 6,423,057 B1 | 7/2002 | He et al. |
| 6,423,082 B1 | 7/2002 | Houser et al. |
| 6,432,118 B1 | 8/2002 | Messerly |
| 6,436,096 B1 | 8/2002 | Hareyama |
| 6,440,130 B1 | 8/2002 | Mulier et al. |
| 6,443,952 B1 | 9/2002 | Mulier et al. |
| 6,443,968 B1 | 9/2002 | Holthaus et al. |
| 6,443,970 B1 | 9/2002 | Schulze et al. |
| 6,451,013 B1 | 9/2002 | Bays et al. |
| 6,451,018 B1 | 9/2002 | Lands et al. |
| 6,454,764 B1 | 9/2002 | Fleenor et al. |
| 6,454,781 B1 | 9/2002 | Witt et al. |
| 6,454,782 B1 | 9/2002 | Schwemberger |
| 6,458,078 B1 | 10/2002 | Luedtke et al. |
| 6,458,128 B1 | 10/2002 | Schulze |
| 6,458,130 B1 | 10/2002 | Frazier et al. |
| 6,458,142 B1 | 10/2002 | Faller et al. |
| 6,461,352 B2 | 10/2002 | Morgan et al. |
| 6,464,689 B1 | 10/2002 | Qin et al. |
| 6,464,702 B2 | 10/2002 | Schulze et al. |
| 6,464,704 B2 | 10/2002 | Schmaltz et al. |
| 6,468,275 B1 | 10/2002 | Wampler et al. |
| 6,468,286 B2 | 10/2002 | Mastri et al. |
| 6,475,217 B1 | 11/2002 | Platt |
| 6,478,030 B1 | 11/2002 | Shaoeton et al. |
| 6,482,202 B1 | 11/2002 | Goble et al. |
| 6,485,490 B2 | 11/2002 | Wampler et al. |
| 6,488,507 B1 | 12/2002 | Stoloff et al. |
| 6,488,680 B1 | 12/2002 | Francischelli et al. |
| 6,491,690 B1 | 12/2002 | Goble et al. |
| 6,491,708 B2 | 12/2002 | Madan et al. |
| 6,493,589 B1 | 12/2002 | Medhkour et al. |
| 6,494,877 B2 | 12/2002 | Odell et al. |
| 6,494,902 B2 | 12/2002 | Hoey et al. |
| 6,497,705 B2 | 12/2002 | Comben |
| 6,500,176 B1 | 12/2002 | Truckai et al. |
| 6,500,188 B2 | 12/2002 | Harper et al. |
| 6,503,263 B2 | 1/2003 | Adams |
| 6,506,189 B1 | 1/2003 | Rittman et al. |
| 6,506,208 B2 | 1/2003 | Hunt et al. |
| 6,510,854 B2 | 1/2003 | Goble et al. |
| 6,511,476 B2 | 1/2003 | Hareyama |
| 6,511,480 B1 | 1/2003 | Tetzlaff et al. |
| 6,514,252 B2 | 2/2003 | Nezhat et al. |
| 6,517,536 B2 | 2/2003 | Hooven et al. |
| 6,517,538 B1 | 2/2003 | Jacob et al. |
| 6,526,320 B2 | 2/2003 | Mitchell |
| 6,527,771 B1 | 3/2003 | Weadock et al. |
| 6,533,784 B2 | 3/2003 | Truckai et al. |
| 6,534,770 B2 | 3/2003 | Miller et al. |
| 6,537,248 B2 | 3/2003 | Mulier et al. |
| 6,537,272 B2 | 3/2003 | Christopherson et al. |
| 6,540,695 B1 | 4/2003 | Burbank et al. |
| 6,543,456 B1 | 4/2003 | Freeman |
| 6,547,783 B1 | 4/2003 | Vilendrer et al. |
| 6,547,786 B1 | 4/2003 | Goble et al. |
| 6,554,829 B2 | 4/2003 | Schulze et al. |
| 6,558,379 B1 | 5/2003 | Batchelor et al. |
| 6,558,383 B2 | 5/2003 | Cunningham et al. |
| 6,561,983 B2 | 5/2003 | Cronin et al. |
| 6,562,037 B2 | 5/2003 | Paton et al. |
| 6,565,559 B2 | 5/2003 | Eggleston |
| 6,565,560 B1 | 5/2003 | Goble et al. |
| 6,569,105 B1 | 5/2003 | Kortenbach et al. |
| 6,569,109 B2 | 5/2003 | Sakurai et al. |
| 6,572,615 B2 | 6/2003 | Schulze et al. |
| 6,579,289 B2 | 6/2003 | Schnitzler |
| 6,582,424 B2 | 6/2003 | Fleenor et al. |
| 6,582,427 B1 | 6/2003 | Goble et al. |
| 6,584,360 B2 | 6/2003 | Francischelli et al. |
| D477,408 S | 7/2003 | Bromley |
| 6,585,732 B2 | 7/2003 | Mulier et al. |
| 6,585,733 B2 | 7/2003 | Wellman |
| 6,585,735 B1 | 7/2003 | Frazier et al. |
| 6,589,200 B1 | 7/2003 | Schwemberger et al. |
| 6,591,719 B1 | 7/2003 | Poole et al. |
| 6,592,582 B2 | 7/2003 | Hess et al. |
| 6,594,518 B1 | 7/2003 | Benaron et al. |
| 6,602,227 B1 | 8/2003 | Cimino et al. |
| 6,602,249 B1 | 8/2003 | Stoddard et al. |
| 6,602,252 B2 | 8/2003 | Mollenauer |
| 6,605,036 B1 | 8/2003 | Wild |
| 6,607,529 B1 | 8/2003 | Jones et al. |
| 6,610,060 B2 | 8/2003 | Mulier et al. |
| 6,611,793 B1 | 8/2003 | Burnside et al. |
| 6,613,048 B2 | 9/2003 | Mulier et al. |
| 6,616,656 B2 | 9/2003 | Brommersma |
| 6,616,660 B1 | 9/2003 | Platt |
| 6,616,661 B2 | 9/2003 | Wellman et al. |
| 6,620,157 B1 | 9/2003 | Dabney et al. |
| 6,620,161 B2 | 9/2003 | Schulze et al. |
| 6,623,482 B2 | 9/2003 | Pendekanti et al. |
| 6,623,515 B2 | 9/2003 | Mulier et al. |
| 6,626,901 B1 | 9/2003 | Treat et al. |
| 6,629,974 B2 | 10/2003 | Penny et al. |
| 6,638,274 B2 | 10/2003 | Yamamoto |
| 6,648,883 B2 | 11/2003 | Francischelli et al. |
| 6,652,514 B2 | 11/2003 | Ellman et al. |
| 6,652,521 B2 | 11/2003 | Schulze |
| 6,656,110 B1 | 12/2003 | Irion et al. |
| 6,656,175 B2 | 12/2003 | Francischelli et al. |
| 6,656,176 B2 | 12/2003 | Hess et al. |
| 6,656,177 B2 | 12/2003 | Truckai et al. |
| 6,660,017 B2 | 12/2003 | Beaupre |
| 6,662,050 B2 | 12/2003 | Olson |
| 6,662,127 B2 | 12/2003 | Wiener et al. |
| 6,663,622 B1 | 12/2003 | Foley et al. |
| 6,663,627 B2 | 12/2003 | Francischelli et al. |
| 6,663,628 B2 | 12/2003 | Peters |
| 6,666,865 B2 | 12/2003 | Platt |

(56) References Cited

U.S. PATENT DOCUMENTS

| | | |
|---|---|---|
| 6,676,660 B2 | 1/2004 | Wampler et al. |
| 6,678,621 B2 | 1/2004 | Wiener et al. |
| 6,679,882 B1 | 1/2004 | Kornerup |
| 6,682,527 B2 | 1/2004 | Strul |
| 6,682,528 B2 | 1/2004 | Frazier et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,692,450 B1 | 2/2004 | Coleman |
| 6,692,489 B1 | 2/2004 | Heim et al. |
| 6,695,837 B2 | 2/2004 | Howell |
| 6,695,838 B2 | 2/2004 | Wellman et al. |
| 6,695,840 B2 | 2/2004 | Schulze |
| 6,699,240 B2 | 3/2004 | Francischelli et al. |
| 6,706,038 B2 | 3/2004 | Francischelli et al. |
| 6,706,039 B2 | 3/2004 | Mulier et al. |
| 6,709,432 B2 | 3/2004 | Ferek-Petric |
| 6,723,091 B2 | 4/2004 | Goble et al. |
| 6,726,683 B1 | 4/2004 | Shaw |
| 6,726,686 B2 | 4/2004 | Buysse et al. |
| 6,733,498 B2 | 5/2004 | Paton et al. |
| 6,736,810 B2 | 5/2004 | Hoey et al. |
| 6,740,084 B2 | 5/2004 | Ryan |
| 6,740,085 B2 | 5/2004 | Hareyama et al. |
| 6,740,102 B2 | 5/2004 | Hess et al. |
| 6,743,229 B2 | 6/2004 | Buysse et al. |
| 6,752,804 B2 | 6/2004 | Simpson et al. |
| 6,755,825 B2 | 6/2004 | Schoenman et al. |
| 6,755,827 B2 | 6/2004 | Mulier et al. |
| 6,755,841 B2 | 6/2004 | Fraser et al. |
| 6,758,846 B2 | 7/2004 | Goble et al. |
| 6,764,487 B2 | 7/2004 | Mulier et al. |
| 6,770,071 B2 | 8/2004 | Woloszko et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,444 B2 | 8/2004 | Messerly |
| 6,775,575 B2 | 8/2004 | Bommannan et al. |
| 6,776,780 B2 | 8/2004 | Mulier et al. |
| 6,780,180 B1 | 8/2004 | Goble et al. |
| 6,786,906 B1 | 9/2004 | Cobb |
| 6,790,217 B2 | 9/2004 | Schulze et al. |
| 6,796,828 B2 | 9/2004 | Ehr et al. |
| 6,796,981 B2 | 9/2004 | Wham et al. |
| 6,807,444 B2 | 10/2004 | Tu et al. |
| 6,807,968 B2 | 10/2004 | Francischelli et al. |
| 6,808,518 B2 | 10/2004 | Wellman et al. |
| 6,808,525 B2 | 10/2004 | Latterell et al. |
| 6,814,745 B2 | 11/2004 | Prestel |
| 6,821,273 B2 | 11/2004 | Mollenauer |
| 6,827,715 B2 | 12/2004 | Francischelli et al. |
| 6,827,717 B2 | 12/2004 | Brommersma et al. |
| 6,827,725 B2 | 12/2004 | Batchelor et al. |
| 6,830,569 B2 | 12/2004 | Thompson et al. |
| 6,832,111 B2 | 12/2004 | Tu et al. |
| 6,832,985 B2 | 12/2004 | Irion et al. |
| 6,832,998 B2 | 12/2004 | Goble |
| 6,835,082 B2 | 12/2004 | Gonnering |
| 6,835,195 B2 | 12/2004 | Schulze et al. |
| 6,837,887 B2 | 1/2005 | Woloszko et al. |
| 6,843,789 B2 | 1/2005 | Goble |
| 6,849,073 B2 | 2/2005 | Hoy et al. |
| 6,852,112 B2 | 2/2005 | Platt |
| 6,855,142 B2 | 2/2005 | Harano et al. |
| 6,855,145 B2 | 2/2005 | Ciarrocca |
| 6,858,028 B2 | 2/2005 | Mulier et al. |
| 6,860,881 B2 | 3/2005 | Sturm |
| 6,860,894 B1 | 3/2005 | Pittman |
| 6,887,240 B1 | 5/2005 | Lands et al. |
| 6,889,694 B2 | 5/2005 | Hooven |
| 6,893,435 B2 | 5/2005 | Goble |
| 6,893,441 B2 | 5/2005 | Brommersma et al. |
| 6,899,710 B2 | 5/2005 | Hooven |
| 6,905,497 B2 | 6/2005 | Truckai et al. |
| 6,905,498 B2 | 6/2005 | Hooven |
| 6,908,472 B2 | 6/2005 | Wiener et al. |
| 6,911,019 B2 | 6/2005 | Mulier et al. |
| 6,913,579 B2 | 7/2005 | Truckai et al. |
| 6,916,318 B2 | 7/2005 | Francischelli et al. |
| 6,918,880 B2 | 7/2005 | Brookner et al. |
| 6,923,803 B2 | 8/2005 | Goble |
| 6,923,804 B2 | 8/2005 | Eggers et al. |
| 6,923,806 B2 | 8/2005 | Hooven et al. |
| 6,926,716 B2 | 8/2005 | Baker et al. |
| 6,929,641 B2 | 8/2005 | Goble et al. |
| 6,929,644 B2 | 8/2005 | Truckai et al. |
| 6,932,810 B2 | 8/2005 | Ryan |
| 6,932,811 B2 | 8/2005 | Hooven et al. |
| 6,937,033 B2 | 8/2005 | Boronkay et al. |
| 6,939,347 B2 | 9/2005 | Thompson |
| 6,942,660 B2 | 9/2005 | Pantera et al. |
| 6,942,662 B2 | 9/2005 | Goble et al. |
| 6,945,972 B2 | 9/2005 | Frigg et al. |
| 6,945,981 B2 | 9/2005 | Donofrio et al. |
| 6,948,503 B2 | 9/2005 | Refior et al. |
| 6,949,098 B2 | 9/2005 | Mulier et al. |
| 6,958,063 B1 | 10/2005 | Soll et al. |
| 6,960,209 B2 | 11/2005 | Clague et al. |
| 6,960,210 B2 | 11/2005 | Lands et al. |
| 6,962,587 B2 | 11/2005 | Johnson et al. |
| 6,962,589 B2 | 11/2005 | Mulier et al. |
| 6,966,907 B2 | 11/2005 | Goble |
| 6,966,909 B2 | 11/2005 | Marshall et al. |
| 6,971,988 B2 | 12/2005 | Orban et al. |
| 6,974,453 B2 | 12/2005 | Woloszko et al. |
| 6,974,454 B2 | 12/2005 | Hooven |
| 6,976,969 B2 | 12/2005 | Messerly |
| 6,979,332 B2 | 12/2005 | Adams |
| 6,984,231 B2 | 1/2006 | Goble et al. |
| 6,984,233 B2 | 1/2006 | Hooven |
| 6,984,826 B2 | 1/2006 | Miller et al. |
| 6,989,010 B2 | 1/2006 | Francischelli et al. |
| 6,994,705 B2 | 2/2006 | Nobis et al. |
| 6,997,735 B2 | 2/2006 | Ehr et al. |
| 6,997,935 B2 | 2/2006 | Anderson et al. |
| 7,001,380 B2 | 2/2006 | Goble |
| 7,001,415 B2 | 2/2006 | Hooven |
| 7,011,657 B2 | 3/2006 | Truckai et al. |
| 7,025,764 B2 | 4/2006 | Paton et al. |
| 7,029,470 B2 | 4/2006 | Francischelli et al. |
| 7,033,351 B2 | 4/2006 | Howell |
| 7,033,354 B2 | 4/2006 | Keppel |
| 7,033,356 B2 | 4/2006 | Latterell |
| 7,041,096 B2 | 5/2006 | Malis |
| 7,041,102 B2 | 5/2006 | Truckai et al. |
| 7,044,948 B2 | 5/2006 | Keppel |
| 7,044,949 B2 | 5/2006 | Orszulak |
| 7,044,950 B2 | 5/2006 | Yamamoto |
| 7,048,687 B1 | 5/2006 | Reuss et al. |
| 7,049,599 B2 | 5/2006 | Miller et al. |
| 7,052,494 B2 | 5/2006 | Goble et al. |
| 7,060,063 B2 | 6/2006 | Marion et al. |
| 7,063,699 B2 | 6/2006 | Hess |
| 7,066,933 B2 | 6/2006 | Hagg |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,090,673 B2 | 8/2006 | Dycus |
| 7,094,202 B2 | 8/2006 | Nobis et al. |
| 7,094,235 B2 | 8/2006 | Francischelli |
| 7,097,644 B2 | 8/2006 | Long |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,104,834 B2 | 9/2006 | Robinson et al. |
| 7,104,989 B2 | 9/2006 | Skarda |
| 7,108,695 B2 | 9/2006 | Witt et al. |

(56) References Cited

U.S. PATENT DOCUMENTS

| | | |
|---|---|---|
| 7,111,769 B2 | 9/2006 | Wales et al. |
| 7,112,201 B2 | 9/2006 | Truckai et al. |
| RE39,358 E | 10/2006 | Goble |
| 7,116,157 B2 | 10/2006 | Ross |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson |
| 7,125,409 B2 | 10/2006 | Truckai et al. |
| 7,126,125 B2 | 10/2006 | Miller et al. |
| 7,131,445 B2 | 11/2006 | Amoah |
| 7,131,860 B2 | 11/2006 | Sartor |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,020 B2 | 11/2006 | Lawes et al. |
| 7,137,980 B2 | 11/2006 | Buysse |
| D533,942 S | 12/2006 | Kerr et al. |
| 7,147,635 B2 | 12/2006 | Ciarrocca |
| 7,147,637 B2 | 12/2006 | Goble |
| 7,147,638 B2 | 12/2006 | Chapman et al. |
| 7,150,097 B2 | 12/2006 | Sremcich |
| 7,150,748 B2 | 12/2006 | Ebbutt |
| 7,150,749 B2 | 12/2006 | Dycus et al. |
| 7,153,300 B2 | 12/2006 | Goble |
| 7,156,843 B2 | 1/2007 | Skarda |
| 7,156,845 B2 | 1/2007 | Mulier et al. |
| 7,156,846 B2 | 1/2007 | Dycus et al. |
| 7,159,750 B2 | 1/2007 | Racenet et al. |
| 7,160,293 B2 | 1/2007 | Sturm et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,105 B2 | 1/2007 | Mulier et al. |
| 7,169,115 B2 | 1/2007 | Nobis et al. |
| 7,169,144 B2 | 1/2007 | Hoey |
| 7,169,145 B2 | 1/2007 | Isaacson |
| 7,169,146 B2 | 1/2007 | Truckai et al. |
| 7,172,591 B2 | 2/2007 | Harano et al. |
| 7,179,254 B2 | 2/2007 | Pendkanti |
| 7,179,258 B2 | 2/2007 | Buysse et al. |
| 7,182,604 B2 | 2/2007 | Ehr et al. |
| 7,186,252 B2 | 3/2007 | Nobis et al. |
| 7,186,253 B2 | 3/2007 | Truckai et al. |
| 7,187,790 B2 | 3/2007 | Sabol |
| 7,189,231 B2 | 3/2007 | Clague et al. |
| 7,189,232 B2 | 3/2007 | Scholl et al. |
| 7,189,233 B2 | 3/2007 | Truckai et al. |
| 7,191,015 B2 | 3/2007 | Lamson et al. |
| 7,195,627 B2 | 3/2007 | Amoah |
| 7,195,630 B2 | 3/2007 | Ciarrocca |
| 7,195,631 B2 | 3/2007 | Dumbauld |
| 7,204,835 B2 | 4/2007 | Latterell et al. |
| 7,207,471 B2 | 4/2007 | Heinrich et al. |
| 7,207,990 B2 | 4/2007 | Lands et al. |
| D541,938 S | 5/2007 | Kerr et al. |
| 7,211,081 B2 | 5/2007 | Goble |
| 7,211,084 B2 | 5/2007 | Goble |
| 7,214,224 B2 | 5/2007 | Goble |
| 7,216,001 B2 | 5/2007 | Hacker et al. |
| 7,220,260 B2 | 5/2007 | Fleming |
| 7,220,951 B2 | 5/2007 | Truckai et al. |
| 7,223,239 B2 | 5/2007 | Schulze et al. |
| 7,223,265 B2 | 5/2007 | Keppel |
| 7,226,447 B2 | 6/2007 | Uchida |
| 7,229,307 B2 | 6/2007 | Ehr et al. |
| 7,232,439 B2 | 6/2007 | Ciarrocca |
| 7,232,440 B2 | 6/2007 | Dumbald et al. |
| 7,235,048 B2 | 6/2007 | Rein et al. |
| 7,235,072 B2 | 6/2007 | Sartor et al. |
| 7,235,073 B2 | 6/2007 | Levine et al. |
| 7,237,708 B1 | 7/2007 | Guy |
| 7,241,296 B2 | 7/2007 | Buysse et al. |
| 7,247,141 B2 | 7/2007 | Makin et al. |
| 7,247,155 B2 | 7/2007 | Hoey et al. |
| 7,250,048 B2 | 7/2007 | Francischelli et al. |
| 7,250,051 B2 | 7/2007 | Francischelli |
| 7,252,667 B2 | 8/2007 | Moses |
| 7,255,694 B2 | 8/2007 | Keppel |
| 7,255,696 B2 | 8/2007 | Goble et al. |
| 7,255,697 B2 | 8/2007 | Dycus et al. |
| 7,259,340 B2 | 8/2007 | Blaha et al. |
| 7,261,711 B2 | 8/2007 | Mulier et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,273,483 B2 | 9/2007 | Weiner et al. |
| 7,276,068 B2 | 10/2007 | Johnson et al. |
| 7,278,994 B2 | 10/2007 | Goble |
| 7,282,048 B2 | 10/2007 | Goble et al. |
| 7,282,049 B2 | 10/2007 | Oraszulak et al. |
| 7,291,161 B2 | 11/2007 | Hooven |
| 7,297,145 B2 | 11/2007 | Woloszko et al. |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,557 B2 | 12/2007 | Wham |
| 7,309,325 B2 | 12/2007 | Mulier et al. |
| 7,309,849 B2 | 12/2007 | Truckai et al. |
| 7,311,560 B2 | 12/2007 | Ehr et al. |
| 7,311,706 B2 | 12/2007 | Schoenman et al. |
| 7,311,707 B2 | 12/2007 | Hagg et al. |
| 7,311,709 B2 | 12/2007 | Truckai et al. |
| 7,322,975 B2 | 1/2008 | Goble et al. |
| 7,329,256 B2 | 2/2008 | Johnson et al. |
| 7,335,997 B2 | 2/2008 | Weiner |
| 7,344,532 B2 | 3/2008 | Goble et al. |
| 7,347,858 B2 | 3/2008 | Francischelli et al. |
| RE40,279 E | 4/2008 | Sluijter et al. |
| D567,943 S | 4/2008 | Moses et al. |
| 7,353,068 B2 | 4/2008 | Tanake et al. |
| 7,354,435 B2 | 4/2008 | Farin et al. |
| 7,354,440 B2 | 4/2008 | Truckai et al. |
| 7,354,443 B2 | 4/2008 | Moll et al. |
| 7,364,577 B2 | 4/2008 | Wham et al. |
| 7,364,578 B2 | 4/2008 | Francischelli et al. |
| 7,364,579 B2 | 4/2008 | Mulier et al. |
| 7,367,972 B2 | 5/2008 | Francischelli et al. |
| 7,367,976 B2 | 5/2008 | Lawes et al. |
| 7,371,246 B2 | 5/2008 | Viola |
| 7,377,902 B2 | 5/2008 | Burbank et al. |
| 7,377,918 B2 | 5/2008 | Amoah |
| 7,377,920 B2 | 5/2008 | Buysse et al. |
| RE40,388 E | 6/2008 | Gines |
| 7,381,209 B2 | 6/2008 | Truckai et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,416,101 B2 | 8/2008 | Shelton |
| 7,416,437 B2 | 8/2008 | Sartor et al. |
| 7,419,487 B2 | 9/2008 | Johnson et al. |
| 7,422,139 B2 | 9/2008 | Shelton et al. |
| 7,422,588 B2 | 9/2008 | Mulier et al. |
| 7,424,965 B2 | 9/2008 | Racenet et al. |
| 7,425,835 B2 | 9/2008 | Eisele |
| 7,426,415 B2 | 9/2008 | Kuhner |
| 7,431,720 B2 | 10/2008 | Pendekanti et al. |
| 7,431,721 B2 | 10/2008 | Paton et al. |
| 7,435,249 B2 | 10/2008 | Buysse et al. |
| 7,435,250 B2 | 10/2008 | Francischelli et al. |
| 7,442,167 B2 | 10/2008 | Dunki-Jacobs |
| 7,442,193 B2 | 10/2008 | Shelds |
| 7,442,194 B2 | 10/2008 | Dumbauld |
| 7,445,621 B2 | 11/2008 | Dumbauld et al. |
| 7,458,972 B2 | 12/2008 | Keppel |
| 7,464,846 B2 | 12/2008 | Shelton et al. |
| 7,470,272 B2 | 12/2008 | Mulier et al. |
| 7,473,250 B2 | 1/2009 | Makin et al. |
| 7,473,253 B2 | 1/2009 | Dycus et al. |
| 7,476,233 B1 | 1/2009 | Wiener et al. |
| 7,481,808 B2 | 1/2009 | Koyfman et al. |

(56) References Cited

U.S. PATENT DOCUMENTS

| | | |
|---|---|---|
| 7,491,199 B2 | 2/2009 | Goble et al. |
| 7,497,858 B2 | 3/2009 | Chapelon et al. |
| 7,811,283 B2 | 10/2010 | Moses et al. |
| 7,841,765 B2 | 11/2010 | Keller |
| 8,561,615 B2 | 10/2013 | Pannell et al. |
| 8,784,417 B2 | 7/2014 | Hanna |
| 8,808,288 B2 | 8/2014 | Rescheke |
| 9,161,813 B2 | 10/2015 | Benamou |
| 2001/0037110 A1 | 11/2001 | Schmaltz |
| 2001/0039417 A1 | 11/2001 | Harano et al. |
| 2002/0052599 A1 | 5/2002 | Goble |
| 2002/0072686 A1* | 6/2002 | Hoey ............... A61B 5/4893 600/587 |
| 2002/0115997 A1 | 8/2002 | Truckai |
| 2002/0120262 A1 | 8/2002 | Bek |
| 2002/0120266 A1 | 8/2002 | Truckai |
| 2002/0128650 A1 | 9/2002 | McClurken |
| 2002/0151884 A1 | 10/2002 | Hoey et al. |
| 2002/0161363 A1 | 10/2002 | Fodor et al. |
| 2002/0165541 A1 | 11/2002 | Whitman |
| 2002/0188294 A1 | 12/2002 | Couture et al. |
| 2003/0004510 A1 | 1/2003 | Wham |
| 2003/0014052 A1 | 1/2003 | Buysse |
| 2003/0060818 A1 | 3/2003 | Kannenberg et al. |
| 2003/0065327 A1 | 4/2003 | Wellman |
| 2003/0065358 A1 | 4/2003 | Frecker et al. |
| 2003/0069571 A1 | 4/2003 | Treat |
| 2003/0109871 A1 | 6/2003 | Johnson |
| 2003/0114845 A1 | 6/2003 | Paton et al. |
| 2003/0114848 A1 | 6/2003 | Cobb |
| 2003/0114851 A1 | 6/2003 | Truckai et al. |
| 2003/0125728 A1 | 7/2003 | Nezhat et al. |
| 2003/0125731 A1 | 7/2003 | Smith et al. |
| 2003/0125734 A1 | 7/2003 | Mollenauer |
| 2003/0139741 A1 | 7/2003 | Goble et al. |
| 2003/0181910 A1 | 9/2003 | Dycus |
| 2003/0199863 A1 | 10/2003 | Swanson et al. |
| 2003/0199870 A1 | 10/2003 | Truckai |
| 2003/0229344 A1 | 12/2003 | Dycus et al. |
| 2003/0236549 A1 | 12/2003 | Bonadio et al. |
| 2004/0006340 A1 | 1/2004 | Latterell |
| 2004/0010289 A1 | 1/2004 | Biggs et al. |
| 2004/0068274 A1 | 4/2004 | Hooven |
| 2004/0068304 A1 | 4/2004 | Paton et al. |
| 2004/0073247 A1 | 4/2004 | Loshakove et al. |
| 2004/0082946 A1 | 4/2004 | Malis et al. |
| 2004/0092922 A1 | 5/2004 | Kadziauskas et al. |
| 2004/0122423 A1 | 6/2004 | Dycus |
| 2004/0162557 A1 | 8/2004 | Tetzlaff et al. |
| 2004/0193148 A1 | 9/2004 | Wham |
| 2004/0215127 A1 | 10/2004 | Kadziauskas et al. |
| 2004/0225288 A1 | 11/2004 | Buysse |
| 2004/0250419 A1 | 12/2004 | Sremich |
| 2005/0004563 A1 | 1/2005 | Racz et al. |
| 2005/0004564 A1 | 1/2005 | Wham et al. |
| 2005/0015125 A1 | 1/2005 | Mioduski et al. |
| 2005/0021027 A1 | 1/2005 | Shields et al. |
| 2005/0033282 A1 | 2/2005 | Hooven |
| 2005/0033352 A1 | 2/2005 | Zepf |
| 2005/0080319 A1 | 4/2005 | Dinkler, II et al. |
| 2005/0090815 A1 | 4/2005 | Francischelli et al. |
| 2005/0096681 A1 | 5/2005 | Desinger et al. |
| 2005/0101951 A1 | 5/2005 | Wham |
| 2005/0107785 A1 | 5/2005 | Dycus |
| 2005/0113817 A1 | 5/2005 | Isaacson |
| 2005/0113819 A1 | 5/2005 | Wham et al. |
| 2005/0124915 A1 | 6/2005 | Eggers et al. |
| 2005/0124987 A1 | 6/2005 | Goble |
| 2005/0137592 A1 | 6/2005 | Nguyen et al. |
| 2005/0149017 A1 | 7/2005 | Dycus |
| 2005/0159745 A1 | 7/2005 | Truckai |
| 2005/0165444 A1 | 7/2005 | Hart |
| 2005/0192568 A1 | 9/2005 | Truckai et al. |
| 2005/0203504 A1 | 9/2005 | Wham |
| 2005/0234447 A1 | 10/2005 | Paton et al. |
| 2005/0245918 A1 | 11/2005 | Sliwa, Jr. et al. |
| 2005/0245922 A1 | 11/2005 | Goble |
| 2006/0020265 A1 | 1/2006 | Ryan |
| 2006/0041254 A1 | 2/2006 | Francischelli et al. |
| 2006/0052777 A1 | 3/2006 | Dumbauld |
| 2006/0064086 A1* | 3/2006 | Odom ............... A61B 18/1442 606/51 |
| 2006/0079788 A1 | 4/2006 | Anderson et al. |
| 2006/0079878 A1 | 4/2006 | Houser |
| 2006/0129146 A1 | 6/2006 | Dycus |
| 2006/0161190 A1 | 7/2006 | Gadberry et al. |
| 2006/0167450 A1 | 7/2006 | Johnson |
| 2006/0173453 A1 | 8/2006 | Gruhl |
| 2006/0217697 A1 | 9/2006 | Lau et al. |
| 2006/0217706 A1 | 9/2006 | Lau et al. |
| 2006/0217707 A1 | 9/2006 | Daniel et al. |
| 2006/0224152 A1 | 10/2006 | Behnke et al. |
| 2006/0224158 A1 | 10/2006 | Odom |
| 2006/0247498 A1 | 11/2006 | Sonadio et al. |
| 2006/0271042 A1 | 11/2006 | Latterell et al. |
| 2007/0016185 A1 | 1/2007 | Tullis et al. |
| 2007/0043352 A1 | 2/2007 | Garrison et al. |
| 2007/0043353 A1 | 2/2007 | Dycus |
| 2007/0062017 A1 | 3/2007 | Dycus et al. |
| 2007/0088202 A1 | 4/2007 | Albrecht |
| 2007/0090788 A1 | 4/2007 | Hansford et al. |
| 2007/0093800 A1 | 4/2007 | Wham et al. |
| 2007/0123847 A1 | 5/2007 | Mihori |
| 2007/0135811 A1 | 6/2007 | Hooven |
| 2007/0142833 A1 | 6/2007 | Dycus |
| 2007/0142834 A1 | 6/2007 | Dumbauld |
| 2007/0156139 A1 | 7/2007 | Schecter |
| 2007/0156140 A1 | 7/2007 | Baily |
| 2007/0167941 A1 | 7/2007 | Hamel et al. |
| 2007/0173811 A1* | 7/2007 | Couture ............ A61B 18/1445 606/45 |
| 2007/0173813 A1 | 7/2007 | Odom |
| 2007/0173814 A1 | 7/2007 | Hixson et al. |
| 2007/0179499 A1 | 8/2007 | Garrison |
| 2007/0191827 A1 | 8/2007 | Lischinsky et al. |
| 2007/0191828 A1 | 8/2007 | Houser et al. |
| 2007/0203481 A1 | 8/2007 | Gregg et al. |
| 2007/0213712 A1 | 9/2007 | Buysse et al. |
| 2007/0260242 A1 | 11/2007 | Dycus et al. |
| 2007/0276363 A1 | 11/2007 | Patton et al. |
| 2007/0282195 A1 | 12/2007 | Masini et al. |
| 2007/0282320 A1 | 12/2007 | Buysse et al. |
| 2007/0282332 A1 | 12/2007 | Witt et al. |
| 2007/0287997 A1 | 12/2007 | Tolmei |
| 2008/0009860 A1 | 1/2008 | Odom |
| 2008/0015563 A1 | 1/2008 | Hoey et al. |
| 2008/0015564 A1 | 1/2008 | Wham et al. |
| 2008/0015567 A1 | 1/2008 | Kimura |
| 2008/0030206 A1 | 2/2008 | Podhajsky et al. |
| 2008/0039831 A1 | 2/2008 | Odom et al. |
| 2008/0045947 A1 | 2/2008 | Johnson et al. |
| 2008/0058802 A1 | 3/2008 | Couture |
| 2008/0082098 A1 | 4/2008 | Tanaka et al. |
| 2008/0091189 A1 | 4/2008 | Carlton |
| 2008/0114356 A1 | 5/2008 | Johnson et al. |
| 2008/0125772 A1 | 5/2008 | Stone et al. |
| 2008/0132893 A1 | 6/2008 | D'Amelio et al. |
| 2008/0167651 A1 | 7/2008 | Tetzlaff et al. |
| 2008/0172048 A1 | 7/2008 | Martin |
| 2008/0188848 A1 | 8/2008 | Deutmeyer et al. |
| 2008/0208246 A1 | 8/2008 | Livneh |
| 2008/0215050 A1 | 9/2008 | Bakos |
| 2008/0215051 A1 | 9/2008 | Buysse et al. |
| 2008/0221565 A1 | 9/2008 | Eder et al. |
| 2008/0228179 A1 | 9/2008 | Eder et al. |
| 2008/0294222 A1 | 11/2008 | Schecter |
| 2008/0300589 A1 | 12/2008 | Paul et al. |
| 2008/0300590 A1 | 12/2008 | Horne et al. |
| 2008/0300591 A1 | 12/2008 | Darin et al. |
| 2009/0012520 A1 | 1/2009 | Hixson et al. |
| 2009/0024126 A1 | 1/2009 | Artale |
| 2009/0248007 A1 | 1/2009 | Falkenstein et al. |
| 2009/0171352 A1 | 7/2009 | Sutter |
| 2009/0275490 A1 | 11/2009 | Milne et al. |

(56) References Cited

U.S. PATENT DOCUMENTS

| | | |
|---|---|---|
| 2009/0275940 A1 | 11/2009 | Malackowski |
| 2012/0010614 A1 | 1/2012 | Couture |
| 2012/0059371 A1 | 3/2012 | Anderson et al. |
| 2012/0083785 A1 | 4/2012 | Roy et al. |
| 2012/0136347 A1 | 5/2012 | Brustad et al. |
| 2012/0197243 A1 | 8/2012 | Sherman et al. |
| 2012/0215220 A1 | 8/2012 | Manzo et al. |
| 2013/0018411 A1 | 1/2013 | Collings et al. |
| 2013/0138101 A1 | 5/2013 | Kerr |
| 2013/0138102 A1 | 5/2013 | Twomey et al. |
| 2013/0197874 A1 | 8/2013 | Heckel |
| 2013/0267951 A1 | 10/2013 | Twomey |
| 2013/0274743 A1 | 10/2013 | Banfalvi |
| 2013/0296843 A1 | 11/2013 | Boudrequx et al. |
| 2013/0345696 A1 | 12/2013 | Behnke, II et al. |
| 2014/0005658 A1 | 1/2014 | Rosenbegr |
| 2014/0088583 A1 | 3/2014 | Singh |
| 2014/0214019 A1 | 7/2014 | Baxter, III et al. |
| 2016/0310203 A1 | 10/2016 | Gaspredes et al. |
| 2016/0310204 A1 | 10/2016 | McHenry et al. |

FOREIGN PATENT DOCUMENTS

| | | |
|---|---|---|
| DE | 1 2005 044918 | 2/2007 |
| EP | 315 338 | 5/1989 |
| EP | 538984 | 4/1993 |
| EP | 570675 | 11/1993 |
| EP | 598202 | 5/1994 |
| EP | 0717967 A2 | 6/1996 |
| EP | 737447 A1 | 10/1996 |
| EP | 878168 | 11/1998 |
| EP | 1054637 | 11/2000 |
| EP | 1 157 666 A1 | 11/2001 |
| EP | 1 500 378 A1 | 1/2005 |
| EP | 1535581 | 6/2005 |
| EP | 1545361 | 6/2005 |
| EP | 1557129 | 7/2005 |
| EP | 1634539 | 3/2006 |
| EP | 1728475 | 12/2006 |
| EP | 1810628 | 7/2007 |
| EP | 1634539 | 2/2008 |
| EP | 1665995 | 2/2008 |
| EP | 1946715 | 7/2008 |
| EP | 2106 762 | 7/2009 |
| EP | 2 111 812 A2 | 10/2009 |
| EP | 2156 802 | 2/2010 |
| EP | 2 301 462 A1 | 3/2011 |
| EP | 2 340 792 A1 | 7/2011 |
| EP | 2 436 327 A1 | 4/2012 |
| EP | 2 436 330 A1 | 4/2012 |
| EP | 2 574 300 A1 | 4/2013 |
| EP | 2 712 568 A2 | 4/2014 |
| EP | 2 777 578 A1 | 9/2014 |
| EP | 3 369 392 A2 | 9/2018 |
| GB | 2157175 | 10/1985 |
| GB | 2 462 453 A | 8/2008 |
| JP | 60-30946 | 2/1994 |
| JP | 83-17935 | 12/1996 |
| JP | 11-070123 | 3/1999 |
| JP | 11-070124 | 3/1999 |
| JP | 11-178833 | 7/1999 |
| JP | 2000-254135 | 9/2000 |
| JP | 2003-135481 | 5/2003 |
| JP | 2003-164463 | 6/2003 |
| JP | 2006-109945 | 4/2006 |
| JP | 2006-167403 | 6/2006 |
| JP | 2007-144201 | 6/2007 |
| JP | 2007-195980 | 8/2007 |
| JP | 2007-195985 | 8/2007 |
| JP | 2008-043789 | 2/2008 |
| JP | 2008-259864 | 10/2008 |
| WO | WO93/015662 | 8/1993 |
| WO | WO97/010764 | 3/1997 |
| WO | WO99/040857 | 8/1999 |
| WO | WO01/012090 | 2/2001 |
| WO | WO04/030553 | 4/2004 |
| WO | WO04/032776 | 4/2004 |
| WO | WO04/032777 | 4/2004 |
| WO | WO2004/082495 | 9/2004 |
| WO | WO2005/004735 | 1/2005 |
| WO | WO05/053785 | 6/2005 |
| WO | WO2006/119245 | 11/2006 |
| WO | WO2006/125558 | 11/2006 |
| WO | WO 2007/044849 A1 | 4/2007 |
| WO | WO07/142601 | 12/2007 |
| WO | WO08/147773 | 12/2008 |
| WO | WO 2009/065140 A1 | 5/2009 |
| WO | WO 2012/110996 A2 | 8/2012 |
| WO | WO 2013/030349 A1 | 3/2013 |

OTHER PUBLICATIONS

International Preliminary Examining Authority/US, International Preliminary Report on Patentability for International Application No. PCT/US2019/049807, titled "Electrosurgical Generator Control System," dated Mar. 18, 2021, 13 pgs.
European Patent Office, Extended European Search Report for European Application No. EP 21215386.0, dated May 24, 2022, 6 pgs.
"New Products" Journal of Medical Engineering and Technology, vol. 19, No. 5 (Sep./Oct. 1995), pp. 189-190.
International Searching Authority/US, The International Search Report and the Written Opinion for International Application No. PCT/US09/39046 titled "Electrosurgical System", dated Jul. 27, 2009.
International Preliminary Examining Authority/US, International Preliminary Report on Patentability for International Application No. PCT/US09/39046, titled "Electrosurgical System", dated Mar. 26, 2010.
European Patent Office, European Search Report for European Application No. EP 10 19 2593 dated Mar. 21, 2011, titled Electrosurgical System.
European Patent Office, European Search Report for European Application No. EP 10 19 2614 dated Apr. 18, 2011, titled Electrosurgical System.
European Patent Office, Extended European Search Report for European Application No. EP 10 19 2580 dated Jul. 21, 2011.
International Preliminary Examining Authority/US, International Preliminary Report on Patentability for International Application No. PCT/US09/39046, titled "Electrosurgical System", dated Jan. 17, 2012.
European Patent Office, The International Search Report and Written Opinion of the International Searching Authority for International Application No. PCT/US2011/054661, dated Mar. 6, 2012.
International Searching Authority/US, The International Search Report and the Written Opinion for International Application No. PCT/US2011/054661 entitled "Electrosurgical System", dated Jun. 3, 2012.
International Searching Authority/US, The International Search Report and the Written Opinion for International Application No. PCT/US09/39046 titled "Electrosurgical System", dated Jun. 2, 2012.
U.S. Appl. No. 12/611,352, filed Nov. 3, 2009, titled Tissue Fusion/Welder Apparatus and Method.
U.S. Appl. No. 12/183,970, filed Jul. 31, 2008, entitled Bipolar Electrosurgical Scissors.
U.S. Appl. No. 12/416,128, filed Mar. 31, 2009, entitled Electrosurgical System.
U.S. Appl. No. 12/416,668, filed Apr. 1, 2009, entitled Electrosurgical System.
U.S. Appl. No. 12/416,695, filed Apr. 1, 2009, entitled Electrosurgical System.
U.S. Appl. No. 12/416,765, filed Apr. 1, 2009, entitled Electrosurgical System.
The International Bureau of WIPO, The International Preliminary Report on Patentability for International Application No. PCT/US2011/054661, entitled Electrosurgical Instruments and Connections Thereto dated Apr. 2, 2013.

(56) References Cited

OTHER PUBLICATIONS

European Patent Office, European Search Report for European Application No. EP 13 17 4814.7 dated Sep. 30, 2013, titled Electrosurgical System.
European Patent Office, European Search Report for European Application No. EP 14199708.0, dated Jul. 10, 2015, entitled "Electrosurgical System."
Bertil Vallfors and Bjorn Bergdahl, Automatically controlled bipolar electrocoagulation—"COA-COMP", Neurosurg. Rev., 1984, pp. 187-190.
US Patent Application No. PCT/US09/39046 filed Mar. 31, 2009, entitled Electrosurgical System.
European Patent Office, European Search Report for European Patent Application No. 12151288, dated Feb. 10, 2012, 8 pgs.
European Patent Office, Supplementary European Search Report for European Patent Application No. 08755322, dated Apr. 18, 2012, 3 pgs.
European Patent Office, Supplementary European Search Report for European Patent Application No. 08755322, dated Jun. 6, 2012, 2 pgs.
U.S. Appl. No. 12/416,751, filed Apr. 1, 2009, entitled Electrosurgical System, now U.S. Pat. No. 8,579,894 issued Nov. 12, 2013.
European Patent Office, Partial European Search Report for European Patent Application No. 15151398.3, dated Jun. 22, 2015, 9 pgs.
International Searching Authority/US, The International Search Report and the Written Opinion for International Application No. PCT/US2015/031452 ,titled "Electrosurgical Fusion Device," dated Dec. 3, 2015, 27 pgs.
International Searching Authority/US, The International Search Report and the Written Opinion for International Application No. PCT/US2015/066473 titled "Bipolar Electrosurgical Sealer and Divider," dated Mar. 31, 2016, 13 pgs.
International Searching Authority/US, The International Search Report and the Written Opinion for International Application No. PCT/US2015/033546 titled "Electrosurgical Seal and Dissection Systems," dated Apr. 22, 2016, 31 pgs.
International Preliminary Examining Authority/US, International Preliminary Report on Patentability for International Application No. PCT/US2015/031452, titled "Electrosurgical System," dated Dec. 1, 2016, 21 pgs.
International Preliminary Examining Authority/US, International Preliminary Report on Patentability for International Application No. PCT/US2015/033546, titled "Electrosurgical Laparoscopic Sealer and Dissector," dated Dec. 15, 2016, 22 pgs.
International Preliminary Examining Authority/US, International Preliminary Report on Patentability for International Application No. PCT/US2015/0066473, titled "Bipolar Electrosurgical Sealer and Divider," dated Jul. 6, 2017, 10 pgs.
European Patent Office, Extended European Search Report for European Application No. EP 17207793.5, dated May 16, 2018, 9 pgs.
European Patent Office, Extended European Search Report for European Application No. EP 18165110.0, dated Jun. 13, 2018, 6 pgs.
International Searching Authority/US, The International Search Report and the Written Opinion for International Application No. PCT/US2019/049768 titled "Electrosurgical Generator Verification System," dated Dec. 11, 2019, 19 pgs.
European Patent Office, Extended European Search Report for European Patent No. 19198318.8, entitled, "Bipolar Electrosurgical Sealer and Divider," dated Dec. 17, 2019, 10 pgs.
European Patent Office, Invitation to Pay Additional Fees for International Application No. PCT/US2019/049807, titled "Electrosurgical Generator Control System", dated Dec. 19, 2019, 16 pgs.
International Searching Authority/US, The International Search Report and the Written Opinion for International Application No. PCT/US2019/049807 titled "Electrosurgical Generator Control System," dated Feb. 12, 2020, 20 pgs.
International Searching Authority/US, The International Search Report and the Written Opinion for International Application No. PCT/US2019/059909 titled "Electrosurgical System," dated Apr. 28, 2020, 23 pgs.
International Preliminary Examining Authority/US, International Preliminary Report on Patentability for International Application No. PCT/US2019/059909, titled "Electrosurgical System," dated May 27, 2021, 15 pgs.

\* cited by examiner

| Tissue name | ρ [S/m] | ε | ε x ρ |
|---|---|---|---|
| BoneMarrow | 0.003852 | 48.969 | 0.18862859 |
| BreastFat | 0.025428 | 30.711 | 0.78091931 |
| Fat | 0.024833 | 34.559 | 0.85820365 |
| BoneCortical | 0.022165 | 174.5 | 3.8677925 |
| Nail | 0.022165 | 174.5 | 3.8677925 |
| Tooth | 0.022165 | 174.5 | 3.8677925 |
| SkinDry | 0.0043646 | 1062 | 4.6352052 |
| BoneCancellous | 0.086731 | 308.16 | 26.727025 |
| Tendon | 0.39075 | 200.69 | 78.4196175 |
| GallBladder | 0.90019 | 101.16 | 91.0812242 |
| Aorta | 0.32389 | 312.32 | 101.157325 |
| BloodVessel | 0.32389 | 312.32 | 101.157325 |
| Bladder | 0.22787 | 534.55 | 121.807909 |
| LungInflated | 0.12301 | 1025 | 126.08525 |
| Dura | 0.50258 | 264.43 | 132.897229 |
| BodyFluid | 1.5003 | 91.35 | 137.052405 |
| VitreousHumor | 1.5003 | 91.35 | 137.052405 |
| Nerve | 0.11094 | 1487.6 | 165.034344 |
| SpinalChord | 0.11094 | 1487.6 | 165.034344 |
| GallBladderBile | 1.4 | 120 | 168 |
| BrainGreyMatter | 0.15187 | 1187 | 180.26969 |
| CerebroSpinalFluid | 2 | 109 | 218 |
| Cerebellum | 0.17248 | 1475 | 254.408 |
| Ovary | 0.35016 | 873.26 | 305.780722 |
| Cervix | 0.55686 | 614.02 | 341.923177 |
| Cartilage | 0.20078 | 1938.6 | 389.232108 |
| Spleen | 0.14706 | 2789 | 410.15034 |
| Liver | 0.1481 | 2769.8 | 410.20738 |
| Trachea | 0.35907 | 1157.6 | 415.659432 |
| Lens | 0.35278 | 1502.1 | 529.910838 |
| LungDeflated | 0.30697 | 1884.3 | 578.423571 |
| MucousMembrane | 0.17798 | 3610 | 642.5078 |
| SkinWet | 0.17798 | 3610 | 642.5078 |
| Colon | 0.27777 | 2370.3 | 658.398231 |
| Kidney | 0.22834 | 3443.3 | 786.243122 |
| Uterus | 0.54947 | 1489.4 | 818.380618 |
| Heart | 0.28072 | 3264.5 | 916.41044 |
| Tongue | 0.33099 | 3252 | 1076.37948 |
| Duodenum | 0.55397 | 2064.7 | 1143.78186 |

FIG. 30

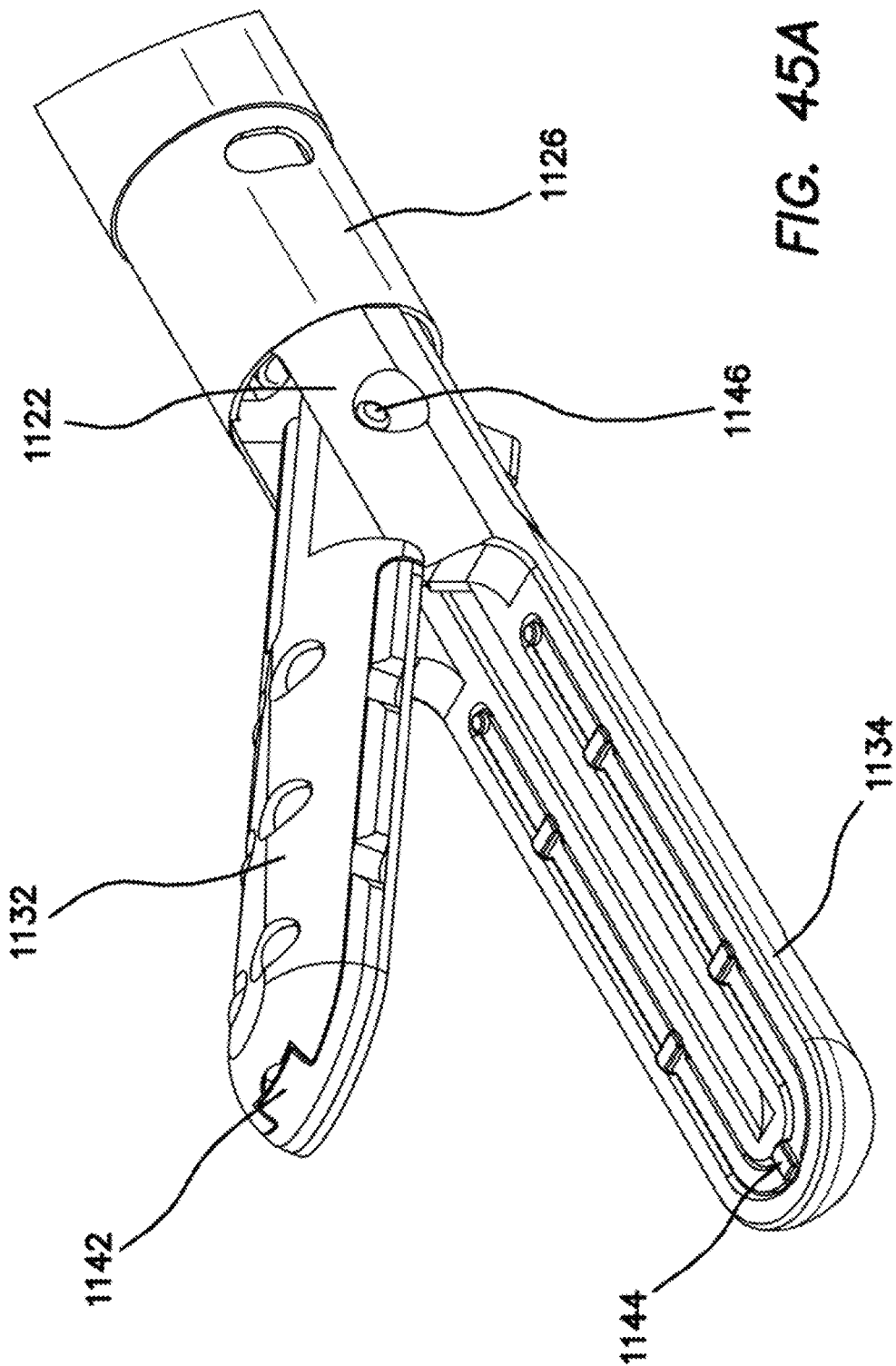

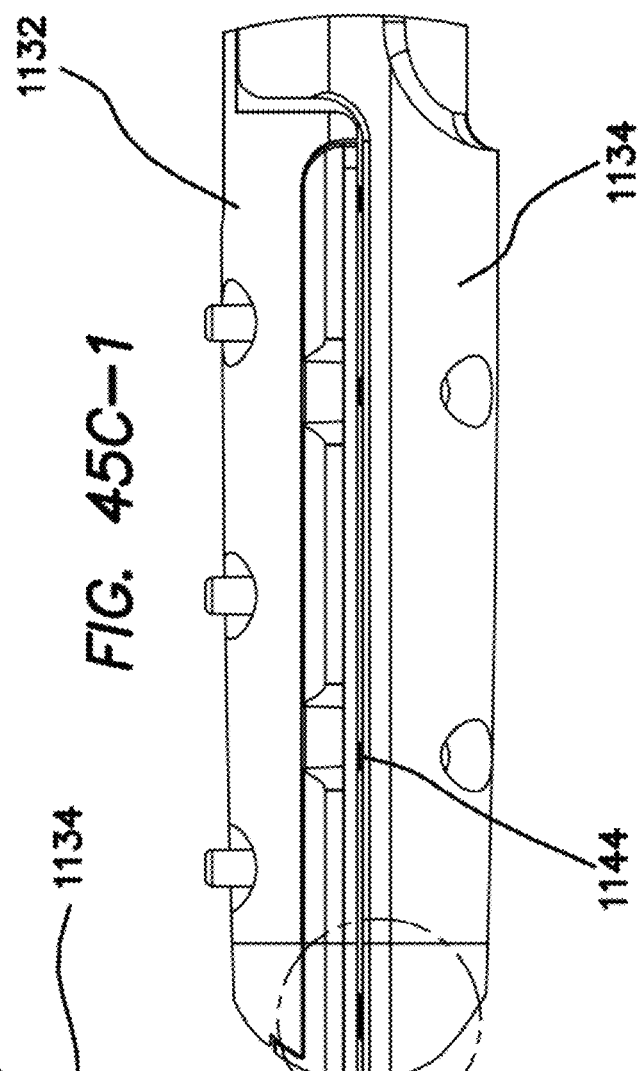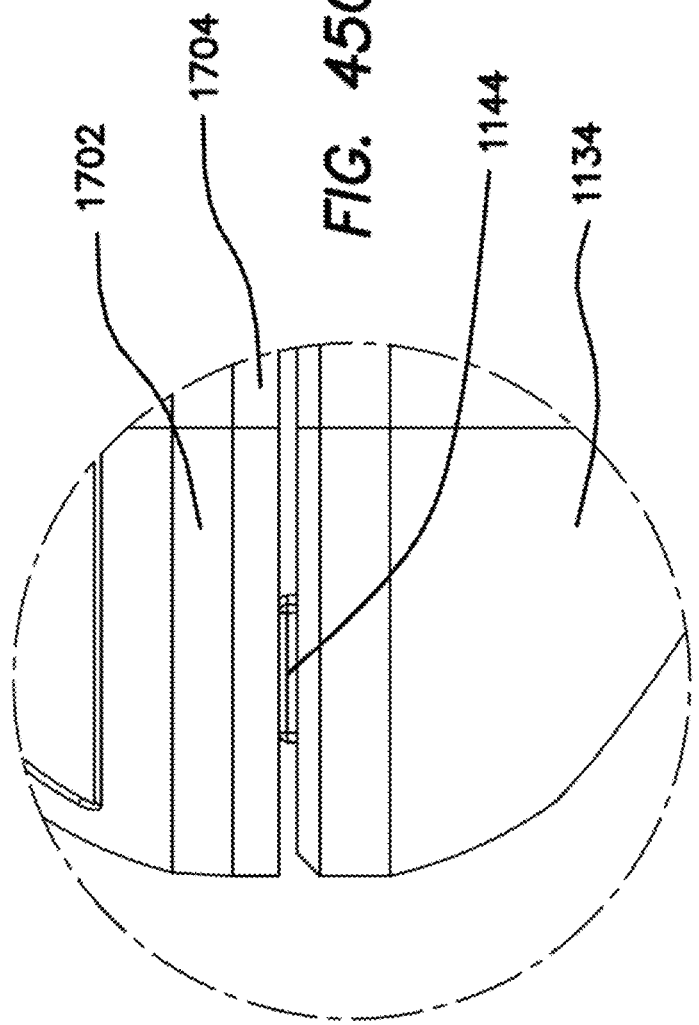

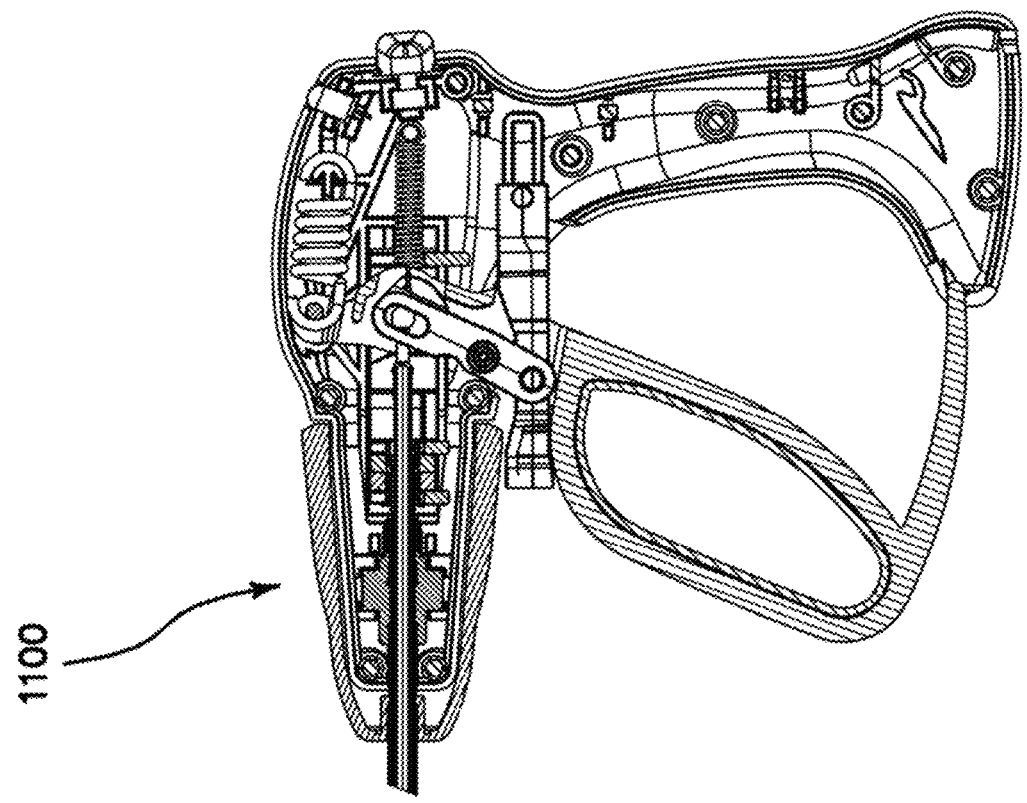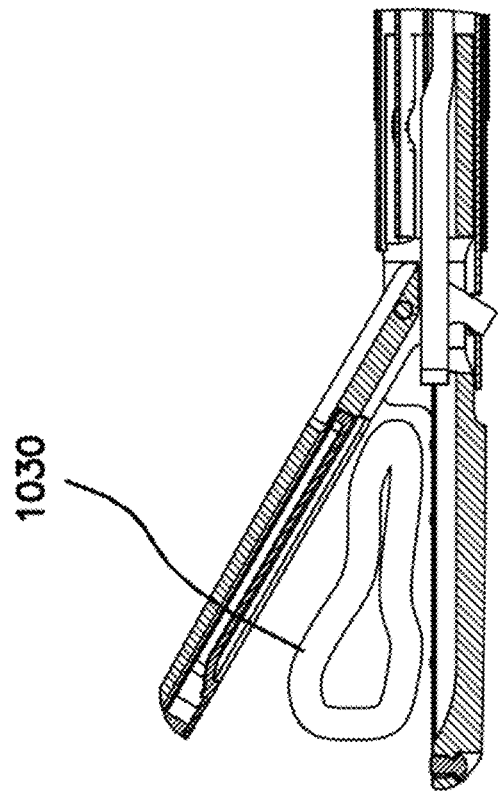
FIG. 46A

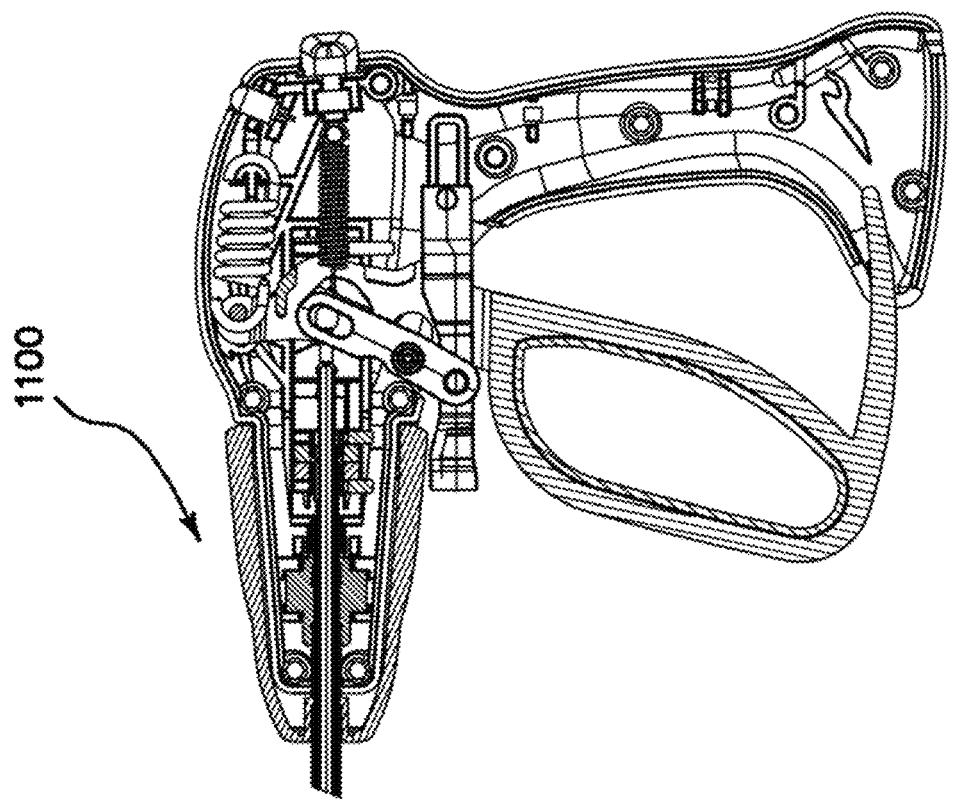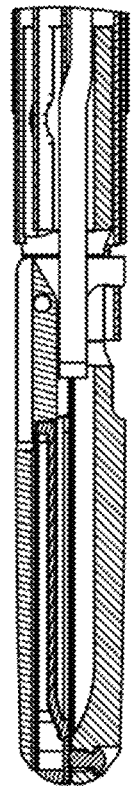
FIG. 46C

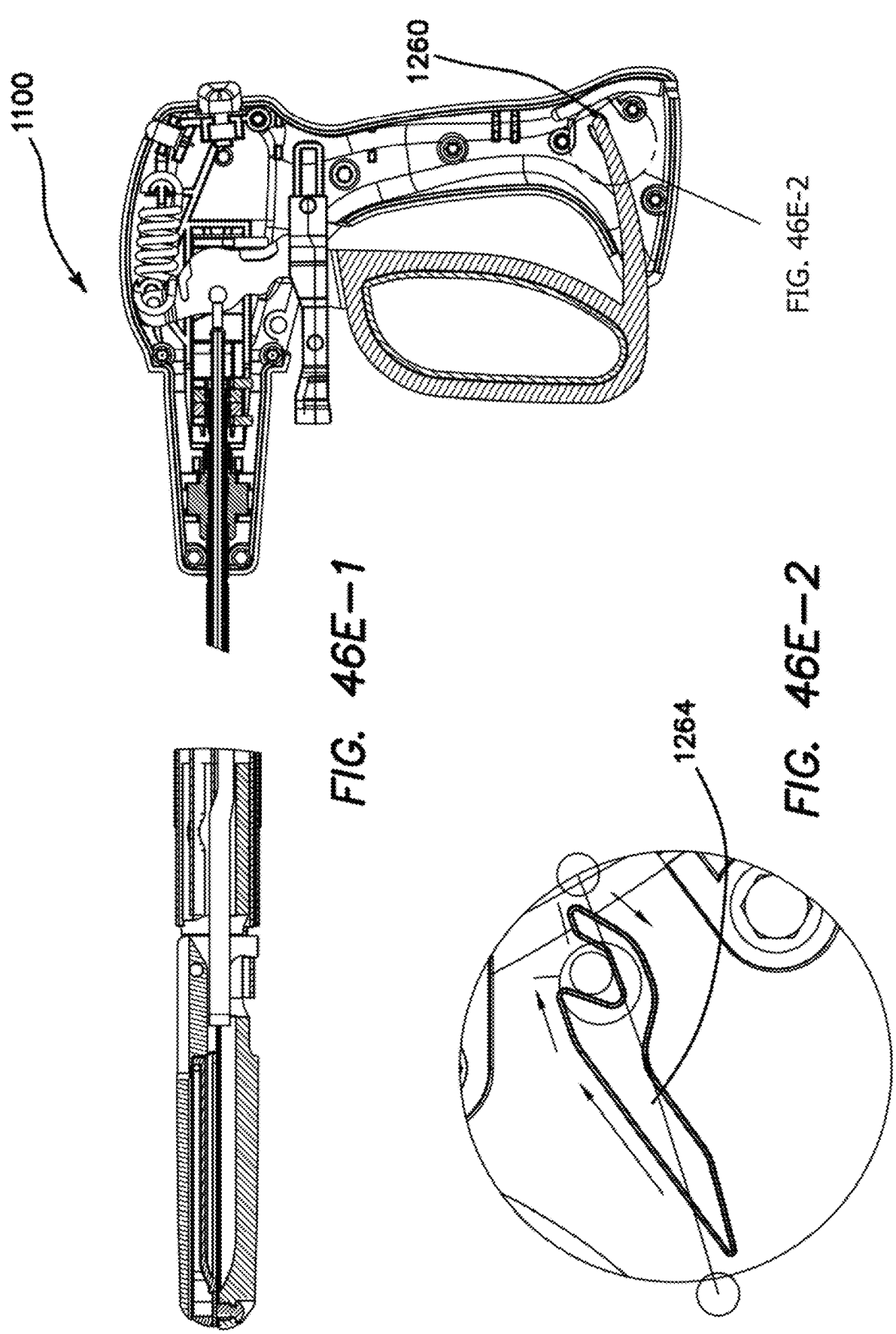

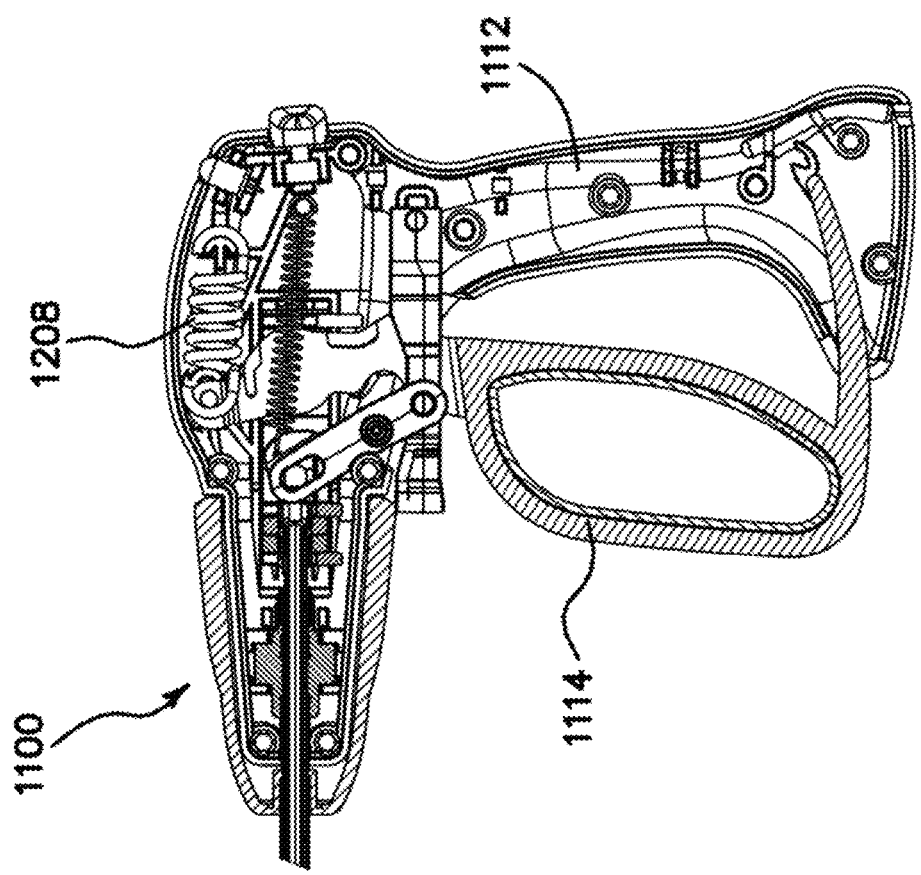
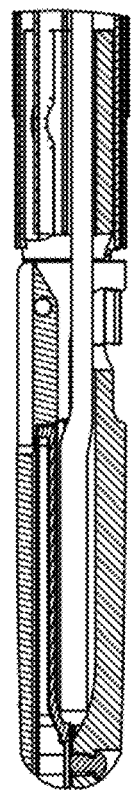
FIG. 46F

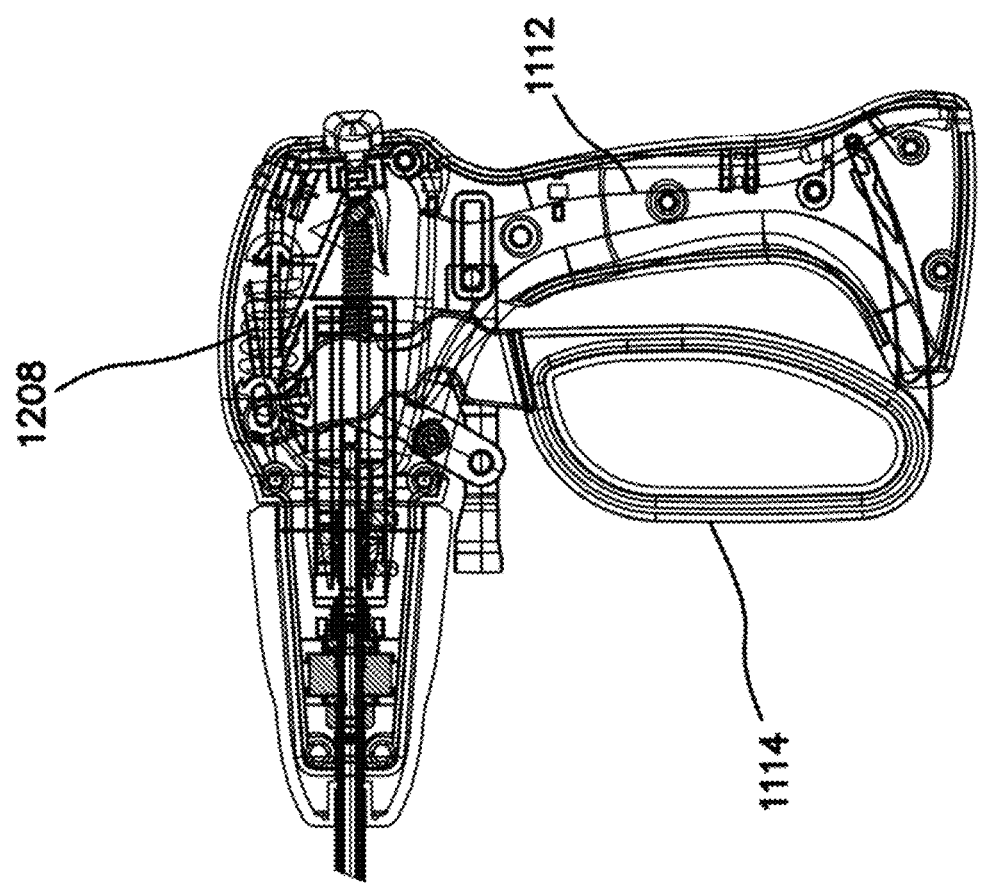
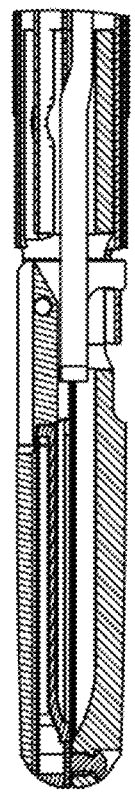
FIG. 46G

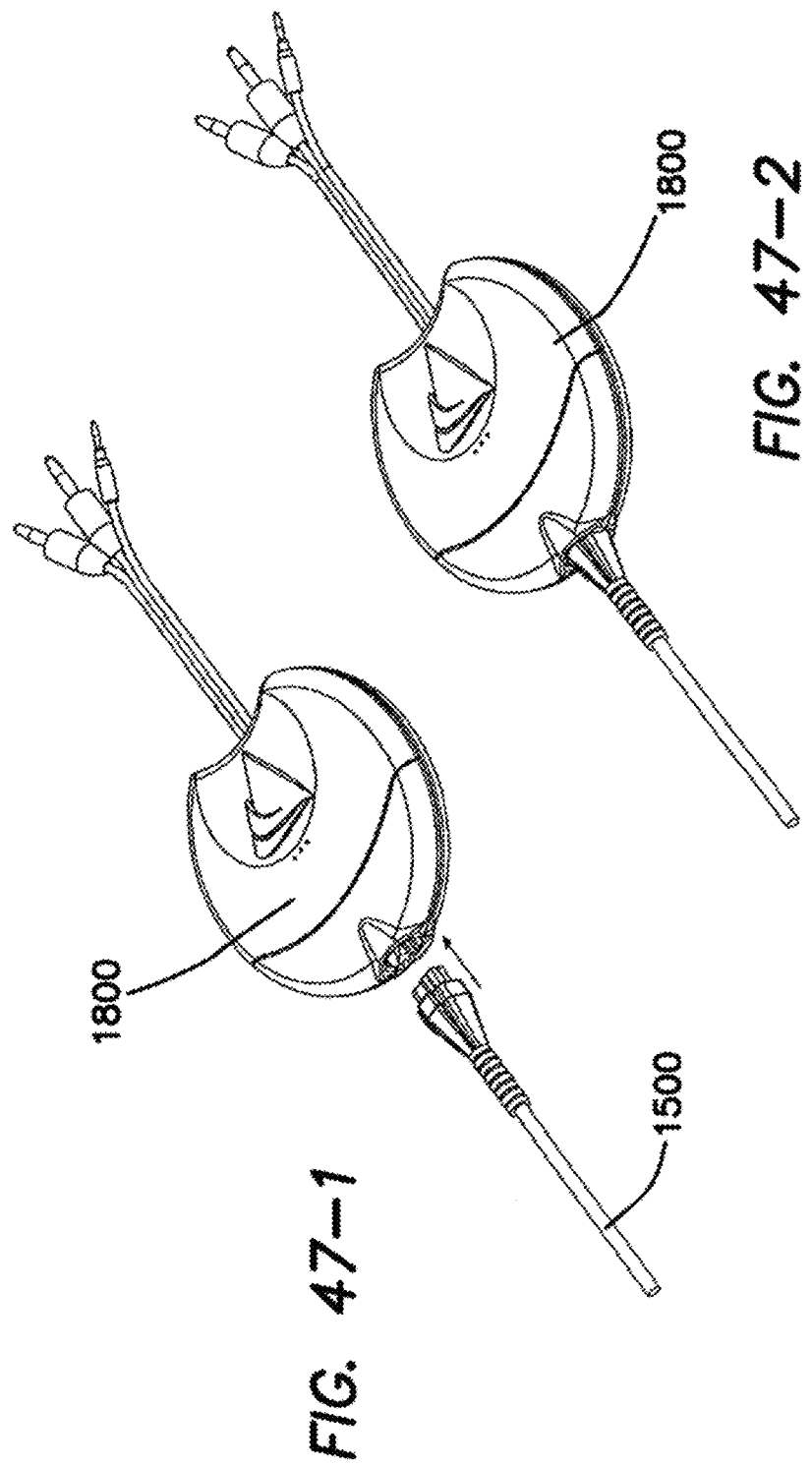

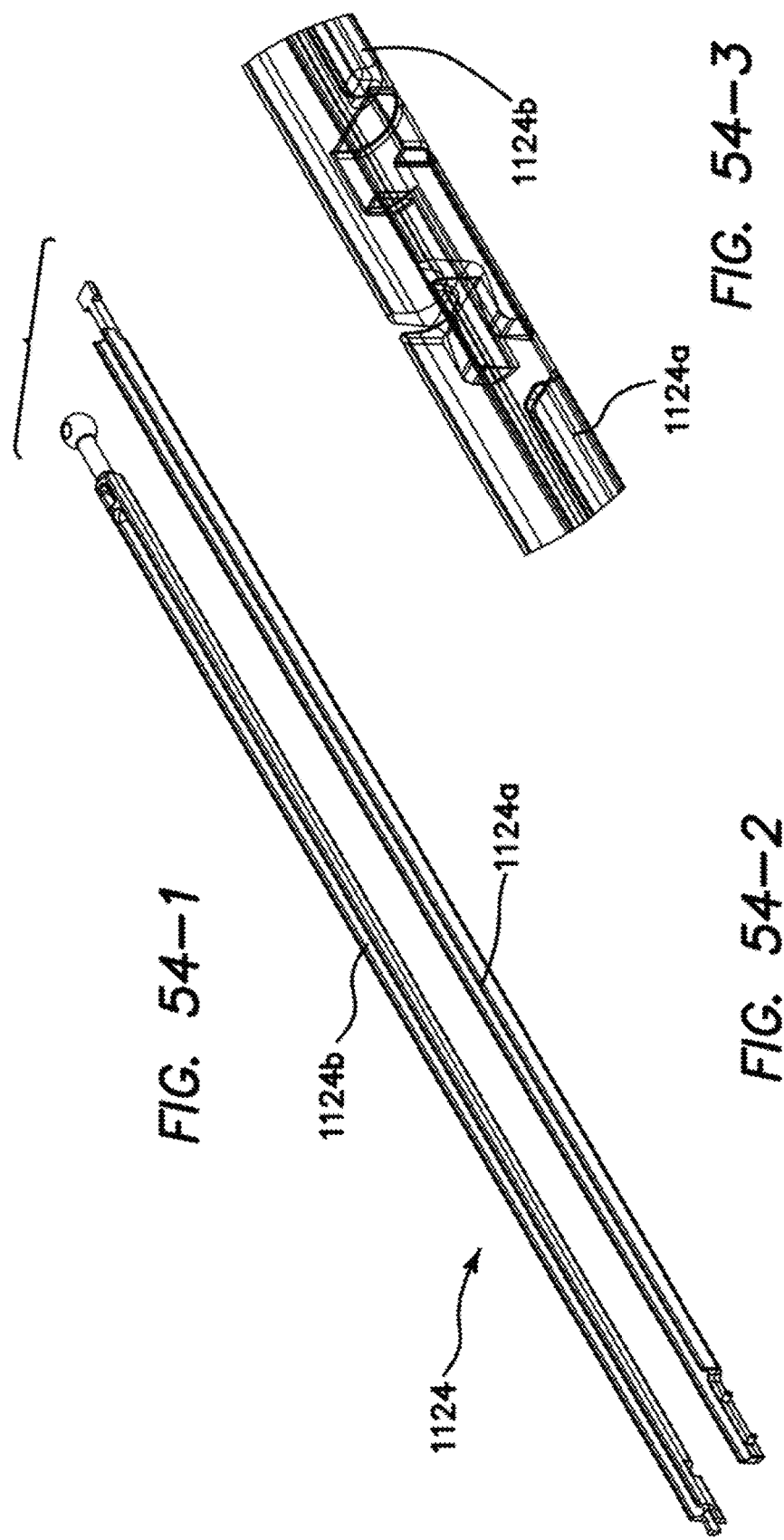

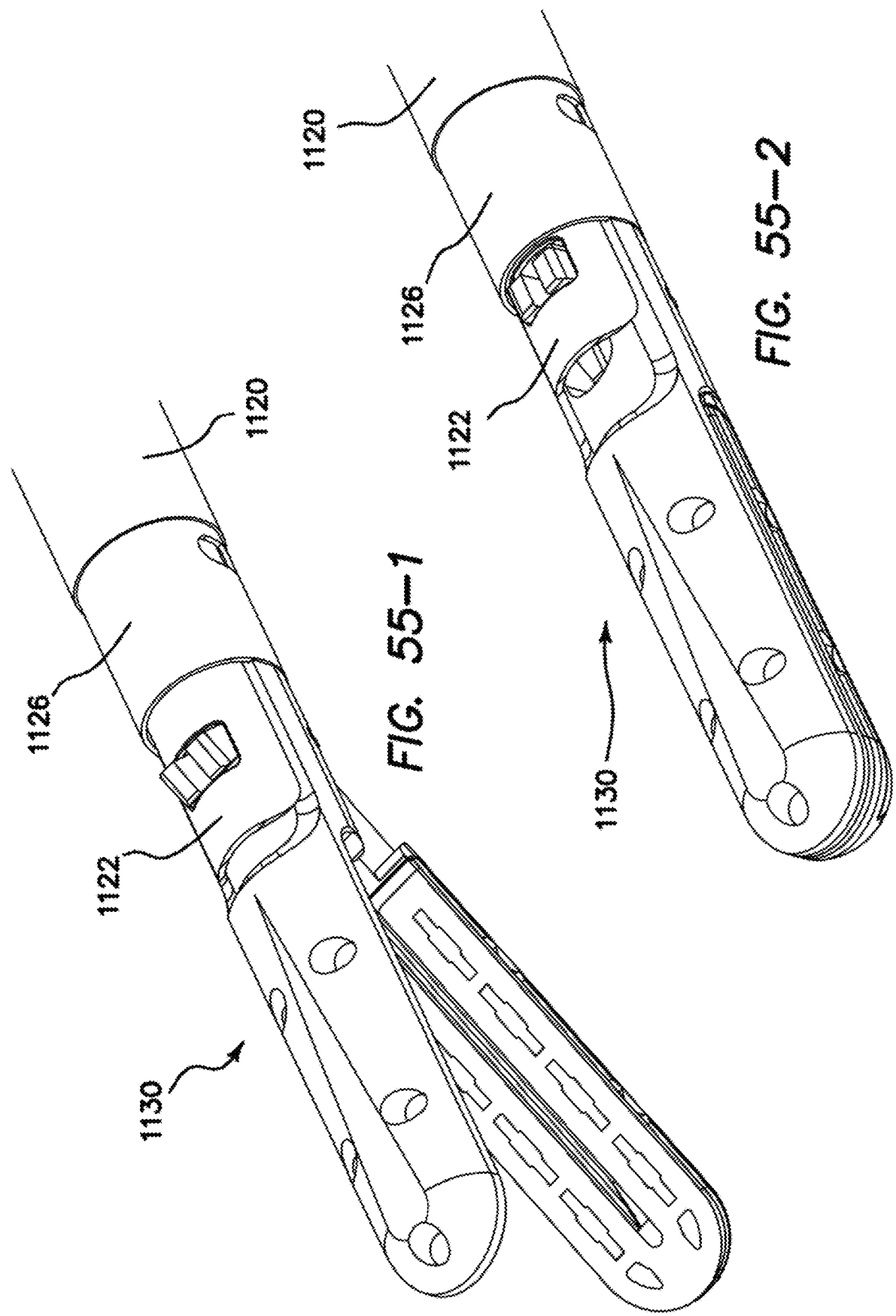

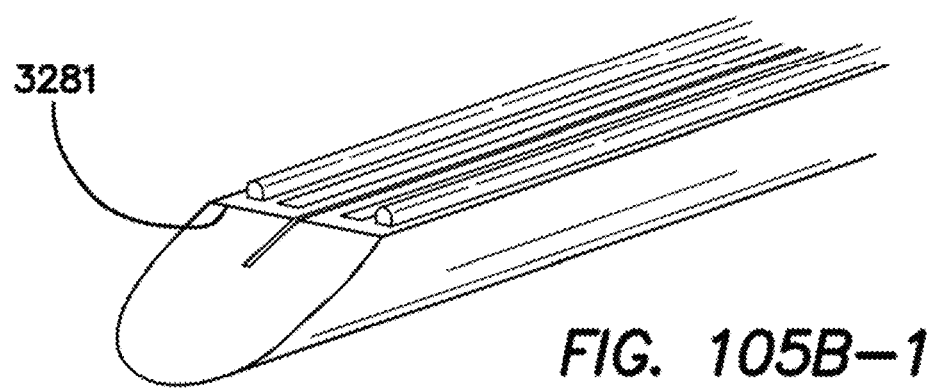
FIG. 105B-1
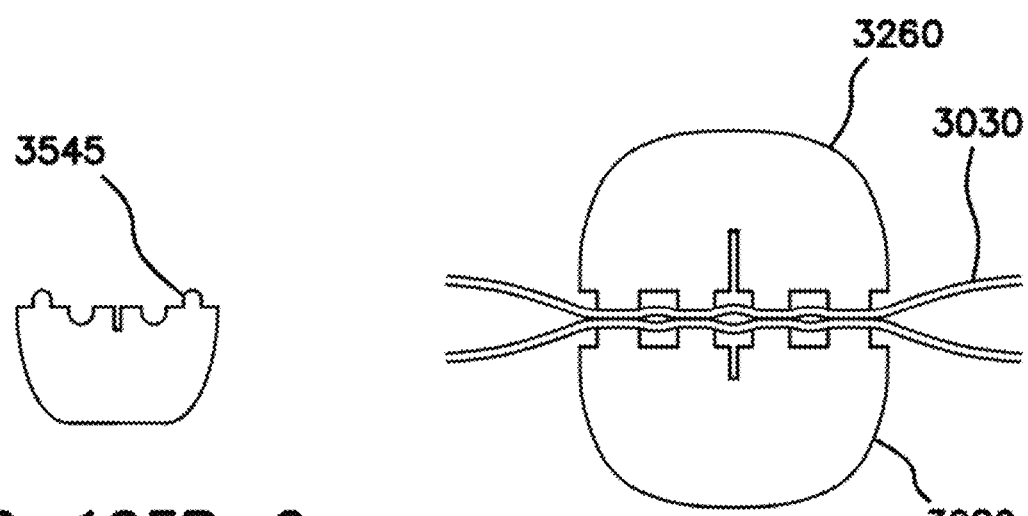
FIG. 105B-2
FIG. 107
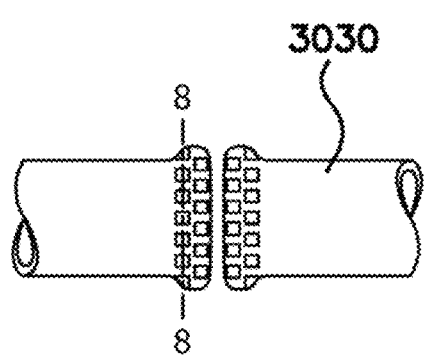
FIG. 108A
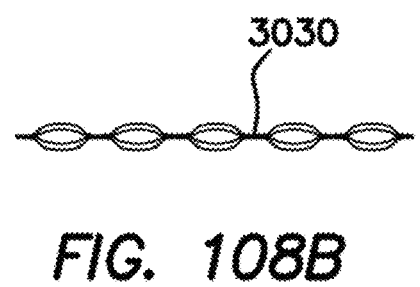
FIG. 108B

ELECTROSURGICAL SYSTEM

CROSS REFERENCE TO RELATED APPLICATIONS

This application is continuation of U.S. patent application Ser. No. 16/448,492, entitled "ELECTROSURGICAL SYSTEM", filed Jun. 21, 2019, currently pending, which is a continuation of U.S. patent application Ser. No. 15/431,595, entitled "ELECTROSURGICAL SYSTEM", filed Feb. 13, 2017, now U.S. Pat. No. 10,342,604, issued Jul. 9, 2019, which is a continuation of U.S. patent application Ser. No. 14/076,469, entitled "ELECTROSURGICAL SYSTEM", filed Nov. 11, 2013, now U.S. Pat. No. 9,566,108, issued Feb. 14, 2017, which is a continuation of U.S. patent application Ser. No. 12/416,751, entitled "ELECTROSURGICAL SYSTEM", filed Apr. 1, 2009, now U.S. Pat. No. 8,579,894, issued Nov. 12, 2013, which is a continuation of U.S. patent application Ser. No. 12/416,128, entitled "ELECTROSURGICAL SYSTEM", filed Mar. 31, 2009, now U.S. Pat. No. 8,568,411, issued Oct. 29, 2013, which claims the benefit of U.S. Provisional Patent Application Ser. No. 61/040,980, entitled "FEEDBACK CONTROL MECHANISM FOR FUSING BIOLOGICAL TISSUE WITH HIGH FREQUENCY ELECTRICAL ENERGY", filed Mar. 31, 2008; U.S. Provisional Patent Application Ser. No. 61/040,994, entitled "FUSING BIOLOGICAL TISSUE WITH HIGH FREQUENCY ELECTRICAL ENERGY", filed Mar. 31, 2008; U.S. Provisional Patent Application Ser. No. 61/040,957, entitled "METHOD AND APPARATUS FOR BLOODLESS TISSUE DISSECTION", filed Mar. 31, 2008; U.S. Provisional Patent Application Ser. No. 61/040,828, entitled "LAPAROSCOPIC BIPOLAR ELECTRICAL INSTRUMENT", filed Mar. 31, 2008; U.S. Provisional Patent Application Ser. No. 61/040,890, entitled "APPARATUS AND METHOD FOR FUSION OF LIVING TISSUE", filed Mar. 31, 2008; U.S. Provisional Patent Application Ser. No. 61/041,045, entitled "WELDING BIOLOGICAL TISSUE WITH HIGH FREQUENCY ELECTRICAL ENERGY", filed Mar. 31, 2008; U.S. Provisional Patent Application Ser. No. 61/041,012, entitled "ELECTRICAL CONTROL CIRCUIT FOR FUSING OF BIOLOGICAL TISSUE WITH HIGH FREQUENCY ELECTRICAL ENERGY", filed Mar. 31, 2008; U.S. Provisional Patent Application Ser. No. 61/115,756, entitled "METHOD AND APPARATUS FOR ELECTROSURGICAL TISSUE DISSECTION", filed Nov. 18, 2008. All of these applications are incorporated herein by reference in their entireties.

BACKGROUND

Field

The present application relates generally to electrosurgical systems and methods. More specifically, the present application relates to an electrosurgical system including an electrosurgical unit with a feedback circuit and an electrosurgical tool.

Discussion of the Relevant Art

Surgical procedures often involve cutting and connecting bodily tissue including organic materials, musculature, connective tissue and vascular conduits. For centuries, sharpened blades and sutures have been mainstays of cutting and reconnecting procedures. As bodily tissue, especially relatively highly vascularized tissue is cut during a surgical procedure, it tends to bleed. Thus, medical practitioners such as surgeons have long sought surgical tools and methods that slow or reduce bleeding during surgical procedures.

More recently, electrosurgical tools have become available that use electrical energy to perform certain surgical tasks. Typically, electrosurgical tools are hand tools such as graspers, scissors, tweezers, blades, needles, and other hand tools that include one or more electrodes that are configured to be supplied with electrical energy from an electrosurgical generator including a power supply. The electrical energy can be used to coagulate, fuse, or cut tissue to which it is applied. Advantageously, unlike typical mechanical blade procedures, application of electrical energy to tissue tends to stop bleeding of the tissue.

Electrosurgical tools typically fall within two classifications: monopolar and bipolar. In monopolar tools, electrical energy of a certain polarity is supplied to one or more electrodes on the tool. A separate return electrode is electrically coupled to a patient. Monopolar electrosurgical tools can be useful in certain procedures, but can include a risk of certain types of patient injuries such as electrical burns often at least partially attributable to functioning of the return electrode. In bipolar electrosurgical tools, one or more electrodes is electrically coupled to a source of electrical energy of a first polarity and one or more other electrodes is electrically coupled to a source of electrical energy of a second polarity opposite the first polarity. Thus, bipolar electrosurgical tools, which operate without separate return electrodes, can deliver electrical signals to a focused tissue area with a reduced risk of patient injuries.

Even with the relatively focused surgical effects of bipolar electrosurgical tools, however, surgical outcomes are often highly dependent on surgeon skill. For example, thermal tissue damage and necrosis can occur in instances where electrical energy is delivered for a relatively long duration or where a relatively high-powered electrical signal is delivered even for a short duration. The rate at which a tissue will achieve the desired coagulation or cutting effect upon the application of electrical energy varies based on the tissue type and can also vary based on pressure applied to the tissue by an electrosurgical tool. However, even for a highly experienced surgeon, it can be difficult for a surgeon to assess how quickly a mass of combined tissue types grasped in an electrosurgical instrument will be fused a desirable amount.

Attempts have been made to reduce the risk of tissue damage during electrosurgical procedures. For example, previous electrosurgical systems have included generators that monitor an ohmic resistance or tissue temperature during the electrosurgical procedure, and terminated electrical energy once a predetermined point was reached. However, these systems have had shortcomings in that they have not provided consistent results at determining tissue coagulation, fusion, or cutting endpoints for varied tissue types or combined tissue masses. These systems can also fail to provide consistent electrosurgical results among use of different tools having different tool and electrode geometries. Typically, even where the change is a relatively minor upgrade to tool geometry during a product's lifespan, the electrosurgical generator must be recalibrated for each tool type to be used, a costly, time consuming procedure which can undesirably remove an electrosurgical generator from service.

SUMMARY

In view of at least the foregoing shortcomings of the previous electrosurgical systems, there is a need in the art to improve control of electrosurgical procedures to enhance consistency of electrosurgical results among electrosurgical tools and tissue types. Accordingly, there is a need for an improved electrosurgical system that can accurately assess an electrical energy application endpoint for a desired electrosurgical procedure. There is also a need for an electrosurgical system that monitors tissue properties during the electrosurgical procedure to assess the energy application endpoint. There is also a need for an improved electrosurgical system that can rapidly accommodate various electrosurgical tools with minimal impact on surgical outcome. To address some or all of these needs and provide various additional advantages as discussed below in greater detail, various embodiments, methods, systems, and apparatuses for electrosurgical procedures are provided.

In various embodiments, methods and apparatuses for bloodless dissection of connective and vascular tissue are provided. The various methods and apparatuses described herein can be used in minimally invasive surgery, particularly laparoscopic surgery.

In certain embodiments, an electrosurgical tool comprises a handle assembly, an elongate shaft, a jaw assembly, and a force regulation mechanism. The handle assembly comprises a stationary handle and an actuation handle movably coupled to the stationary handle. The elongate shaft extends distally from the handle. The elongate shaft has a proximal end and a distal end defining a central longitudinal axis therebetween. The jaw assembly is positioned on the distal end of the elongate shaft. The jaw assembly comprises a first jaw and a second jaw. The first jaw has an inner surface, an outer surface, and at least one electrode disposed on the inner surface. The second jaw has an inner surface, an outer surface, and at least one electrode disposed on the inner surface. The jaw assembly is actuatable by movement of the ff from an open configuration in which the inner surface of the first jaw is spaced apart from the inner surface of the second jaw to a closed configuration in which the inner surface of the first jaw is proximate the inner surface of the second jaw. The force regulation mechanism couples the handle assembly to the jaw assembly. The force regulation assembly is configured such that in the closed configuration, the jaw assembly delivers a gripping force between the first jaw and the second jaw between a predetermined minimum force and a predetermined maximum force.

In other embodiments, an electrosurgical tool is provided comprising a handle assembly, an elongate shaft, and a jaw assembly. The handle assembly comprises a moveable actuation handle. The elongate shaft extends distally from the handle. The elongate shaft has a proximal end and a distal end defining a central longitudinal axis therebetween. The jaw assembly is positioned on the distal end of the elongate shaft. The jaw assembly comprises a first jaw, a second jaw, and a blade. The first jaw has an inner surface, an outer surface, a proximal end and a distal end, and at least one electrode disposed on the inner surface. The second jaw has an inner surface, an outer surface, a proximal end and a distal end and at least one electrode disposed on the inner surface. The blade is advanceable along the inner surface of the first jaw along a cutting path defined between a retracted position adjacent the proximal end and an advanced position between the proximal end and the distal end. The jaw assembly is actuatable from an open configuration to a closed configuration by movement of the actuation handle. The at least one electrode on the first jaw and the at least one electrode on the second jaw define a sealing area enclosing the cutting path of the blade.

In other embodiments, an electrosurgical tool is provided comprising a handle assembly, an elongate shaft, and a jaw assembly. The elongate shaft extends distally from the handle assembly. The shaft having a proximal end and a distal end defining a central longitudinal axis therebetween. The jaw assembly is positioned on the distal end of the elongate shaft. The jaw assembly comprises a first jaw and a second jaw. The first jaw has an inner surface, an outer surface, a proximal end and a distal end, and at least one fusion electrode disposed on the inner surface. The second jaw has an inner surface, an outer surface, a proximal end and a distal end and at least one fusion electrode disposed on the inner surface and a cutting electrode disposed on the outer surface.

In certain embodiments, an electrosurgical system for performing surgical procedures on body tissue of a patient comprises an electrosurgical generator and an electrosurgical tool. The electrosurgical tool comprises a memory module storing tool data. The electrosurgical generator is configured to receive the tool data from the memory module and apply an electrosurgical signal profile to the electrosurgical tool based on the tool data.

In other embodiments, an electrosurgical generator for performing surgical procedures on body tissue of a patient comprises a power supply, a signal generation module, and a first tool port. The signal generation module is electrically coupled to the power supply. The signal generation module is configured to generate a radiofrequency signal. The first tool port is configured to interface with an electrosurgical tool having tool data stored therein. The first tool port is adapted to receive the tool data stored on the electrosurgical tool and to supply the radiofrequency signal from the signal generation module to the tool.

In some embodiments, a controller for electrosurgical tools comprises a first actuator, a second actuator, and a tool selector. The first actuator is movable between an on position and an off position for actuating a first electrosurgical action when in the on position. The second actuator is movable between an on position and an off position for actuating a second electrosurgical action when in the on position. The tool selector has a first state wherein the controller is adapted to be operatively coupled to a first electrosurgical tool and a second state wherein the controller is adapted to be operatively coupled to a second electrosurgical tool.

In certain embodiments, a surgical tool can comprise jaw elements having a plurality of electrodes to be used for both electrosurgical coagulation and cutting. The electrodes can be powered in a first configuration to provide coagulation—leading to hemostasis of small vascular vessels and tissue—and powered in a second configuration for electrosurgical cutting of the coagulated tissue. The two powered configurations can be generated by addressing different electrodes on the jaw elements and applying them with voltages appropriate for electrosurgical coagulation and/or cutting. In some embodiments, the surgical tool can initially be powered in the first configuration to provide coagulation, and then can be powered in the second configuration for electrosurgical cutting. In other embodiments, the electrosurgical tool can be powered only in a coagulating configuration to achieve tissue hemostasis, only in a cutting configuration to dissect tissue, or in a cutting configuration followed by a coagulation configuration.

At the same time, various embodiments of the surgical tools described herein can include different electrode configurations. I.e., while in one embodiment only the lower jaw is utilized to provide both coagulation and cutting functions, another embodiment can also employ the upper jaw element to be used in the coagulation and/or cutting process. In yet another embodiment, each jaw element can carry multiple electrode elements, greatly increasing the functionality of the tool. A specific electrode arrangement can allow for tools that are more suitable for particular surgical procedures.

Another aspect of the surgical tools described herein relates to activation and deactivation of one or multiple electrodes, based on the position of the jaw elements. This position-based actuation allows, for example, activation of the upper jaw electrodes only in a near-closed position of the tool (or, in other embodiments, in an opened or near-opened position of the tool). In some embodiments, electrical switches in the jaw element driving mechanism can be positioned in a hand-piece of the surgical tool to selectively activate and deactivate one or multiple electrodes based on a position of the jaw elements. In other embodiments, the activation and deactivation can be performed by sliding contacts that are assembled in the hand-piece.

Yet another aspect of the surgical tools described herein is the automated switching from coagulation to cutting, enabled by use of a multi-electrode generator. Here, a tissue feedback mechanism triggers both switching from one set of coagulation electrodes (applied with voltages appropriate for coagulation) to another set of cutting electrodes (applied with voltages appropriate for cutting). As such, each individual tool electrode can be relayed through a bus-bar connection to any polarity of choice of the power supply. In addition, tool position switches in the hand tool can provide with logic switching for the population of different coagulation and/or cutting settings, depending on the specific tool position.

In certain embodiments, an electrosurgical tool is provided comprising a first jaw, a second jaw, a first electrode, a second electrode, and a third electrode. The second jaw is pivotable with respect to the first jaw. The first electrode is positioned on the first jaw. The second electrode is positioned on the first jaw. The third electrode is positioned on the first jaw. The electrosurgical tool can be selectively configurable in a coagulation configuration such that at least one of the first, second, and third electrodes is electrically coupled with a source of electrical energy having a first polarity and at least one other of the electrodes is electrically coupled with a source of electrical energy having a second polarity generally opposite the first polarity and in a cutting configuration such that one of the first, second, and third electrodes is electrically coupled with a source of electrical energy having a cutting voltage and at least one other of the electrodes is configured to be a return electrode.

In other embodiments, an electrosurgical tool having a proximal end and a distal end is provided comprising a distal end-piece, an elongate shaft, a handle assembly, and a switching mechanism. The distal end-piece is positioned at the distal end of the tool. The distal end-piece comprises a first jaw element, a second jaw element, and a plurality of electrodes. The first and second jaw elements are movable relative to one another between an open position and a closed position. The plurality of electrodes is disposed on at least one of the first jaw element and the second jaw element. The plurality of electrodes is selectively configurable in one of a coagulation configuration and a cutting configuration. The elongate shaft has a distal end connected to the distal end-piece and a proximal end. The handle assembly is positioned at the proximal end of the tool and connected to the proximal end of the elongate shaft. The handle assembly comprises a hand-piece and a trigger. The trigger is pivotally coupled to the hand-piece and operably coupled to the distal end-piece such that movement of the trigger relative to the hand-piece moves the first and second jaw elements relative to one another. The switching mechanism is electrically coupled to the distal end-piece to selectively configure the plurality of electrodes in one of the coagulation configuration and the cutting configuration.

In other embodiments, a method for substantially bloodless dissection of biological tissue is provided. The method comprises positioning an electrosurgical tool adjacent tissue to be dissected, measuring tissue properties to determine the switching point from coagulation to cutting, applying electrical energy to the electrosurgical tool, assessing the tissue coagulation (phase shift) through a feedback loop, switching a configuration of the electrosurgical tool, and applying electrical energy to the electrosurgical tool in a cutting configuration. The electrosurgical tool comprises a plurality of electrodes configurable in one of a coagulation configuration and a cutting configuration. Applying electrical energy to the electrosurgical tool comprises applying electrical energy to the electrosurgical tool in the coagulation configuration to achieve hemostasis in the tissue. Switching the electrosurgical tool comprises switching the electrosurgical tool to the cutting configuration.

In some embodiments, a method for controlling an output of an electrosurgical generator operatively coupled to a bipolar electrosurgical device is provided. The method comprises measuring a phase angle, determining a target phase angle, measuring the phase angle of a second measurement signal, and ceasing delivery of a treatment signal. Measuring the phase angle comprises measuring a phase angle of a first measurement signal applied to tissue of a patient via at least one electrode of the electrosurgical device. The first measurement signal is applied to the tissue prior to treatment of the tissue by the electrosurgical device. Determining a target phase angle comprises determining a target phase angle using the phase angle of the first measurement signal. Following delivery of a treatment signal comprises following delivery of a treatment signal to the tissue. Measuring the phase angle of a second measurement signal comprises measuring the phase angle of a second measurement signal applied to the tissue. The treatment signal is capable of causing modification of the tissue. Ceasing delivery of the treatment signal comprises ceasing delivery of the treatment signal to the tissue when the phase angle of the second measurement signal reaches the target phase angle.

In other embodiments, a method for controlling an output of an electrosurgical generator operatively coupled to a bipolar electrosurgical device is provided. The method comprises determining permittivity and conductivity of tissue, determining a threshold phase angle, measuring a phase angle, and ceasing the delivery of the treatment signal. Determining permittivity and conductivity of tissue comprises determining permittivity and conductivity of tissue of a patient using a measurement signal. The measurement signal is applied to tissue of a patient via at least one electrode of the electrosurgical device. The measurement signal is applied to the tissue prior to modification of the tissue by the electrosurgical device. Determining a threshold phase angle comprises determining a threshold phase angle based on the permittivity and the conductivity of the tissue. Measuring a phase angle comprises measuring a phase angle of a signal applied to the tissue. Ceasing the delivery of the treatment signal comprises ceasing the delivery of the treatment signal to the tissue when the phase angle of the signal reaches the threshold phase angle.

In other embodiments, a method of characterizing tissue prior to the delivery of electrosurgical energy to the tissue via a bipolar electrosurgical device is provided. The method comprises measuring phase angle, determining the product of the relative permittivity and conductivity, and characterizing the tissue. Measuring phase angle comprises measuring phase angle of a measurement signal applied to tissue of a patient via at least one electrode of the electrosurgical device. The measurement signal is applied to the tissue at a predetermined frequency prior to modification of the tissue by the electrosurgical device. Determining the product of the relative permittivity and conductivity comprises determining the product of the relative permittivity and conductivity of the tissue using the phase angle measurement and the predetermined frequency. Characterizing the tissue comprises characterizing the tissue based on the product of the relative permittivity and conductivity of the tissue.

In other embodiments, a method of characterizing tissue prior to the delivery of electrosurgical energy to the tissue via a bipolar electrosurgical device is provided. The method comprises generating a measurement signal, determining a treatment endpoint condition, and stopping delivery of a treatment signal. Generating a measurement signal comprises generating a measurement signal applied to tissue of a patient positioned between at least two jaw members of an electrosurgical device. At least one of the jaw members comprises an electrode. The measurement signal is delivered to the tissue via the electrode and applied to modification of the tissue by the electrosurgical device. Determining a treatment endpoint condition comprises determining a treatment endpoint condition using the measurement signal. The treatment endpoint condition is determined substantially independently of the dimensions of the tissue positioned between the at least two jaw members. Stopping delivery of a treatment signal comprises stopping delivery of a treatment signal to the tissue when the treatment endpoint condition is reached. The treatment signal is capable of causing modification of the tissue.

In other embodiments, an electrosurgical system for application of treatment energy to a patient involved in bipolar electrosurgery is provided. The system comprises an electrosurgical generator, an electrosurgical control unit, and an electrosurgical tool. The electrosurgical generator is configured to generate and output a treatment energy along with a measurement signal. The electrosurgical control unit is configured to direct the output of treatment energy and a measurement signal. The electrosurgical tool is removably connected to one of the electrosurgical generator and the electrosurgical control unit and arranged to contact tissue and apply the treatment energy and the measurement signal to the tissue. The electrosurgical control unit measures permittivity and conductivity of the tissue through the application of the measurement signal.

BRIEF DESCRIPTION OF THE DRAWINGS

The present inventions may be understood by reference to the following description, taken in connection with the accompanying drawings in which the reference numerals designate like parts throughout the figures thereof.

FIG. 30 is a table of dielectric constants or permittivity and conductivities for various types of biological tissue, arranged by increasing values of the product of dielectric constants and tissue conductivity.

FIGS. 45A, 45B-1, 45B-2, 45C-1, and 45C-2 are views of a jaw assembly of a laparoscopic sealer/divider of FIG. 41A.

FIGS. 46A, 46B, 46C, 46D, 46E-1, 46E-2, 46F, and 46G are cross-sectional side views of a laparoscopic sealer/divider of FIG. 41A.

FIGS. 47-1 and 47-2 are perspective views of a controller of a laparoscopic sealer/divider of FIG. 41A.

FIGS. 49-1, 49-2, and 49-3 are top level views of electrode configurations of a laparoscopic sealer/divider of FIG. 41A.

FIGS. 52-1 and 52-2 provide views of a jaw assembly of a laparoscopic sealer/divider of FIG. 41A.

FIGS. 54-1, 54-2, and 54-3 provide views of portions of a shaft assembly of a laparoscopic sealer/divider of FIG. 41A.

FIGS. 55-1 and 55-2 provide views of a jaw assembly of a laparoscopic sealer/divider of FIG. 41A.

FIG. 105B-1 is an enlarged perspective view of a clamping jaw showing a plurality of current intensifying elements comprising linear "spicket-and-sockets". FIG. 105B-2 is a cross-sectional view of the clamping jaw of FIG. 105B-1.

FIG. 107 shows a cross-section view of a clamping jaw with an exemplary compressed artery with an application of electrical or thermal energy.

FIGS. 108a and b are views of an exemplary portion of an artery sealed and cut (108a top plan view, 108b along 8-8).

Figure 109A:
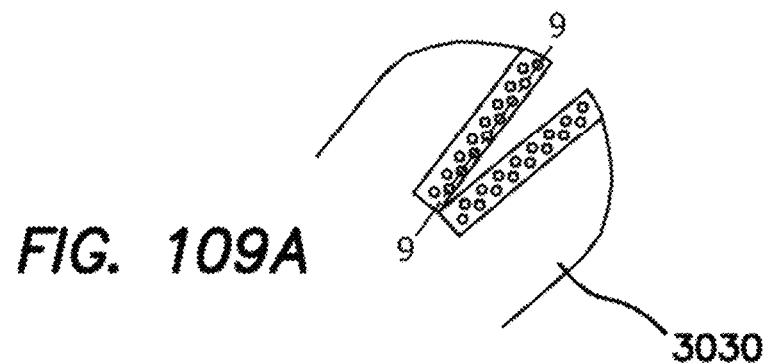
Figure 109B:
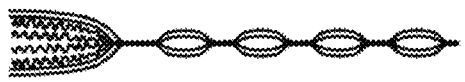

FIGS. 109a and b are views of an exemplary portion of tissue sealed and cut (109a top plan view, 109b along 9-9).

Figure 110:
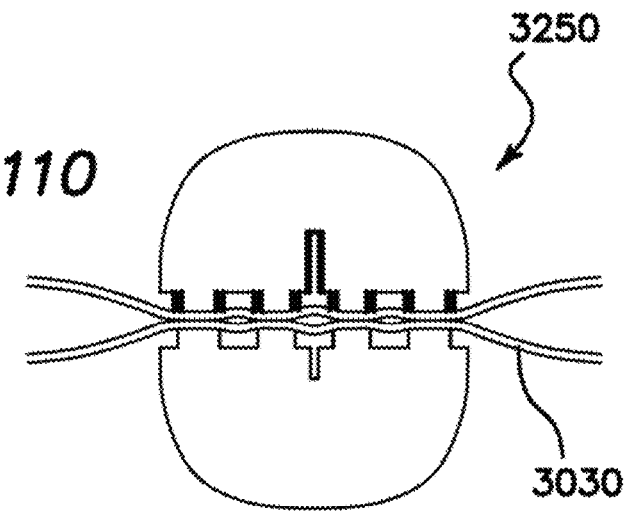

FIG. 110 shows a cross-sectional view of a clamping jaw with an exemplary compressed artery with an application of ultrasonic energy.

Figure 111:
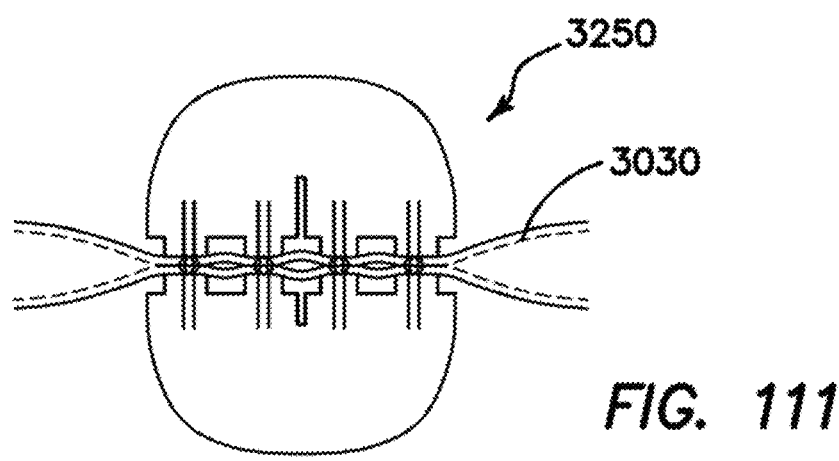

FIG. 111 shows a cross-sectional view of a clamping jaw with an exemplary compressed artery with an application of UV or IR radiant energy.

DETAILED DESCRIPTION

The following description is provided to enable any person skilled in the art to make and use the surgical tools and perform the methods described herein and sets forth the best modes contemplated by the inventors of carrying out their inventions. Various modifications, however, will remain apparent to those skilled in the art. It is contemplated that these modifications are within the scope of the present disclosure.

Electrosurgical System

Figure 1A:
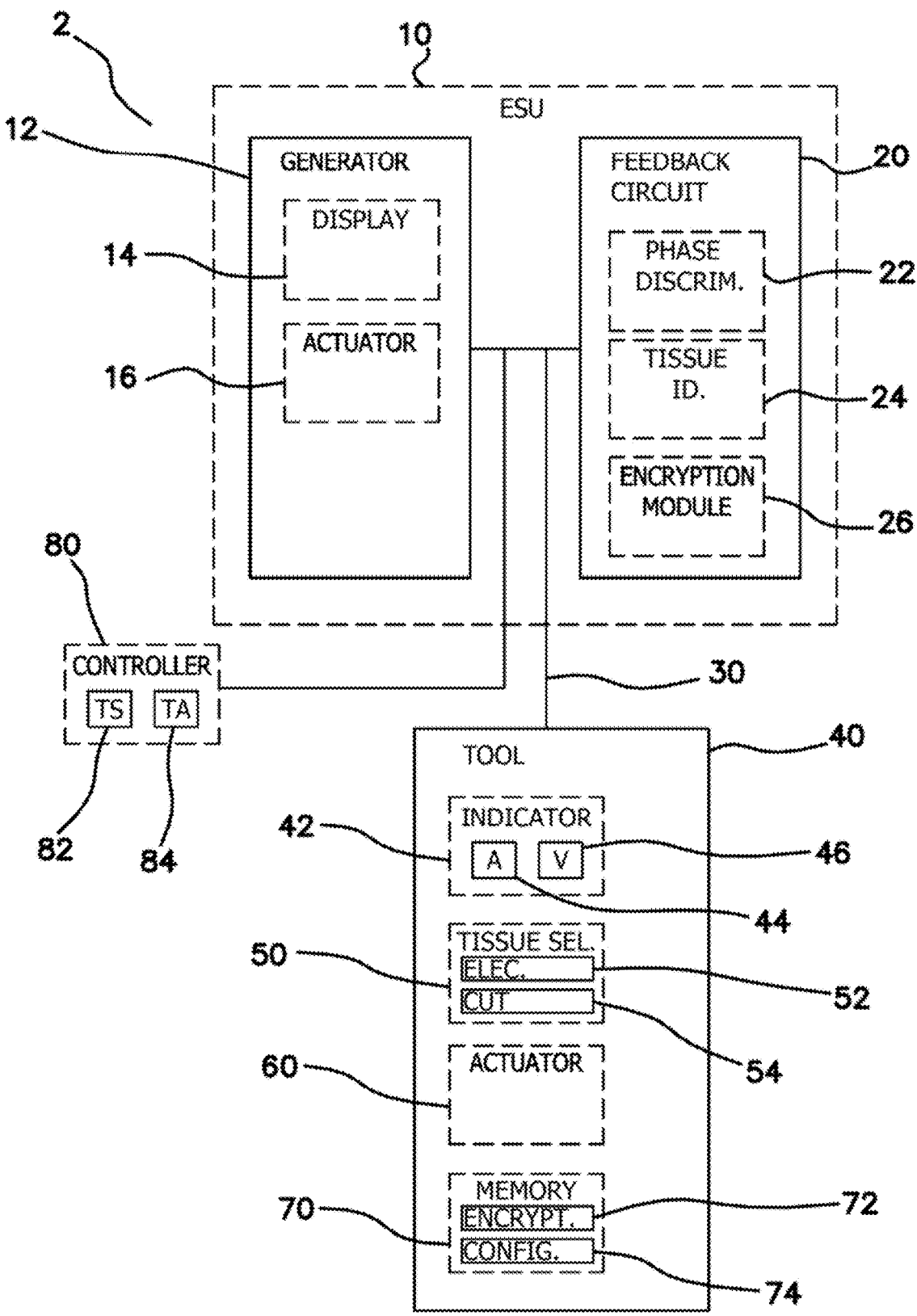
FIG. 1A is a schematic block diagram of an embodiment of electrosurgical system.

FIG. 1A illustrates a schematic diagram of an electrosurgical system 2. The electrosurgical system 2 can comprise an electrosurgical unit (ESU) 10 and an electrosurgical tool 40. The electrosurgical tool 40 can be electrically coupled to the electrosurgical unit 10. In some embodiments, an electronic coupler 30 such as an electrical wire, wire bundle, or cable can electrically couple the electrosurgical tool 40 to the ESU 10. In some embodiments, the electrosurgical system 2 can optionally further comprise an external tool controller 80.

With continued reference to FIG. 1A, the electrosurgical unit 10 can comprise a generator 12 and a feedback circuit 20. The generator 12 can include an actuator 16 such as a power supply and a signal processor configured to generate a radiofrequency (RF) electrosurgical signal. The generator 12 can further comprise a display 14. The display 14 can be configured to indicate the status of the electrosurgical system 2, including, among other information, the status of the actuator 16 and the status of the electrosurgical tool 40 electrically coupled to the electrosurgical unit 10.

With continued reference to FIG. 1A, the feedback circuit 20 of the ESU 10 can comprise a phase discriminator 22, a tissue identifier 24, and an encryption module 26. In some embodiments, the phase discriminator 22 can be electrically coupled to the tissue identifier 24. The phase discriminator 22 can be configured to receive information from the electrosurgical tool 40 electrically coupled to the ESU 10. In some embodiments, the information from the electrosurgical tool 40 comprises information regarding an applied voltage and a supplied current to the electrosurgical tool, and the phase discriminator 22 can be configured to calculate a phase difference between the applied voltage and the supplied current. The encryption module 26 can be configured to transmit and receive data formatted in an encrypted protocol. The encrypted protocol can be one of several commercially-available encryption protocols, or, in some embodiments can be a purpose developed encryption protocol.

Figure 1B:
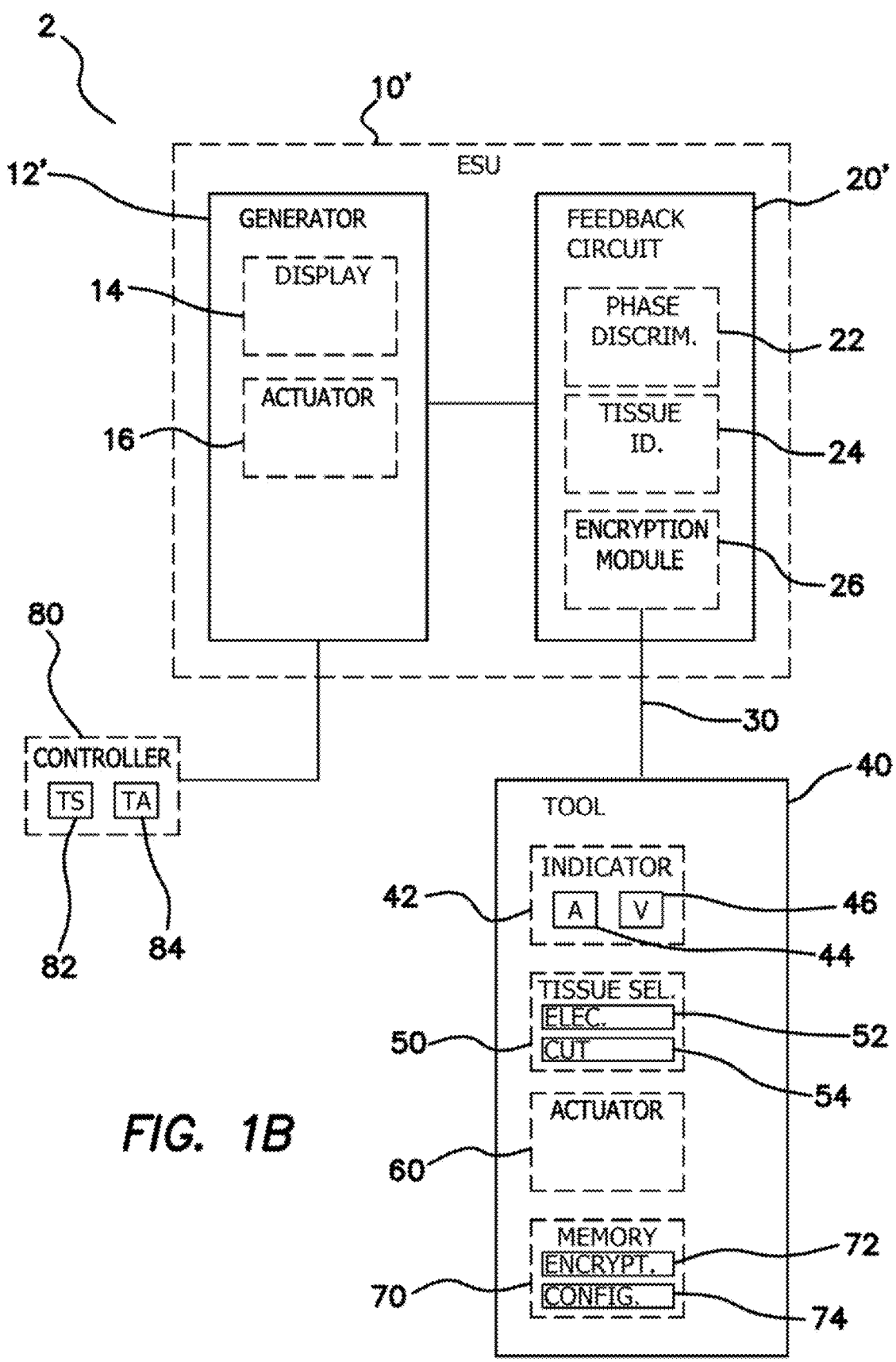
FIG. 1B is a schematic block diagram of another embodiment of electrosurgical system.

With continued reference to FIG. 1A, In some embodiments, the feedback circuit 20 can be one or more integrated circuits, printed circuit boards, or other processor collocated with the generator 12 within an integrated ESU 10. As Illustrated in FIG. 1B, In other embodiments, the feedback circuit 20' can be electrically coupled to a stand-alone generator 12' to form an ESU 10'. The tool 40 can be electrically coupled to the feedback circuit 20'. Other aspects of electrosurgical systems having a stand-alone generator 12' and feedback circuit 20' can be substantially similar to systems having an integrated ESU discussed with respect to FIG. 1A.

With continued reference to FIG. 1A, the tool 40 can comprise an indicator 42, a tissue selector 50, an actuator 60, and a memory 70. In some embodiments, the indicator 40 can comprise an audio indicator 44 such as a speaker, a chime, a clicker device, or another audio generation device. In some embodiments, the indicator 40 can comprise a visual indicator 46 such as a lamp, an LED, a display, a counter, or another visual indication device. In some embodiments, the visual indicator 46 comprises a multi-color LED. In some embodiments, the tool 40 comprises both an audio indicator 44 and a visual indicator 46.

The tissue selector 50 can comprise an electrode assembly 52 and a cutting tool 54. In various embodiments, various electrode assemblies can be configured to perform a desired electrosurgical procedure such as, for example, coagulation, cutting, or fusion, on a particular tissue. In some embodiments, the electrode assembly 52 can be configured for use as a vascular sealer. In other embodiments, the electrode assembly 52 can be configured for use as a bariatric stapler. In still other embodiments, the electrode assembly 52 can be configured for use as a tissue cutting device. In some embodiments, the cutting tool 54 can be a mechanical element such as a stationary or moveable blade or sharpened edge. In other embodiments, the cutting tool 54 can be an electrosurgical element such as an energizable wire or filament.

With continued reference to FIG. 1A, the actuator 60 can be operatively coupled to the tissue selector 50 to selectively select tissue. For example, in some embodiments, the tissue selector 50 can include a jaw-based grasper, and the actuator can comprise an actuation mechanism to selectively move the grasper from an open position to a closed position. In other embodiments, it is contemplated that other tissue selectors can be used in the electrosurgical system 2. In some embodiments, the actuator 60 can also be configured to selectively energize the electrodes. For example, the actuator 60 can comprise a switch or button on the tool.

With continued reference to FIG. 1A, the tool 40 can further comprise a memory 70. In some embodiments, the memory 70 comprises an encryption module 72 and a configuration device module 74. The encryption module 72 can be configured to facilitate an encrypted information exchange with the encryption module 26 on ESU 10. The configuration device module 74 can store operational parameter information about the tool 40. For example, in some embodiments, the configuration device module 74 can store information regarding the electrode assembly, the number of uses and total operational time of use of the tool, and other operational parameters.

With continued reference to FIG. 1A, the electrosurgical system 2 can further comprise an external tool controller 80 electrically coupling the ESU 10 to the tool 40. In some embodiments, the external tool controller 80 comprises a tool selector 82 such as a switch. The external tool controller 80 can allow for multiple devices to connect thereto. A tool selector 82 allows selection of one of the multiple devices to be energized. For example the tool selector 82 can comprise a dial, switch, or toggle. The tool actuator 84 can selectively electrically couple the selected tool 40 with the ESU 10. 3

Figure 2A:
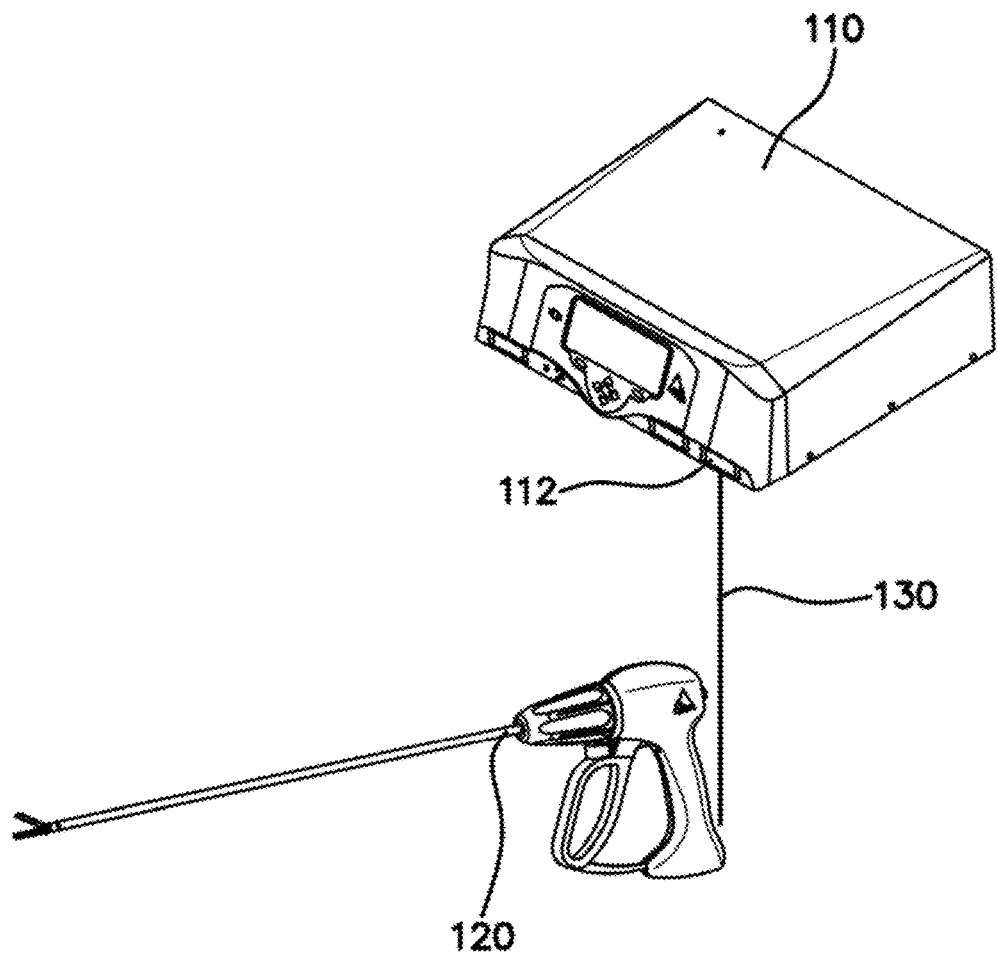
FIG. 2A is a perspective view of components of one embodiment of an electrosurgical system.

With reference to FIG. 2A, an exemplary embodiment of electrosurgical system 102 is illustrated including an ESU 110, and an electrosurgical fusion tool 120. The electrosurgical fusion tool 120 can be electrically coupled to the ESU 110 by an electrical coupler 130 such as with an cabled connection to a tool port 112 on the ESU 110. In the illustrated embodiment, the electrosurgical fusion tool 120 comprises a tissue sealer and divider, as discussed in further detail below with respect to FIGS. 41A-55. The electrosurgical fusion tool 120 comprises visual indicators 122 such as multi-color LEDs positioned there on to apprise a user of the status of the tool. In other embodiments, the electrosurgical fusion tool 120 can be electrically coupled to a generator or a different electrosurgical unit. In some embodiments, a manual controller such as a hand of foot switch can be electrically coupled to the ESU 110 or the electrosurgical fusion tool 122 to allow selective control of the tool.

Figure 2B:
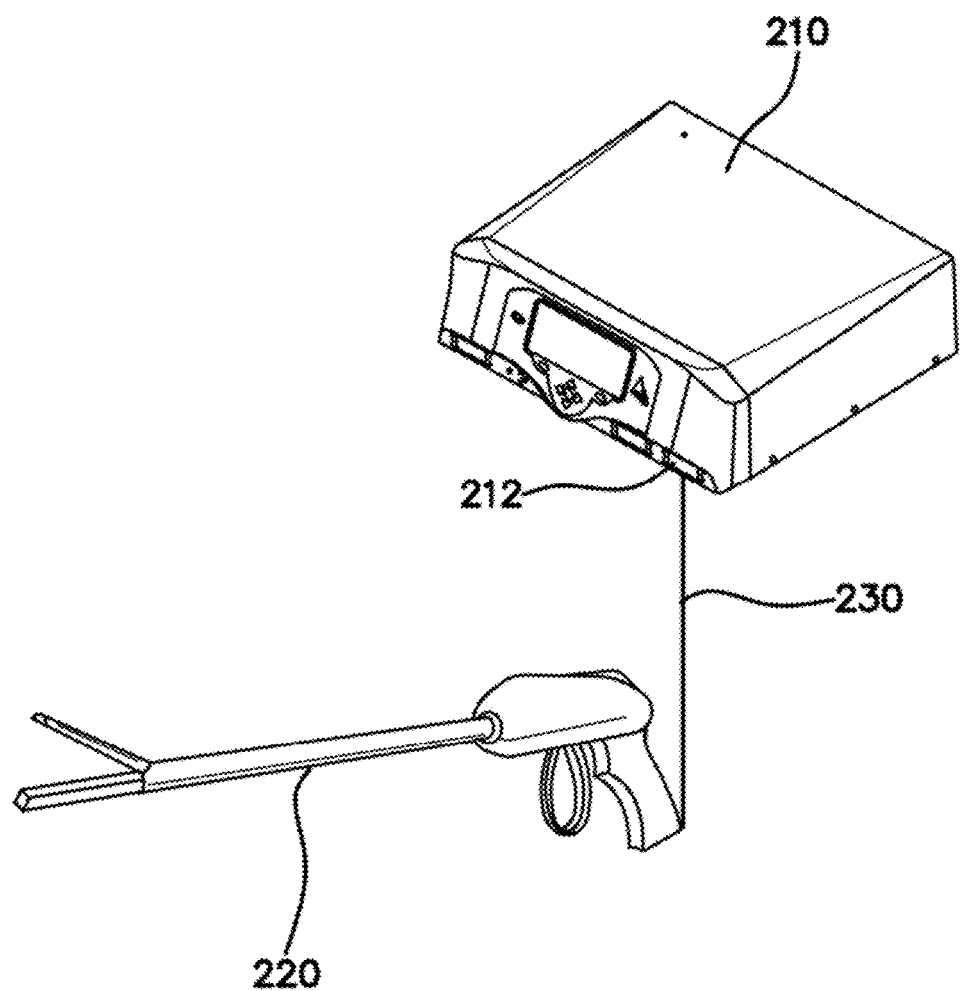
FIG. 2B is a perspective view of components of one embodiment of an electrosurgical system.

With reference to FIG. 2B, an exemplary embodiment of electrosurgical system 202 is illustrated including an ESU 210, and an electrosurgical tool 220. The electrosurgical tool 220 can be electrically coupled to the ESU 210 such as with a cabled connection to a tool port 212 on the ESU 210. In the illustrated embodiment, the electrosurgical tool 220 comprises an electric cutting and coagulation tool, as discussed in further detail below with respect to FIGS. 56-65. The electrosurgical tool 220 comprises visual indicators 222 such as multi-color LEDs positioned there on to apprise a user of the status of the tool. In other embodiments, the electrosurgical tool 220 can be electrically coupled to a generator or a different electrosurgical unit. In some embodiments, a manual controller such as a hand of foot switch can be electrically coupled to the ESU 210 or the electrosurgical fusion tool 222 to allow selective control of the tool.

Figure 2C:
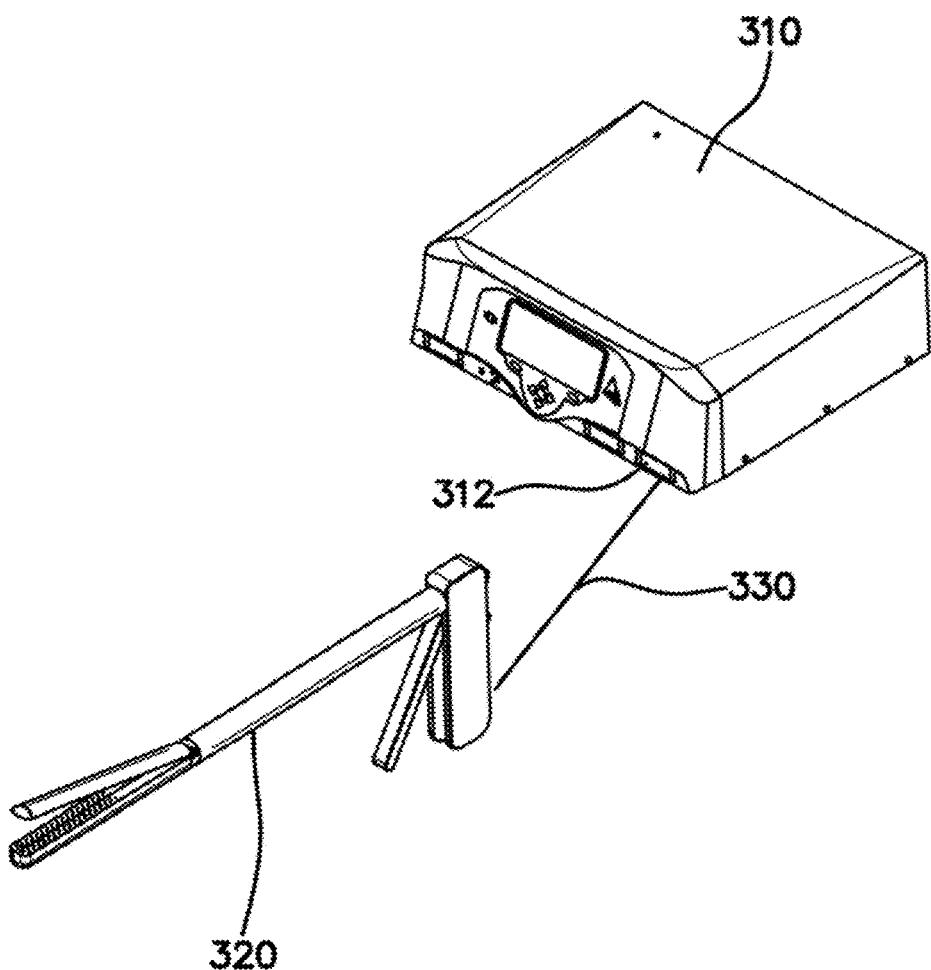
FIG. 2C is a perspective view of components of one embodiment of electrosurgical system.

With reference to FIG. 2C, an exemplary embodiment of electrosurgical system 2302 is illustrated including an ESU 310, and an electrosurgical tool 320. The electrosurgical tool 320 can be electrically coupled to the ESU 310 such as with a cabled connection to a tool port 312 on the ESU 310. In the illustrated embodiment, the electrosurgical tool 320 comprises an electrosurgical stapling tool, as discussed in further detail below with respect to FIGS. 66-111. The electrosurgical tool 320 comprises visual indicators 322 such as multi-color LEDs positioned thereon to apprise a user of the status of the tool. In other embodiments, the electrosurgical tool 320 can be electrically coupled to a generator or a different electrosurgical unit. In some embodiments, a manual controller such as a hand of foot switch can be electrically coupled to the ESU 310 or the electrosurgical tool 322 to allow selective control of the tool.

Integrated Electrosurgical Unit

Figure 3A:
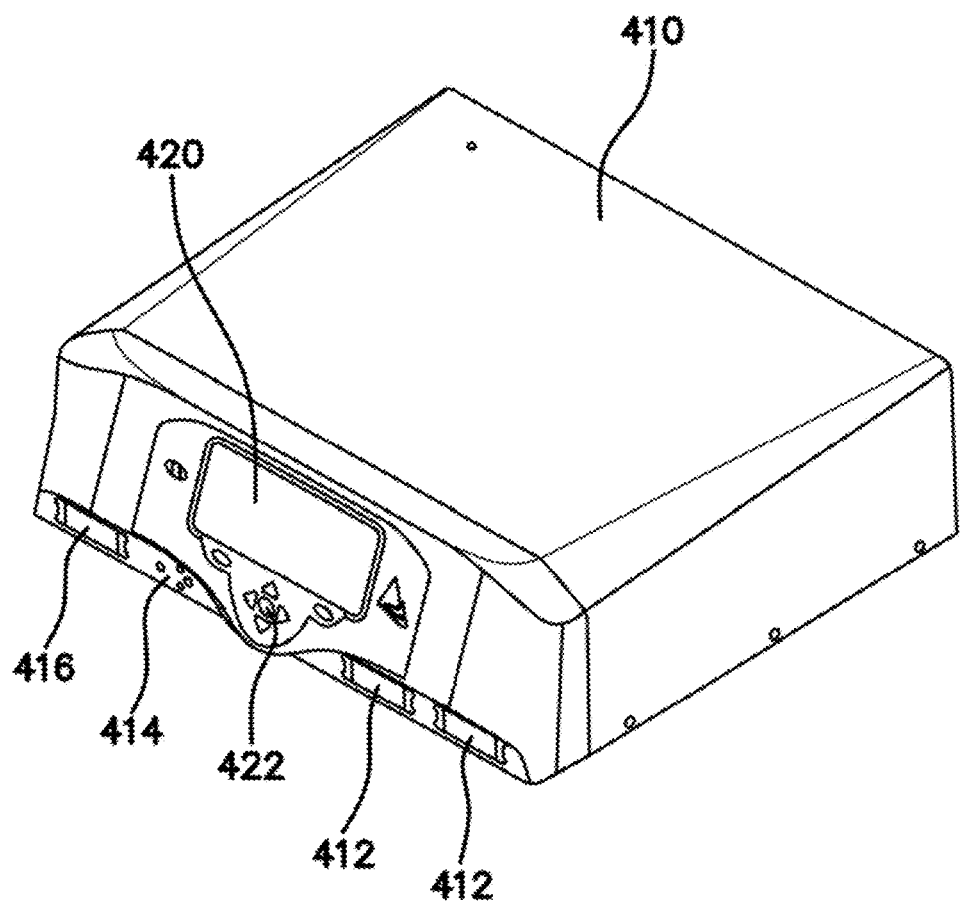
FIG. 3A is a perspective view of an electrosurgical unit for use in an electrosurgical system.
Figure 3B:
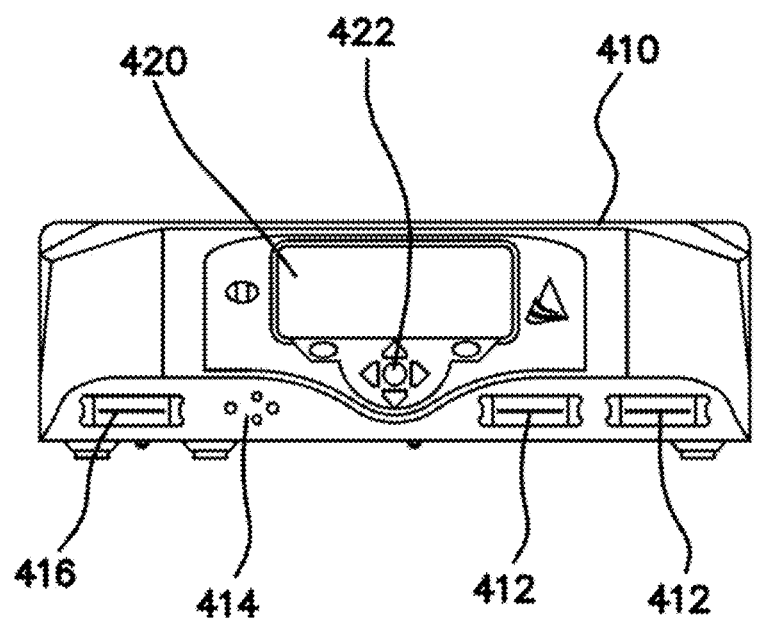
FIG. 3B is a front view of the electrosurgical unit of FIG. 3A.
Figure 3C:
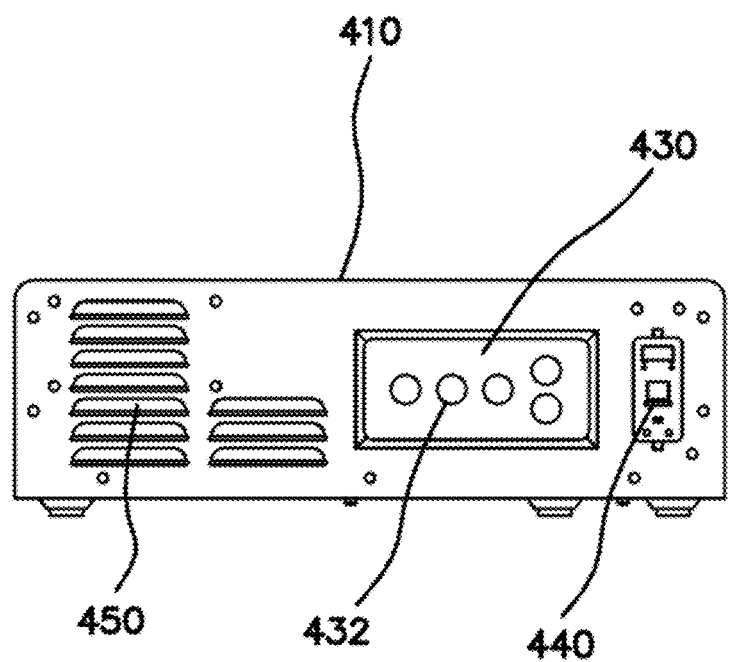
FIG. 3C is a rearview of the electrosurgical unit of FIG. 3A.

With reference to FIGS. 3A-3C, of electrosurgical unit 410 is illustrated in perspective, front, and rear views. The electrosurgical unit 410 can be an integrated ESU as discussed above with respect to FIG. 1A, and can comprise a generator and a feedback circuit. In some embodiments, the housing or console of the electrosurgical unit 410 can be sized and configured to fit on a standard operating room cart or storage rack. In some embodiments, the housing or console of the electrosurgical unit 410 can be configured to be stackable with other surgical electrical equipment.

With reference to FIGS. 3A-3B, a perspective view of the electrosurgical unit 410 is illustrated. In the illustrated embodiment, the electrosurgical unit 410 comprises two dedicated tool ports 412, one bipolar tool port 414, and one electrical power port 416. In other embodiments, electrosurgical units can comprise different numbers of ports. For example, in some embodiments, an electrosurgical unit can comprise more or fewer than two dedicated teleports 412, more or fewer than one bipolar tool port 414, and more or fewer than one power port 416.

With continued reference to FIGS. 3A-3B, each dedicated tool port 412 is configured to be coupled to electrosurgical tool having a memory, as described above with respect to FIG. 1A. Thus the dedicated tool ports 412 can be electrically coupled to the feedback circuit of the electrosurgical unit 410 as well as the generator. In some embodiments, the dedicated tool ports 412 can comprise multi-pin connectors comprising a plurality of electrical connection pins or pin receptacles. In some embodiments, the connectors can comprise more than 10, for example 20 pins or pin receptacles. As discussed above with respect to FIG. 1A, and discussed in further detail below, the dedicated tool ports 412 can be configured for encrypted transmission and reception of data from an electrically coupled electrosurgical tool.

With continued reference to FIGS. 3A-3B, the bipolar tool port 414 can include a plug configured to receive a conventional bipolar electrosurgical tool. The bipolar tool port 414 can be coupled to the generator of the electrosurgical unit 410. In some embodiments, the bipolar tool port 414 is not coupled to the feedback circuit of the electrosurgical unit 410. Thus, advantageously, the electrosurgical unit 410 can energize both specialized electrosurgical tools, as described in further detail here and, conventional bipolar electrosurgical tools. Accordingly, the electrosurgical unit 410 can be used in place of a standalone bipolar electrosurgical generator without requiring additional rack or cart space in a surgical workspace.

With continued reference to FIGS. 3A-3B, the electrical power port 416 can be coupled to the generator of the electrosurgical unit 410. The electrical power port 416 can be configured to supply direct current. For example, in some embodiments, the electoral power port 416 can provide approximately 12 Volts DC. The electrical power port 416 can be configured to power a surgical accessory, such as a respirator, pump, light, or another surgical accessory. Thus, advantageously, in addition to replacing electrosurgical generator for standard bipolar tools, the electrosurgical unit 410 can also replace a surgical accessory power supply. In some embodiments, replacing presently-existing generators and power supplies with the electrosurgical unit 410 can reduce the amount of storage space required on storage racks cards or shelves in the number of mains power cords required in a surgical workspace.

With continued reference to FIGS. 3A-3B, the electrosurgical unit 410 can comprise a display 420. In some embodiments, the display can comprise a multi-line display capable of presenting text and graphical information such as for example an LCD panel display, which, in some embodiments can be illuminated via backlight or sidelight. In some embodiments, the display 420 can comprise a multi-color display that can be configured to display information about a particular tool electrically coupled to the electrosurgical unit 410 and a color that corresponds to a standard color associated with a surgical procedure (such as, for example cutting operations displayed in yellow text and graphics, fusion or welding operations displayed in purple, and coagulation displayed in blue, bloodless dissection operations can be displayed in yellow and blue). In some embodiments, as discussed in further detail below, the display can be configured to simultaneously indicate status data for a plurality of tools electrically coupled to the electrosurgical unit 410. In some embodiments, a user can toggle the display 420 between presenting status of multiple electrically connected tools and status of a single electrically connected tool. Further exemplary aspects of the display are discussed generally with respect to FIGS. 4A and 4B, and more specifically with respect to operation of the system below.

With continued reference to FIGS. 3A-3B, the electrosurgical unit can comprise a user interface such as, for example a plurality of buttons 422. The buttons 422 can allow user interaction with the electrosurgical unit such as, for example, requesting an increase or decrease in the electrical energy supplied to one or more tools coupled to the electrosurgical unit 410. In other embodiments, the display 420 can be a touch screen display thus integrating data display and user interface functionalities. In some embodiments, the electrosurgical unit 410 can comprise an audible indicator, such as a speaker or chime to alert a user of a possible error, the termination of electrical energy supplied, or other conditions. In some embodiments, the electrosurgical unit 410 can be configured such that the audible indicator can sound a particular sound during cutting operations, a different sound during fusion or welding operations, and another distinct sound during coagulation operations to provide audible feedback to a user.

With reference to FIG. 3C, a rearview of the electrosurgical unit 410 is illustrated. In the illustrated embodiment, the rear of the electrosurgical unit 410 includes a rear panel 430. The rear panel 430 can include various ports, such as a controller port 432 configured to be electrically coupled to an external controller such as a foot pedal controller, as described above with respect to FIG. 1A. The rear panel 430 can also include a grounding lug. In other embodiments, one or more controller ports and/or the grounding lug can be located on another face of the electrosurgical unit 410, for example on the front face or a side face. The rear face of the electrosurgical unit 410 can include a power module 440 including a mains power port configured to be plugged into an AC power mains such as a wall socket and a master power switch for powering the electrosurgical unit 410 on and off. In other embodiments, the master power switch can be positioned on another face of the electrosurgical unit 410, for example on the front face or a side face. The rear phase of the electrosurgical unit 410 can also include a heat exchange feature, such as, for example slots, a grill, or a plurality of louvers 450. In other embodiments, the heat exchange feature can be positioned on another face of the electrosurgical unit 410, for example on the front face or a side face. The heat exchange feature can enhance air or other fluid cooling of the generator, the feedback circuit, and other electrical components housed within the electrosurgical unit 410 console.

Figure 4A:
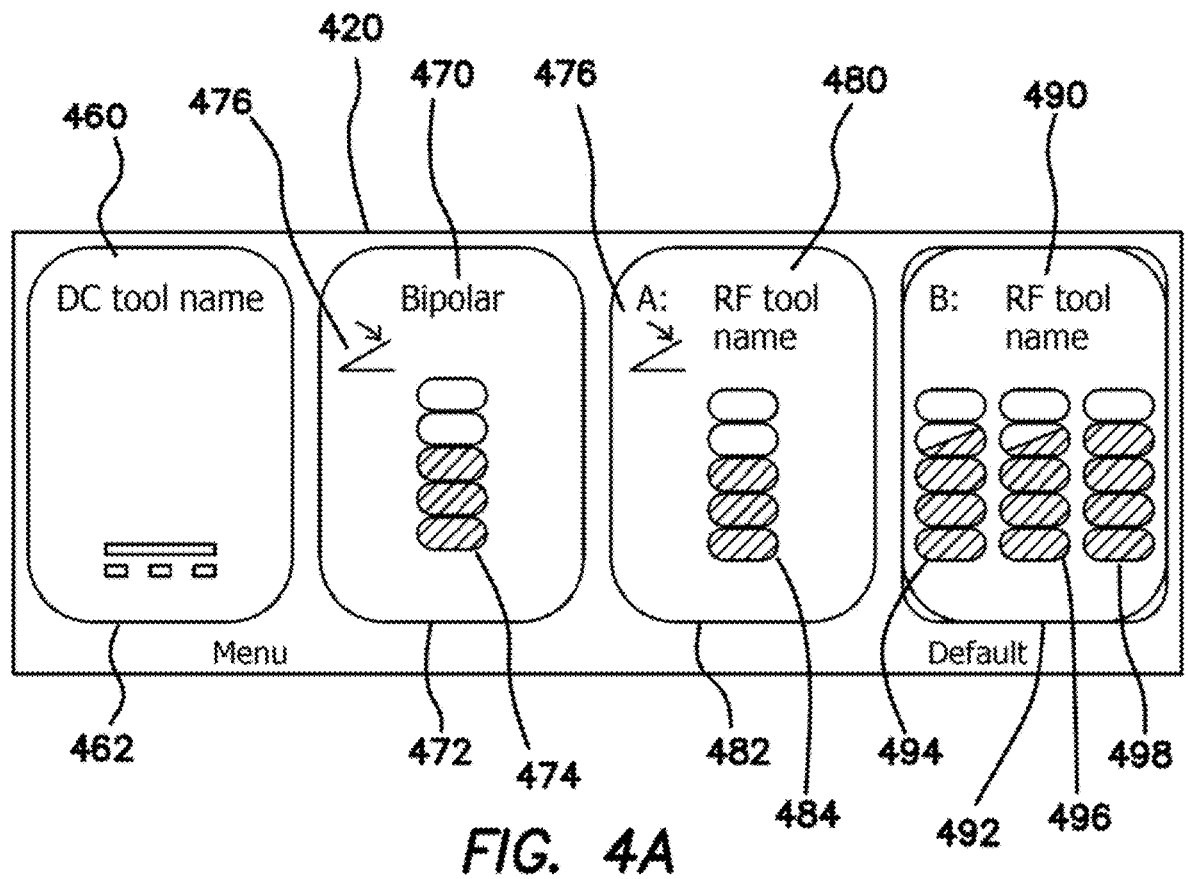
FIG. 4A is an exemplary screenshot of a display of the electrosurgical unit of FIG. 3A.

With reference to FIG. 4A, an exemplary screen shot of the display is illustrated. In the illustrated embodiment, the display 420 can be portioned to display status information for ADC tools 460, a bipolar tool 470, a first radiofrequency electrosurgical tool 480, and a second radiofrequency electrosurgical tool 490, corresponding to the four ports on the front panel of the electrosurgical unit 410 discussed above with respect to FIGS. 3A, 3B in the illustrated screenshot, a first section 462 displays information regarding the DC tool 460. A second section 472 displays information regarding the bipolar electrosurgical tool 470. A visual indicator such as a status bar graph 474 can be used to illustrate a proportion of total available electrical energy to be applied to the bipolar electrosurgical tool 470 when actuated. As discussed above, the visual indicator can be color-coded to indicate a surgical procedure to be performed. A third section 482 can display information regarding a first radiofrequency electrosurgical tool 480 with a visible indicator such as a status bar graph 484. A fourth section 492 can display information regarding a second radiofrequency electrosurgical tool 490 with separate visual indicators or bar graphs 494, 496, 498 for each type of surgical operation that can be performed for that tool. For example an electrosurgical tool operable to cut, coagulate, or fuse tissue could have three color-coded bar graphs. The display 420 can also include a controller icon, such as a foot pedal icon 476 positions in a section corresponding to a tool to which a foot pedal is electrically coupled.

Figure 4B:
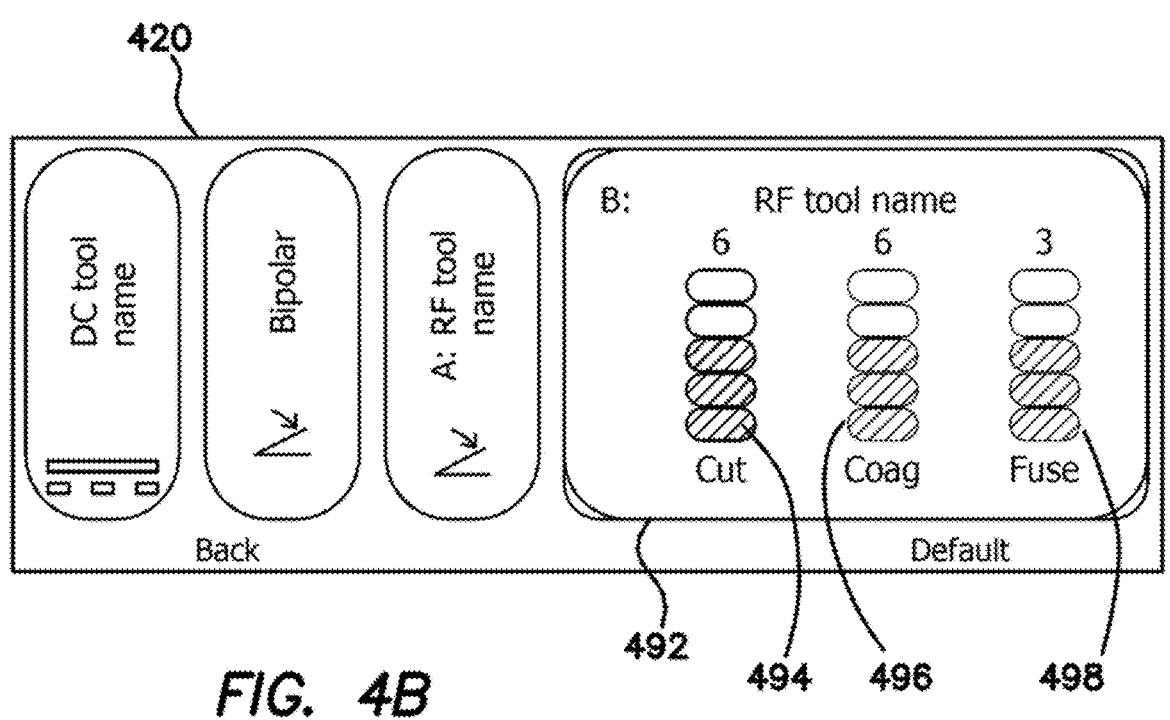
FIG. 4B is another exemplary screenshot of the display of the electrosurgical unit of FIG. 3A.

With reference to FIG. 4B, another exemplary screen shot of the display 420 is illustrated. It is illustrated, the display has been configured to maximize information presentation of the section 492 corresponding to the second of electrosurgical tool. As discussed above, in some embodiments electrosurgical unit can be configurable display status information regarding a single tool electrically coupled thereto. In some embodiments, the electrosurgical unit can allow user manipulation of energy levels applied to electrosurgical tool. In one configuration, energy levels for an electrosurgical tool can be adjusted proportionally for each type of electrosurgical procedure to be performed by the tool. For example, a user can increase or decrease a master energy level which correspondingly increases or decreases the energy levels supplied to you electrosurgical operation performed by the tool, which can be reflected in the bar graphs 494, 496, 498 on the display 420. In another configuration, energy levels for electrosurgical tool can be manipulated in a procedure-specific manner. For example, a user can increase or decrease in energy level corresponding to one of the electrosurgical procedures performed by specific electrosurgical tool while leaving energy levels for other electrosurgical procedures unchanged. This change can be reflected in one of the bar graphs on the display 420, for example, the cut bar graph 494.

Electrosurgical System Phase Angle Operation

Electrosurgical Unit

Generally, an electrosurgical unit is provided that includes an electrosurgical generator, an electrosurgical controller and one or more electrosurgical tool. The controller can be incorporated in or attached to the generator with the tool attached to the controller.

In one embodiment, a controller is attachable to various electrosurgical generators. The generator attached to the controller provides the supply of RF energy as directed by the controller. The controller provides feedback control and preprogrammed settings for the various attachable generators. This is largely enabled by using an internal measurement signal that is independent from the attached generator. In other words, regardless of the driving frequency of the drive signal the generator generates (which has an impact on the end point measurement, e.g., the phase shift), the measurement signal and hence the final phase shift remains the same.

Figure 5:
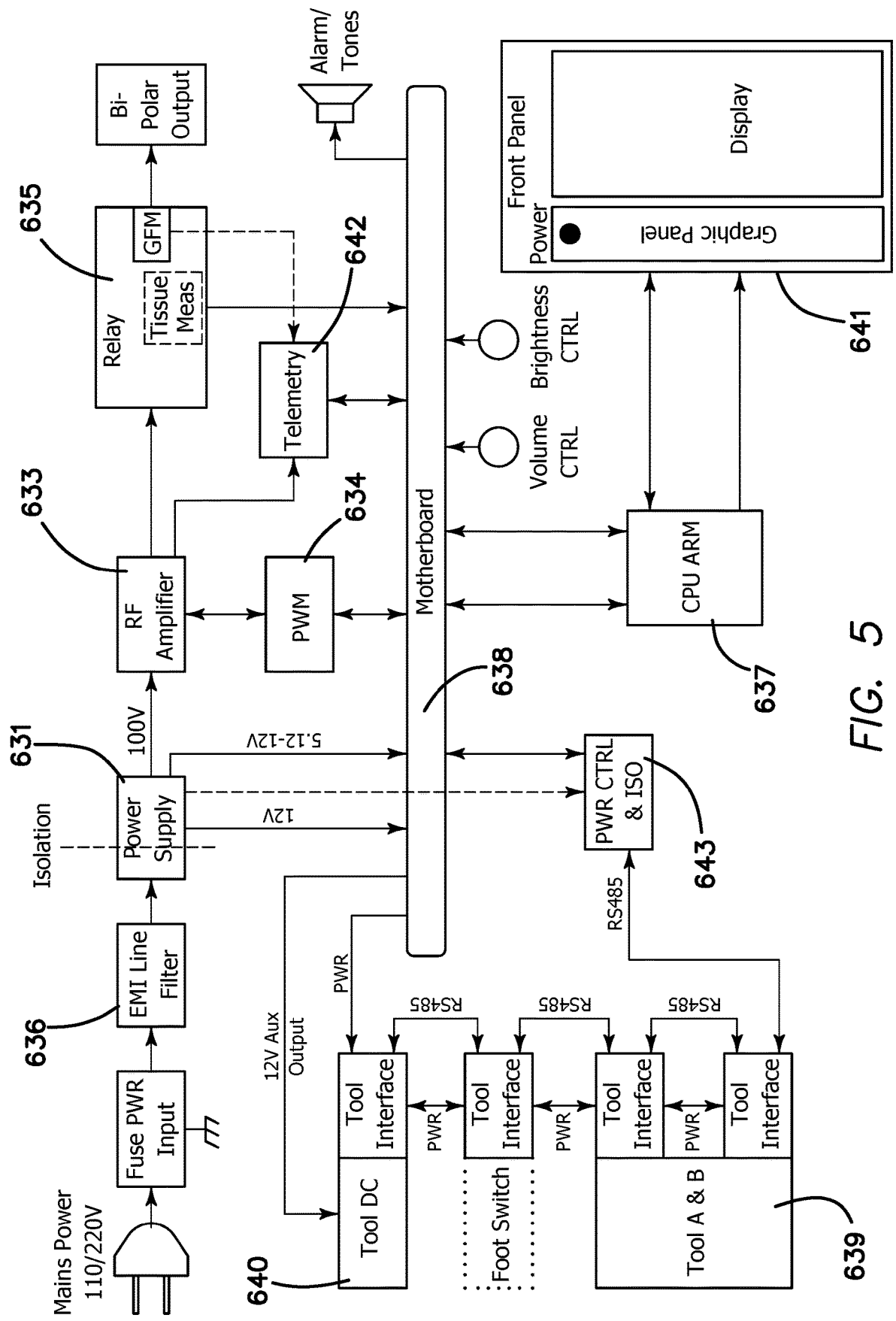
FIG. 5 is a block diagram of various embodiments of an electrosurgical unit.

Referring to FIG. 5, in one embodiment, an electrosurgical generator includes an RF amplifier, pulse width modulator (PWM) and relays. The electrosurgical generator is coupled to a 120 Hz Voltage main input. The main input is isolated with a low leakage isolation transformer of a power supply 631. The power supply provides operational voltages for the control processor 637 and the RF amplifier 633. Additionally, the power supply includes two 50 VDC output modules connected in series to provide a total output of 100 VDC and 8 Amps. RF power is generated by the RF amplifier, e.g., a switched mode low impedance RF generator that produces the RF output voltage. In one embodiment, a 600 peak cut voltage for cutting and 10 Amp current for coagulation/fusing is generated.

Fusing tissue in one embodiment involves applying RF current to a relatively large piece of tissue. Because of the potentially large tool contact area tissue impedance is very low. Accordingly, to deliver an effective amount of RF power, the current capability of the RF amplifier is large. As such, where a typical generator might be capable of 2 to 3 amps of current, the RF amplifier of the generator can supply more than 5 Amps RMS into low impedance loads. This results in rapid tissue fusion with minimal damage to adjacent tissue.

The RF amplifier circuitry has redundant voltage and current monitoring. One set of voltage and current sensors are connected to the PWM circuitry and are used for servo control. The voltage and current can also be read by the processor 637 using an analog to digital converter (ADC) located on the PWM circuitry. The PWM circuitry also has an analog multiplier, which calculates power by computing the product of the voltage and current. The PWM circuitry uses the average value of voltage and current and does not include a phase angle and thus is actually calculating Volt Amps Reactive (VAR) rather than actual power. A second set of voltage and current sensors are also connected to the Telemetry circuitry 642. The signals are connected to an ADC for redundant monitoring of the voltage and current. The processor multiplies the voltage and current readings to verity that power output does not exceed 400 Watts. The Telemetry circuitry has monitoring circuits that are completely independent of the PWM circuitry. This includes the ADC, which has an independent voltage reference.

The RF amplifier in one embodiment is a switching class D push pull circuitry. As such, the amplifier can generate large RF voltages into a high tissue impedance, as well as large RF currents into low tissue impedance. The output level of the RF amplifier is controlled by Pulse Width Modulation (PWM). This high voltage PWM output signal is turned into a sine wave by a low pass filter on the RF amplifier. The output of the filter is the coagulation output of the RF amplifier. The output is also stepped up in voltage by an output transformer resulting in the cut output of the RF amplifier. Only one output is connected to the control servo on the PWM circuitry at a time and only one output is selected for use at a time.

Coupled to the RF amplifier is the PWM circuitry 634. The PWM 634 in one embodiment receives voltage and current set points, which are input by the user through a user interface, to set the output level of the RF amplifier. The user sets points are translated into the operating levels by digital to analog converters of the PWM. The user sets points are translated into the operating levels by digital to analog converters of the PWM. The set points in one embodiment include a maximum voltage output, maximum current output, maximum power output, and a phase stop. The servo circuit of the PWM circuitry controls the RF output based on the three set points. The servo circuit as such controls the output voltage of the RF amplifier so that the voltage, current, and power set points are not exceeded. For example, the output of the ESG is restricted to be less than 400 watts. The individual voltage and current set point can be set to exceed 400 watts depending on the tissue impedance. The power servo however limits the power output to less than 400 watts.

The RF output voltage and current are regulated by a feedback control system. The output voltage and current are compared to set point values and the output voltage is adjusted to maintain the commanded output. The RF output is limited to 400 Watts. Two tool connections are supported by using relays 635 to multiplex the RF output and control signals. The EMI line filter 636 limits the RF leakage current by the use of an RF isolation transformer and coupling capacitors.

The cut and coagulation output voltages of the RF amplifier are connected to the relay circuitry 635. The relay circuitry in one embodiment contains a relay matrix, which steers the RF amplifiers output to one of the three output ports of the electrosurgical unit. The relay matrix also selects the configuration of the tool electrodes. The RF output is always switched off before relays are switched to prevent damage to the relay contacts. To mitigate against stuck relays steering RF to an idle output port each output port has a leakage current sensor. The sensor looks for unbalanced RF currents, such as a current leaving one tool port and returning through another tool port. The current sensors on are located on the Relay PCB, and the detectors and ADC are on the Telemetry PCB. The CPU monitors the ADC for leakage currents. Any fault detected results in an alarm condition that turns off RF power.

The relay circuitry also contains a low voltage network analyzer circuit used to measure tool impedance before RF power is turned on. The circuit measures impedance and tissue phase angle. The processor 637 uses the impedance measurement to see if the tool is short-circuited. If a Tool A or B output is shorted the system warns the user and will not turn on RF power. The RF amplifier is fully protected against short circuits. Depending on the servo settings the system can operate normally into a short circuit, and not cause a fault condition.

Voltage and current feedback is provided using isolation transformers to insure low leakage current. The control processor 637 computes the power output of the RF amplifier and compares it to the power set point, which in one embodiment is input by the user. The processor also monitors the phase lag or difference between current and voltage. Additionally, in one embodiment, the processor matches the different phase settings, which depend on tissue types to the monitored phase difference. The processor as such measures a phase shift of tissue prior to any application of RF energy. As will be described in greater detail below, the phase measurement is proportional to tissue permeability and conductivity that uniquely identifies the tissue type. Once the tissue type is identified, the phase angle associated with an end point determination of that tissue type can be determined. The generator in one embodiment has three RF output ports (Tool A, Tool B and generic bipolar). The tool A and B ports 639 are used to connect smart tools, while the generic bipolar port 640 supports standard electro surgical tools. Audible tones are produced when the RF output is active or an alarm condition exists.

The hand and foot controls are also isolated to limit leakage current. The control processor checks the inputs for valid selections before enabling the RF output. When two control inputs from the switches are simultaneously activated the RF output is turned off and an alarm is generated. Digital to analog converters are used to translate control outputs into signals useable by the Analog Servo Control. The control set points are output voltage and current. The analog to digital converter is used to process the analog phase angle measurement. Voltage RMS, current RMS, and power RMS information from the controller is also converted into a form usable for presentation to the user. The digital I/O bus interface 638 provides digital communication between the user, controller and hand/foot switches. Isolation circuitry is used to eliminate a possible leakage path from the electrosurgical generator. It also provides communication between the user and the generator though a data channel protocol.

In one embodiment, there are four tool Interface circuits in the unit. These circuits are used to electrically isolate the user input switches from mains power inside the system. The four tool interface circuits are identical and have an on board microprocessor to read the user switch inputs as well as the tool crypto memory and script memories. The switch closure resistance is measured with an ADC to eliminate a contaminated switch contact being read as a closure. Switch closures below 300 Ohms are valid, while any reading above 1000 Ohms is open. Readings between 300 and 1000 Ohms are considered to be faulty inputs.

The four tool interface circuits communicate with the processor using an RS485 network. Each tool interface circuit has jumpers to select its address and location in the unit. The RS485 interface is isolated to eliminate any potential leakage current paths. One tool interface circuit is connected to each of the Tool A and B ports. A third tool interface circuit is connected to the DC output port, and the fourth circuit is connected to the rear panel foot switch inputs. The processor is the network master and each of the four circuits is a network slave. The processor polls each circuit for input. The tool interface circuitry can only reply to commands. This makes the network deterministic and prevents any kind of dead lock. Each Tool Interface circuit is connected to a System OK logic signal. If a system error is detected by a Tool Interface circuit, this signal is asserted. The processor monitors this signal and indicates a fault. This signal also has a hardware connection to the PWM circuit and will disable the RF amplifier when asserted. A system error could be two input switches activated at the same time, or a loss of communication with the processor. The Tool A & B ports as well as the DC port have a micro switch that detects when a tool is plugged into the receptacle. Until this switch is depressed the Tool Interface circuit front panel connections are configured off to prevent any leakage current flowing from front panel connections. Once the switch is depressed the Tool Interface allows the processor to initiate reads and writes to the tool crypto memory and script memory. Once a tool is detected a window opens in the user interface display showing the type of tool connected and status. The generic bipolar port supports legacy tools, which do not have any configuration memory. The tissue measurement circuitry is used to monitor the bipolar connection contacts. When a bipolar tool is connected the tool capacitance is detected and the processor opens the bipolar tool window on the user interface display and shows status for the bipolar tool. The DC port is used to interface with 12 Volt DC powered custom surgical tools. When a tool is plugged into this port a window opens in the user interface display showing the type of tool connected and status. When the DC tool script commands power on, the processor closes a relay on the Power Control and Isolation circuitry 643 turning on the isolated 12 Volt tool power.

The power control and isolation circuitry 643 has two other features. It controls the 100 Volt power supply that drives the RF amplifier. This power supply is turned on by a relay controlled from the PWM circuitry. The processor commands this power supply on via the PWM circuitry. If the PWM circuitry is reset or detects a fault condition, the relay will not operate leaving the 100 Volt power supply off. Also located on the power control and isolation circuitry is a RS485 isolation circuit that adds an extra layer of isolation.

The front panel interface circuitry 641 is used to connect the front panel control switches and LCD display to the processor. The front panel interface circuitry also contains a microprocessor, which is powered by an isolated standby power supply, which is on whenever the main power switch is on. When the front panel power switch is pressed, the microprocessor uses a relay on the Power Control and Isolation circuitry to turn on the main logic power supply. When the button is pressed to turn power off, the microprocessor signals a power off request to the processor. When the processor is ready for power to be turned off it signals the microprocessor to turn off power. The power control relay is then opened, turning off the main power supply.

In one embodiment, the generator accepts only single switch input commands. With no RF active, e.g., RF energy applied, multiple switch closures, either from a footswitch, tool, or a combination of footswitch and tool are ignored. With RF active, dual closures shall cause an alarm and RF shall be terminated. The footswitch in one embodiment includes momentary switches providing activation of the application of RF energy. The switches for example when manipulated initiates activation of the RF energy for coagulation, for cutting and/or sequenced coagulation or cutting. A two-position pushbutton on the foot pedal switch allows toggling between different tools. The active port is indicated on the display of the generator and an LED on the hand tool.

In one embodiment, all RF activation results in a RF ON Tone. Activation tone volume is adjustable, between 40 dBA (minimum) and 65 dB (maximum) with a rear panel mounted control knob. The volume control however does not affect audio volume for alarms. Also, in one embodiment, a universal input power supply is coupled to the generator and operates over the input voltage and frequency range without the use of switches or settings. A programming port in one embodiment is used to download code to the generator and is used to upload operational data.

The generator in one embodiment provides output power has a 12V DC at 3 Amps. Examples of such tools that use DC power are, but are not limited to, a suction/irrigation pump, stapler, and a morcellator (tool for dividing into small pieces and removing, such as a tumor, etc.). The DC connector has intuitive one-way connection. Similar to the other tool receptacles, a non-sterile electronic chip module is imparted into the connector of the appropriate DC-powered hand tool by a one-time, one-way locking mechanism. Tool-specific engravings on both the connector and chip module ensure that the chip module fits only to the type of tool for which it has been programmed. The chip connector allows tool recognition and the storage of data on tool utilization. The DC connector is also configured to prevent improper insertion. The generator is also configured to recognize the attached DC-powered tool. The generator reads configuration data from the tool connector, allowing tool recognition and the storage of tool utilization data.

The controller in one embodiment recognizes the tool upon the tool being attached to the controller. Based on the recognized tool, the generator accesses and initiates specific operations and setting parameters utilized to configure the controller to properly apply RF energy as desired by the tool. For example, parameters set includes but not limited to an automatic preset of the output voltage, activation of specific output pins (connected to tool) or determination of the feedback cycle.

In one embodiment, the controller supplies control signals and/or power to a connected tool to indicate when they are active via a LED and/or a distinctive audio tone. The controller is also arranged to display when and/or which specific tool is active. The controller also prevents the tool from being reused after certain expiration of the tool shelf life, or a specific time period after the first tool activation.

In one embodiment, phase measurement is a relative measurement between two sinusoidal signals. One signal is used as a reference, and the phase shift is measured relative to that reference. Since the signals are time varying, the measurement cannot be done instantaneously. The signals must be monitored long enough so that difference between them can be determined. Typically the time difference between two know points (sine wave cross through zero) are measured to determine the phase angle. In the case of the phase controller, the device makes the output sine wave with a precise crystal controlled clock. That exact same clock is use to read the input samples with the analog to digital converter. In this way the output of the phased controller is exactly in phase with the input of the phase controller. The phase controller in one embodiment compares the input sine wave signal to a reference sine wave to determine the amount of phase shift.

The phase controller does this comparison using a mathematical process known as a Discreet Fourier Transform (DFT). In this particular case 1024 samples of the input signal are correlated point by point with both a sine function, and a cosine function. By convention the cosine part is called real, and the sine part is called imaginary. If the input signal has no phase shift the result of the DFT is 100% real. If the input signal has a 90-degree phase shift the result of the DFT is 100% imaginary. If the result of the DFT has both a real and imaginary component, the phase angle can be calculated as the arctangent of ratio of the imaginary and real values.

It should be appreciated that the phase angle calculation is independent of units of the real and imaginary numbers. Only the ratio matters. The phase results of the phase controller are also independent of gain and no calculation of impedance is made in the process of calculating the phase angle. By performing a DFT, the phase controller encodes the phase measurement as a pair of numbers.

A user interacts with the electrosurgical unit via a graphical panel display and associated switches 641. The front panel switches allow interaction with LCD display menus generated on the graphical panel display. The menus allow language selection, and modification of tool set points. In one embodiment, only when a tool is plugged in and detected by the unit, parameters can be changed for that tool.

The electrosurgical unit as described above includes one or more receptacles in which electrosurgical tools connect to the unit. Through this connection, a tool and unit communicate with each other. Connecting the tool also causes the controller to update the display of the system to show tool information and current intensity.

Figure 6:
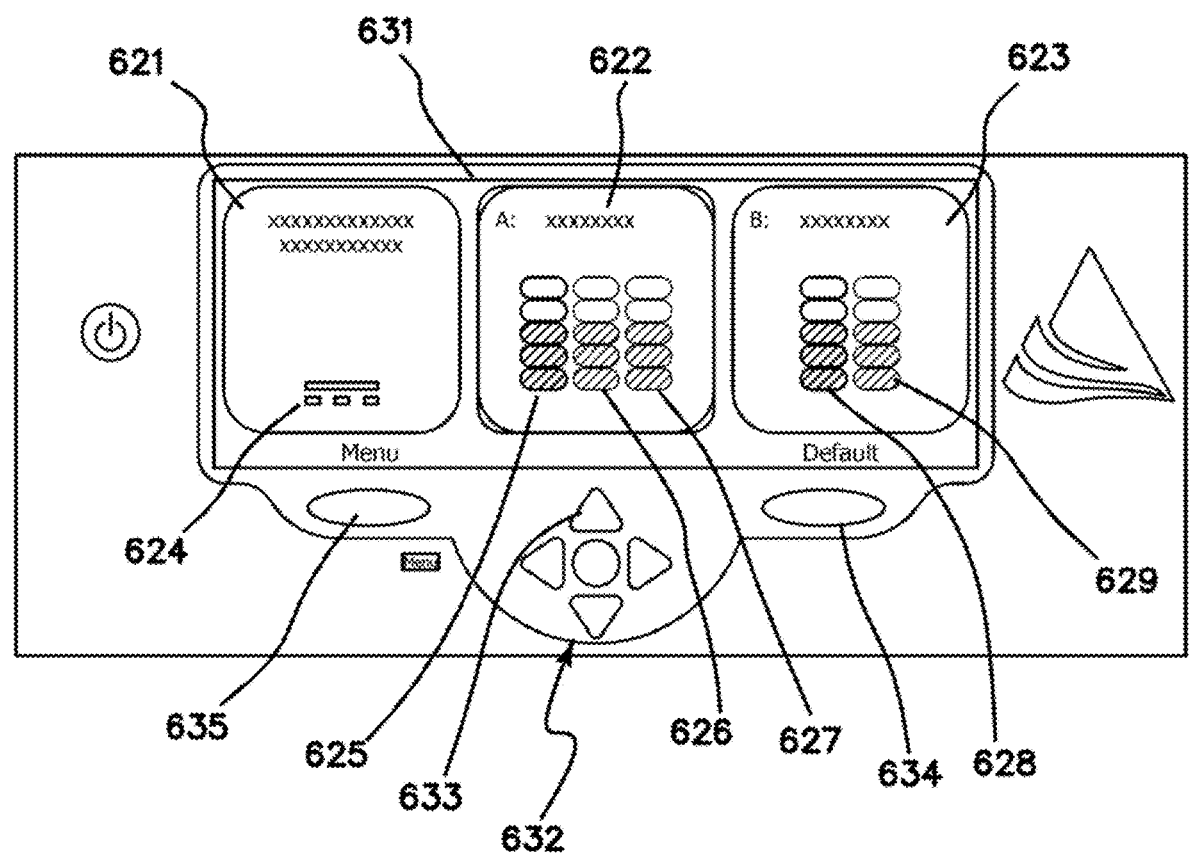
FIG. 6 is a front view of a user interface of an electrosurgical unit.

An example of a display or user interface 641 is shown in FIG. 6. The user interface provides tool information such as tool status for each connected tool and allows a user to modify set points, e.g., the application or intensity of the RF energy. The user interface in one embodiment also shows the tool settings for functions for each connected tool. In the illustrated embodiment, three tools are connected to the generator. Accordingly, a suction/irrigation pump display 621, a Kii fusion tool display 622 and a spatula tool display 623 are shown. Associated operations or actions available for each tool are also provided in which the suction/irrigation pump has an on/off setting 624; the Kii fusion tool has relative power settings for cut 625, coagulation 626 and fuse 627; and the spatula tool has relative power settings for cut 628 and coagulation 629.

Figure 7:
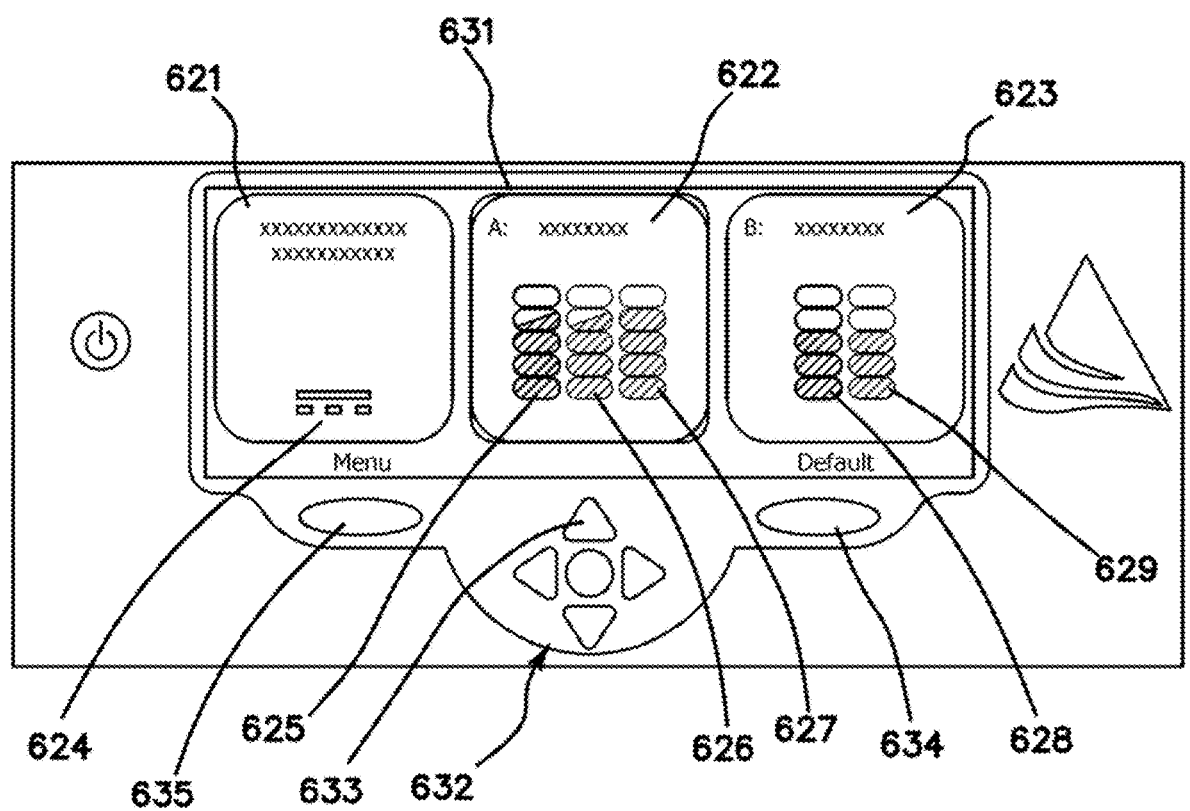
FIG. 7 is a front view of a user interface of an electrosurgical unit.
Figure 8:
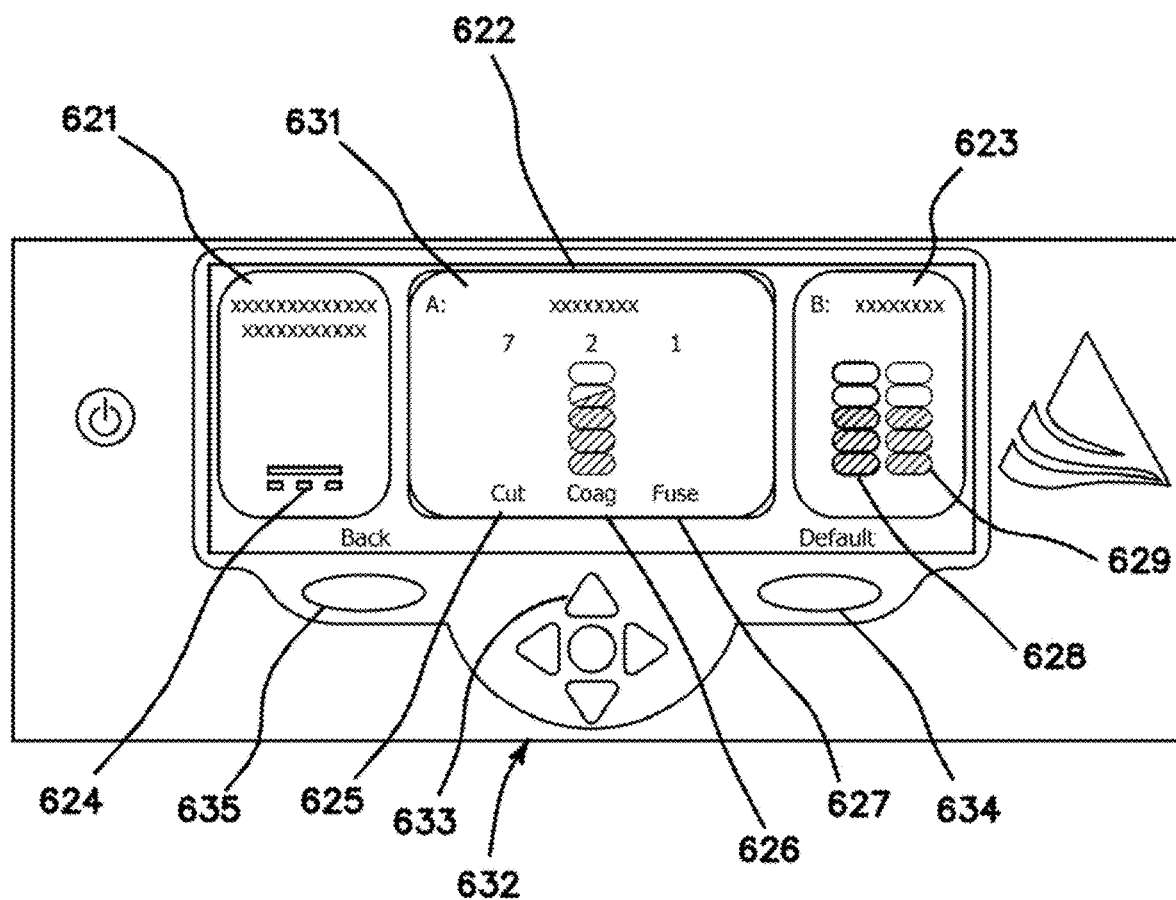
FIG. 8 is a front view of a user interface of an electrosurgical unit.

In one embodiment, the user interface allows a simultaneous change to all settings for a selected tool (indicated by the highlighted rim 631) by pushing single button from the navigation buttons 632. For example, as shown in FIG. 7, pushing the "up" button 633 will simultaneously change the cut, coagulation and fuse relative power settings for the connected Kii fusion tool. Additionally, the settings can be changed individually by navigating into a sub menu, as shown in FIG. 8. In the illustrated case, the coagulation level of the Kii fusion tool is changed without changing the cut and/or fuse relative power setting. By selecting the default button 634, the settings for all tool functions of the selected tool are returned to the default setting. Also, as warranted by the context, an associated button operation and corresponding label can vary as shown in button 635 being a menu button in FIG. 7 and a back button in FIG. 8.

Figure 9:
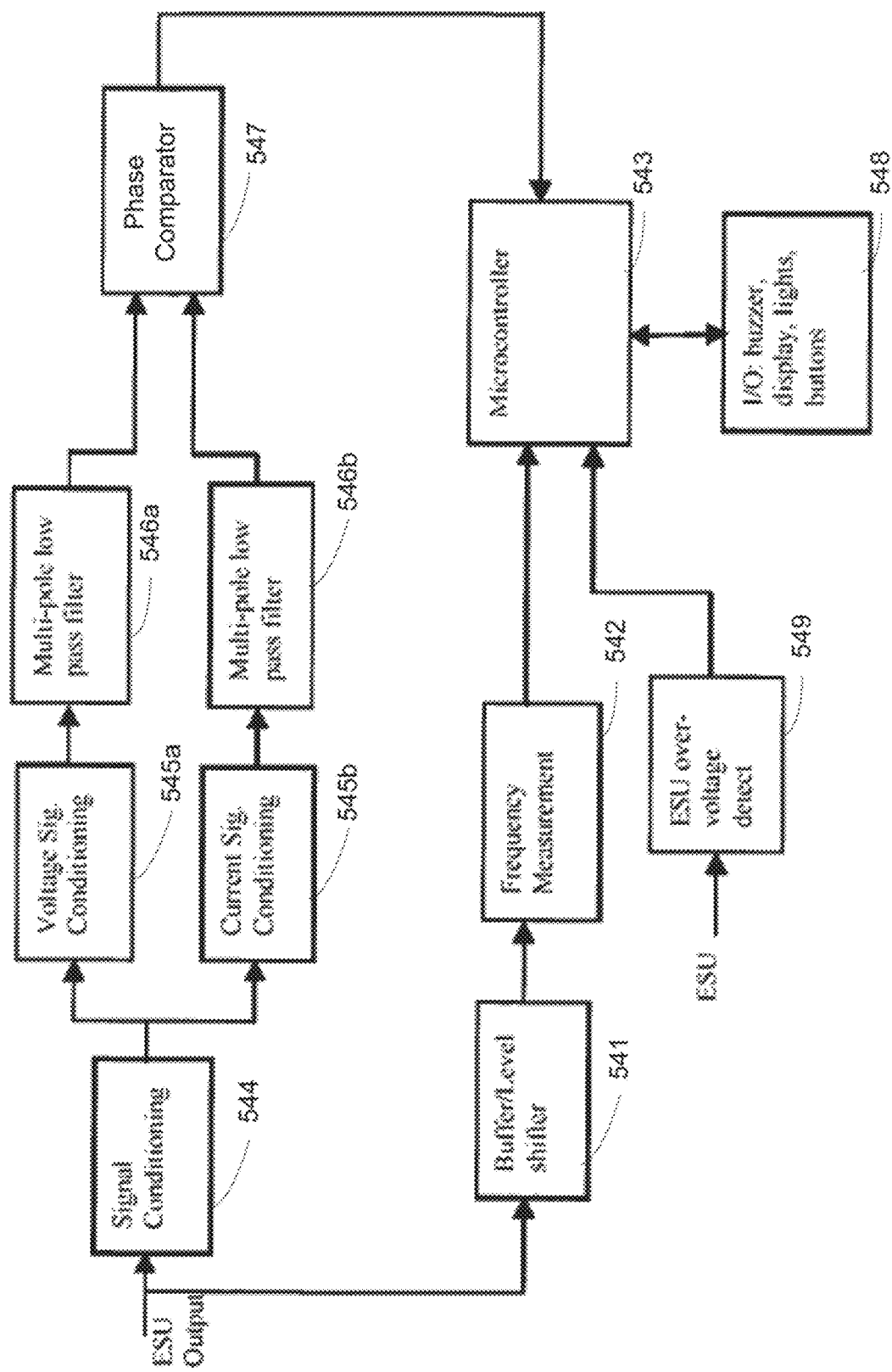
FIG. 9 is a block diagram of an electrosurgical unit.

A block diagram illustrating a controller in accordance with various aspects of the invention is shown in FIG. 9. As shown, the output of a generator is fed into circuitry that determines the frequency of the driving signal and circuitry to measure the phase shift between voltage and current applied to the tissue. The voltage applied by the generator is sent through a buffer/level shifter 541 that reduces the amplitude of the output voltage. The signal is processed to deliver the frequency of the generator output via frequency measurement 542 and fed into a microcontroller 543. The frequency of the driving signal can directly impact the phase shift. Similarly, the generator output is sent through a signal conditioning circuitry 544 to reduce high-frequency noise, and then conditioned via voltage and current conditioning 545*a-b* and filtered by multi-pole low pass filter 546*a-b* to deliver signals to represent applied voltage and current. Both signals representing voltage and current are measured for phase shift using a phase comparator 547. The output of the phase comparator is fed into the microcontroller 543. Depending on the frequency of the electrosurgical unit used, which can determine the final phase shift to be reached, the microcontroller compares the output of the phase comparator with the trigger level determined by the driving frequency of the generator. When such trigger level is achieved, i.e., the tissue fusion or welding is completed, the microcontroller 543 causes the tissue to be disconnected from the generator and indicates that state by acoustical or visual indicators 548 (buzzer, display, lights, etc.). An over-voltage detector 549 is also provided that is supplied the generator output to detect excessive voltage the condition of which is supplied to the microcontroller 543.

Figure 10:
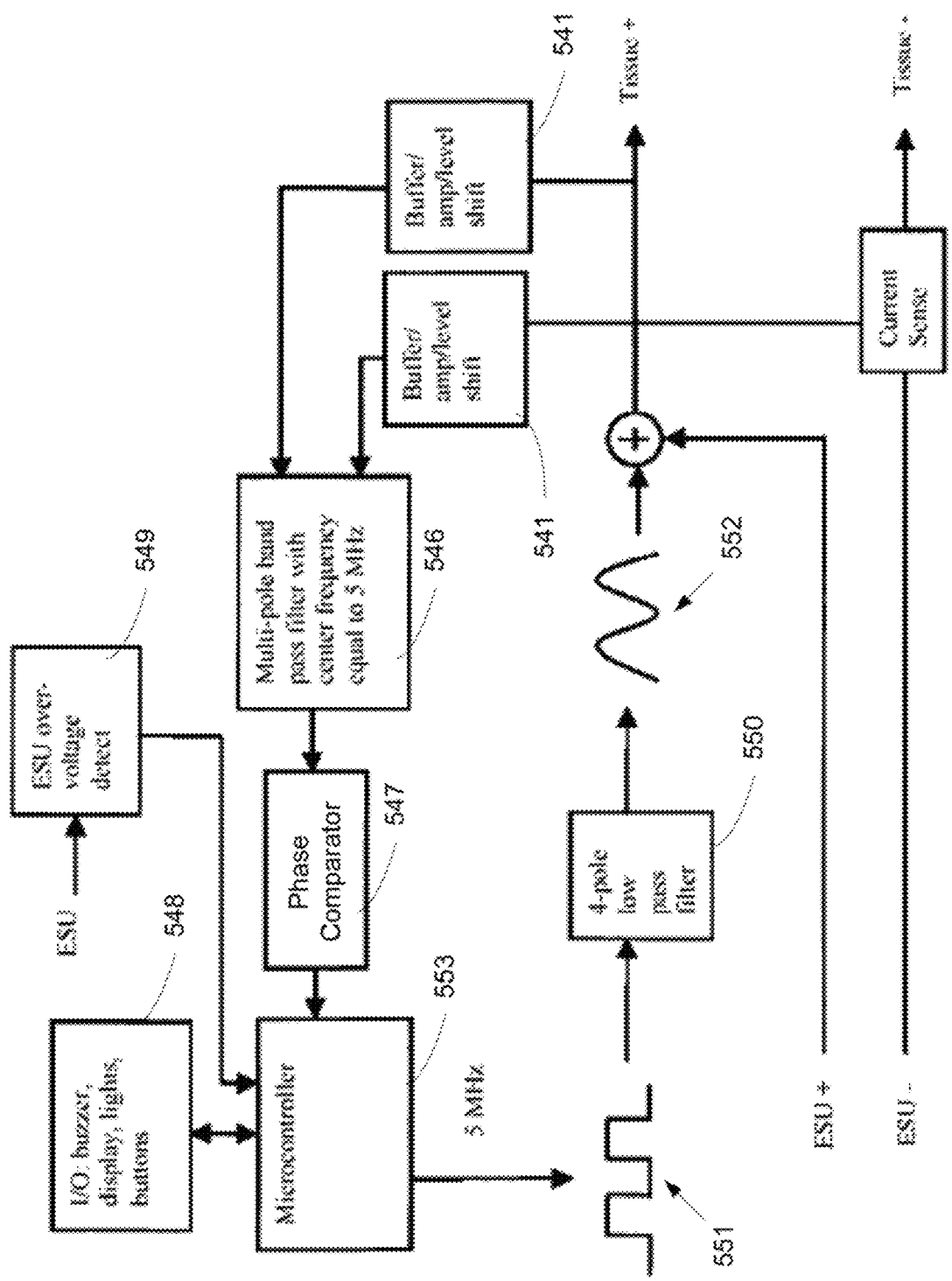
FIG. 10 is a block diagram of an electrosurgical unit.
Figure 11:
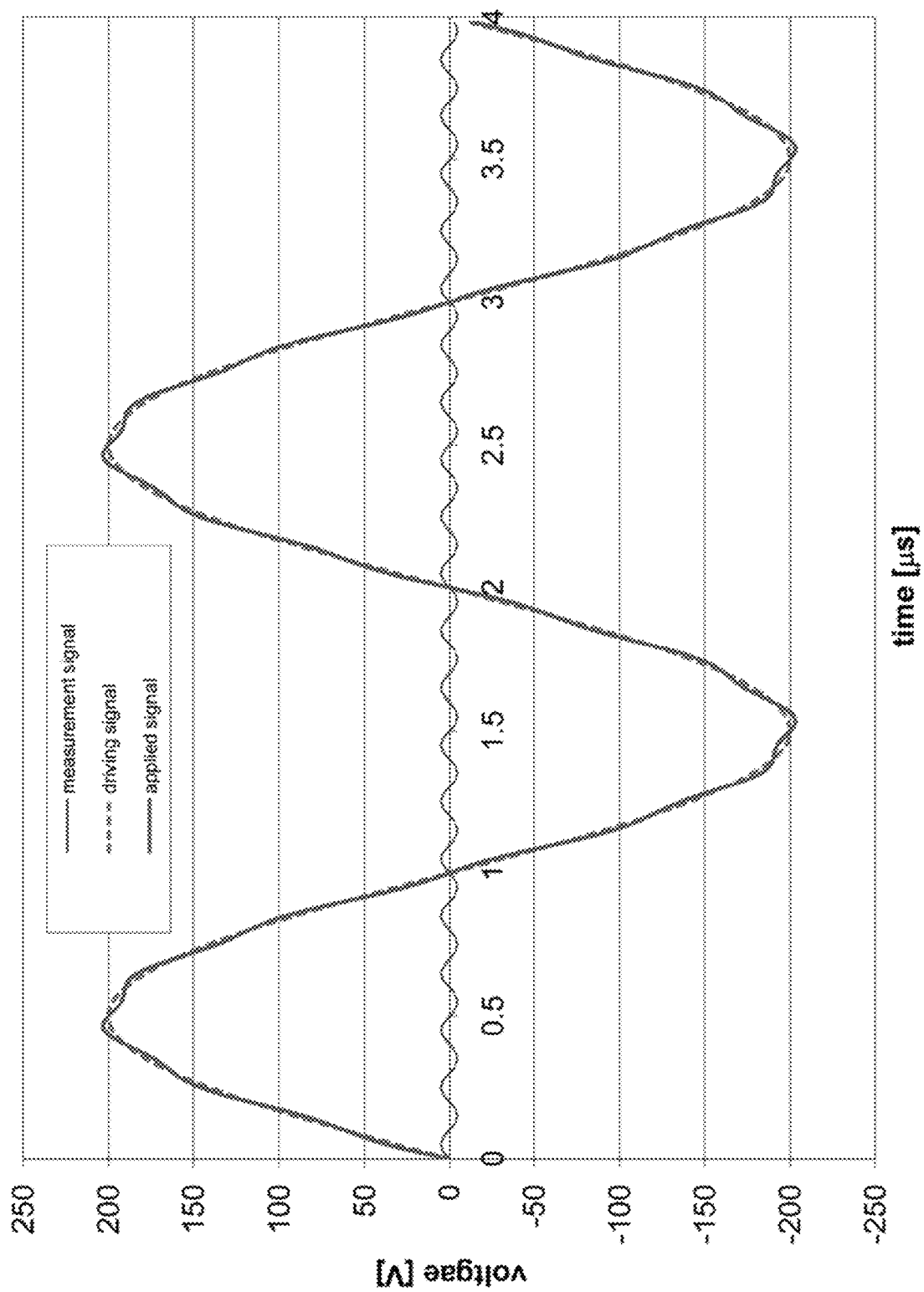
FIG. 11 is a graphical representation of a high voltage driving signal at low frequency relative to a low voltage measurement voltage at a high frequency.

FIG. 10 shows a block diagram of a controller in accordance with various embodiments of electrosurgical unit utilizing the phase shift between voltage and current to determine the end-point of the fusion process. A microcontroller 553 delivers a low-voltage square-wave signal 551 at 5 MHz, which is converted by a 4-pole low pass filter 550 into a low-voltage sin-wave signal 552 at 5 MHz. The low-voltage 5 MHz signal is superimposed to the output of the generator, which is typically in the 100 to 200V range at frequencies of 300 to 500 kHz. As an example, the superimposed voltage signal of a 200V driving voltage at 500 kHz and a 5V measurement voltage at 5 MHz is shown in FIG. 11.

Figure 12:
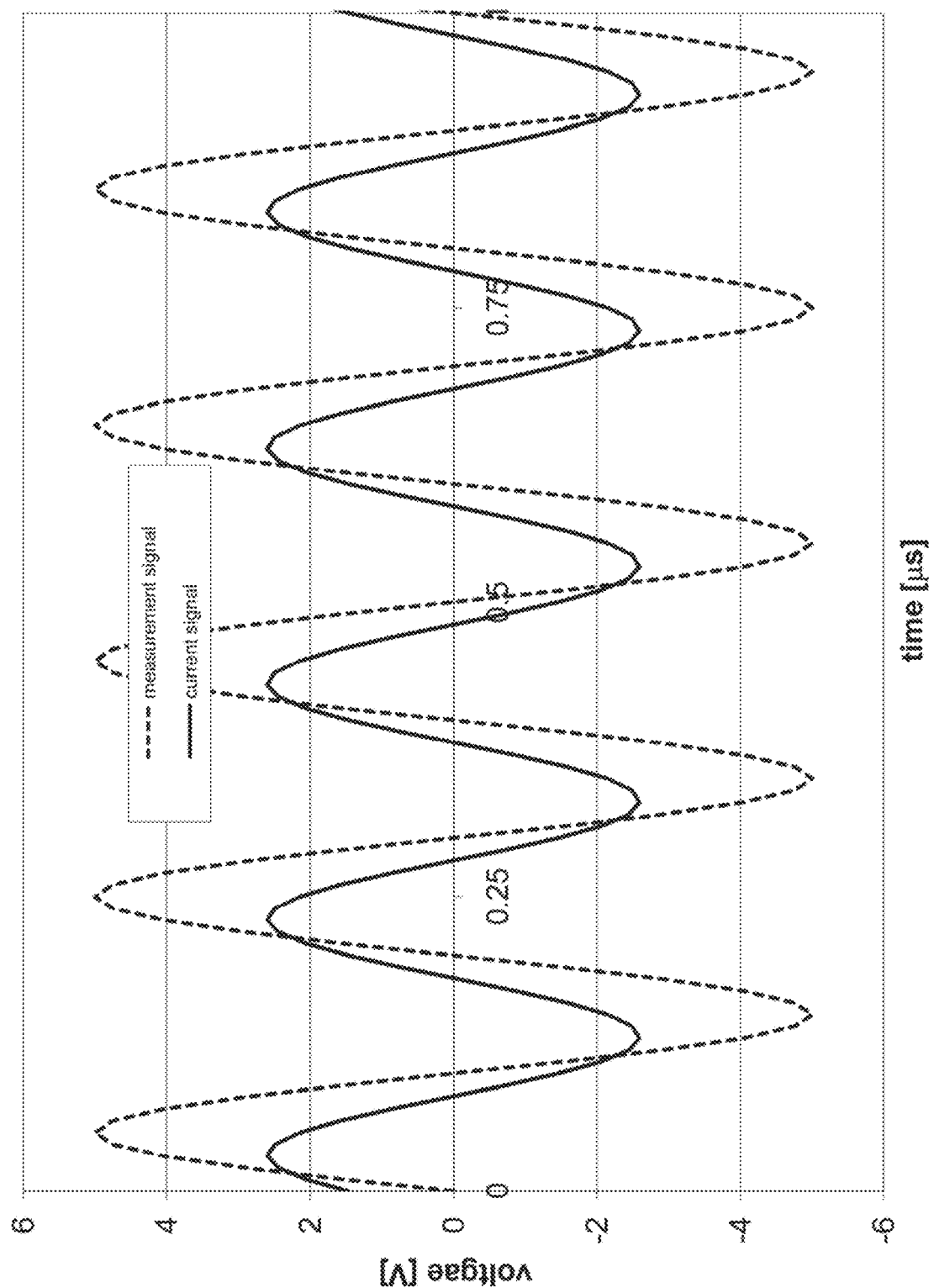
FIG. 12 is a graphical representation of filtered measurement and current signals for a time near the end of the fusion process.

The combined voltages are then applied to the tissue and, just as in the previous example, also conditioned through a buffer/level shifter circuitry for processing. Similarly, the current through the tissue is measured and also conditioned for processing. The processed voltage (and current) signal containing the high voltage (and high current) signal at 300 to 500 kHz from the ESU, as well as low voltage (low current) signal at 5 MHz are sent through a multi-pole band pass filter centering at 5 MHz. The filter discriminates the signal from the ESU, leaving only the two signals at 5 MHz for measuring the phase shift in a phase comparator. The filtered signals for both the voltage and current at 5 MHz are illustrated in FIG. 12 at a time near the end of the fusion process.

The measured phase shift is fed into a microcontroller, which compares the reading with a pre-determined level indicative to the completion of the fusion process at 5 MHz frequency. Again, when such a trigger level is achieved, i.e., the tissue fusion or welding is completed, the microcontroller 553 will cause the tissue to be discontinued from the generator and indicate that state by acoustical or visual indicator 548 (buzzer, display, lights, etc.).

Figure 13:
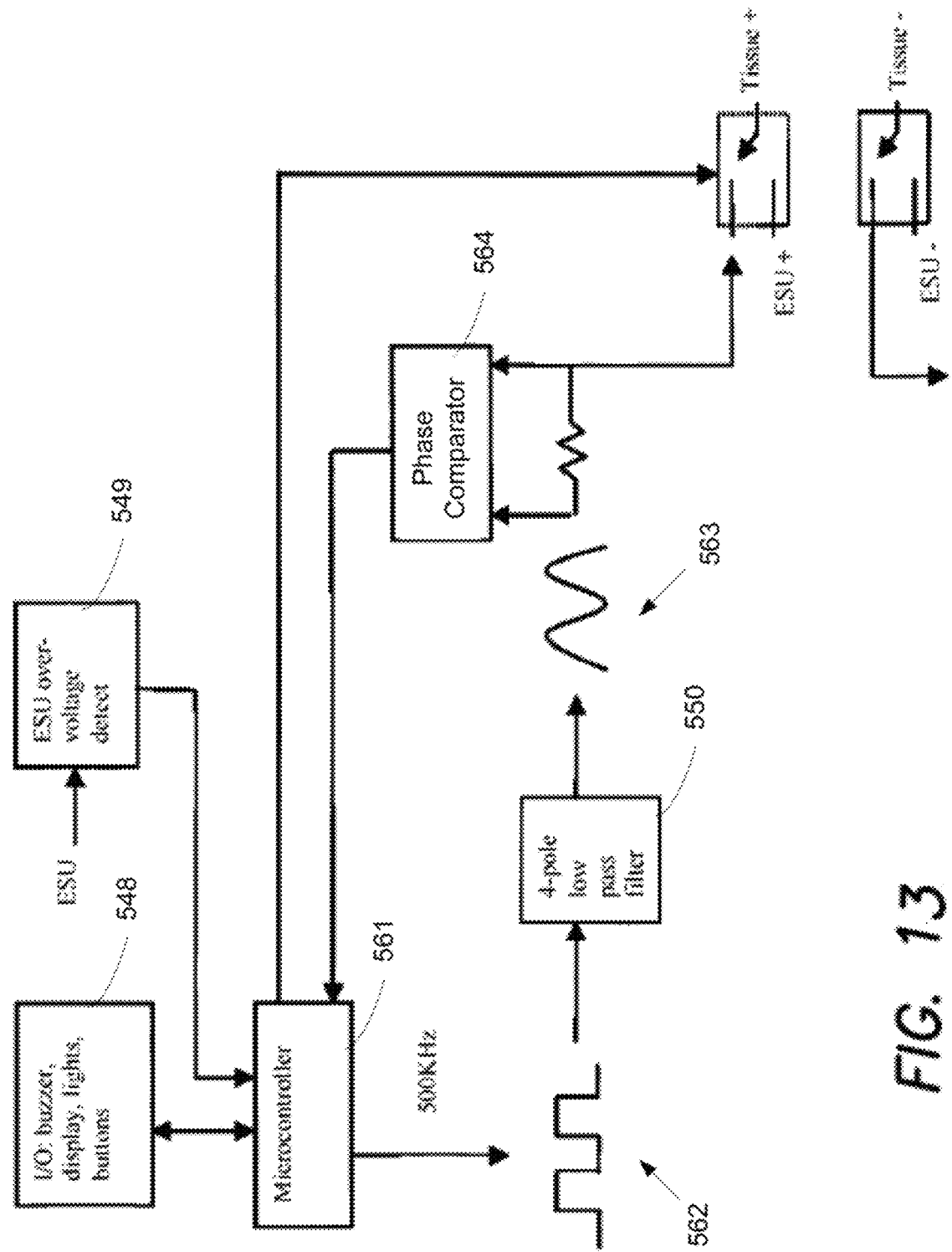
FIG. 13 is a block diagram of an electrosurgical unit.

FIG. 13 shows a schematic block diagram of one aspect of a controller. As shown, a microprocessor 561 times the switching of the tissue between the output of a generator and an internal measurement circuit. As a result, the tissue is periodically assessed for the status of the fusion process by measuring the phase shift of a low-voltage and low-current measurement signal. Depending on the value of the obtained phase shift, the tissue is either switched back to the high-voltage output of the generator for further fusion, or permanently disconnected from the generator. As such, the internal circuit comprises of a microprocessor 561 generating a low-voltage square wave signal 562 at 500 kHz that is transferred into a low-voltage sinusoidal wave 563 at 500 kHz. This signal is applied to the tissue, and analyzed by a phase comparator 564 only when it electrically disconnected from the generator during regular measurement intervals.

In one embodiment, the phase shift is derived directly from the driving signal, i.e., the voltage and current supplied by the electrosurgical generator to the tissue. In one embodiment, an electrical circuit modifies the driving voltage having one (sinusoidal) frequency by superimposing a measurement signal at a vastly different frequency. As a result, electrical energy for the fusion process is provided at one frequency, while simultaneously applying as second signal at a second frequency for measurement. Separation of the two different signals by using band pass filters in the measurement circuit allows continuous measurement of the phase shift during the electrosurgical fusion or welding process. In one embodiment, the controller periodically interrupts the supply of electrosurgical energy to assess the status of the fusion or welding process by applying a low-voltage measurement signal. Depending on the phase shift obtained during the measurement cycle, the controller switches the driving signal from the generator back to the tissue or isolates the tissue. In one embodiment, the controller interrupts the tissue fusion or welding process at a pre-determined level of phase shift by terminating the supply of RF energy from the generator to the tissue.

Figure 14:
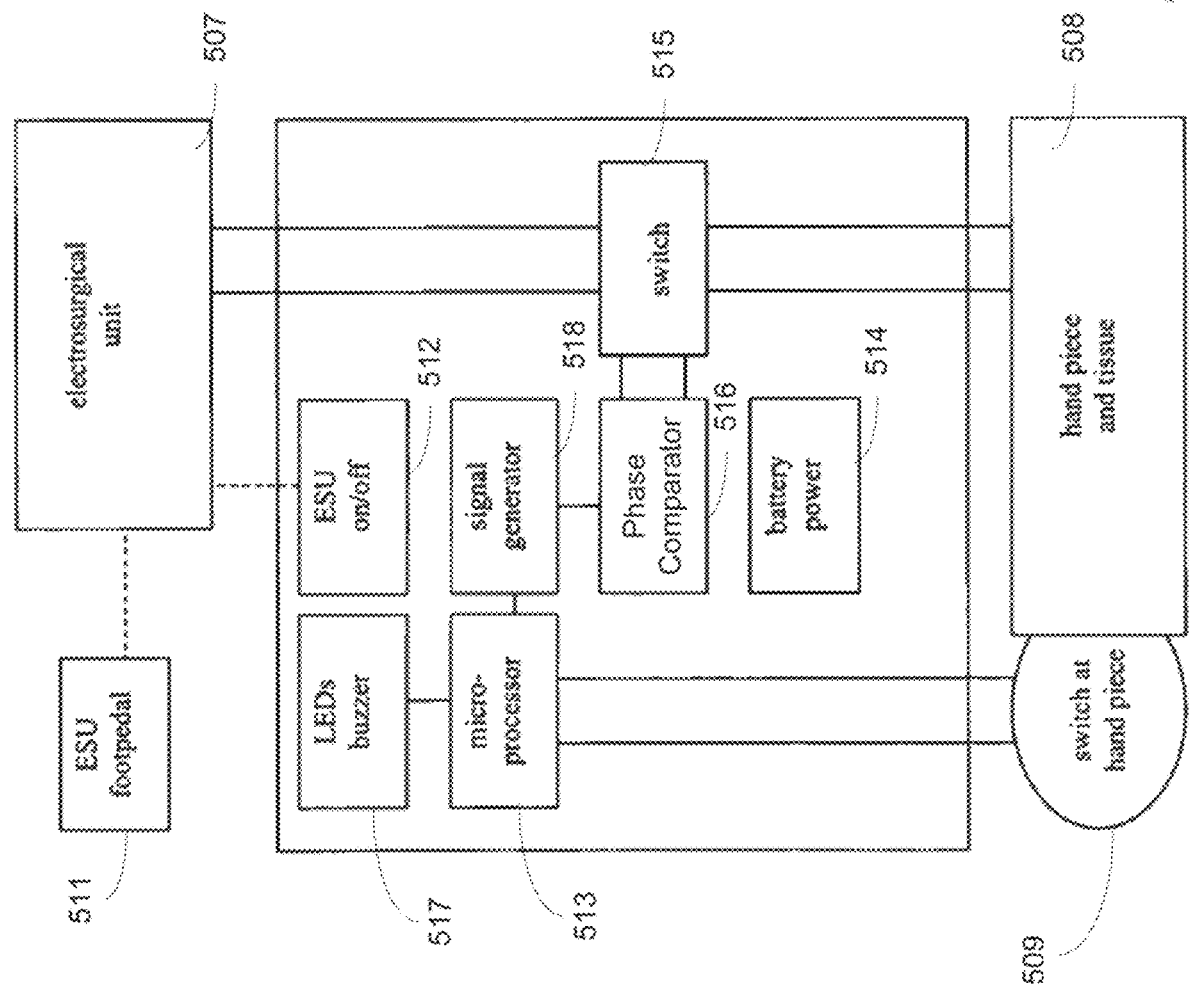
FIG. 14 is a block diagram of an electrosurgical unit.

FIG. 14 depicts a controller or control unit in accordance with aspects of the present invention for the controlled fusion or welding of biological tissue. As shown, the control unit is connecting the bipolar power outlet of a generator 507 to the tool 508 that is arranged to compress vessels or tissue. The tool also houses a switch 509 that activates the fusion process. If the generator is equipped with an input for hand activation (rather than using a foot pedal 511 or other intermediary device), a third connection 512 from the control unit to the generator allows activation of the generator with the same hand switch.

The controller in one embodiment includes a processor 513 that controls the switching of the tissue between the direct output of the generator and an internal measurement circuit, e.g., switch 515. It is powered with an internal battery power module 514. The timed switching causes the tissue to be fused in intervals while periodically measuring the status of the tissue. As such, the measurement signal is a 500 kHz sinusoidal low voltage signal, generated by a signal generator 518 when fed with a 500 kHz square wave from the microprocessor 513. When the low-voltage sinusoidal measurement signal is applied to the tissue, a phase comparator 516 measures the phase shift between the applied measurement voltage and the current caused by application of the measurement voltage. Depending on the result analyzed or processed by the processor, the tissue will be either be switched back to the generator, or disconnected from the generator accompanied by an acoustical and/or visual indication via LEDs/buzzers 517.

Figure 15:
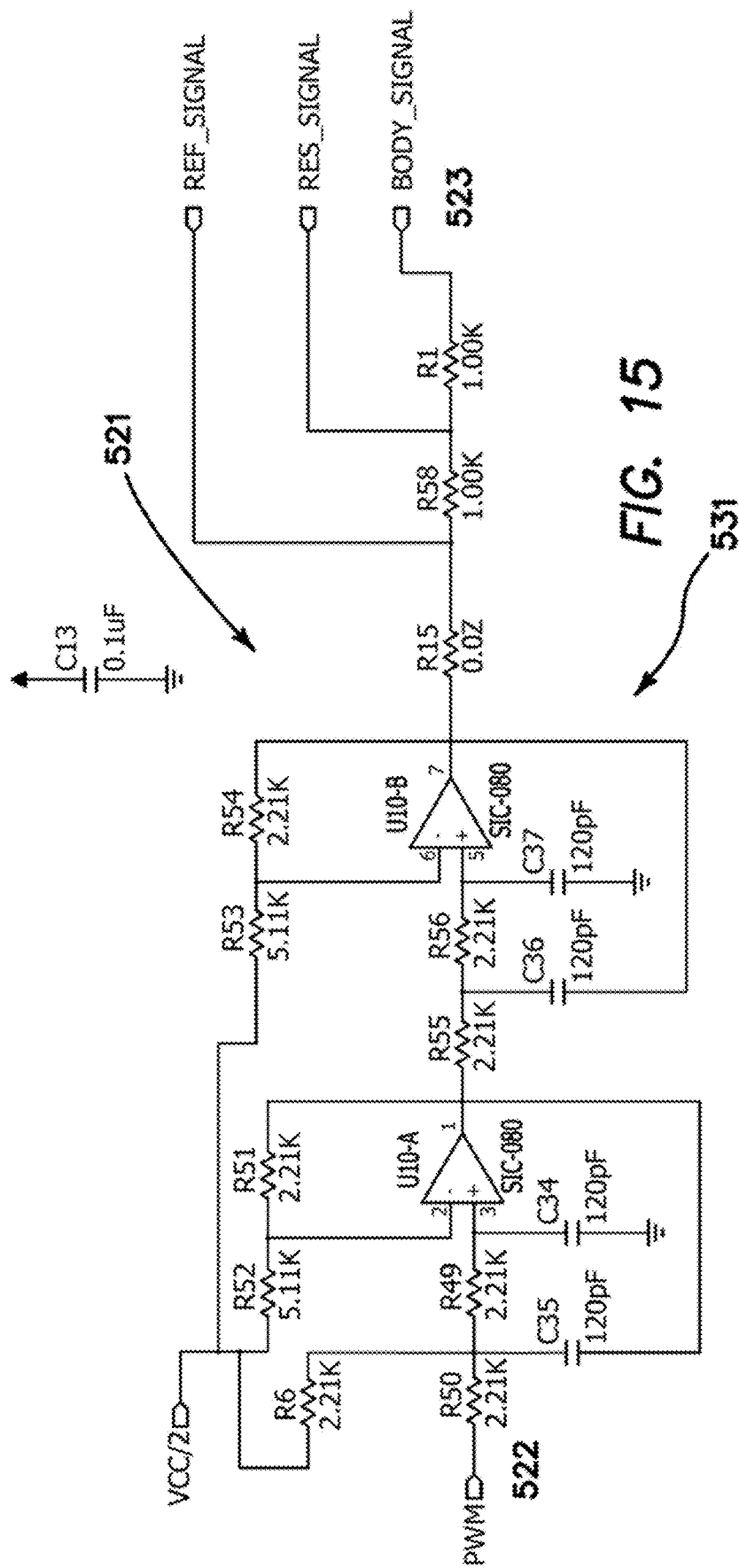
FIG. 15 is a schematic diagram of an external measurement circuitry of an electrosurgical unit.

FIG. 15 shows in one embodiment of the external measurement circuit that generates the low-voltage sinusoidal signal used to measure the phase shift. It is generated by passing a 500 kHz square wave through a 4-pole low-pass active filter 531. The 4-pole low pass filter removes higher harmonic components and passes the sinusoidal fundamental frequency. The 500 KHz square wave is generated via the PWM peripheral 522 in the microcontroller 524.

Figure 16:
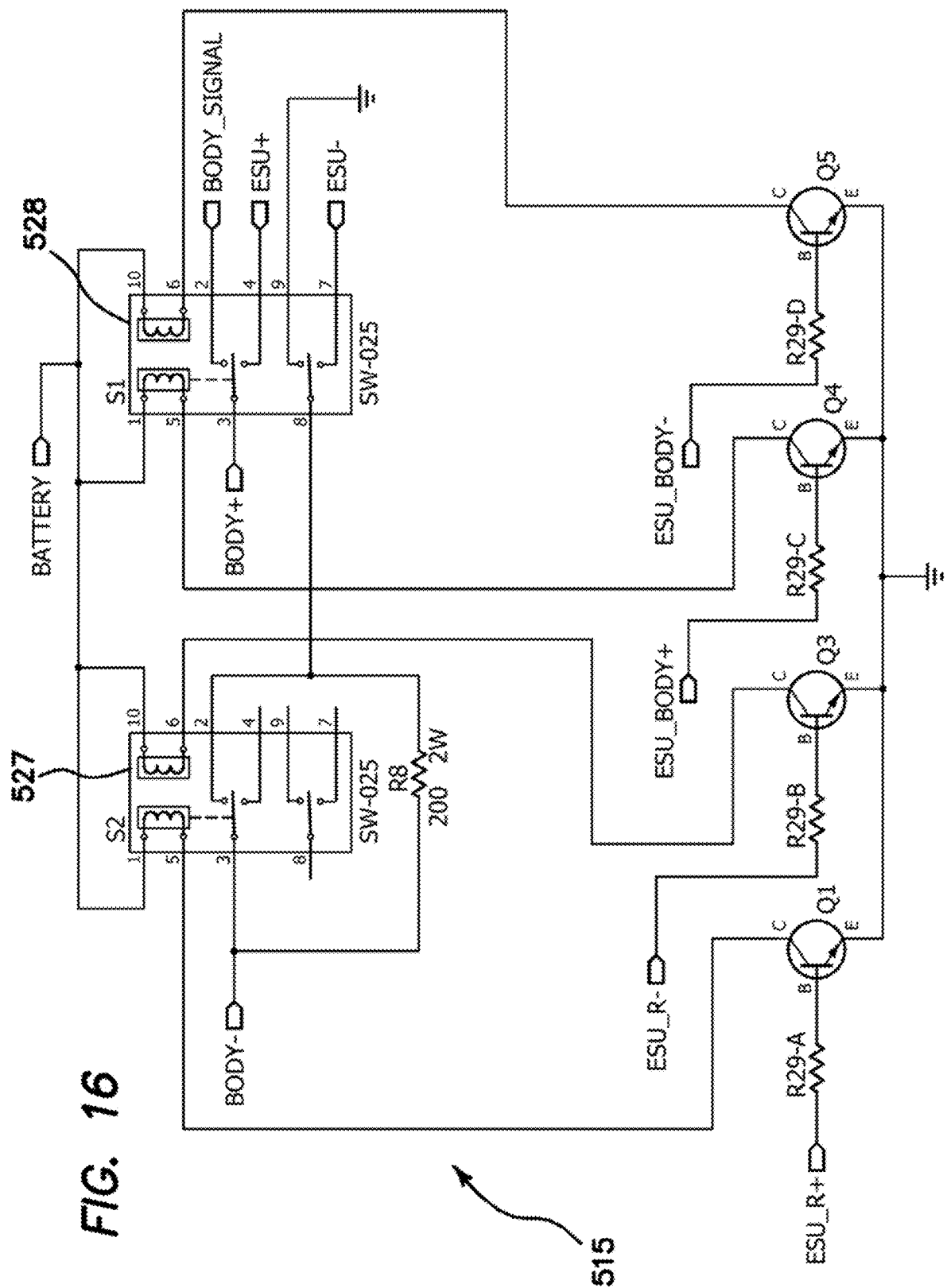
FIG. 16 is a schematic diagram of switch circuitry of an electrosurgical unit.

FIG. 16 illustrates switch 515 configured to switch between the application of the drive signal and the measurement signal, e.g., the 500 kHz, 5 Volt peak-to-peak sine wave reference signal, from the generator. Although the use of a solid-state switch to implement the switching offers a long operational life and inherent current surge control, it can be difficult to block the relatively high voltage (~200 VAC) and high frequency (~500 KHz) signal generated by a typical generator in bipolar coagulation mode. As such, two double pole, double-throw mechanical relays 527,528 are used. The first relay 527 switches between the generator and the reference signal. The second relay 528 limits the current surge, which can damage the relay and create an electromagnetic interference (EMI) pulse that can disrupt the low-voltage circuitry. Additionally, this protects the tissue against complications or issues caused by electrical arcing. Since most generators are constant power devices, the highest voltages occur during conditions of no load. By first switching in the generator through a series resistor, the output voltage of the generator is shared across the resistor, limiting the voltage imparted to the tissue. Furthermore, the resistor serves as an energy limiter, enabling high conductive channels in the tissue to fuse before the full power of the generator is applied.

In one embodiment, switching takes place in the following sequence. When switching from the low voltage measurement or reference signal to the generator, the first relay 528 switches out both ends of the reference and switches in one generator lead directly and one through a 100 Ohm resistor. The 100 Ohm resistor limits the surge current to two amps for a 200 Volt source. If a shorted output occurs, 400 watts are dissipated in the 3 Watt resistor, which would quickly burn up. However, approximately 50 milliseconds after the first relay 528 switches in the generator, a second relay 527 switches out the 100 Ohm resistor, keeping it from burning up and allowing the full power of the generator to be delivered to the tissue. When the device switches the other way (from the ESU to the reference signal), it first switches in the 100 Ohm resistor, reducing the current, and then switches out the generator entirely. This sequence reduces inductive kickback and EMI generation.

The relays 527,528 in one embodiment are of a latching type. Most mechanical relays draw a fair amount of power in their non-default state (an electrical current is needed to fight the force of the returning spring). Since the controller is equipped with a battery of limited power capacity, two latching type relays are used. These relays only use current to transition between two stable states and can operate at a much lower power level.

Figure 17:
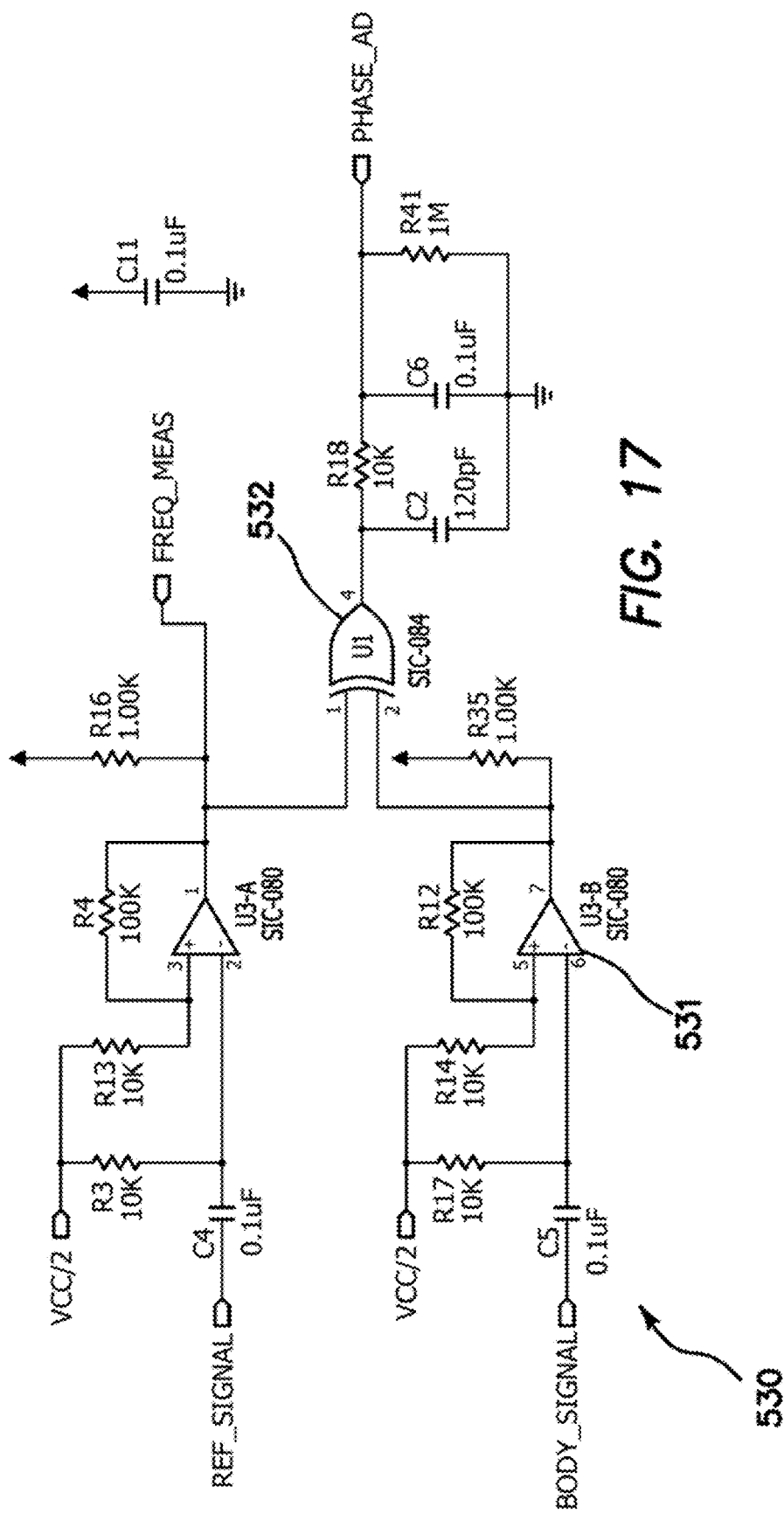
FIG. 17 is a schematic diagram of a phase comparator or detection circuitry of an electrosurgical unit.

The phase detection circuitry 530 is shown in FIG. 17, which measures the phase shift between the two above-mentioned sine waves. The first part of the circuit level-shifts the sine wave to the same DC value as a reference voltage. The level-shifted signal is then sent to the negative input of a comparator 531. The positive input is connected directly to the DC reference voltage. A small amount of hysteresis is used to reduce switching noise. The output of the comparator is a square wave with the same phase as the input sine wave. These two signals are sent to an exclusive "OR" gate 532. The output of the gate is high when one of the two inputs is high, and low otherwise. The duty cycle of the output is therefore linearly related to the phase of the two input square waves. The duty cycle is converted to a DC voltage through a low pass filter, which is measured by the analog to digital converter peripheral of the microcontroller.

Figure 18:
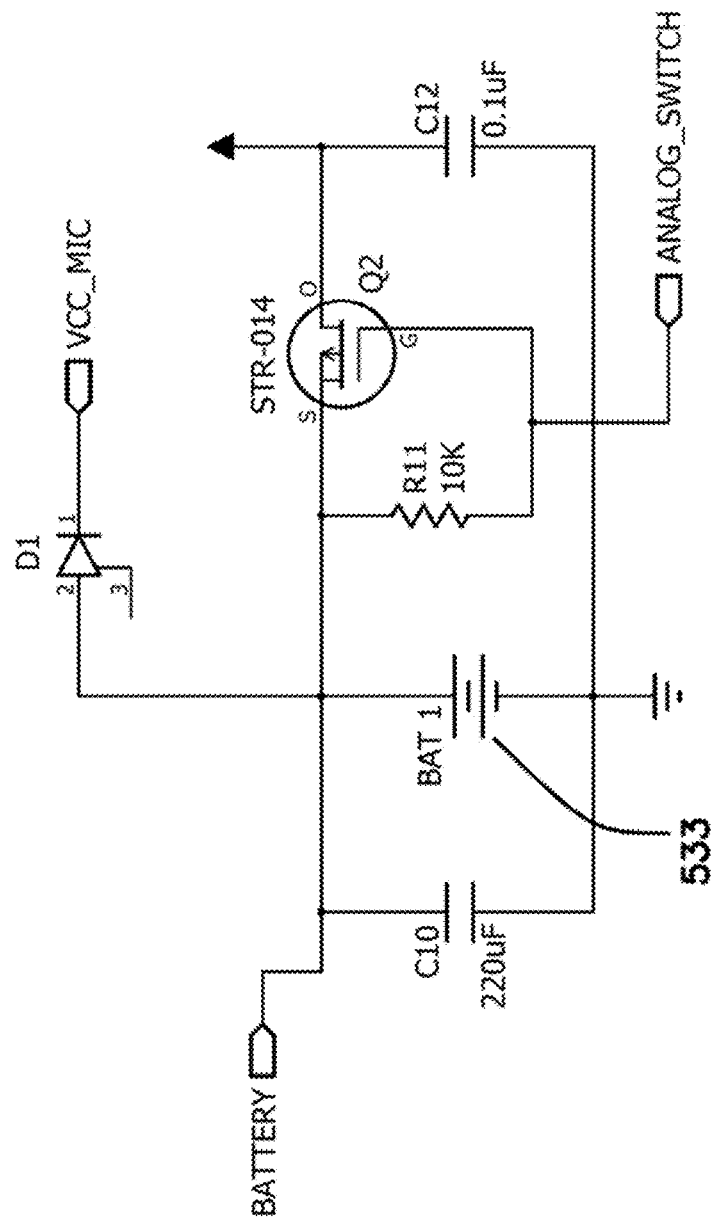
FIG. 18 is a schematic diagram of a battery power circuitry of an electrosurgical unit.

FIG. 18 shows the battery power circuit that is powering the control circuit by two low-capacity coin cells. The battery provides a life of 500 fusing cycles over a 5-hour time span. When a specific number of seals, or a specific time limit have been reached, the controller issues a warning and ceases operating. The controller manages its power demand around the power characteristics of the specific batteries used. The controller includes management controls that prevent specific operations from occurring simultaneously that may exceed the power capacity of the batteries, power down selected portions of the circuit between fusing cycles, and slow the microcontroller oscillator down from 4 MHz to 32 kHz between fusing cycles.

Figure 19:
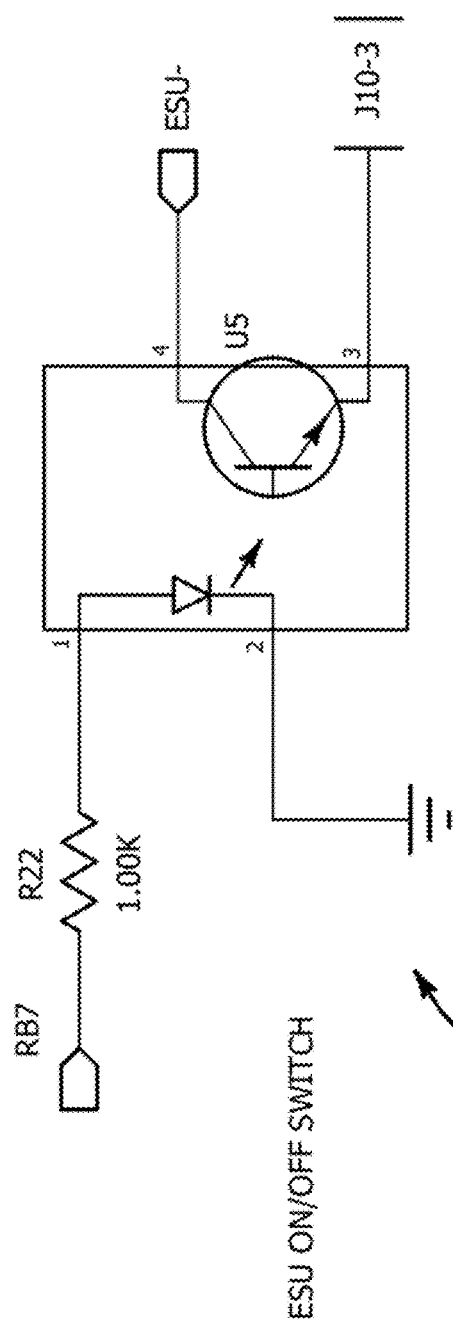
FIG. 19 is a schematic diagram of an input interface of an electrosurgical unit.

FIG. 19 shows an input port 534 adapted for connecting to a tool. With engagement of a switch on the tool, the controller takes initial measurements on the tissue (shorting, etc.) and based on the initial measurements activates the generator to supply electrosurgical power that is passed and controlled by the controller.

As many generators can exclusively (but also alternatively, with the surgeons preference) be activated with a foot-pedal, the controller accommodates such a scenario. For example, if the generator is activated with a foot switch while subsequent activation of the hand switch on the tool occurs, the controller allows switching-in of the output of the generator.

Figure 20:
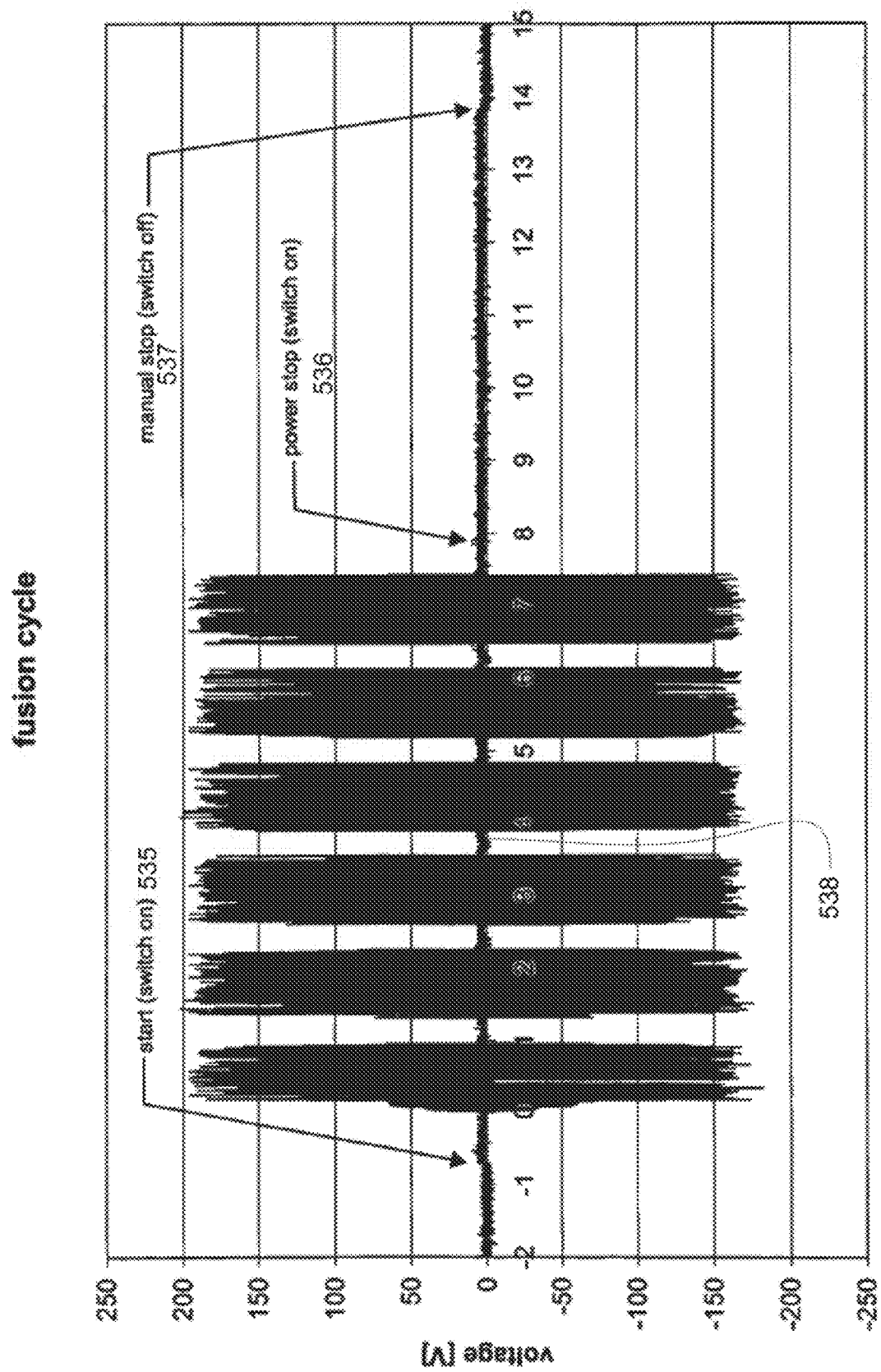
FIG. 20 is a graphical representation of experimental data for the voltage applied to the tissue during a typical a vessel fusion process.

The result of using the control circuit described above is shown in FIG. 20, showing the effective voltage applied to the biological tissue as function of time. As shown in this specific example of porcine renal arteries, the tissue is being exposed to 6 high-power fusion intervals of about 850 ms time duration, interrupted by 5 measurement cycles of about 300 ms.

In one embodiment, the fusion process starts with depressing a switch on the tool, which starts an initial measurement sequence. This point in time is marked start (switch on) 535. The tool in one embodiment checks the resistance between the two electrodes and if the phase shift is within an acceptable range. Verifying the phase shift prevents an attempt to re-fuse already fused tissue. Based on the results of the initial check, the controller switches-in the activated output of the generator to the tissue. This starts the application of RF energy to the compressed tissue. After about 850 ms, the controller disconnects the tissue from the generator and switches back to the first tissue assessment phase. Depending on the result, the tissue gets heated further, or remains disconnected from the generator to remain on the measurement circuit. The latter case is marked "power stop (switch on)" 536. In this case, an acoustical and/or visual signal is given off the unit, indicated that the tissue is sealed (or that shorting of the electrodes has occurred). The supply of the measurement signal to the tissue is ended when the switch on the tool is released, marked "manual stop (switch off)" 537. At this point, all supply of energy to the tissue is terminated.

Figure 21:
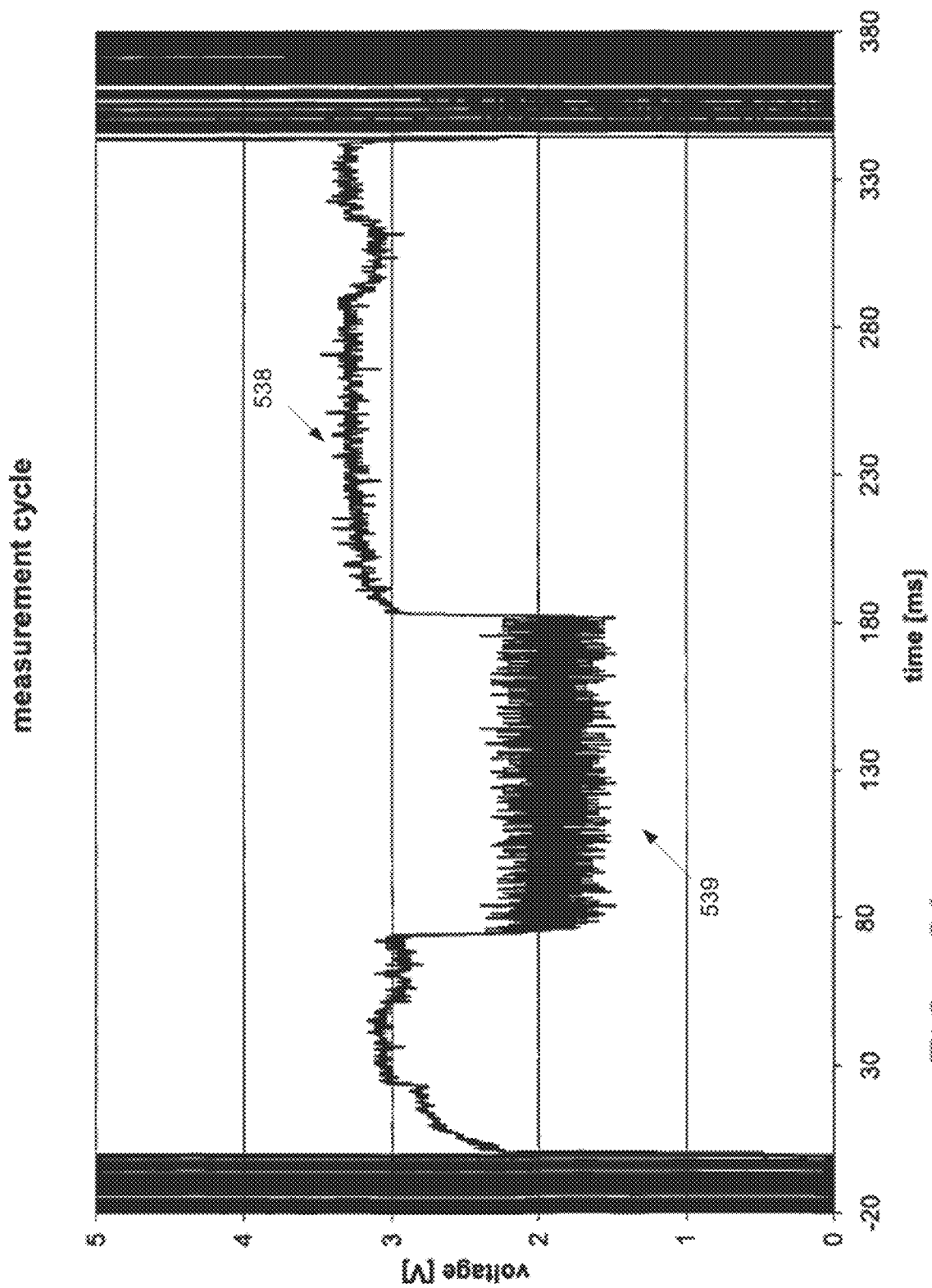
FIG. 21 is a graphical representation of experimental data for the voltage applied to the tissue during the measurement cycle.
Figure 22:
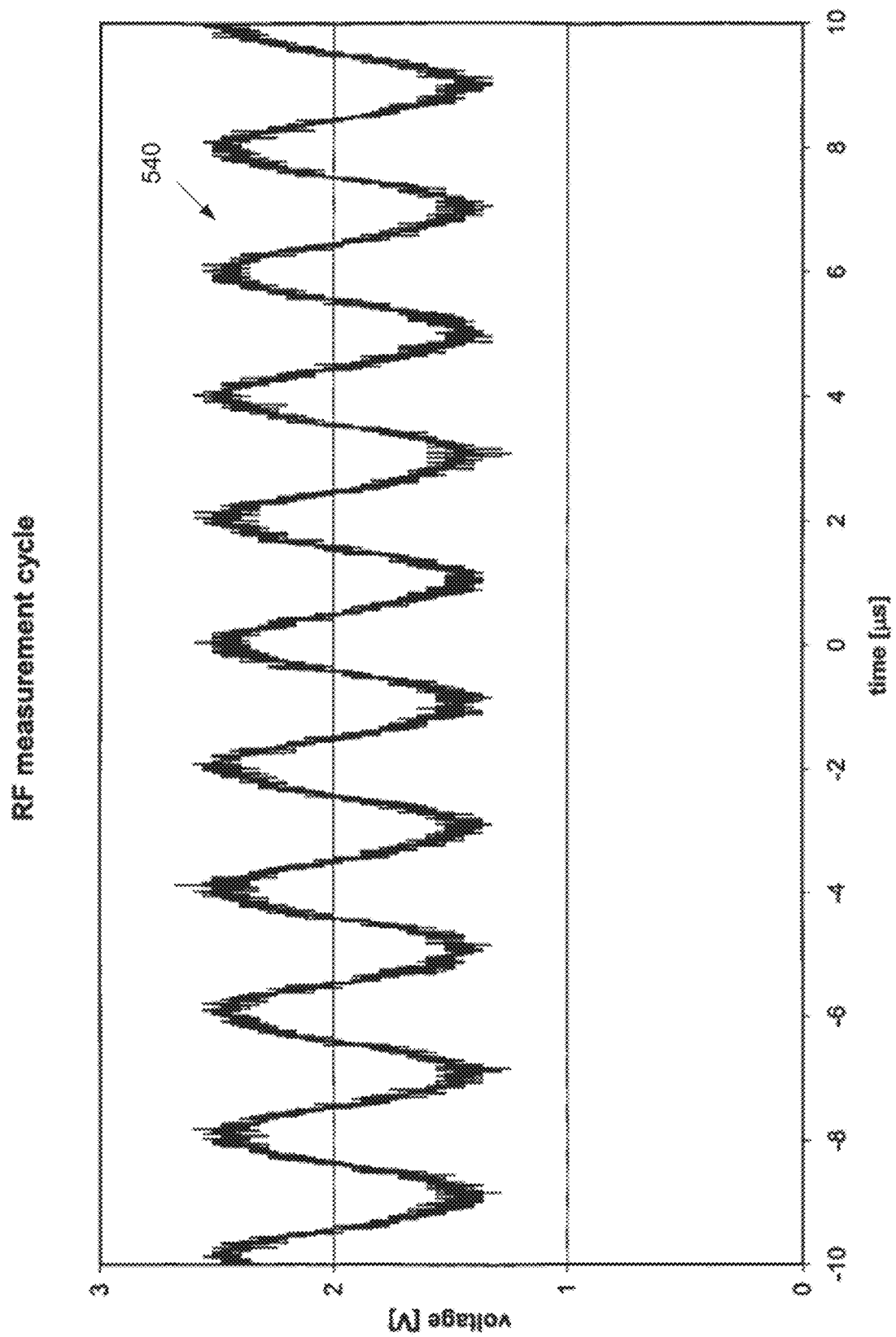
FIG. 22 is a graphical representation of experimental data for the voltage applied to the tissue during the RF measurement cycle to determine the phase shift through the tissue.

A more detailed analysis of the measurement cycle 538 is shown in FIGS. 21 and 22, showing that additional measurements (other than the phase shift) can be included in that measurement period. Such measurements, for example, could prevent attempting to fuse already fused tissue, or powering of electrically shorted electrodes.

In FIG. 22, a more detailed analysis of the measurement plateau 539 of 2V in FIG. 21. As shown, a detailed view of the low-voltage measurement signal 540 at 500 kHz used to determine the phase shift through the tissue during the RF measurement cycle.

Electrosurgical Systems and Processes

Electrosurgical systems and processes in various embodiments apply monopolar or bipolar high-frequency electrical energy to a patient during surgery. Such systems and processes are particularly adapted for laparoscopic and endoscopic surgeries, where spatially limited access and visibility call for simple handling, and are used to fuse blood vessels and weld other biological tissue and in one aspect to cut, dissect and separate tissue/vessels. In particular embodiments, the systems and processes include the application of RF energy to mechanically compressed tissue to (a) desiccate the tissue, and (b) to denature collagens (type I-III) and other proteins, which are abundant in most biological tissue. As heating of collagens to an appropriate temperature causes them to unfold, shrink or denature, the system enables the sealing of capillaries and blood vessels during surgery for permanent occlusion of the vessels. As described in greater detail below, as an example, arteries up to seven millimeters can be occluded and dissected by radio frequency (RF) energy and mechanical pressure.

When concurrently applying controlled high-frequency electrical energy to the compressed tissue, the tissue is compressed with a relatively high pressure (about 10-20 kg/cm2), and the tissue is supplied with sufficient electrical energy to denature proteins and remove sufficient water in the tissue. During this process, the applied voltages are sufficiently reduced to avoid electrical arcing (typically <200V RMS).

When applying electrical energy in the described manner stated above, the tissue quickly moves through the following fusion/welding process. Starting at body temperature the tissue (a) heats quickly, leading to (b) cell rupture, expelling of juices (mainly water and salt ions), (c) unraveling and "activation" of collagens and elastin in the blood vessels at about 60-650 C, and (d) desiccation of the vessel. Here, the desiccation process can be seen by the release of water in form of steam where the vessel temperature has reached about 1000 C. The reduction of water in presence of unraveled collagen and elastin strands leads to formation of bonds between collagen strands, leading to a strong and elastic seal of the tissue. As confirmed by measurements, the strongest (highest burst pressure) vessel fusions are obtained when the vessels have been heated to at least 70° C., pressurized with about 10-20 kg/cm2, and then desiccated by about 40-50% of their original water content.

Electrically, the tissue can be characterized during the fusion process by its impedance, which is typically starting at 10-100 Ohms purely ohmic resistance. During the fusion process, the purely ohmic resistance reduces by 20-50% before it increases by two orders of magnitude. As the resistance approaches a final value, the impedance of the tissue gradually increases in capacitive behavior with a phase shift of about 20 degrees. The tissue will exhibit a pronounced capacitive behavior at the end of the fusion process with a phase shift of about 40 degrees, even though the ohmic component will remain nearly unchanged during this phase.

Figure 23:
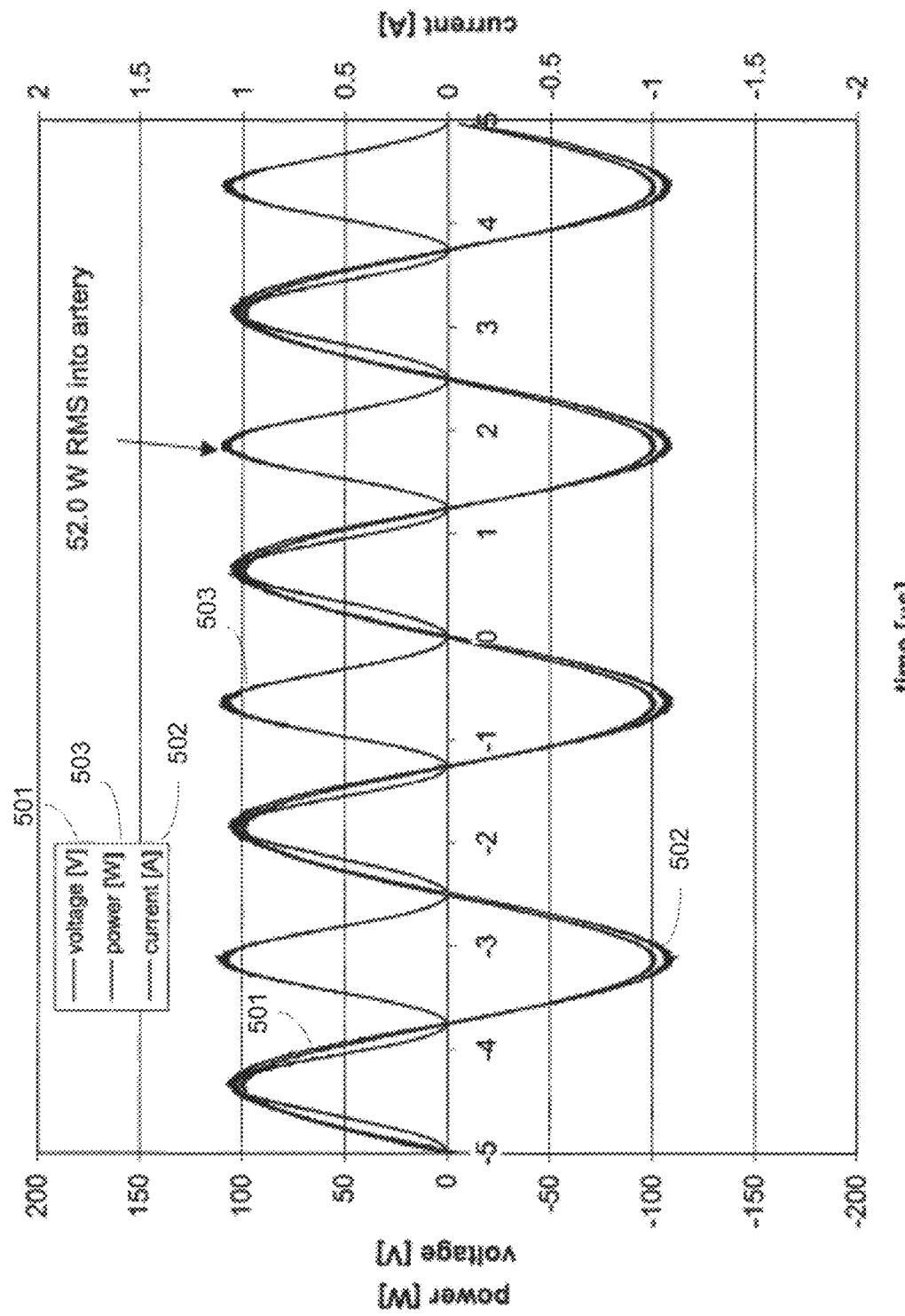
FIG. 23 is a graphical representation of a sample of experimental data for a typical vessel sealing process, showing a temporal showing a temporal snapshot of applied voltage, electrical current, and dissipated power at 1 second into the fusion.

Referring now to FIG. 23, graphical representation exemplifying experimental data for the sealing of a four-millimeter diameter porcine renal artery in accordance with various embodiments of electrosurgical system is shown. The fusion process is performed by compressing the artery with 0.75 millimeter wide electrodes with a compression load of three pounds, and by energizing it with a voltage-stabilized electrosurgical power supply using 200V at 60 W maximum power setting. Voltage 501, current 502 and electrical power 503 in the beginning of the fusion process (1 second) are shown. As can be seen, the sinusoidal voltage and current are substantially in-phase, e.g., the phase difference or angle equals zero. At this time, the impedance of the artery is purely ohmic with a value of about 100 Ohms.

Figure 24:
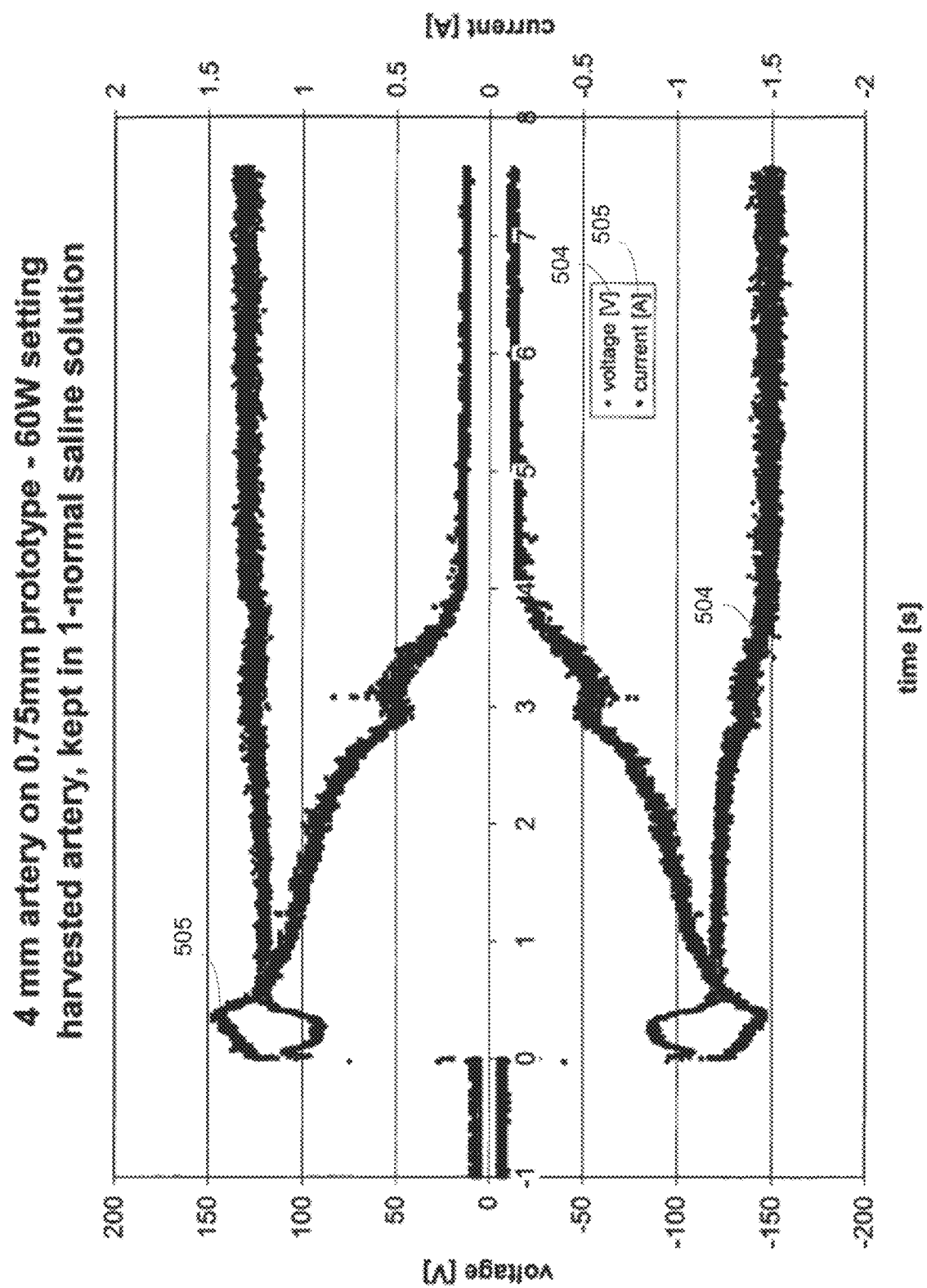
FIG. 24 is a graphical representation of a sample of experimental data for a typical vessel sealing process, showing the peak voltage and peak electrical current as function of fusion time.

The temporal progression of the applied peak voltage and peak current for the same-sized artery is provided in FIG. 24. The applied voltage quickly stabilizes to a constant value, which is an artifact of the voltage-stabilized power supply. Regardless of the applied load, voltage-stabilized electrosurgical power supplies regulate the output voltage to a pre-set value since the voltage has a dominant impact on the electrosurgical effect. In contrast to the voltage, the current driven through the artery increases from an initial 1 A to 1.5 A at 0.5 s, and then gradually reduces over the next three seconds to about 0.2 A. For the remaining 4 seconds of the fusion time the peak value of the current remains nearly unchanged.

Figure 25:
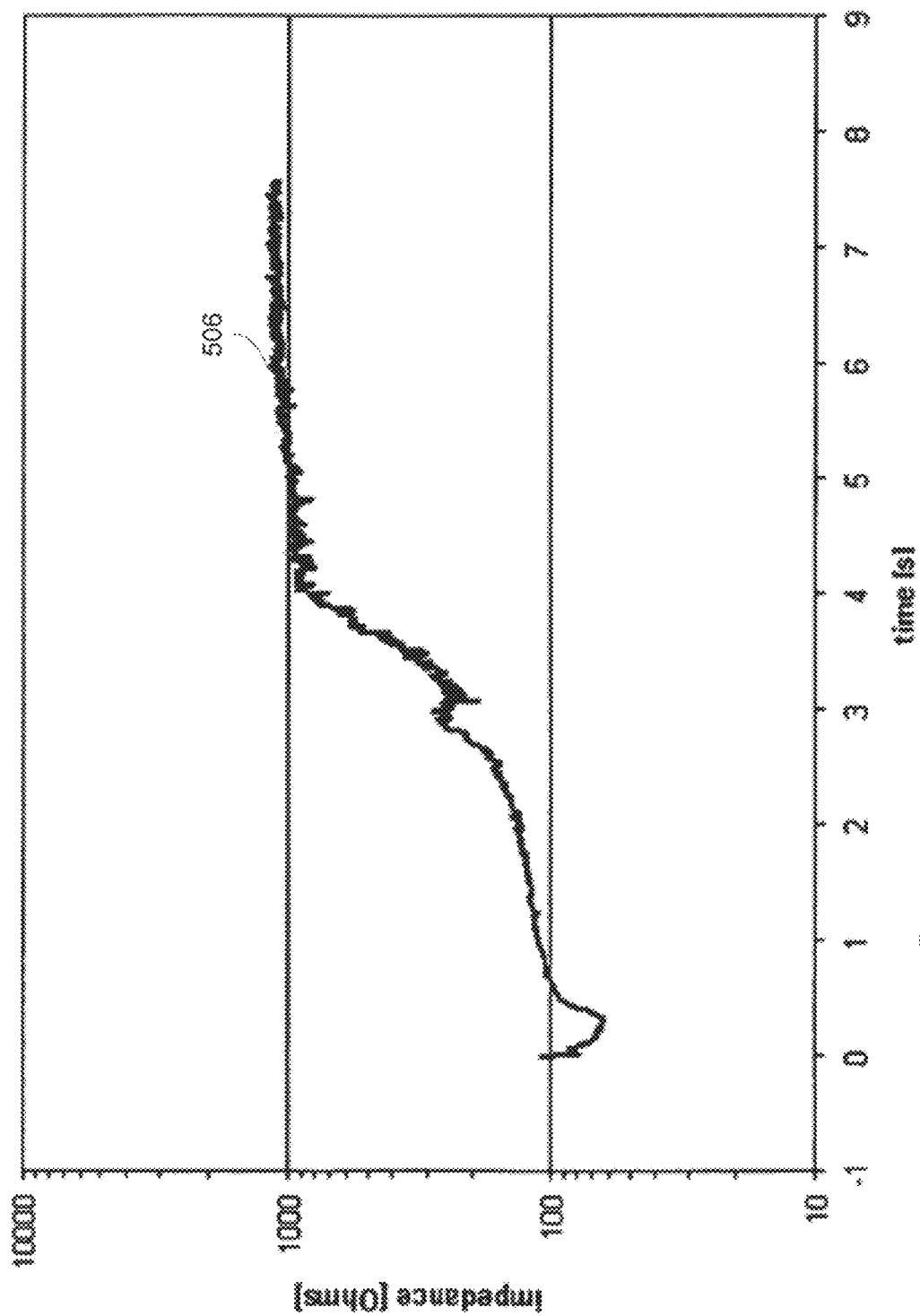
FIG. 25 is a graphical representation of a sample of experimental data for a typical vessel sealing process, showing the vessel impedance as function of fusion time.

Another way to depict the information from FIG. 24 is shown in FIG. 25, showing the impedance 506 of the artery as function of fusion time. The initial impedance of the harvested artery is 75 Ohms. With application of high frequency electrical energy the artery heats quickly, leading to shrinkage of collagens, rupture of cell membranes, and the ultimate expelling of trapped liquid (mainly water and ions). As a result, the impedance has reduced to about 54 Ohms. Further supply of electrical energy starts to desiccate the artery, resulting in an impedance increase. At about 4 seconds into the fusion process the impedance of the artery starts to stabilize, with a slow increase of the impedance from about 800 Ohms to about 1,200 Ohms.

Figure 26:
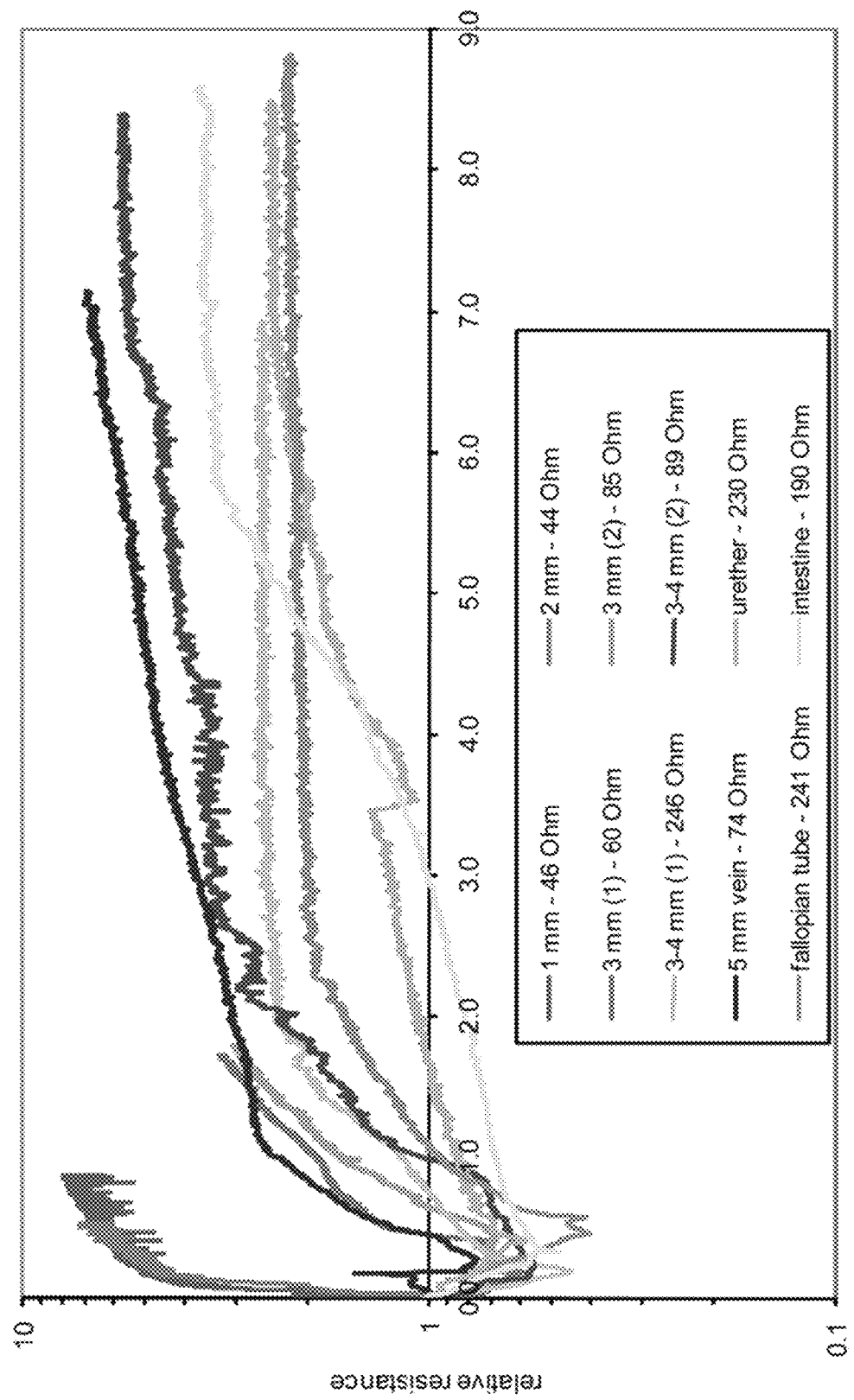
FIG. 26 is a graphical representation of a vessel sealing and tissue welding process in accordance with various embodiments of the present invention showing the relative impedances of various tissues as a function of time.

The fusion process could be terminated (a) at a fixed and absolute resistance (for example 2 k Ohms), which would neglect both the size and type of tissue, (b) at a specific multiple of the time where the ohmic resistance is minimal, (c) at a specific multiple of the time where the ohmic resistance is the same as the initial one, or (d) at a specific multiple of the time where the ohmic resistance is a certain factor of the minimal one. However, considering burst pressure of fused arteries and thermal spread, the termination of the fusion process is determined to be in the flattened part of the impedance curve. As can be seen in FIG. 25, however, this region is also an inexact range for impedance measurements. Similarly, each succession of (a) to (d) becomes better in determining the end-point of the fusion time (resulting in the highest desired bursting pressure with the least desired thermal spread). Utilizing the ohmic resistance only as termination criterion can lead to incomplete results. This can be more pronounced when fusing differently sized tissues (even of same nature), also exemplified in FIG. 26 showing the relative resistance (relative to the initial resistance) of various-sized arteries and other tissue as a function of fusion time.

Termination of the fusion process for same-material tissue (i.e., arteries) cannot be controlled with desired precision by specifying one relative ohmic load (e.g., when the resistance reaches 3 times the initial resistance). Instead, the relative change in resistance depends on the size of the vessel, i.e., <2 mm arteries seal in fractions of a second (where the resistance about doubles compared to the initial resistance), about 3 mm arteries seal in about 2 seconds (where the resistance about triples), and 15 mm arteries/veins seal in about 7 seconds (where the resistance increases by a factor of 5). At the same time, some arteries may not follow that characterization (e.g., a 3-4 mm artery would not reach more than 2.5 times the initial resistance). Instead, the fusion process should end within the flat region in FIG. 25. As previously described, precision is difficult in the flat region with the function of time at different fusion times.

Phase Based Monitoring

In one aspect, the determination of the end-point of the fusion process is given by monitoring the phase shift of voltage and current during the fusion process. Unlike impedance, the phase shift changes much more pronounced at times where the artery desiccates and the fusion completes, and hence offers a more sensitive control value than the impedance. This can be seen when monitoring the voltage and current as function of time at different fusion times, as is shown in FIG. 23 for the beginning of the fusion process.

In FIG. 23, the beginning of the fusion shows that the applied voltage and current are in phase (with a shift of about −3 degrees), revealing that the artery behaves dominantly like an ohmic load of about 75 ohms. Further supply of energy leads to heating of the artery, an initial reduction in impedance (caused by shrinking of collagens, cell membrane rupture and expelling of mainly water and dissolved ions), and a subsequent increase in impedance. During this period of vessel fusion, the phase difference between voltage and current remains small with minimal changes, indicating that the artery is purely ohmic.

Figure 27:
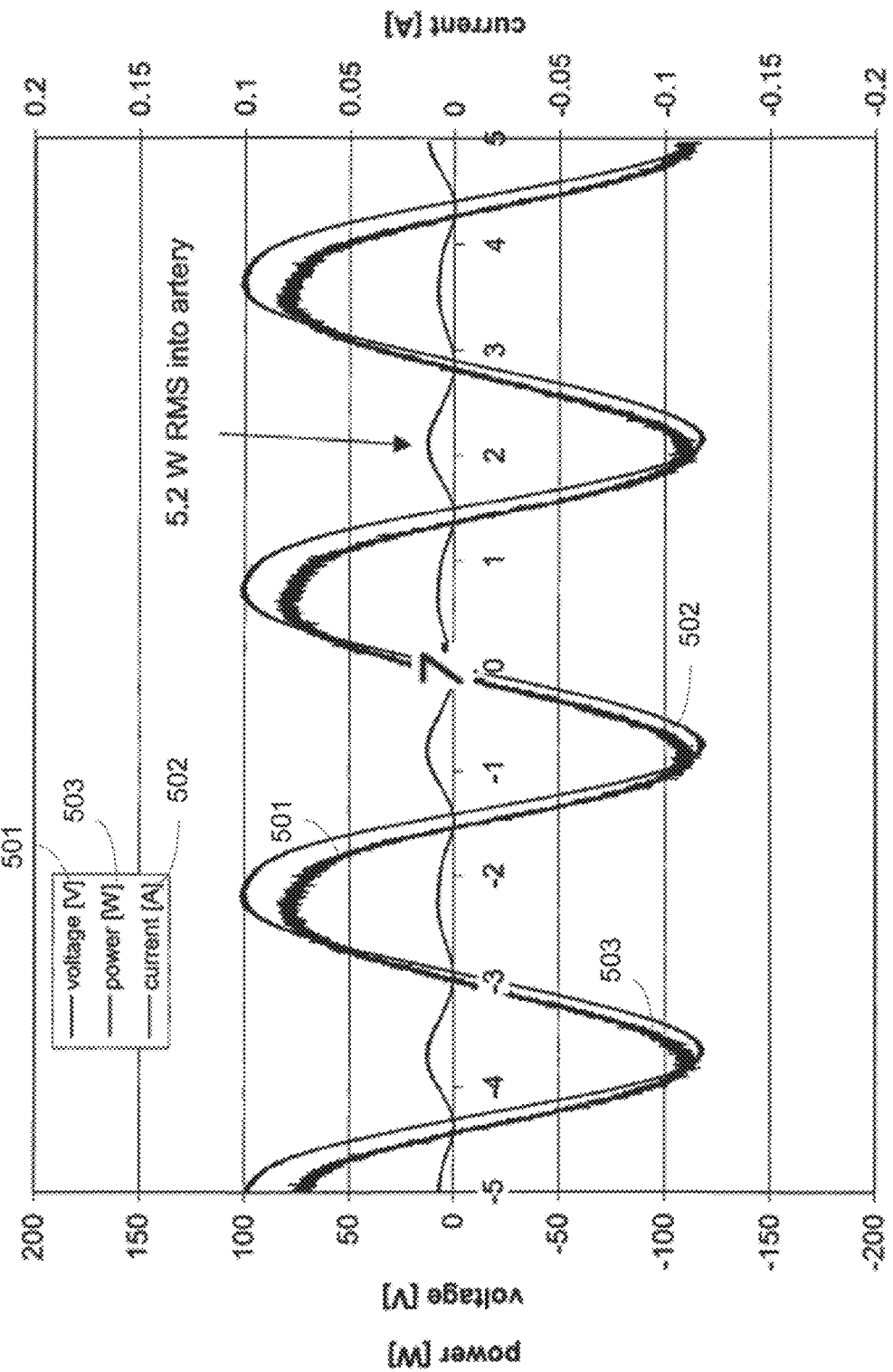
FIG. 27 is a graphical representation of a fusion/vessel sealing process in accordance with various embodiments of the present invention showing a temporal snapshot of applied voltage, electrical current, and dissipated power at 4 seconds into the fusion process.
Figure 28:
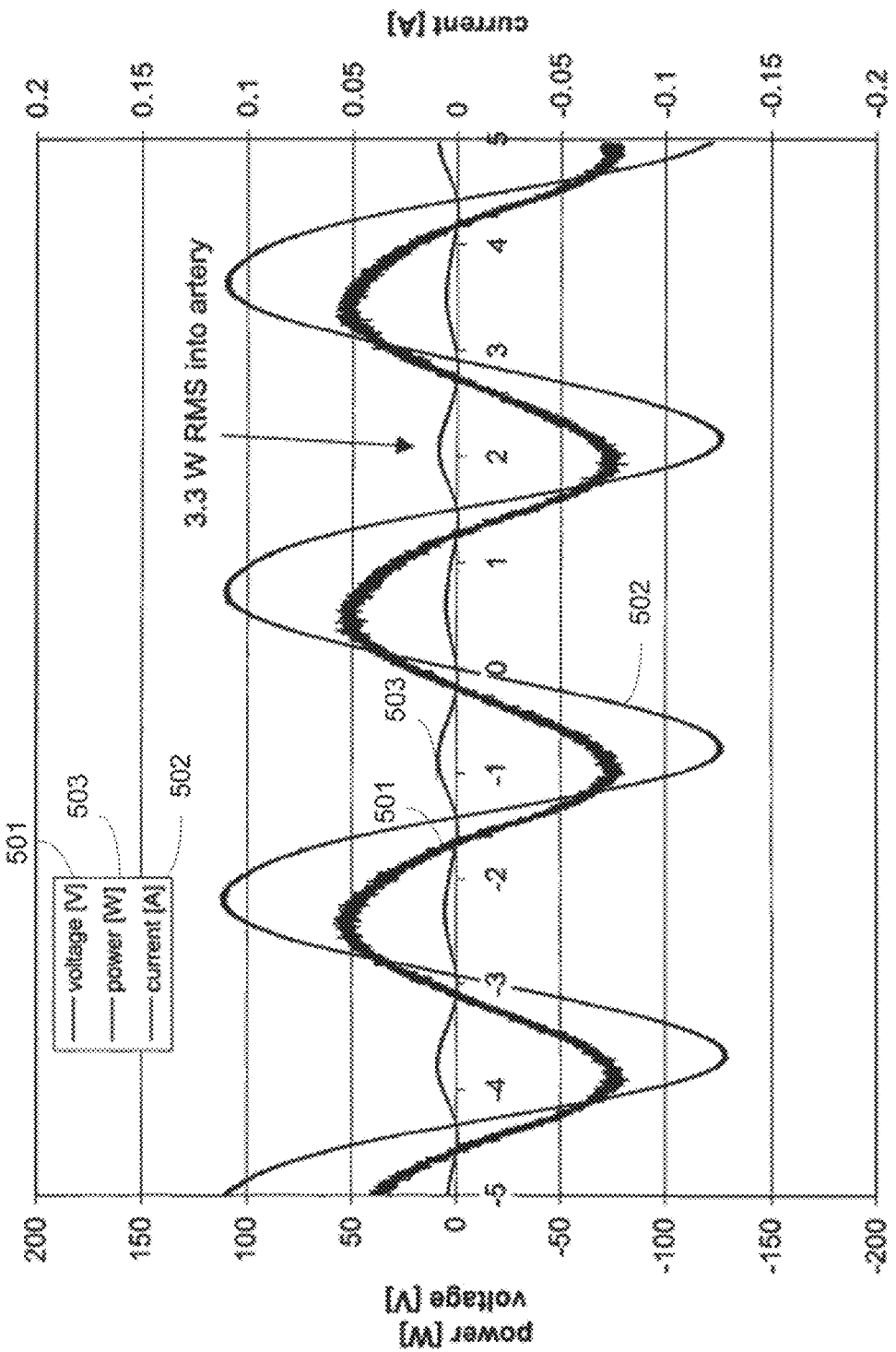
FIG. 28 is a graphical representation for a fusion/vessel sealing process showing a temporal snapshot of applied voltage, electrical current, and dissipated power at 7 seconds into the fusion process.
Figure 29:
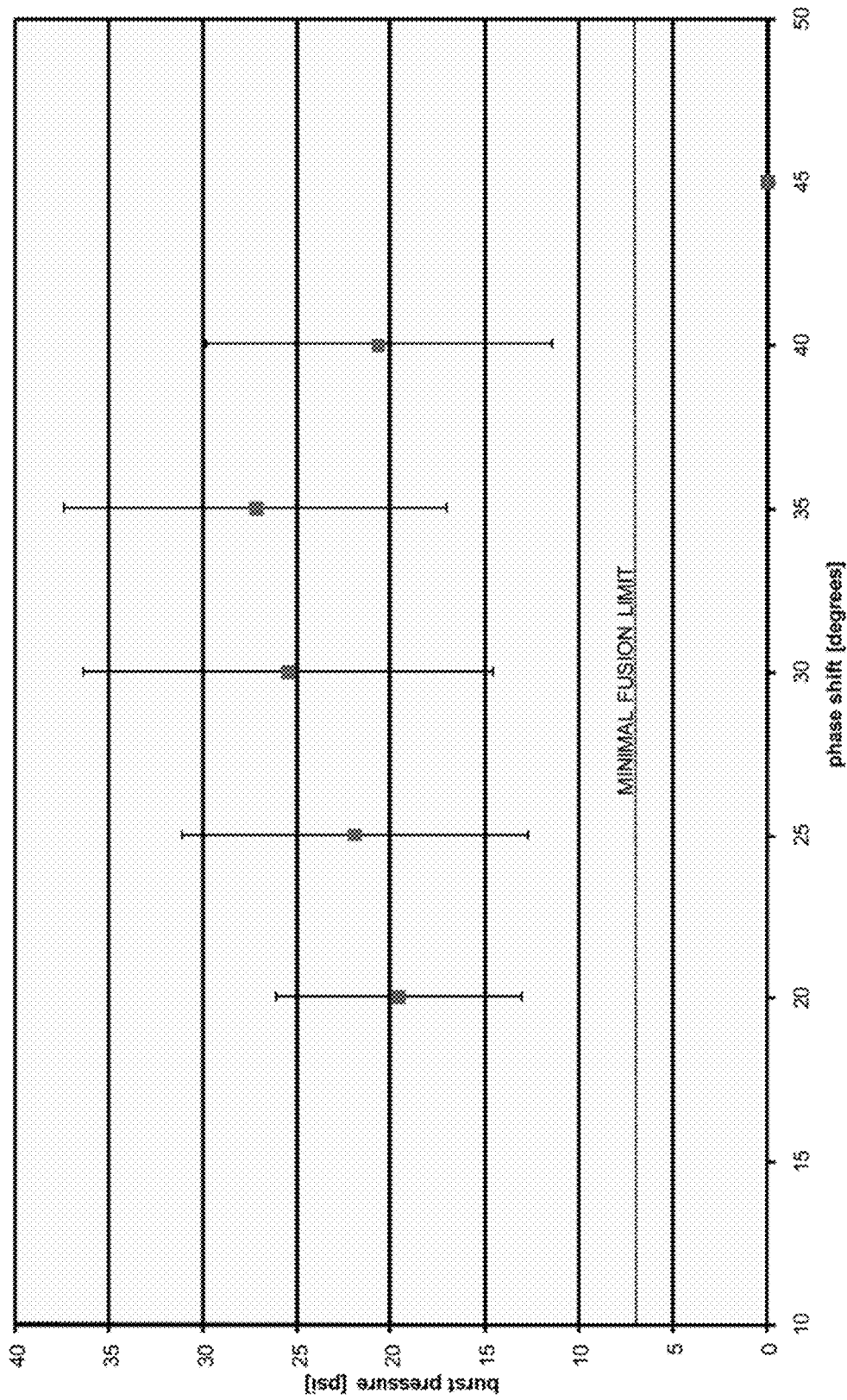
FIG. 29 is a graphical representation of bursting pressure as a function of phase shift used in end point determination.

The artery is not fully desiccated, and thus the seal is not complete. Referring to FIG. 27, at 4 seconds into the fusion process, the phase difference slowly increases to −10 degrees (current leads). While further supply of electrical energy does not significantly change the value of the resistance (see FIG. 24), it does cause a pronounced increase in phase difference between voltage and current. This can be seen in FIG. 28 at 7 seconds into the fusion process, showing a phase difference of about 25 degrees. The vessel fusion process continues and yields the desired burst pressures at the least desired thermal spread when the phase difference or angle reaches about 35-40 degrees as shown in FIG. 29. Also, as shown the phase angle reaches about 20 to 40 degrees. Similarly, the phase difference or angle necessary to result in welding of other tissue reaches about 45-50 degrees for lung tissue, and 60 to 65 degrees for small intestine. However, for all types of tissue, reaching a high end of the phase range can lead to excessively long sealing times. Accordingly, as will be described in greater detail below, the application of RF energy, i.e., drive signal, via an electrosurgical generator in conjunction with the measuring or monitoring of phase shift, i.e., a measurement signal, via an electrosurgical controller are provided to fuse or weld vessels and tissue in accordance with various embodiments of electrosurgical system.

Endpoint Determination Based on Tissue Properties

Using the phase difference between voltage and current as a control value in the fusion or welding process, instead of the impedance, can be further shown when characterizing the tissue electrically. When considering vessels and tissue to be a time-dependent ohmic resistor R and capacitor C in parallel (both of which depend on the tissue size and type) the phase difference can be obtained with $$R = \frac{\rho \cdot d}{A},$$

where R is the ohmic resistance, ρ the specific resistance, A the area, and d the thickness of the fused tissue, $$X_c = \frac{1}{\omega \cdot C},$$

where $X_c$ is the capacitive impedance, ω the frequency, and C the capacity of the tissue, and $$C = \frac{\varepsilon \cdot \varepsilon_0 \cdot A}{d},$$

where ε and $\varepsilon_0$ are the relative and absolute permittivity.

The phase difference φ can then be expressed as $$\varphi = \arctan\left(\frac{X_c}{R}\right) = \arctan\left[(\omega \cdot \varepsilon \cdot \varepsilon_0 \cdot \rho)^{-1}\right].$$

As such, the difference between monitoring the phase difference φ as opposed to the (ohmic) resistance R is that φ depends on the applied frequency ω and material properties only (namely, the dielectric constant ε and the conductivity ρ), but not on tissue dimensions (namely the compressed tissue area A and tissue thickness d). Furthermore, the relative change in phase difference is much larger at the end of the fusion process than the change in tissue resistance, allowing for easier and more precise measurement.

Figure 31:
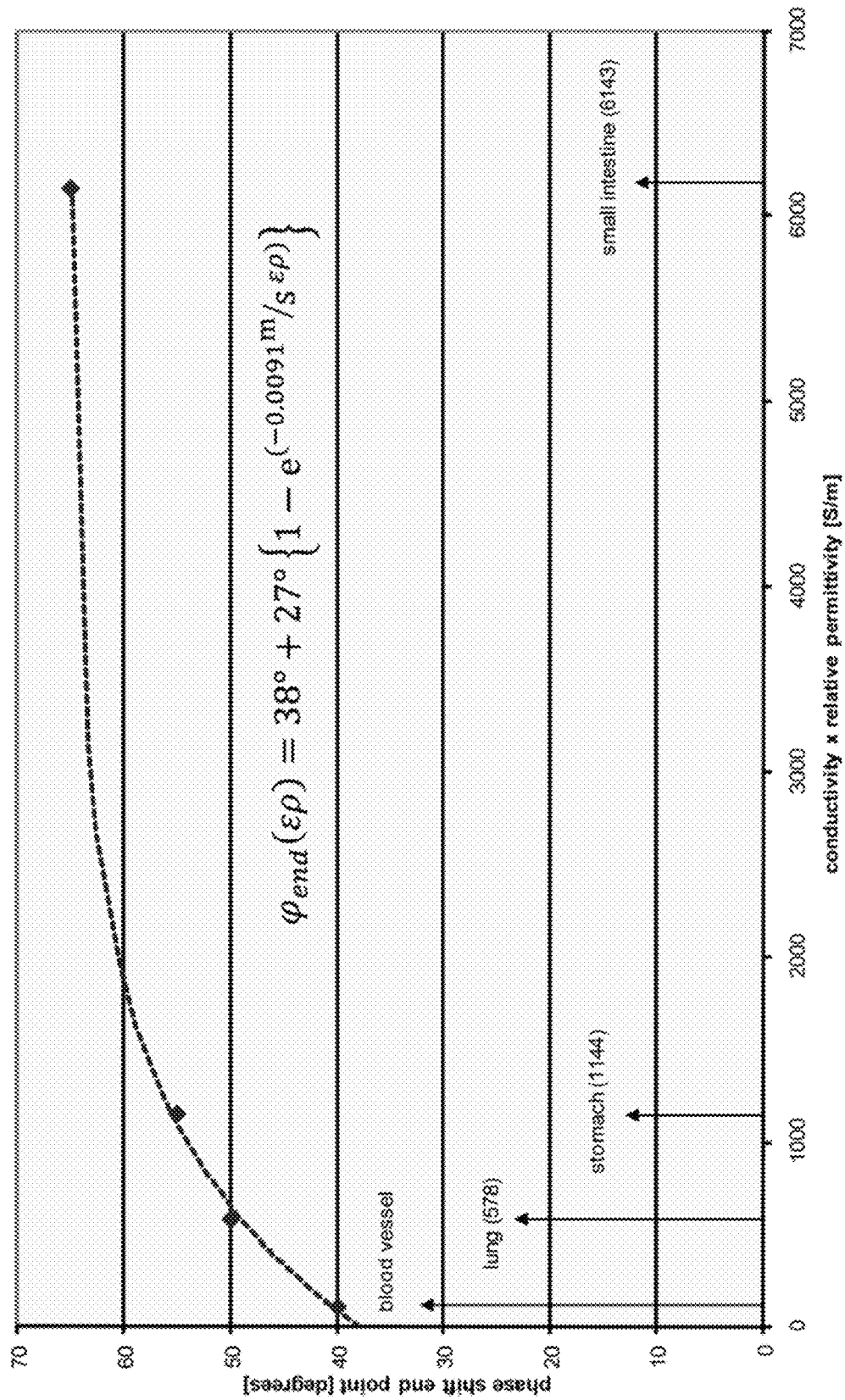
FIG. 31 is a graphical representation of empirically determined phase shifts to adequately fuse and/or weld various types of biological tissue.
Figure 32:
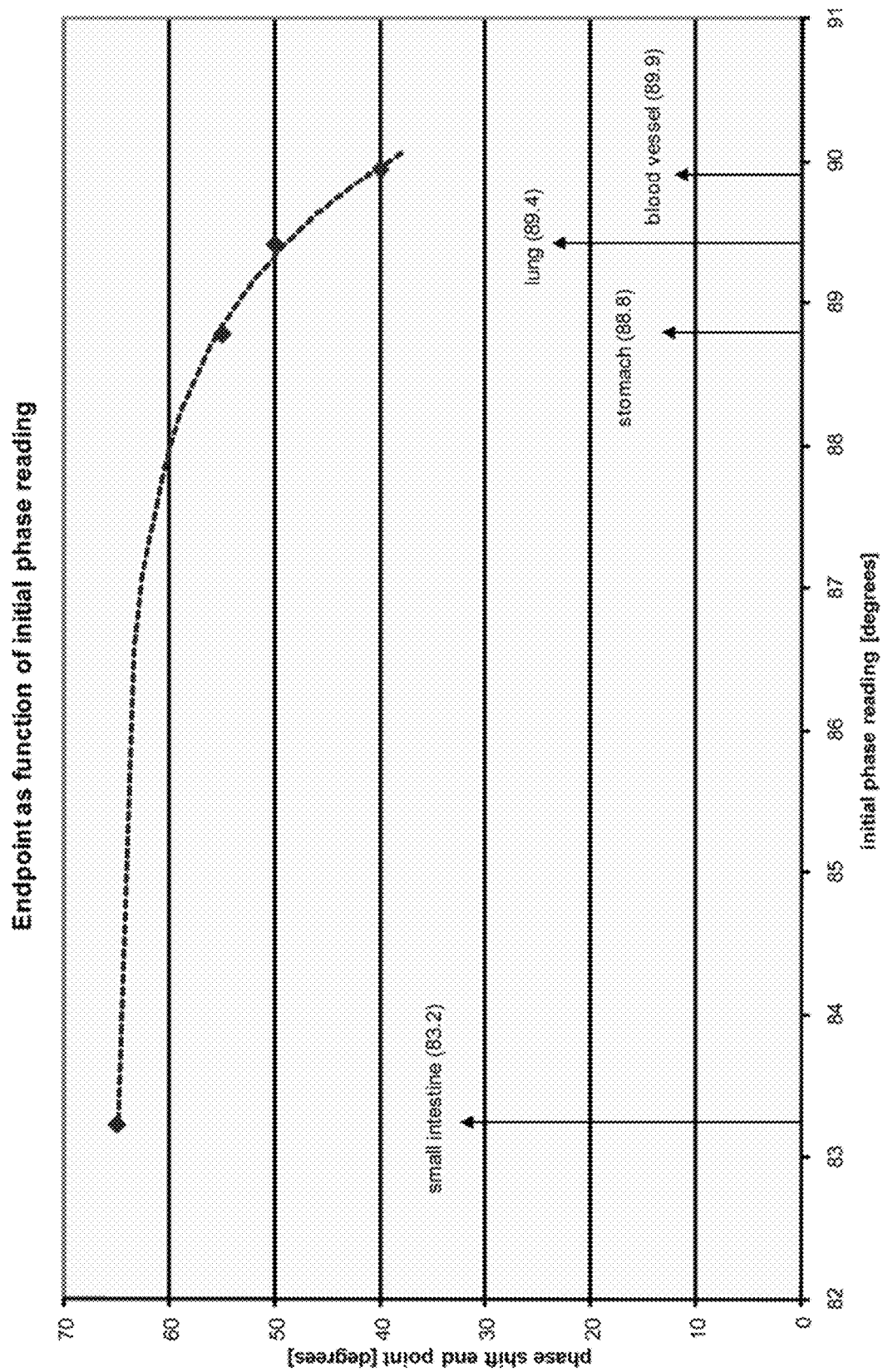
FIG. 32 is a graphical representation of endpoint phase shifts relative to initial phase shift measurements of various types of biological tissue.

In addition, with measurement of the initial dielectric properties of the tissue (dielectric constant ε and conductivity ρ) at a certain frequency, the type of tissue can be determined. The dielectric properties for various types of biological tissue, arranged by increasing values of the product of dielectric constant ε and conductivity ρ) are given in FIG. 30 at a frequency of 350 kHz (which is in the frequency range of a typical electrosurgical generator). By measurement of the product of dielectric constant ε and conductivity ρ of the tissue (which are material characteristics and independent of tissue dimensions) before the actual tissue fusion or welding process, the phase shift required to adequately fuse or seal the specific biological tissue can be determined from FIG. 30. The phase shift required to reliably fuse or seal the respective type of tissue is measured as function of the product of dielectric constant ε and conductivity ρ of the tissue (at 350 kHz). FIGS. 31 and 32 further emphasize this function in which in FIG. 31, end-point determination is shown as a function of an initial phase reading and in FIG. 32, end point determination is shown as a function of tissue properties (conductivity times relative permittivity). The function of tissue properties can also be expressed as $\phi end=38+29[1-\exp(-0.0091\rho\varepsilon)]$.

As a result, (a) measurement of the dielectric properties of the tissue and (b) control and feedback of the phase difference allows for a precise control and feedback mechanism for various tissue types, regardless of the tissue size and allows employing standard electrosurgical power supplies (which individually run in a very close range of frequencies). It should be noted that however that specific frequency of the tissue properties measurement is performed can be the same or different from the specific frequency of the phase If the tissue measurement is based on the driving frequency of the generator, and various generators are used (all of which run in a close range of frequencies) though, the end points will be different. Hence, for such a case, it can be desirable to (1) use an external measurement signal (which is at the same frequency), or (b) utilize a stand-alone generator.

As such, the controller is configured to determine the product of dielectric constant and conductivity, as well as the phase difference between the applied voltage and current to monitor and control the tissue fusion or welding process. In particular, control and feedback circuitry of the controller determines when the phase difference reaches the phase shift value determined by the result of the dielectric and conductivity measurements. When this threshold is reached, the fusion or welding process is terminated. An indicator, e.g., visual or audible, is provided to signal the termination and in one aspect the controller restricts (completely, nearly completely or to a predetermined minimum) further delivery of electrical energy through the electrodes. As such, the tool generating the seal, weld or connection of the tissue provides atraumatic contact to the connecting tissue and provides enough burst pressure, tensile strength, or breaking strength within the tissue.

Capacitive Load Compensation of Connected Tools

In one embodiment, measuring and accounting for the tool capacitance and tool resistance is provided for consistent initial tissue assessment (conductivity and permittivity) which provides the tissue-specific endpoint of the process (i.e., coag, fuse, or weld). In another aspect of the invention, measuring and accounting for the tool capacitance and tool resistance is provided for consistent tissue feedback measurements (phase shift) which ensures consistent tissue modification results (i.e., coag, fuse or weld).

Figure 33:
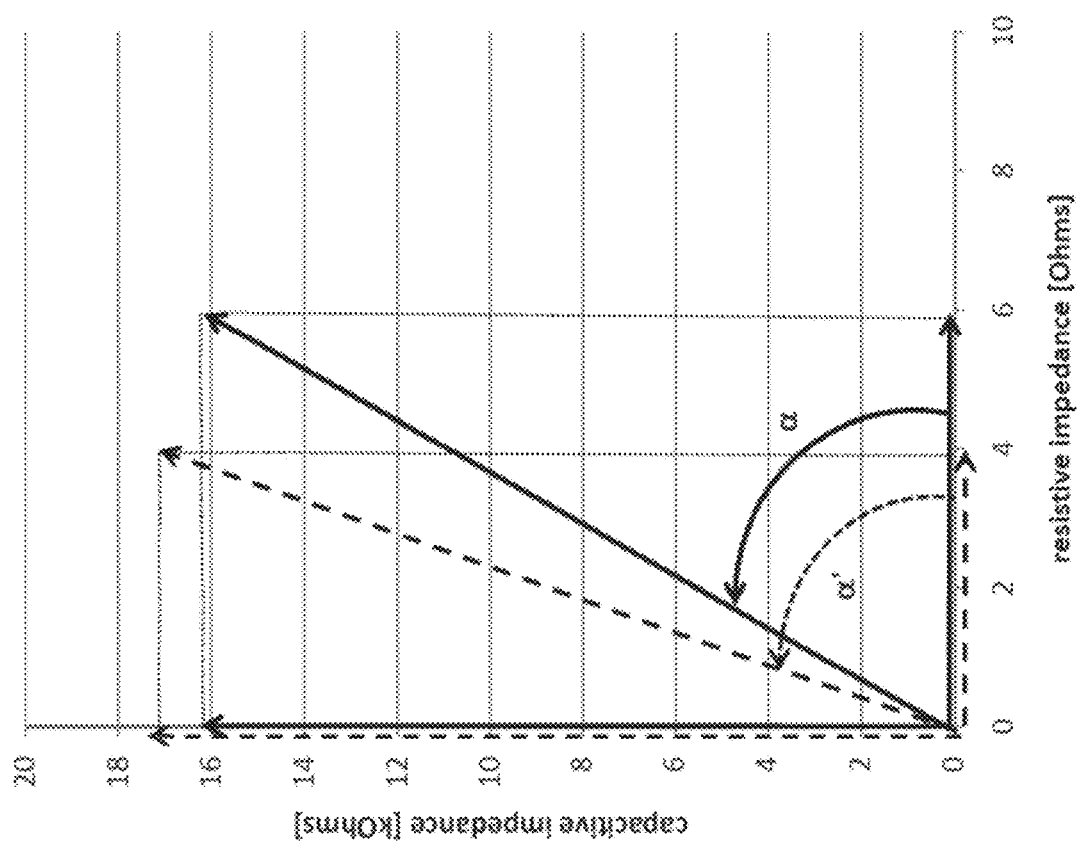
FIG. 33 is a graphical representation of a phase diagram of two electrosurgical tools and their associated capacitance and resistance.

FIG. 33 shows phase diagrams of two electrosurgical tools. As can be seen, both tools are electrically represented as a resistive or ohmic load (originating mainly from the wire harness 1500 connecting the hand tool to the generator, as well as the connections within the hand tools), as well as a capacitive load (originating mainly from the tool jaws, as well as the wire harness 1500 connecting the hand tool to the generator). In a phase diagram, the tool can be characterized by a phase angle α.

The values of the ohmic and capacitive impedances found in typical arrangements of tools are in the range of 1-10 Ohms for the ohmic load and 1-100 kOhms for capacitive resistances (several ten to several hundred pF capacitance at several 100 kHz). Even for two equal tools variations in the tool characteristics (such as wire connections, harness length, etc.) can lead to different phase angles α and α' for the same tool. As will be shown in the following, these variations can lead to different tissue measurement results, used both before and during tissue assessment.

Figure 34:
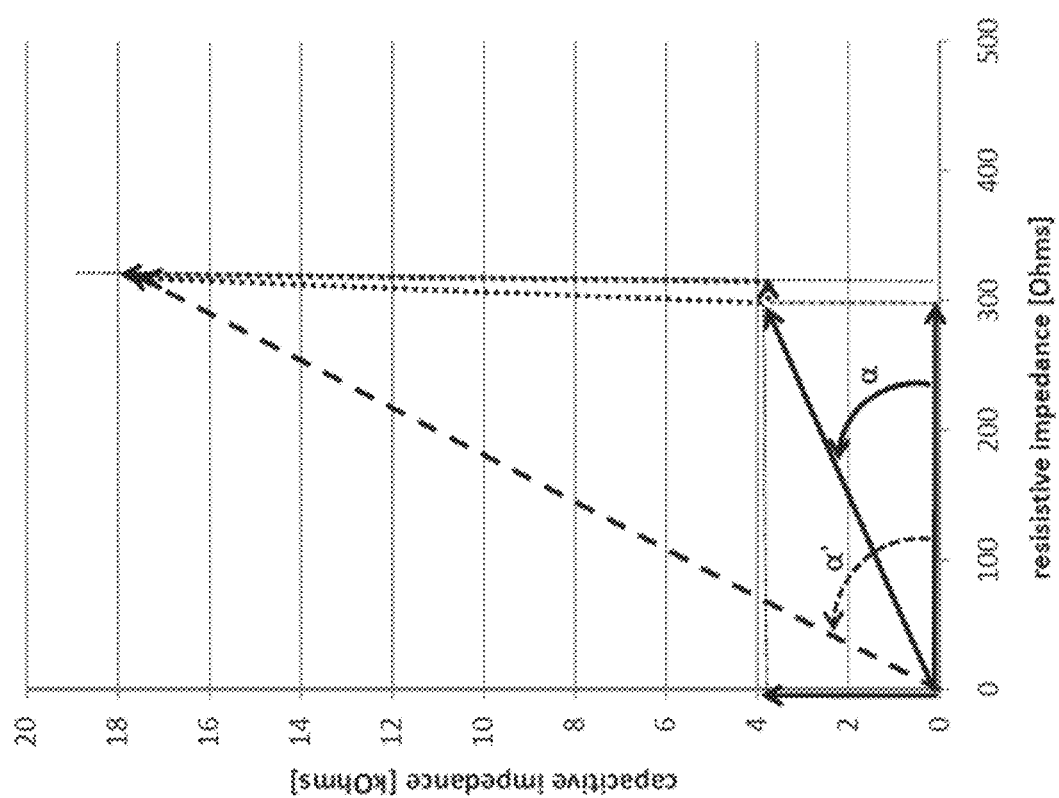
FIG. 34 is a graphical representation of a phase diagram of an electrosurgical tool in tissue contact and the associated capacitance and resistance.

As shown in FIG. 34, the phase diagram of an electrosurgical tool that is in contact with tissue composes of the resistive and capacitive component of the tool (dotted arrows) which add to the ohmic and capacitive component of the tissue (solid arrows) to present a total load to the electrosurgical generator (dashed line). For tissue measurement techniques that rely on the phase shift of voltage and current, the presence of the tool significantly alters the results of the intended tissue measurement by the apparent phase.

In this context, the presence of the tool (impedance) does not pose an actual problem if the tissue measurement before powering (to determine end point of fuse/weld), or during powering (to determine the end point of the fuse/weld) has been defined with the very same tool (i.e., tool impedance). Instead, variances of the tool impedances lead to different results in both the initial tissue assessment (pointing to an inaccurate endpoint) and tissue feedback measurement (determining the end point of the fuse/weld).

As such, the controller used to measure the phase shift during the tissue modification process can be used to initially determine the initial tool impedance (e.g., during plug-in of the tool connector to the electrosurgical generator), where tolerances/changes in the tool characteristics are then accounted for in the tissue measurement algorithm. This will allow for tissue measurement values which are independent of the ohmic and capacitive values and/or tolerances of the specific electrosurgical tool.

Accordingly, generally speaking, when tool capacitance increases, the endpoint phase shift decreases. In particular, when the tool capacitance increases, the capacitive impedance decreases ($X=1/\omega C$). Decreased capacitive impedance leads to a smaller or decreased end point phase shift. Similarly, when tool resistance increases, the end point phase shift decreases.

Also, from an initial tissue determination perspective, generally speaking, when tool capacitance increases, the apparent initial phase shift decreases compared to the "ideal" value. The "ideal" value being a tool having zero or near zero capacitance. Similarly, when tool resistance increases, the apparent initial phase shift decreases compared to the "ideal" value. As such, when the tool capacitance ($C=\varepsilon\varepsilon_0 A/d$) and/or the tool resistance ($R=\rho\ d/A$) increase, there is an increase in permittivity and/or conductivity which reflects a decrease in tan φ, i.e., a decrease in phase. In one example, an electrosurgical tool having a capacitance of 160 pF had an initial phase shift of 9-59 degrees versus a tool having a capacitance of 230 pF having an initial phase shift of 6-23 degrees. Additionally with tissue permittivity and conductivity product values being inversely proportional with the initial phase shift, when tool capacitance and/or resistance increases, the apparent tissue permittivity and conductivity product value increases compared to the "ideal" value.

Figure 35:
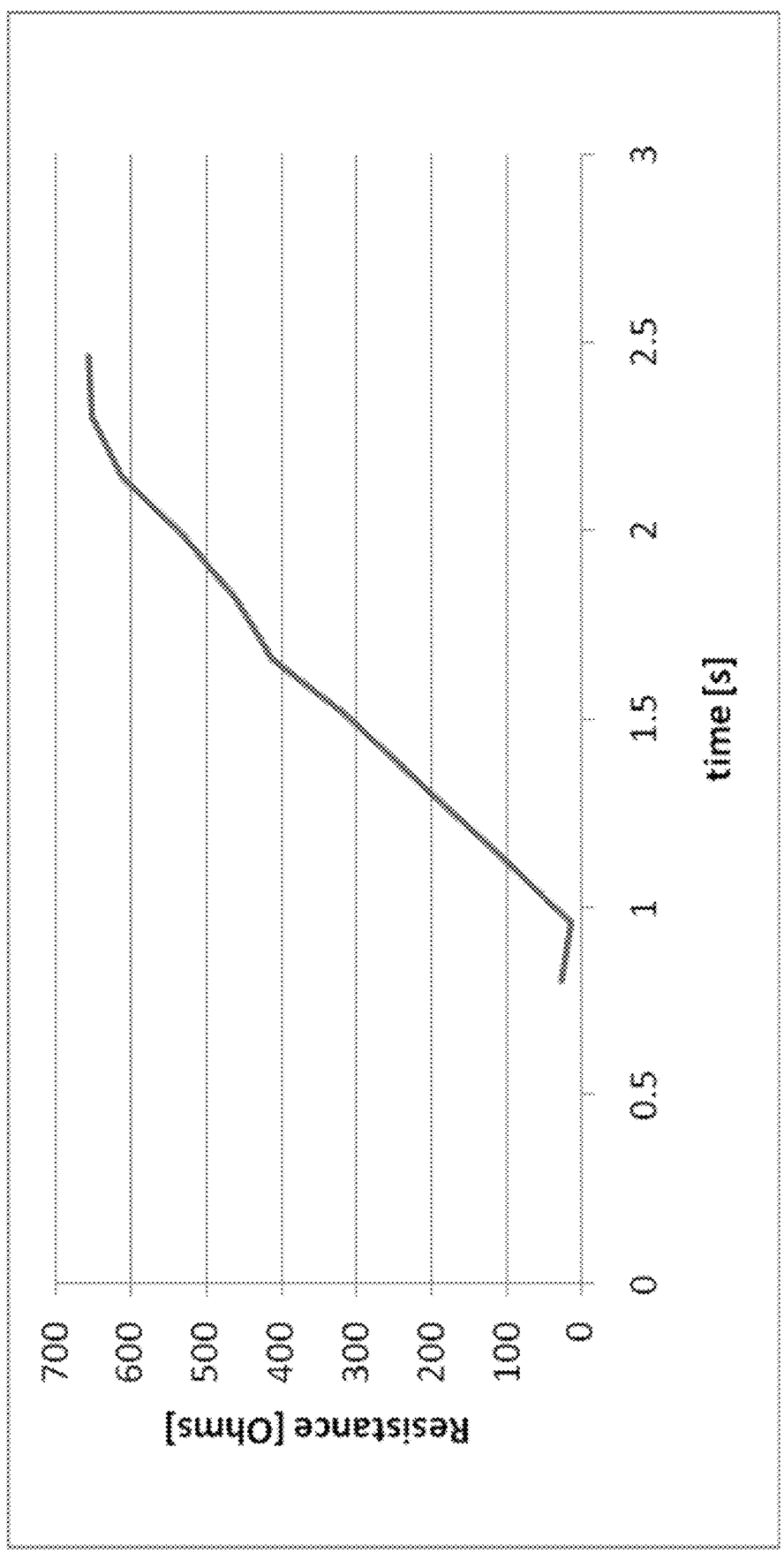
FIG. 35 is a graphical representation of the ohmic resistance of a porcine renal artery during the electrosurgical fusion process.

FIG. 35 shows the ohmic resistance of a porcine renal artery during the electrosurgical fusion process. As was shown previously, the fusion process of blood vessels and/or welding of tissue can be better controlled when the phase difference or angle between applied voltage and incurred current is measured and used to interrupt the fusion/sealing process. Depending on the type of tissue, the end point has been found to be ideal at about 40 degrees (blood vessels) or 60 degrees (intestines), respectively.

Figure 36:
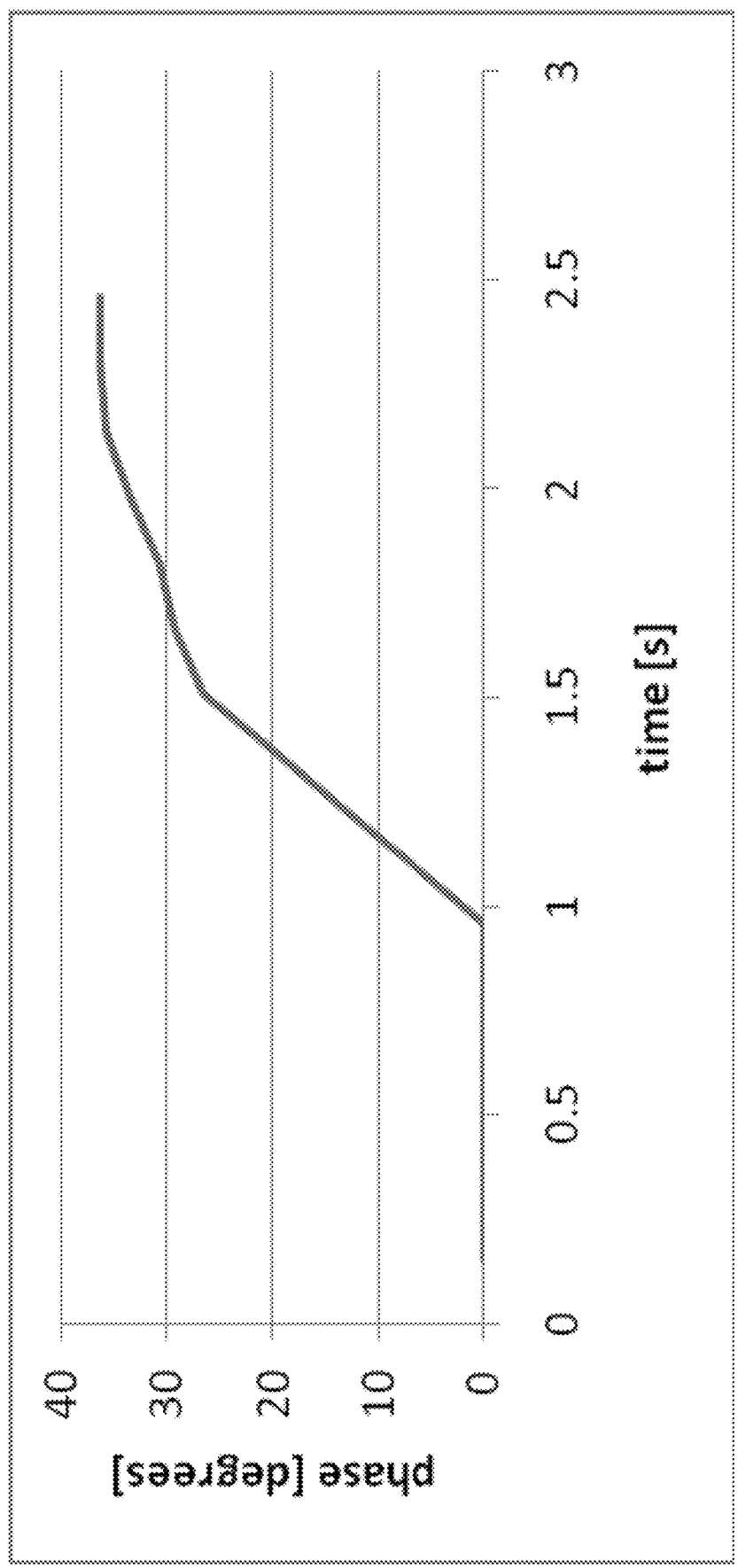
FIG. 36 is a graphical representation of phase shift during the electrosurgical fusion process.
Figure 37:
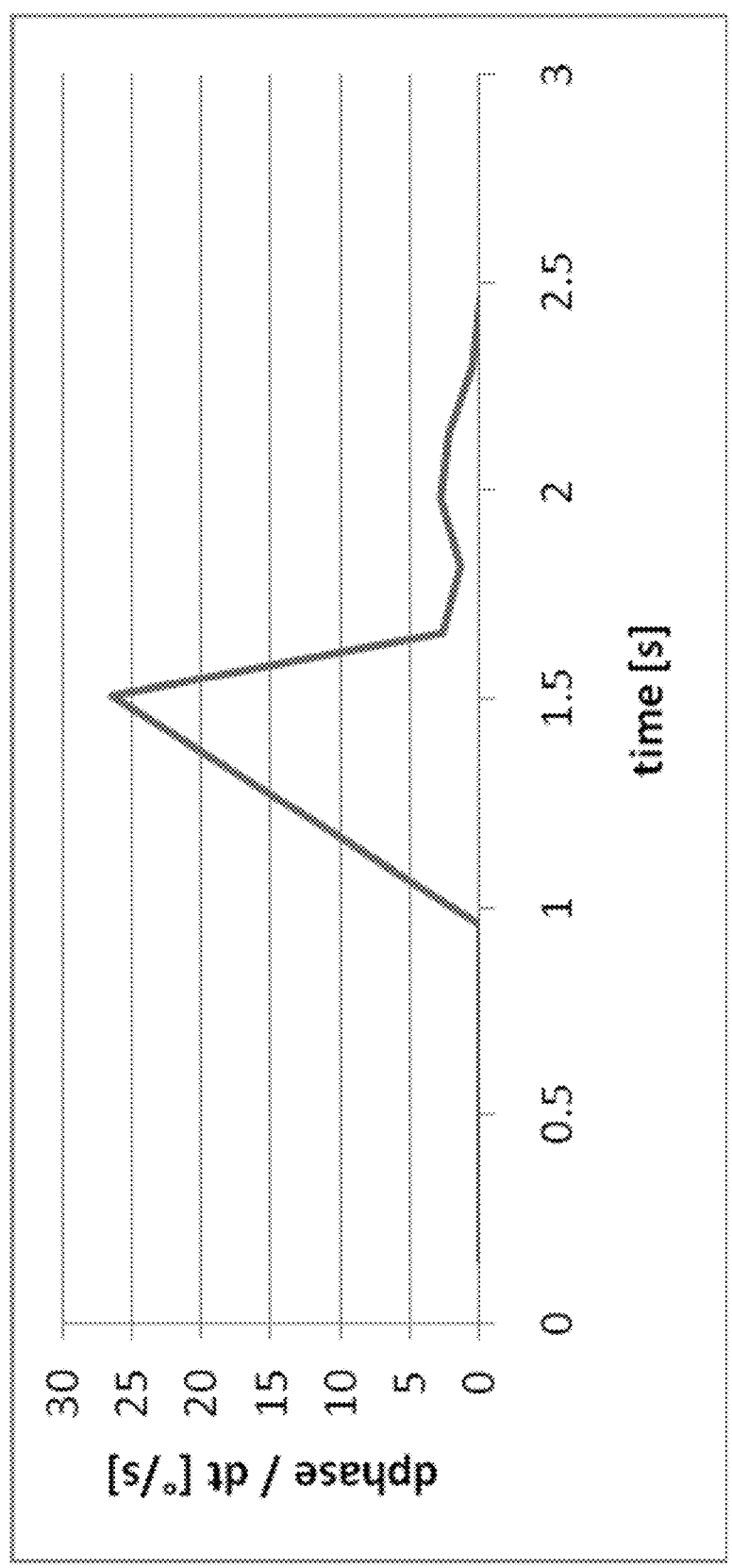
FIG. 37 is a graphical representation of the derivate of the phase shift during the electrosurgical fusion process.

Instead of the tissue quickly reaching a pre-determined phase (ranging from 40 to 60 degrees, depending on type of tissue), the measured phase shift approaches the cut-off threshold asymptotically. This is shown in FIG. 36 for the same seal as given in FIG. 35. As can be seen, the phase shift quickly increases during the initial fusion process, but then increases slowly for the remainder of the seal. The asymptotic approach can require a significant amount of time to reach the final phase threshold (e.g., 40 degrees). As such, instead of depending on the phase value to reach a definite value alone, additionally the derivate of the phase can be used to avoid asymptotic approaches to a finalized phase value. The derivative of the phase value of the same seal is shown in FIG. 37. As shown, the phase changes (increases) strongly during the first 0.5 s into the seal and changes little for the remainder of the seal. After about 1.5 s sealing time, the derivative of the phase dp/dt reaches a pre-determined value of 0.1 degrees/second to terminate the seal (independent of the actual phase reading).

Figure 38:
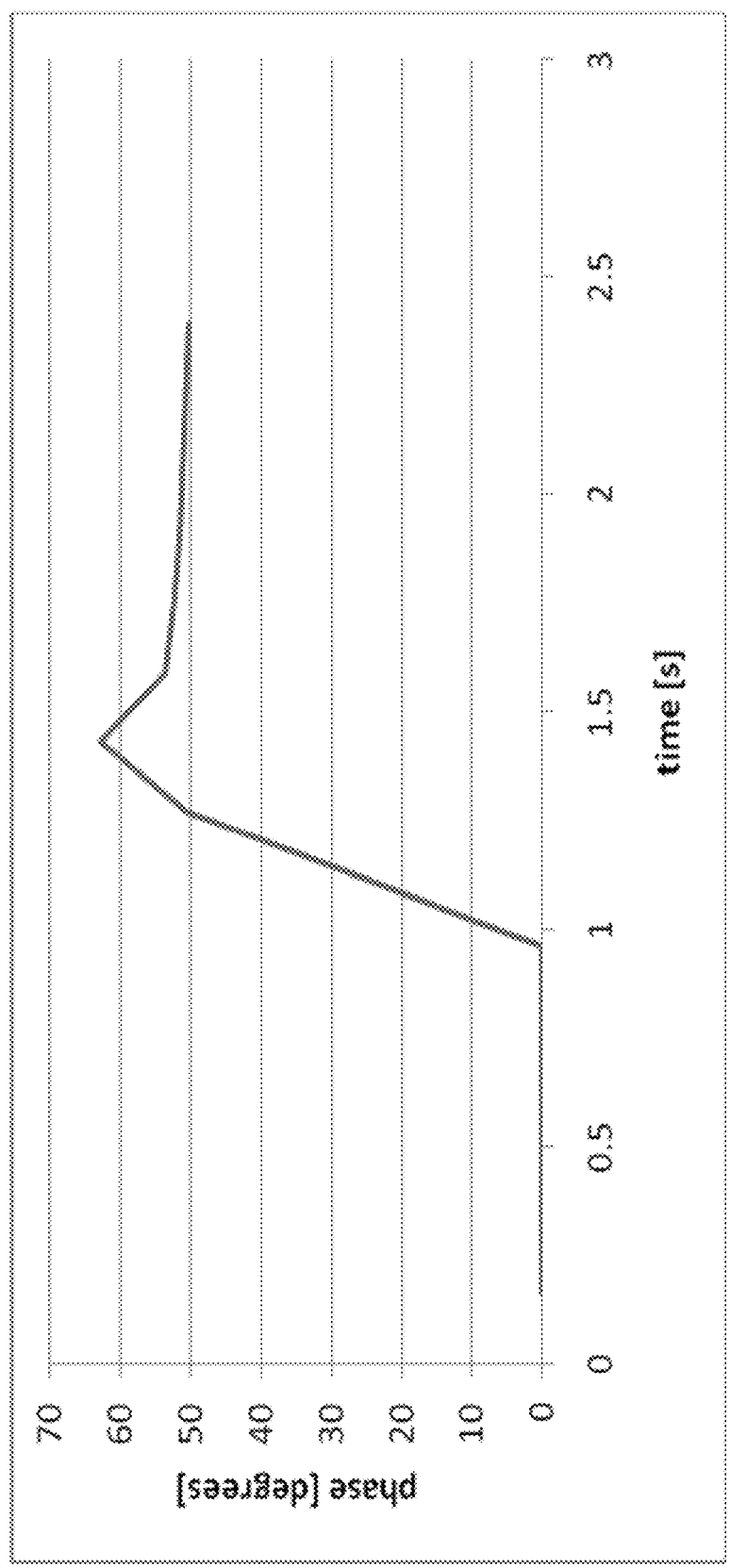
FIG. 38 is a graphical representation of phase shift during the electrosurgical fusion process.

Additionally, the determined phase value can be overshot without being detected, for example, when the phase trip level is reached during the read out time of the processor controlling the power supply. In such cases, the processor may not recognize that the final phase stop has been reached. This is shown in FIG. 38 for welding of porcine intestines. As can be seen, the phase shift overshoots a pre-determined phase threshold of 60 degrees, but instead reaches an asymptotic steady-state level of 50 degrees. Instead of relying on the phase value to reach a definite value alone, the derivate of the phase is also used to ensure the seal to end.

Figure 39:
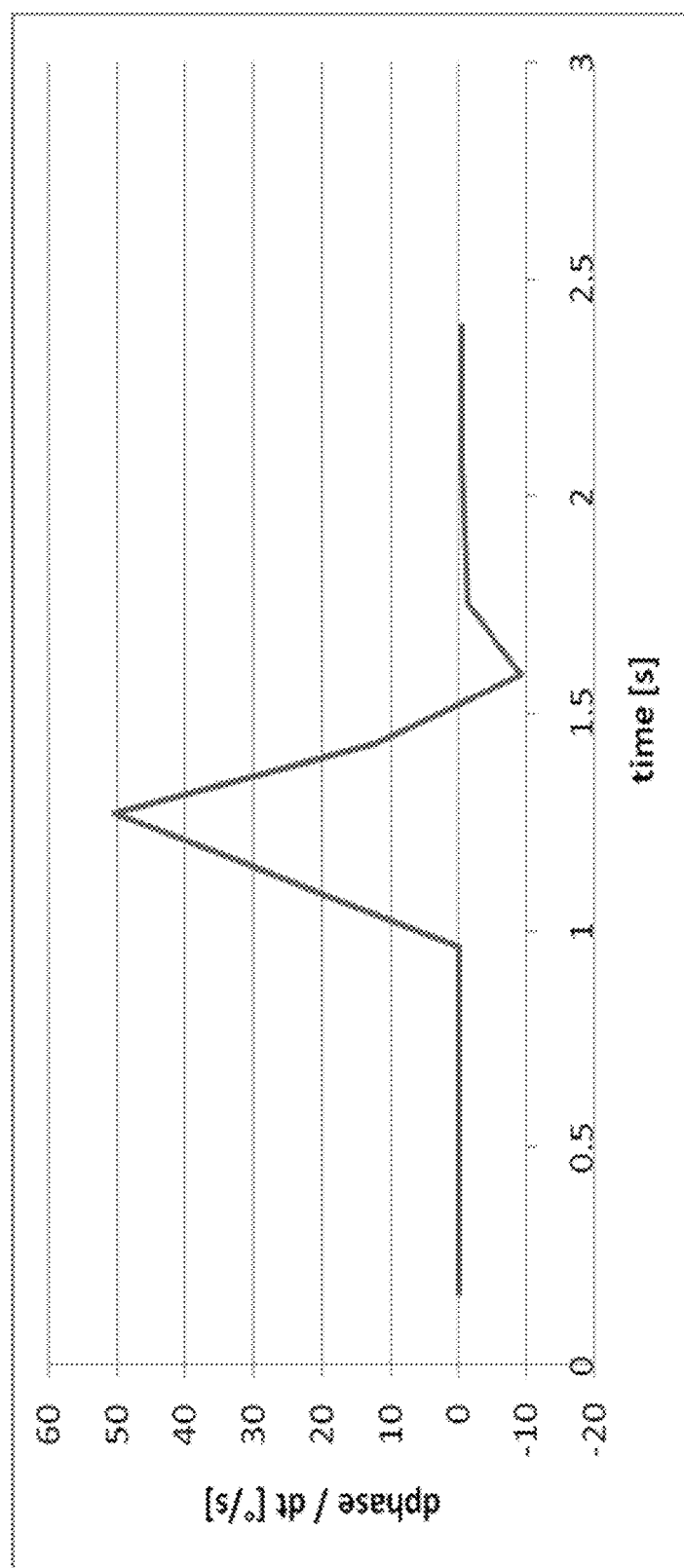
FIG. 39 is a graphical representation of the derivate of the phase shift during the electrosurgical fusion process.

The derivative of the phase value of the same seal is shown in FIG. 39. As shown, the phase changes (increases) strongly during the first 0.25 s into the weld and changes only little for the remainder of the seal. At about 1.5 s into the weld, the derivative of the phase dp/dt reaches a pre-determined value of 0.1 degrees/second and terminates the weld (independent of the actual phase reading). The derivate of the phase in one embodiment is set to 0.02 degrees per second. A range of phase derivate from 0.2 to 0.01 degrees per second has also been found to be acceptable. In the latter case, the derivate of the phase angle reading provides a safety feature for terminating a seal/weld.

As previously described and described throughout the application, the electrosurgical generator ultimately supplies RF energy to a connected electrosurgical tool. The electrosurgical generator ensures that the supplied RF energy does not exceed specified parameters and detects faults or error conditions. In various embodiments, however, an electrosurgical tool provides the commands or logic used to appropriately apply RF energy for a surgical procedure. An electrosurgical tool includes memory having commands and parameters that dictate the operation of the tool in conjunction with the electrosurgical generator. For example, in a simple case, the generator can supply the RF energy but the connected tool decides how much energy is applied. The generator however does not allow the supply of RF energy to exceed a set threshold even if directed to by the connected tool thereby providing a check or assurance against a faulty tool command.

In one embodiment, each tool comes with an integrated circuit that provides tool authentication, configuration, expiration, and logging. Connection of tools into the receptacles or ports initiates a tool verification and identification process. Tool authentication in one embodiment is provided via a challenge-response scheme and/or a stored secret key also shared by the controller. Other parameters have hash keys for integrity checks. Usages are logged to the controller and/or to the tool integrated circuit. Errors in one embodiment can result in unlogged usage. In one embodiment, the log record is set in binary and interpreted with offline tools or via the controller.

In one embodiment, connection of a standard bipolar tool into the standard bipolar outlet will not actively check the tool. However, the controller recognizes a connection so that the information on the bipolar outlet can be displayed on the monitor or user interface of the unit. The display reserves a field for the bipolar outlet before the outlet is activated. In one embodiment, the controller uses time measurement components to monitor a tool's expiration. Such components utilize polling oscillators or timers, real-time calendar clocks and are configured at boot time. Timer interrupts are handled by the controller and can be used by scripts for timeouts. Logging also utilizes timers or counters to time-stamp logged events.

The tool in one embodiment has memory integrated with or removable from the tool. A tool algorithm or script within the tool's memory is loaded into a script interpreter of the generator. The script provides commands and parameters readying the tool for use when connected to the generator. Upon activation of a switch coupled to the tool, the controller detects the switch closure, and authenticates the tool, checks the tool's expiration status, and initializes internal data structures representing the receptacle's tool. A subsequent activation of the tool switch initiates an event that causes the script to direct the generator to supply RF energy. The controller logs the usage to both the tool and the generator. When the tool is disconnected from the receptacle of the generator, the controller resets the information associated with the receptacle. The controller constantly monitors the generator for proper operation. Unrecoverable errors and faults are announced and further operation of the system is prevented. All faults are stored in the controller's memory and/or the tool's memory.

Data from a specific procedure (e.g., from power-up to power-down) is stored on each tool. The tool additionally holds the data from a procedure, i.e., the number of tool uses, the power setting and faults. Each tool in one embodiment holds the information from all other tools as well. Tool memory includes but is not limited to the following parameters: serial number of generator, time stamp, tissue assessment and endpoint setting for each tool use, cut, coagulation, weld, power setting, duration of RF and endpoint (auto stop, fault, manual stop, etc.).

The generator logs usage details in an internal log that is down loadable. The generator has memory for storage of code and machine performance. The generator has reprogrammable memory that contains instructions for specific tool performance. The memory for example retains a serial number and tool use parameters. The generator stores information on the type of tools connected. Such information includes but is not limited to a tool identifier, e.g., a serial number of a connected tool, along with a time stamp, number of uses or duration of use of the connected tool, power setting of each and changes made to the default setting. The memory in one embodiment holds data for about two months or about 10,000 tool uses and is configured to overwrite itself as needed.

In one embodiment, the controller includes a state machine interpreter module that parses tool scripts. Tool scripts represent a tool process for a specific or given tool. The tool scripts are stored on memory connected to or integrated with a tool, the controller or a combination thereof. The state machine interpreter module responds to specific events, such as a switch activation/de-activation, tool positions or exceeding measurement thresholds. The module upon response controls the output of RF energy and/or electrode activation. In one embodiment, an interpreter module is provided for each tool input receptacle. The controller detects tool events and forwards the detected event to the appropriate interpreter module. The module in turn requests actions of the controller based on the detected event which provides output to the connected tool associated with the appropriate tool input receptacle and also the appropriate interpreter module.

In one embodiment, the controller has a specific or predetermined fixed tool script for a specific input receptacle. As such, only this tool script is used for the tool connected to the particular input receptacle. The interpreter module includes an event detector and a script parser. The event detector receives and identifies tool events, such as a switch activation/de-activation event or a measurement event (e.g., phase threshold exceeded). The event detector formulates requests to the controller to control RF output, output selection and/or selection of outputs, changes to the display and audio tones. Other events detected include detecting hand and foot switches, jaw switches, phase over and phase under-after-over events, shorts and opens, tool script states. The script parser interprets the tool scripts. Keywords in the scripts assist the script parser to extract operational commands and data for tool operation based on a detected event identified by the event detector. In addition to the voltage, current, etc. set points, a tool script specifies the RF source as from the CUT or the COAG source. The script also specifies which electrodes get connected to RF+, RF−, or allowed to float. Because the script controls the electrode configuration, and can set thresholds that trigger events, a script can completely reconfigure tool during its use.

The script controls the voltage and current output settings as well as sequences of voltage and current settings. For example the permittivity and conductivity of blood vessels is the same independent of size. A small blood vessel will fuse very rapidly while a large vessel may take several seconds. Applying a large amount of current to a small vessel may cause excess tissue damage, while using a small amount of current will take an unacceptably long time to perform the fusion function. So to modify tool performance the script can initially command a small amount of RF current, and if fusion endpoint is not reached in less than one second, a high current is commanded to speed the fusion of a large vessel. Another script usage to modify tool performance to switch from one operation (coagulation) to another operation (cut) is to reconfigure the tool electrodes and ESG output to simplify a multistep process such as fuse and cut. When the clinician starts the process the script will first setup the unit for the fusion, measure the tissue phase angle that indicates the fusion endpoint. RF power is then turned on until the fusion endpoint is reached. The unit will then turn off RF power and beep to indicate that fusion is complete. The unit then switches the electrodes to the cut configuration, sets the RF output for cut, and restarts the RF output. The cut operation is stopped by the clinician when the cut is completed.

Figure 40:
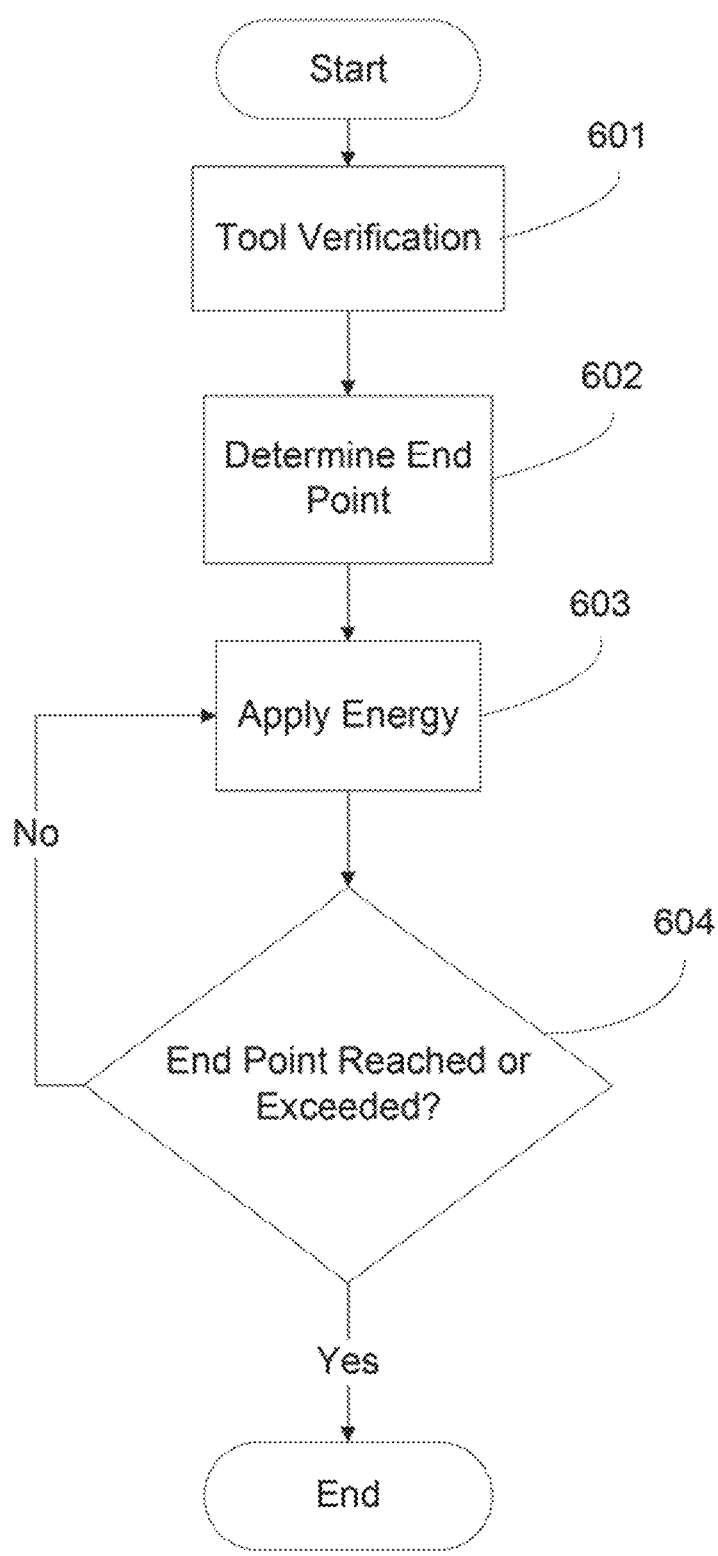
FIG. 40 is a block diagram of a fusion or welding process of an electrosurgical unit.

Referring to FIG. 40, an overview of tool operations is provided. A tool connected to the electrosurgical generator is verified 601. The endpoint is determined 602. The tool applies energy 603, e.g., RF energy, and continues until an endpoint is reached or an error condition is detected. Upon determination of an endpoint being reached or exceeded 604, the tool is deactivated (e.g., application of energy is stopped) ending the process.

Based on the tool algorithm for the connected tool, the tool verification and determination of an end point can vary. In particular, a tool short is determined by measuring resistance at a tissue contacting surface of the tool. If the resistance is less than ten (10) Ohms, a tool short condition is recognized. In accordance with various embodiments, the product of measured tissue permittivity and conductivity or an initial phase shift is utilized to determine the end point for a connected tool.

In accordance with various embodiments, phase shift and/or a phase rate of change is measured throughout the process to determine if an endpoint is reached or exceeded. Also, timeout parameters, e.g., a timer or counter reaching or exceeding a set time limit, or a fault condition stops or interrupts the process even if the determined end point is not reached or exceeded.

Handheld Electrosurgical Tools

As described generally above and described in further detail below, various handheld electrosurgical tools can be used in the electrosurgical systems described herein. For example, electrosurgical graspers, scissors, tweezers, probes, needles, and other instruments incorporating one, some, or all of the aspects discussed herein can provide various advantages in an electrosurgical system. Various embodiments electrosurgical tool are discussed below. It is contemplated that one, some, or all of the features discussed generally below can be included in any of the embodiment of tool discussed below. For example, it can be desirable that each of the tools described below include a memory for interaction with a feedback circuit as described above. However, in other embodiments, the tools described below can be configured to interact with a standard bipolar power source without interaction of a tool memory. Furthermore, although it is contemplated that certain aspects of these embodiments can be combined with certain aspects of other electrosurgical tools within the scope of this application. Certain aspects of these electrosurgical tools are discussed generally herein, and in more detail with respect to various embodiments below.

As discussed above with respect to FIGS. 1A and 1B, and electrosurgical tool can desirably include a memory. The memory can include an encryption module and a configuration device module. The configuration device module can store certain types of tool data. For example the configuration device module can store operational parameters for the tool, including software to be transferred to an electrosurgical unit upon successful electrical connection to the electrosurgical unit. These operational parameters can include data regarding various electrosurgical procedures to be performed by the tool and corresponding energy level ranges and durations for these operations, data regarding electrode configuration of a tool, and data regarding switching between electrodes to perform different electrosurgical procedures with the tool. Advantageously, unlike prior art electrosurgical systems, changes to tool profiles and periodic tool updates can be rapidly made without downtime to electrosurgical generators, as the software for tool operation can reside in electrosurgical tool itself, rather than the generator. Accordingly, updates can be made during tool production.

The configuration device module can further store a data log comprising, for example, a record of information of each previous tool use. For example, in some embodiments, the data log can contain timestamp data including an electrosurgical unit identifier, a log of electrosurgical procedures perform by the tool, and along of durations and energies applied to the tool. In some embodiments, it can be desirable that use of a particular tool is limited to a maximum usage period or number of procedures, especially where electrosurgical tool has not been configured for sterilization and reuse. Accordingly, in some embodiments, the configuration device module can be configured to prevent operation of a tool after a predetermined usage or number of procedures. In some embodiments, a tool can comprise a mechanical lockout in addition to or in place of the data log, such as a breakaway single-use connector to reduce the possibility of unintended reuse.

In some embodiments, it is desirable that the tool communicate with the electrosurgical unit through an encrypted protocol. Accordingly, the memory can further store an encryption module, or encryption key to facilitate this encrypted communication.

As discussed above with respect to FIG. 18 and one be, it can be desirable that an electrosurgical tool for use in the electrosurgical system includes one or more audio and/or visual indicators. In some embodiments, the electrosurgical tool can include an array of LEDs, or a multi-color LED assembly such as a three-color LED assembly capable of generating many combined colors. The visual indicator can be configured to illuminate with a color corresponding to the type of electrosurgical procedure performed by the tool. Were a tool is configured to perform multiple different types of electrosurgical procedures, desirably the visual indicator updates to reflect the currently-selected electrosurgical procedure. Thus, advantageously, a user can tell, while watching the surgical field, what type of electrosurgical procedure the tool is configured to perform.

Electrosurgical Fusion Tool

Figure 41A:
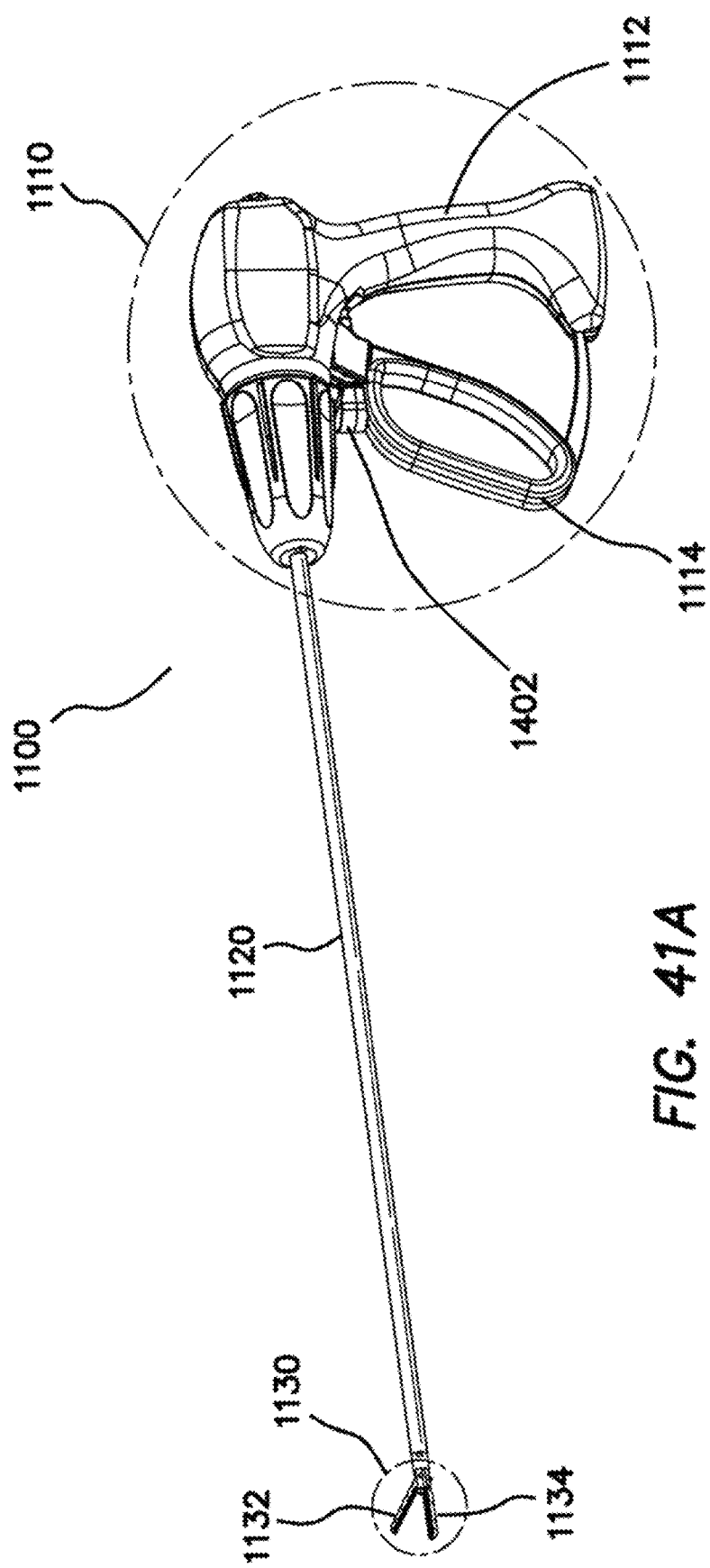
FIG. 41A is a perspective view of an embodiment of laparoscopic sealer/divider.
Figure 41B:
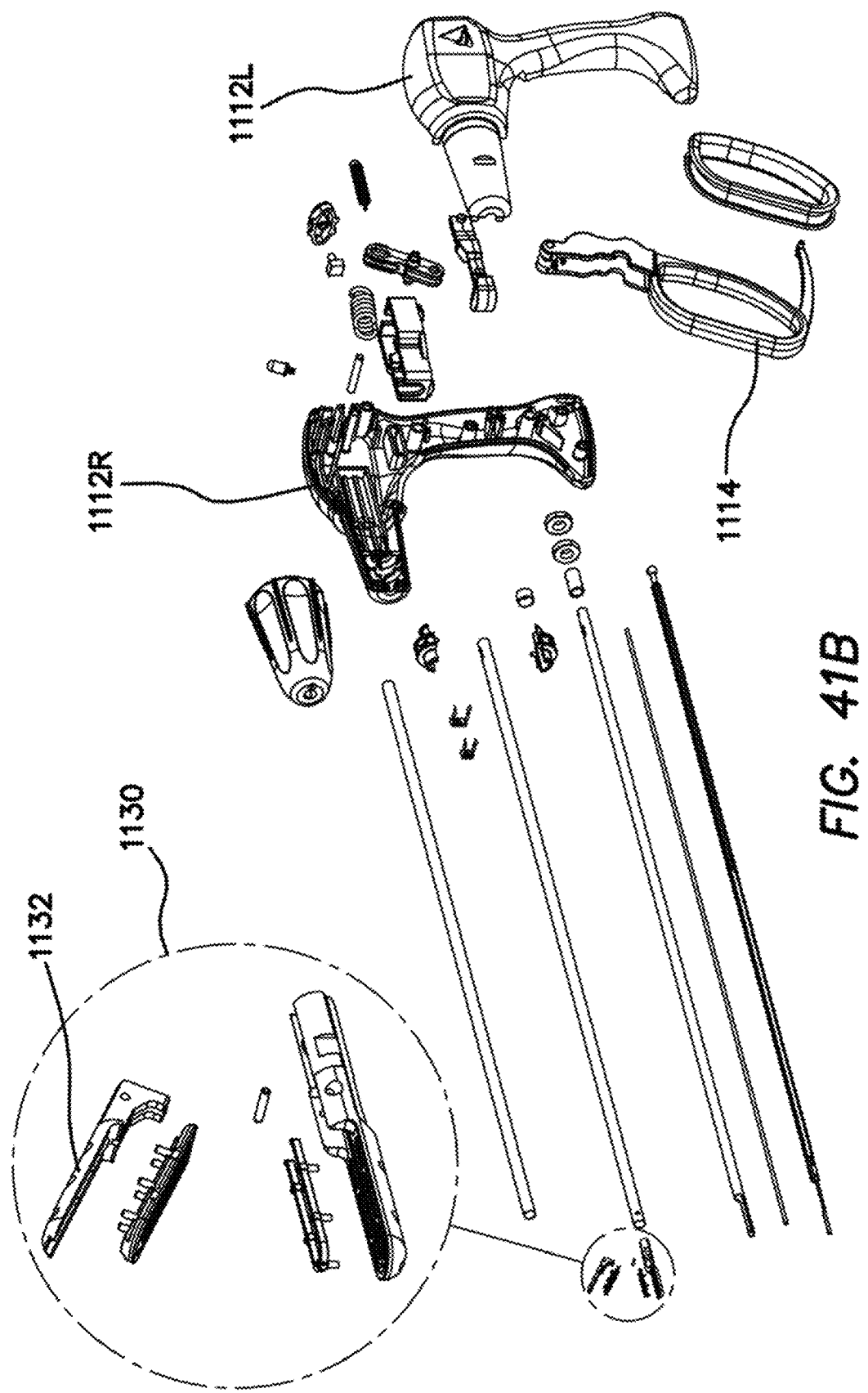
FIG. 41B is a disassembled view of a laparoscopic sealer/divider of FIG. 1A.

With reference to FIGS. 41A-41B, one embodiment of a hand held laparoscopic sealer/divider or fusion tool 1100 is provided. In the illustrated embodiment, the sealer/divider comprises a handle assembly 1110, an elongate shaft 1120 extending from the handle assembly 1110, and a jaw assembly 1130 positioned on the elongate shaft 1120 opposite the handle assembly 1110. The elongate shaft 1120 has a proximal end and a distal end defining a central longitudinal axis therebetween. In the illustrated embodiment, the handle assembly 1110 comprises a pistol-grip like handle. The elongate shaft 1120 and the jaw assembly 1130, in one embodiment, are sized and shaped to fit through a 5 mm diameter trocar cannula or access port. In other embodiments, the elongate shaft and jaw assembly can be sized and configured to fit through trocar cannulae or access ports having other standard, or non-standard sizes. In FIG. 41A, the handle assembly 1110 is shown in a first or initial position in which the jaws are open.

With reference to FIGS. 41A-42B, the handle assembly 1110 comprises a stationary handle 1112 and an actuation handle 1114 movably coupled to the stationary handle. In the illustrated embodiment, the stationary handle 1112 comprises a housing formed of right 1112R and left 1112L frames. In other embodiments, the stationary handle 1112 can be a single component, or can be a housing formed of more than two pieces. In the illustrated embodiment, the actuation handle 1114 is slidably and pivotally coupled to the stationary housing, as discussed in further detail below. In operation, the actuation handle 1114 can be manipulated by a user, e.g., a surgeon to actuate the jaw assembly, for example, selectively opening and closing the jaws.

Figure 42A:
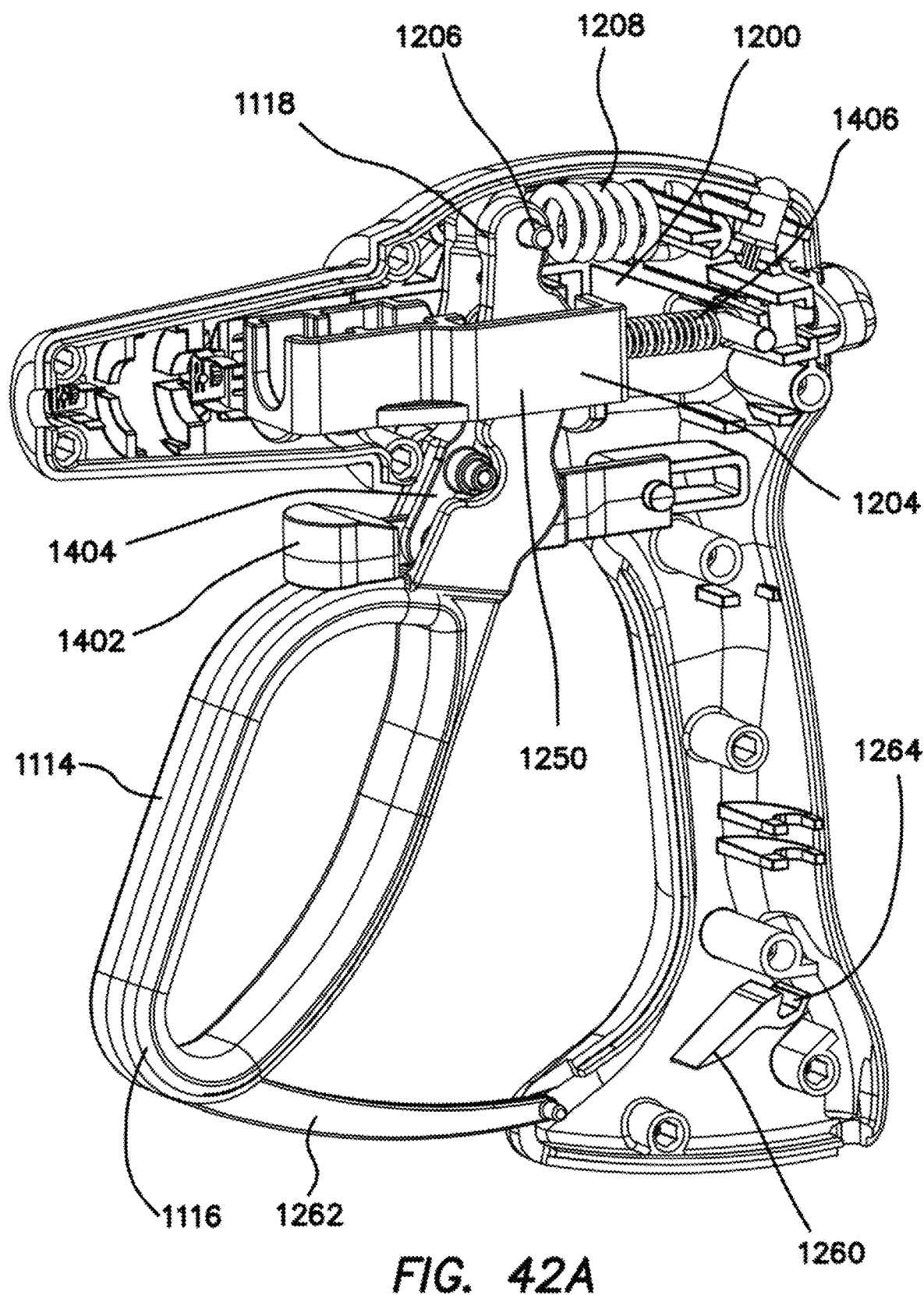
FIGS. 42A-42C are views of an actuator of the laparoscopic sealer/divider of FIG. 41A.
Figure 42B:
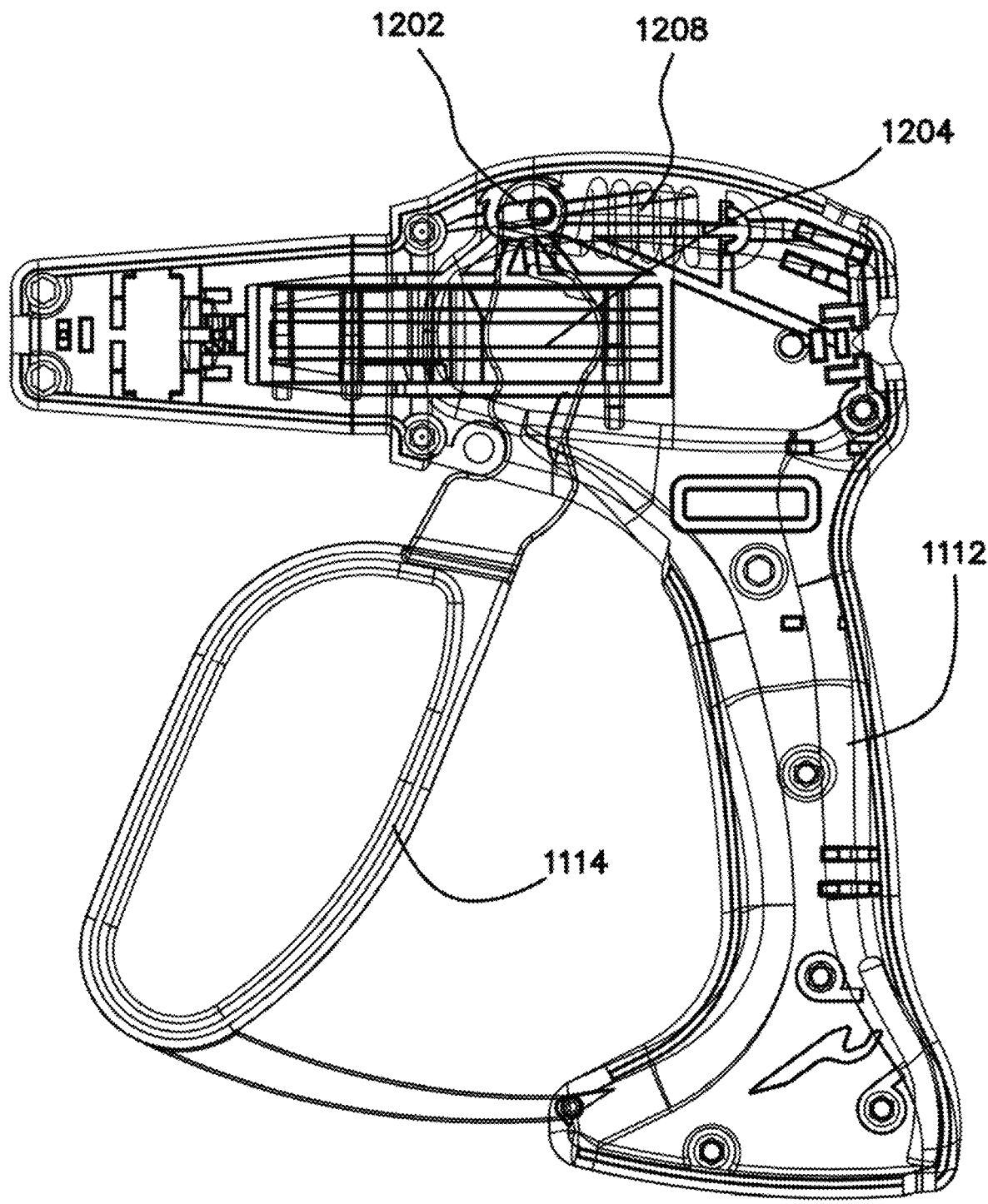

With continued reference to FIGS. 42A-42B, in the illustrated embodiment, the actuation handle 1114 is coupled to the stationary handle 1112 to form a force regulation mechanism 1200 coupling the handle assembly 1110 to the jaw assembly 1130. Desirably, the force regulation mechanism 1200 can be configured such that in a closed configuration, the jaw assembly 1130 delivers a gripping force between the first jaw 1132 and the second jaw 1134 between a predetermined minimum force and a predetermined maximum force.

With continued reference to FIGS. 42A-42B, in the illustrated embodiment, the actuation handle 1114 is coupled to the stationary handle 1112 at two sliding pivot locations 1202, 1204 to form the force regulation mechanism 1200. The actuation handle 1114 has a first end 1116 including a gripping surface formed thereon, and a second end 1118 opposite the first end 1116. In the illustrated embodiment, the actuation handle 1114 is coupled to a pin 1206 adjacent the second end 1118. In some embodiments, the actuation handle 1114 can be integrally formed with a protrusion extending therefrom defining a pin surface, while in other embodiments, a pin can be press-fit into an aperture in the actuation handle. The 1206 pin can be contained within slots in the stationary handle 1112, such as corresponding slots formed in the right and left handle frames 1112R, 1112L of the stationary handle housing. These slots can allow the sliding pin 1206 to move over a predetermined range. In some embodiments, the slots can be configured to define a desired actuation handle path as the actuation handle is moved from the first position corresponding to open jaws to a second position corresponding to closed jaws. For example, the illustrated embodiment includes generally linear slots formed in the stationary handle 1112 at an angle from the central longitudinal axis of the elongate shaft 1120. In other embodiments, the slots can be formed generally parallel to the central longitudinal axis. In some embodiments, the slots can be curvilinear.

In the illustrated embodiment, the force regulation mechanism 1200 includes a biasing member such as a trigger spring 1208 that biases the pin in a proximal direction towards the rear of the pin slots in the right and left handle frames (see, for example, FIG. 42B). The trigger spring 1208 and the actuation handle 1114 can pivot freely or unhindered at their attachment point 1202. The biasing member 1208 can be preloaded to a predetermined force. In operation, as a predetermined force is exerted on the actuation handle 1114, a biasing force exerted by the trigger spring 1208 is overcome, and the second end 1118 of the actuation handle 1114 can translate generally distally, guided by the pin in the slots.

While the illustrated embodiment includes a pin-in-slot arrangement coupling one pivot point of the actuation handle to the stationary handle, in other embodiments, it is contemplated that other connections can be formed. For example, in some embodiments, a slot can be formed in the actuation handle and a mating projection can be formed in the stationary handle. Furthermore, while the illustrated embodiment includes a tension coil spring forming the biasing member, in other embodiments, other biasing members are contemplated. For example, the biasing member can comprise a compression spring, a torsion spring, an elastomeric band, a fluid-filled shock absorbing unit, or another suitable biasing device.

With continued reference to FIGS. 42A-42B, in the illustrated embodiment, the actuation handle 1114 is slidably and pivotably coupled to the stationary handle 1112 at a location between the first and second ends 1116, 1118 of the actuation handle. An actuation member such as a pull block 1250 can be coupled to the actuation handle. In the illustrated embodiment, an actuation path of the pull block 1250 is defined by rails formed in the right and left handle frames 1112L, 1112R. When the actuation handle 1114 is moved proximally, the pull block 1250 also moves, effectively closing the jaws thereby clamping any tissue between the jaws. In the illustrated embodiment, the rails guide the pull block 1250 to slide proximally and distally while limiting movement in other directions. In other embodiments, various other guide members such as a pin-in-slot arrangement can define the actuation path of the actuation member.

As illustrated, the pull block 1250 comprises a generally rectangular prismatic structure having a generally open top and bottom faces and a substantially closed proximal end. The actuation handle 1114 can extend through the top and bottom faces of the pull block 1250. An edge of the actuation handle 1114 can bear on the proximal end of the pull block 1250 such that movement of the actuation handle 1114 relative to the stationary handle can move the pull block 1250 generally longitudinally along the actuation path defined by the rails. A distal end of the pull block 1250 can be coupled with an actuation shaft such as an actuation tube, bar, or rod, which can extend longitudinally along the elongate shaft of the sealer/divider. Thus, in operation, movement of the actuation handle 1114 from the first position to the second position translates the pull block 1250 longitudinally within the stationary housing, which correspondingly translates the actuation rod generally linearly along the longitudinal axis with respect to the elongate shaft. Movement of this actuation tube can control relative movement of the jaws in the jaw assembly.

With continued reference to FIGS. 42A and 42B, in some embodiments, the sealer/divider can include a latch mechanism 1260 to maintain the actuation handle 1114 in the second position with respect to the stationary handle. In the illustrated embodiment, the actuation trigger comprises an extended latch arm 1262 which can engage a matching latch 1264 contained within actuation handle 1112 for holding the actuation trigger at a second or closed position. In other embodiments, it is contemplated that the one portion of the latch mechanism can be formed on a portion of the actuation handle 1114 adjacent the second end of the actuation handle 1114, and a mating portion of the latch mechanism can be formed on the actuation handle 1112. In still other embodiments, it is contemplated that a portion of the latch mechanism can be formed on the pull block 1250 and a mating portion of the latch mechanism can be formed on the stationary housing.

In some embodiments, the jaw assembly 1130 of the sealer/divider comprises an advanceable cutting blade 1400 (FIG. 44B) that can be coupled to a blade actuator such as a blade trigger 1402 positioned on the handle assembly 1110. A blade actuation mechanism 1404 can operatively couple the blade trigger to the cutting blade. In the illustrated embodiment, the blade trigger 1402 is positioned on a proximal surface of the handle assembly such that it can be easily operated in a pistol-grip fashion. As illustrated, the blade actuation mechanism 1404 comprises a pivoting blade advancement link that transfers and reverses the proximal motion of the blade trigger 1402 to a blade actuation shaft assembly coupled to the cutting blade. In other embodiments, the blade trigger 1402 can be positioned elsewhere on the actuation handle 1112 such as on a distal surface of the actuation handle 1112 such that distal movement of the blade trigger 1402 can advance the cutting blade distally without transfer of advancement directions via a linkage. In operation, a user can move the blade trigger 1402 proximally to advance the cutting blade 1400 from a retracted position to an extended position. The blade actuation mechanism 1404 can include a biasing member such as a blade return spring 1406 to biases the blade advancement lever distally within the actuator and thereby bias the cutting blade 1400 into the retracted position.

Figure 42C:
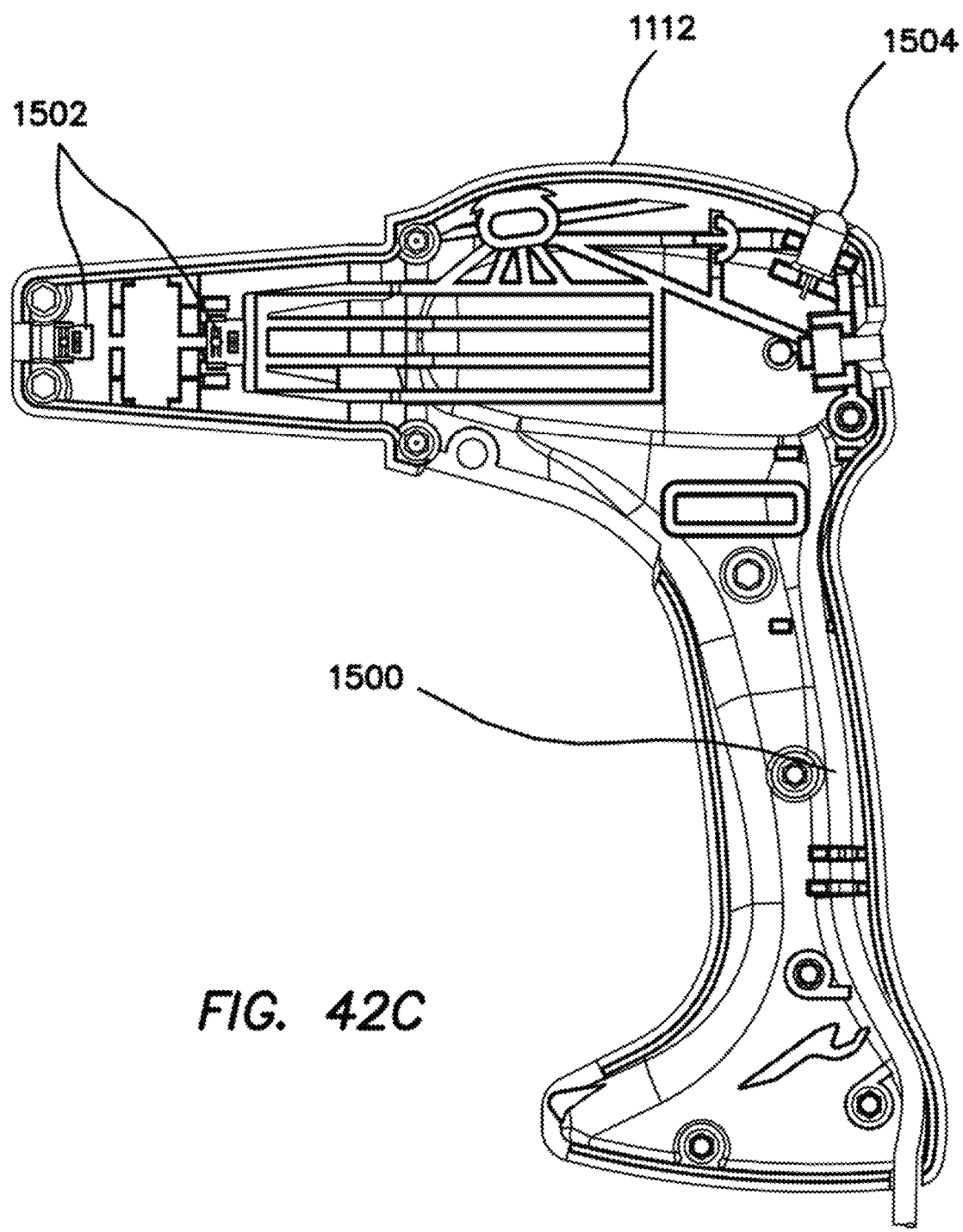

With reference to FIG. 42C, the handle assembly also comprises a wire harness 1500. The wire harness 1500, in certain embodiments, comprises six insulated individual electrical wires or leads contained within a single sheath. As illustrated, the wire harness 1500 can exit the housing of the actuation handle 1112 at a lower surface thereof and can run generally upwards along the interior of the actuation handle 1112. In other embodiments, other wire routings can be made. For example, in some embodiments, the wire harness 1500 can exit a lower portion of the proximal surface of the actuation handle 1112. The wires within the harness can provide electrical communication between the sealer/divider and an electrosurgical generator and/or accessories thereof, as discussed above.

In certain embodiments of sealer/divider, inside the actuation handle 1112, two of the leads are attached to rotational coupling clips 1502 configured to allow infinite rotation of the jaw assembly 1130, as discussed in greater detail below, two of the other leads are attached to a visible indicator 1504, such as a multi-colored LED, and the remaining two leads are attached to a switch 1506. In some embodiments, the switch 1506 is connected to a user manipulated activation button and is activated when the activation button is depressed. In one aspect, once activated, the switch 1506 completes a circuit by electrically coupling the two leads together. As such, an electrical path is then established from an electrosurgical generator to the actuator to supply radio frequency power to one of the two leads attached to the rotational coupling clips 1502.

Figure 43:
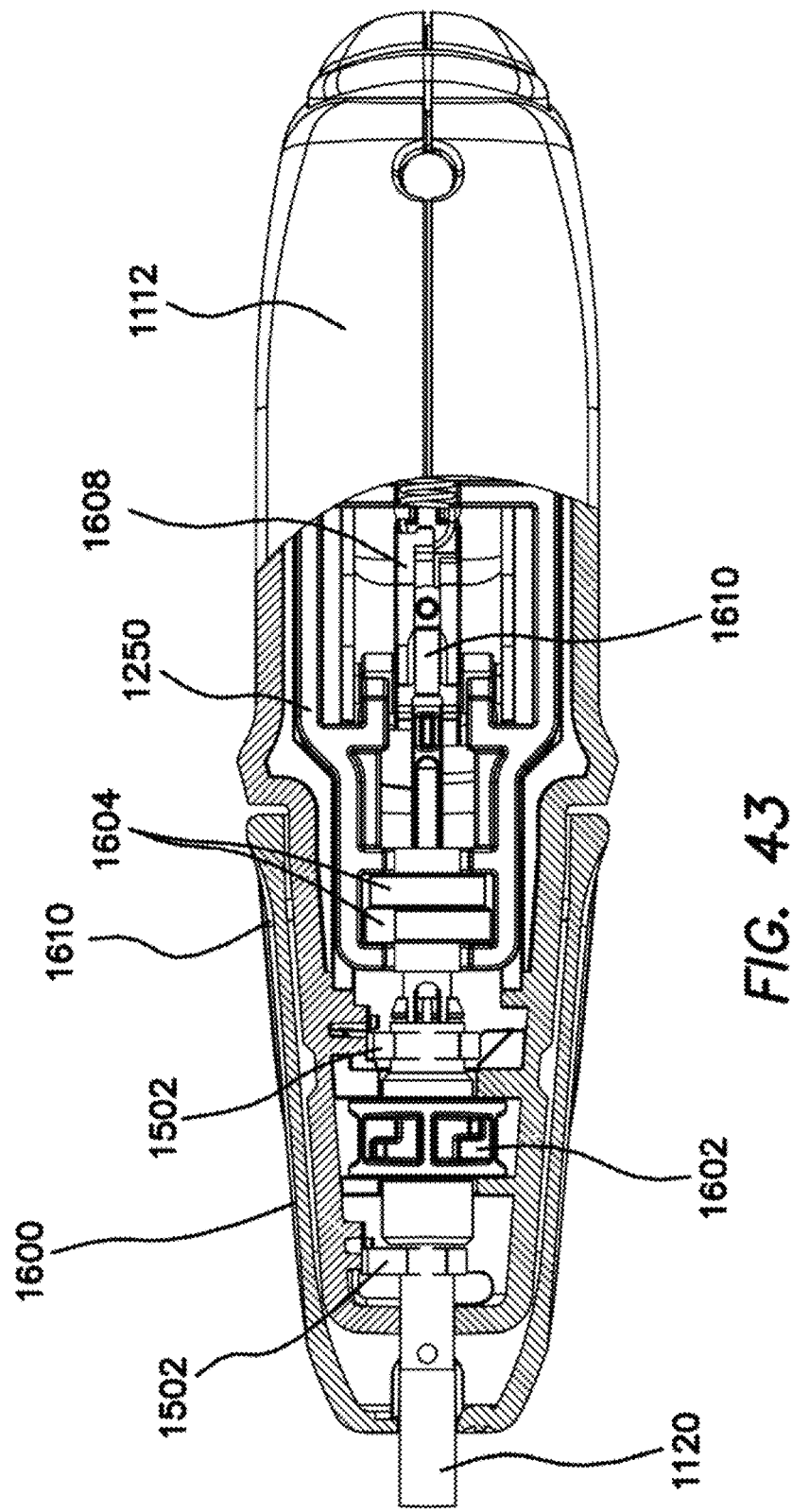
FIG. 43 is a top cross-sectional view of an actuator of a laparoscopic sealer/divider of FIG. 41A.

Referring now to FIG. 43, the handle assembly is coupled to a rotational shaft assembly 1600. In certain embodiments, coupling of the handle assembly to the rotational shaft assembly 1600 is configured to allow infinite 360 degree rotation of the jaw assembly 1130 with respect to the handle assembly. In the illustrated embodiment, the handle assembly 1110 connects to the shaft 1120 at five locations or connections providing a continuous 360 degree rotation of the entire shaft while simultaneously allowing complete actuation of the actuation handle 1114, e.g., sealing and/or dividing of the vessel. As illustrated, the first two connections are rotational coupling clips 1502 which make contact with the rotational shaft assembly at the actuation tube and conductive sleeve. The next area of engagement or the third connection is a rotational hub assembly 1602 which is located between the two rotational coupling clips 1502.

With continued reference to FIG. 43, the rotational shaft assembly 1600 is desirably contained within the right and left handle frames such that proximal and distal movement of the jaw assembly 1130 with respect to the handle assembly 1110 is prevented while allowing for rotational movement. For example, inwardly-extending flanges can be formed on the actuation handle 1112 that interfere with proximal and distal movement of the rotational hub assembly 1602, rotational coupling clips 1502, or other components of the rotational shaft assembly 1600. The fourth connection is at a plurality of threaded nuts 1604 and the pull block 1250. The fifth connection is between the blade lever 1608 and a rear blade shaft 1606. The rotation shaft assembly 1600 can also comprises a rotation knob 1610 which is fixed to the outer cover tube. The rotation knob 1610 allows the surgeon to rotate the shaft of the device while gripping the handle. While the rotational shaft assembly 1600 is illustrated as having five connection locations with the actuation handle 1112, in some embodiments, a rotational shaft assembly can have fewer connection locations, such as for example, 1, 2, 3, or 4 connection locations. In still other embodiments, it can be desirable that a rotational shaft assembly has more than 5 connection locations, such as, for example 6, 7, 8, or more than 8 connection locations.

Desirably, the rotational shaft assembly 1600 provides the vessel sealer/divider with continuous 360 degree rotation throughout operation of the electrosurgical instrument. By using rotational coupling clips 1502 for the electrical connections to the shaft, the shaft can operate, e.g., deliver RF energy, at any orientation or rotation of the jaw assembly 1130 relative to the handle assembly. Thus, advantageously, the surgeon is provided more surgical options for the placement and activation of the sealer/divider. Advantageously, with a rotational shaft assembly 1600, the wires and electrical and mechanical connections, as such, do not interfere with continuous, infinite rotation of the shaft. To maintain a bipolar connection through the rotational shaft assembly 1600, one of the electrical connections is electrically isolated from other conductive portions of the shaft.

As discussed in further detail below, in some embodiments, the sealer/divider can be configured to grasp with a gripping force within a predetermined range. In one embodiment, an overall tolerance stack-up over the length of the shaft can be controlled so that the force applied to the jaw assembly 1130 from the handle assembly can be maintained accurately within the predetermined range. The overall length of the shaft 1120 can be controlled by using threaded nuts 1604 and a threaded coupling. The threaded nuts 1604 can be adjusted to tightly control the length of the elongate shaft 1120. The length is controlled by maintaining the location of the threaded nuts 1604 in relation to the hub portions of the shaft. In the illustrated embodiment, attached to the distal end of the actuation tube is a threaded coupling. Attached to the threaded coupling are two threaded nuts, which are configured to engage with the pull block 1250. The pull block 1250 engages with the threaded nuts 1604 which are attached to the rear of the actuation tube, causing the actuation tube to move proximally. The described interaction can also be reversed so that the threaded nuts 1604 and coupling are attached to an outer cover tube rather than the actuation tube. In other embodiments, other length adjustment mechanisms can be used to control the overall tolerance stack-up such as a lock screw to selectively secure the position of the pull block 1250 at a desired location relative to the actuation tube or toothed ratchet interfaces defining set distance relationships between the pull bock and the actuation tube. In other embodiments, a length adjustment mechanism can be positioned at the distal end of the elongate shaft, e.g., where the elongate shaft interfaces with the jaw assembly 1130.

Referring to FIGS. 44A-44D, the elongate shaft 1120 can comprise a plurality of actuation members extending therethrough. In the illustrated embodiment, the elongate shaft comprises an actuation tube 1122 coupling the jaw assembly 1130 with the handle assembly 1110 and a blade actuation shaft assembly 1124 coupling the blade trigger 1402 with the cutting blade. In some embodiments, the blade actuation shaft assembly 1124 comprises a two-piece shaft having a proximal portion and a distal portion. The proximal portion of the blade shaft assembly can terminate at a proximal end at an interface node 1126. In the illustrated embodiment, the interface node 1126 comprises a generally spherical protrusion portion which is adapted to engage the blade advancing lever. In other embodiments, the interface node can comprise other geometries such as cubic or rectangular prismatic protrusions. In the illustrated embodiment, the proximal portion of the blade shaft is operatively coupled to the distal portion of the blade shaft assembly 1124. The distal portion of the blade shaft can comprise a mount at its distal end for attachment of the cutting blade. In the illustrated embodiment, the mount comprises at least one heat stake post. In certain embodiments, both the proximal and distal portions of the blade shaft are at least partially positioned within a generally tubular section of the actuation tube 1122. (see, e.g., FIG. 44C).

Figure 44A:
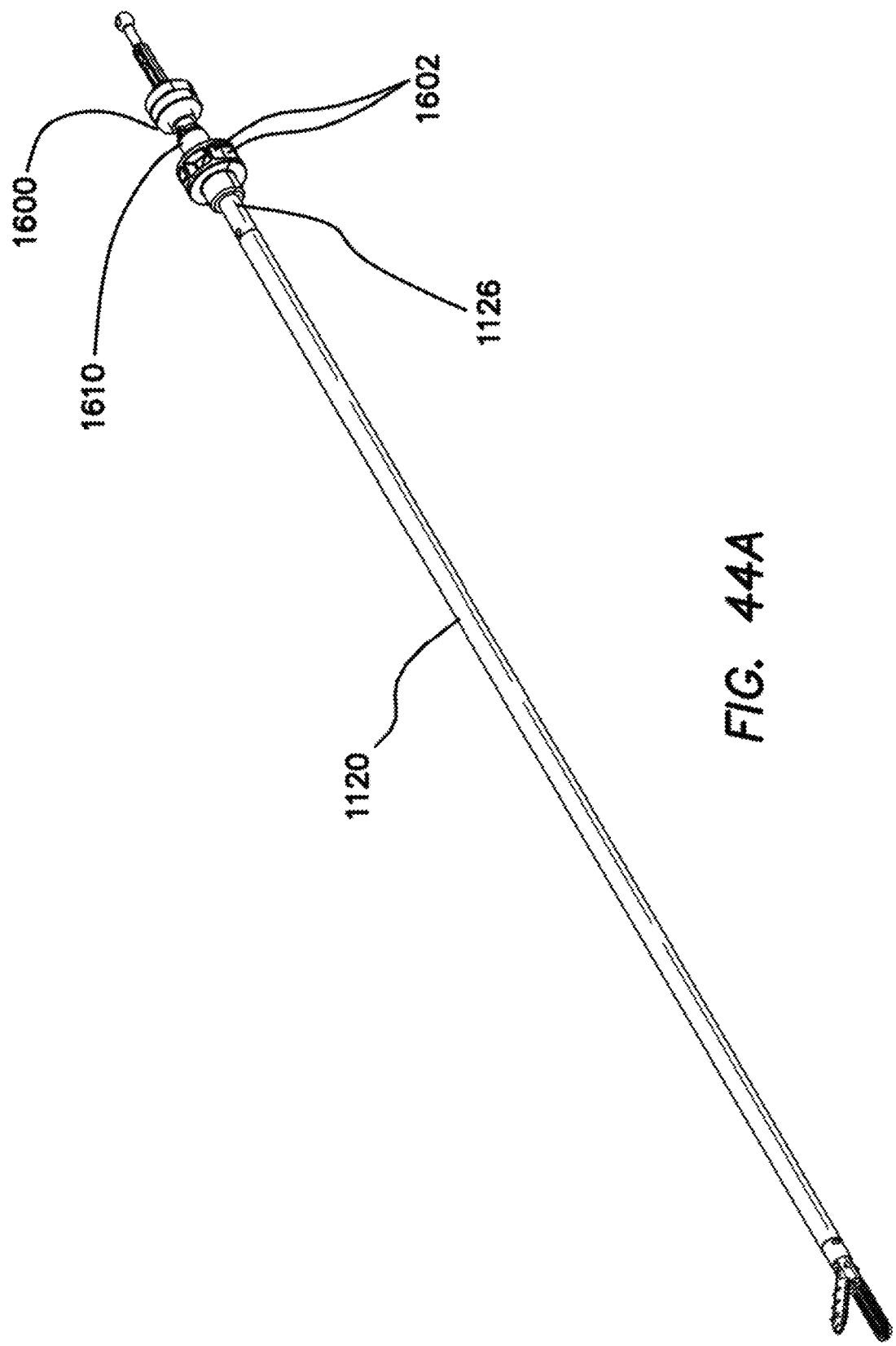
FIGS. 44A, 44B, 44C-1, 44C-2, 44C-3, and 44D are views of a shaft assembly of a laparoscopic sealer/divider of FIG. 41A.
Figure 44B:
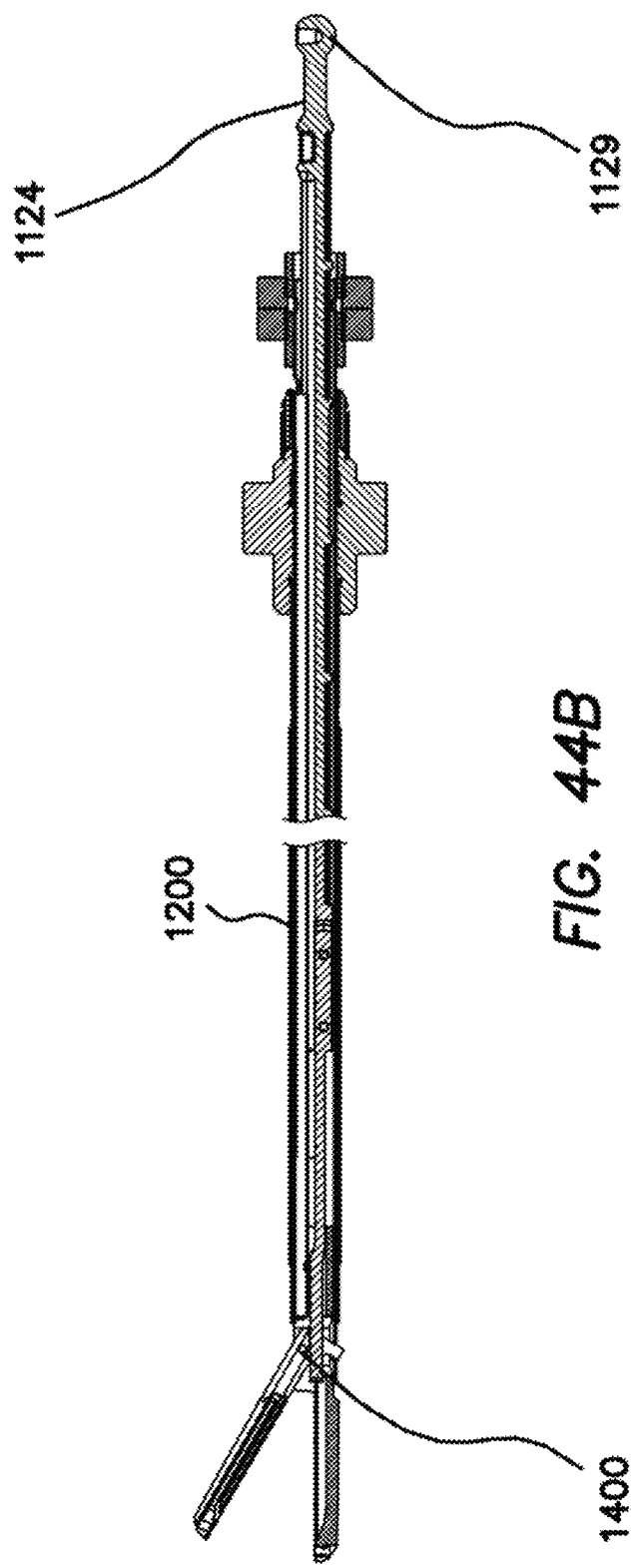
Figures 1, 44C:
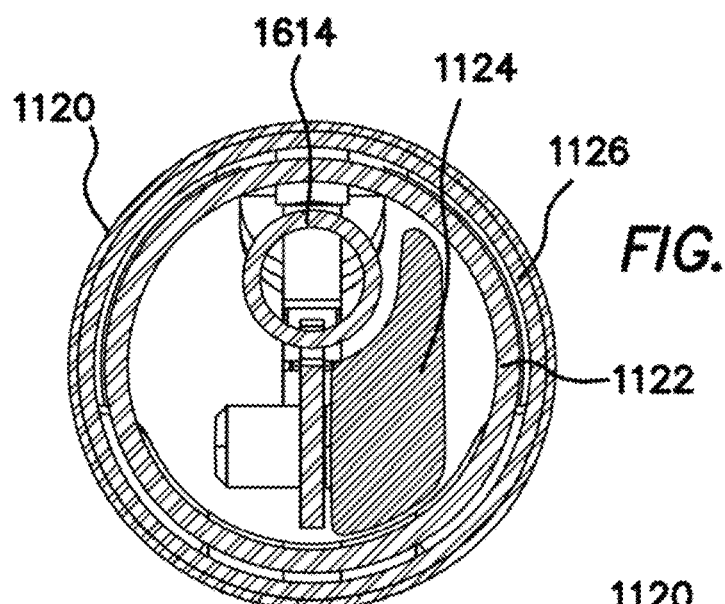
Figures 2, 44C:
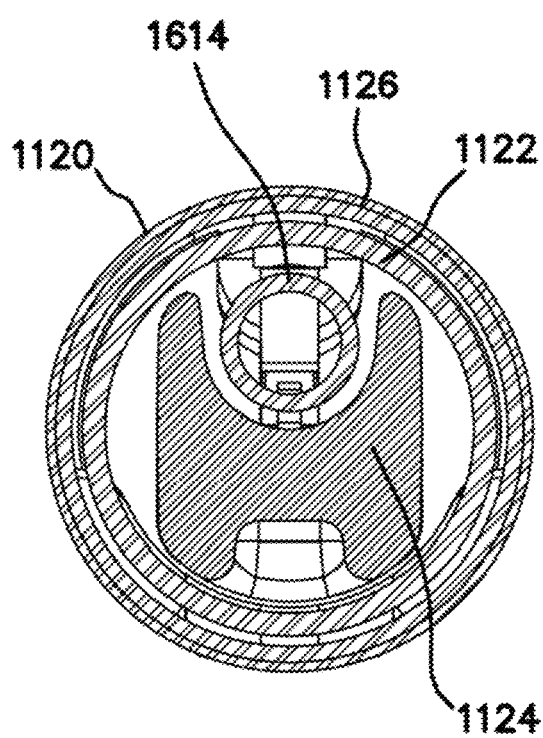
Figures 3, 44C:
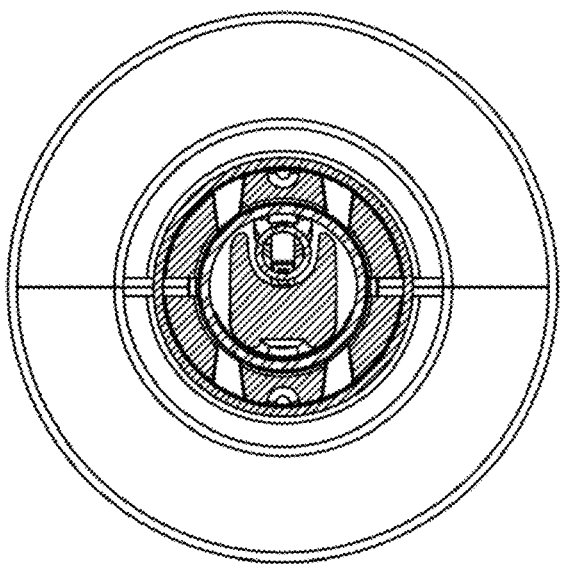
Figure 44D:
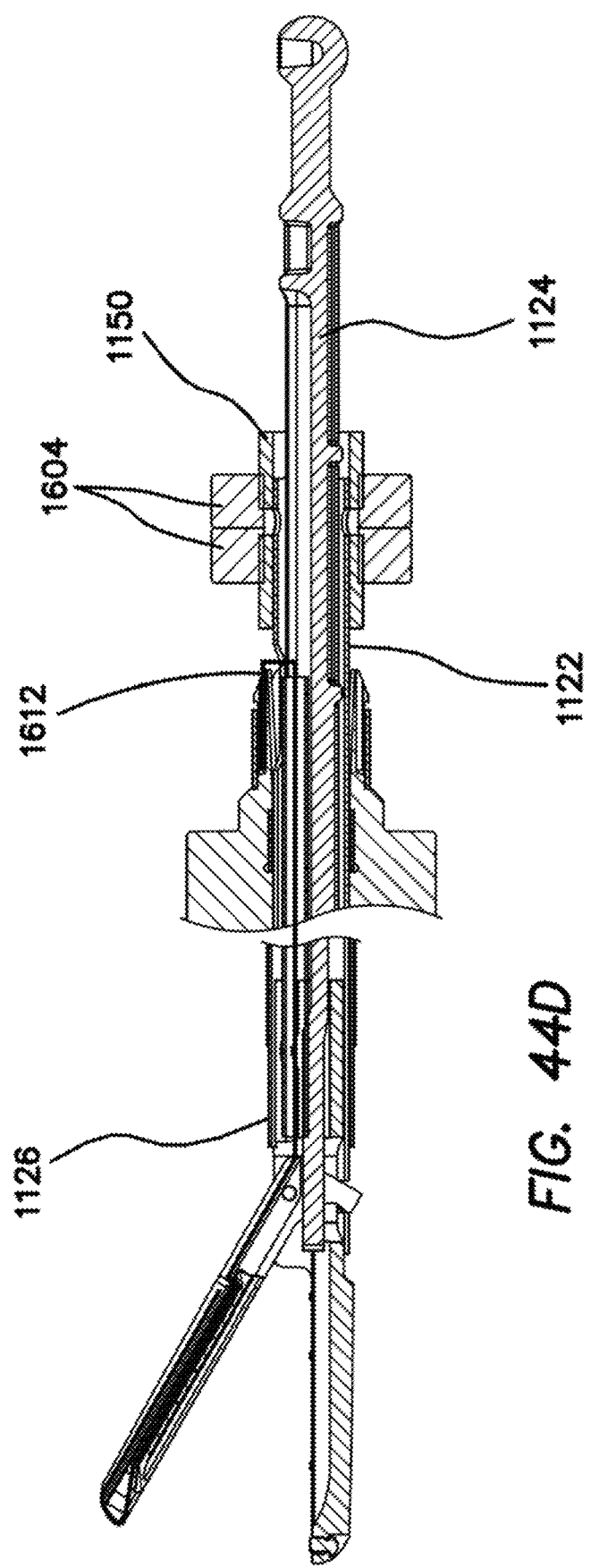

As discussed above with respect to length adjustment of the elongate shaft 1120, in the illustrated embodiment attached to the distal end of the actuation tube 1122 is a threaded coupling 1150 (FIG. 44D). As illustrated, attached to the threaded coupling 1150 are two thread nuts 1604, which are configured to engage with the pull block 1250. In the illustrated embodiment, the actuation tube 1122 is housed within an outer cover tube. While the actuation tube 1122 is illustrated as a generally tubular member that can be nested within the outer cover tube 1126, and that can have a blade actuation shaft 1124 nested within it, in other embodiments, a non-tubular actuation member can be used, for example, a shaft, a rigid band, or a link, which, in certain embodiments can be positioned generally parallel to the blade actuation shaft within the outer cover tube.

With continued reference to FIG. 44A, in the illustrated embodiment, attached to the distal end of the outer cover tube 1126 is the rotational shaft assembly 1600. The rotational shaft assembly 1600 comprises two mating hubs 1602 and a conductive sleeve 1610. In the illustrated embodiment, the hubs 1602 snap together, engaging with the outer cover tube. In other embodiments, the hubs can be of a monolithic construction and configured to interface with mating features on the outer cover tube. The conductive sleeve 1610 can be attached to the proximal portion of the assembled hubs after they are attached to the outer cover tube. When the conductive sleeve 1610 is attached to the rear of the assembled hubs 1602, the sleeve 1610 traps the exposed end of an isolated wire 1612 (see FIG. 44D). In the illustrated embodiment, the isolated wire 1612 extends from its entrapment point under the conductive sleeve through a slot in the actuation tube 1122 and then inside a protective sleeve 1614. The protective sleeve 1614 and isolated wire 1612 extend distally inside the actuation tube 1122, towards the jaw assembly 1130. In other embodiments, the isolated wire can be formed integrally with a protective sheath and no separate protective sleeve is present in the actuation tube.

Figures 1, 45B:
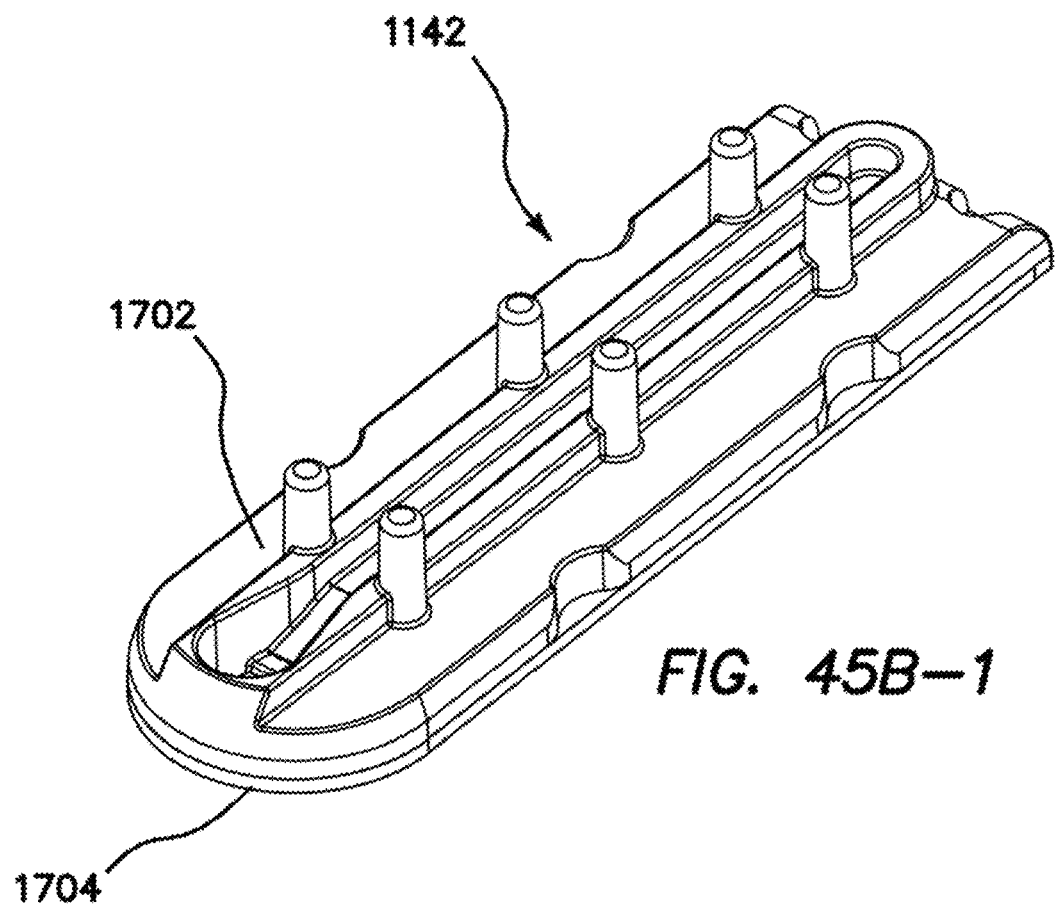
Figures 2, 45B:
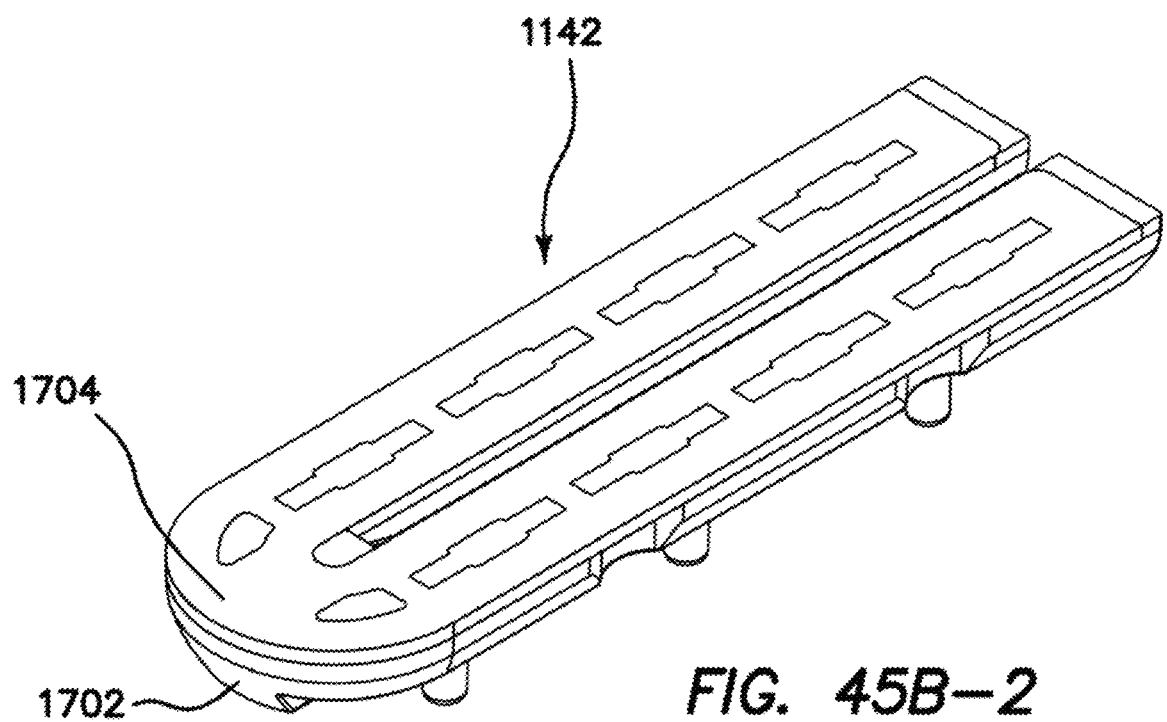

With reference to FIGS. 45A-45C, attached to the distal end of the elongate shaft 1120 is the jaw assembly 1130. In certain embodiments, the jaw assembly 1130 comprises a lower jaw 1134, upper jaw 1132, upper conductive assembly 1142, lower nonconductive spacer 1144, and jaw pivot pin 1146. In the illustrated embodiments, the jaw pivot pin 1146 pivotally couples the upper and lower jaws 1132, 1134 and allows the upper jaw 1132 to pivot relative to the lower jaw 1134. In other embodiments, other pivotal couplings are contemplated. As illustrated, the proximal portion of the upper jaw 1132 extends through the lower jaw 1134 and into a hole in the actuation tube 1122.

In some embodiments, one jaw can be fixed with respect to the elongate shaft 1120 such that the opposing jaw pivots with respect to the fixed jaw between an open and a closed position. For example, in the illustrated embodiment, the proximal portion of the lower jaw 1134 extends inside the cover tube 1126 and is crimped in place, fixing the jaw assembly 1130 to the rotation shaft assembly 1600. Thus, in the illustrated embodiment, the upper jaw 1132 is moveable with respect to a fixed lower jaw 1134. In other embodiments, both jaws can be pivotally coupled to the elongate shaft such that both jaws can pivot with respect to each other.

Attached to the upper jaw 1132 is the upper conductive assembly 1142, which comprises a nonconductive portion 1702 and a conductive pad 1704 (see FIG. 45B). The nonconductive portion 1702 isolates the conductive pad 1704 from the upper jaw 1132, likewise isolating it from the rest of the shaft assembly 1120. The isolated wire 1612 can be routed to electrically couple the conductive pad 1704 on the upper jaw 1132 to the wiring harness 1500 in the handle assembly 1110. In the illustrated embodiment, the isolated wire 1612 extends from the distal end of the protective sleeve which is housed at the proximal end of the lower jaw and extends into the upper jaw 1132. The upper jaw 1132 can have a slot positioned to receive the isolated wire. The isolated wire 1612 then extends through a hole in the upper jaw 1132 and drops into a slot in the nonconductive portion. The isolated wire then extends to the distal end of the nonconductive portion and drops through to the conductive pad (see FIG. 44D).

The jaw assembly 1130 can include one or more nonconductive space maintaining members such as spacers 1144 to reduce the risk that electrodes on the upper jaw 1132 and lower jaw 1134 can come into direct contact and create a short. In the illustrated embodiment, the lower nonconductive spacer 1144 is housed inside the u-groove portion of the lower jaw and contains space maintaining protrusions which prevent the conductive pad from contacting the lower jaw (see FIG. 45C).

Figure 46B:
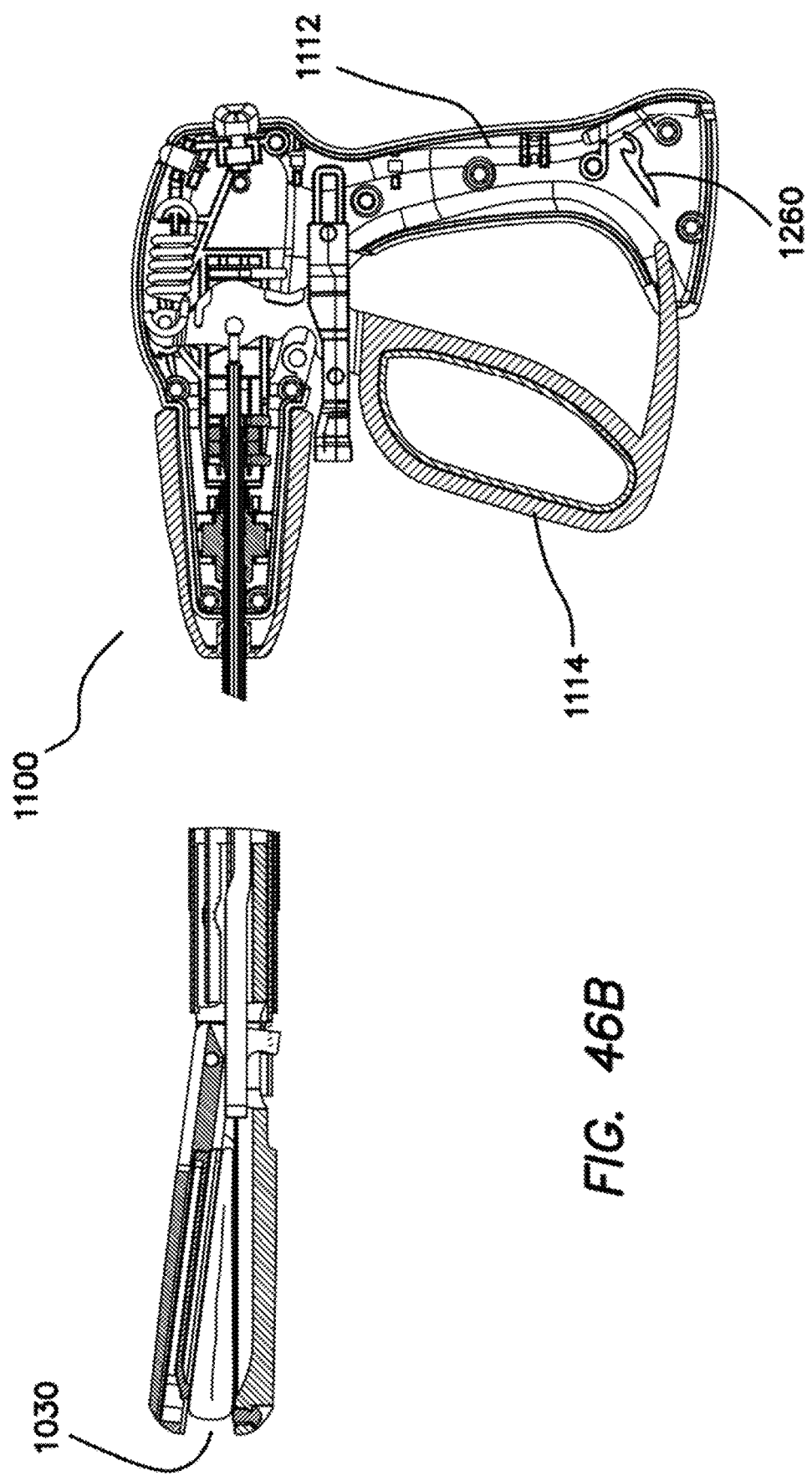
Figure 46D:
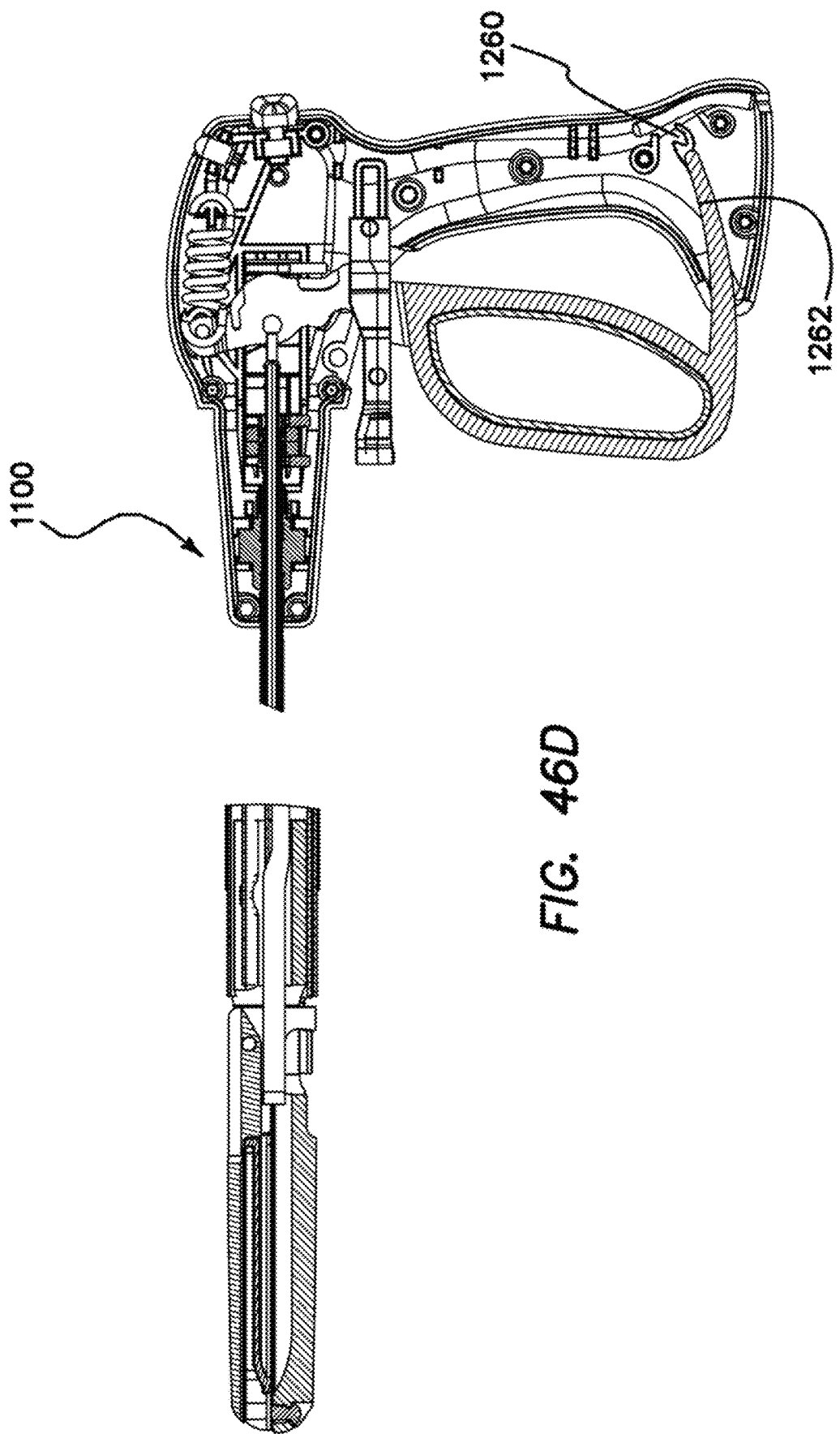
Figure 48A:
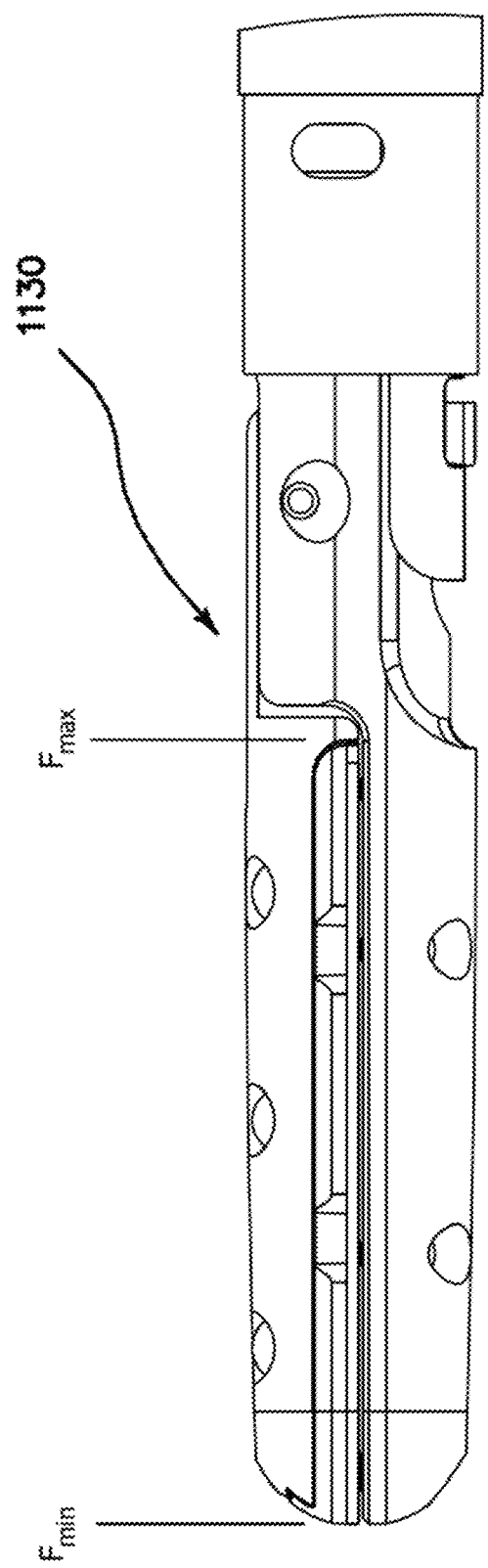
FIG. 48A is a side view of a jaw assembly of a laparoscopic sealer/divider of FIG. 41A.
Figure 48B:
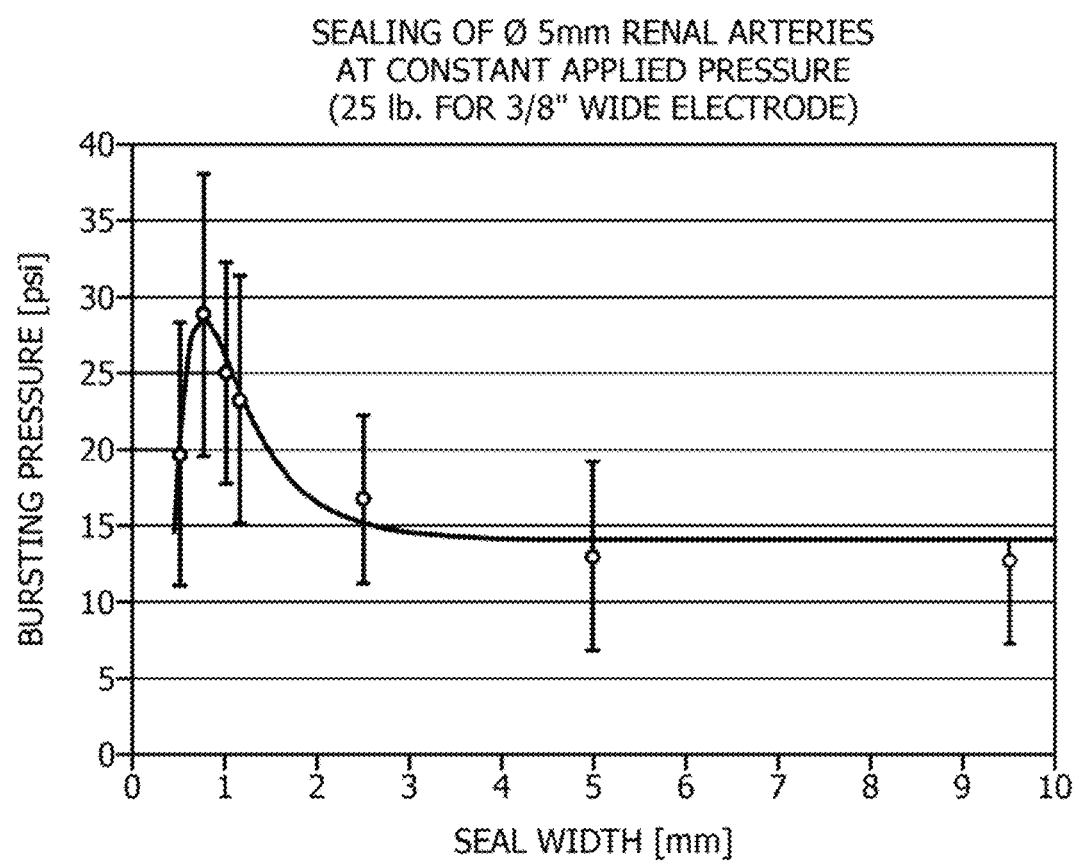
FIGS. 48B-48C are graphical representations of exemplary vessel sealing pressures provided by a laparoscopic sealer/divider of FIG. 41A.
Figure 48C:
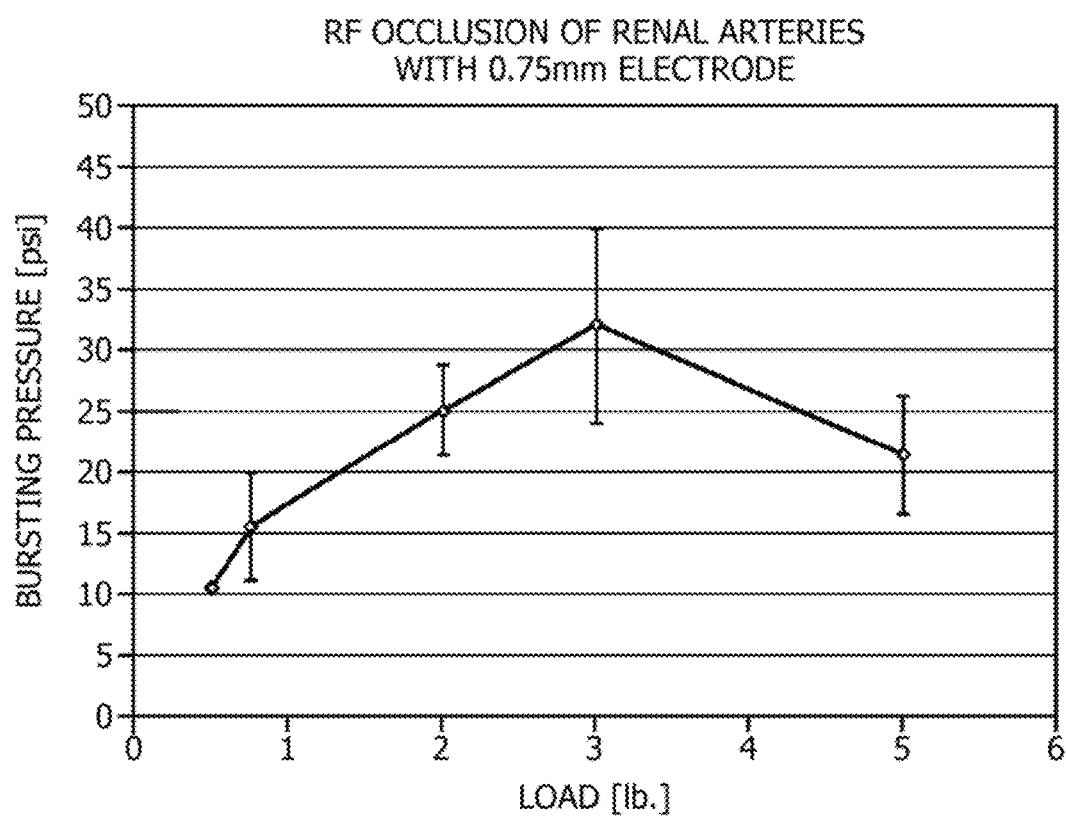
Figures 1, 2, 3, 49:
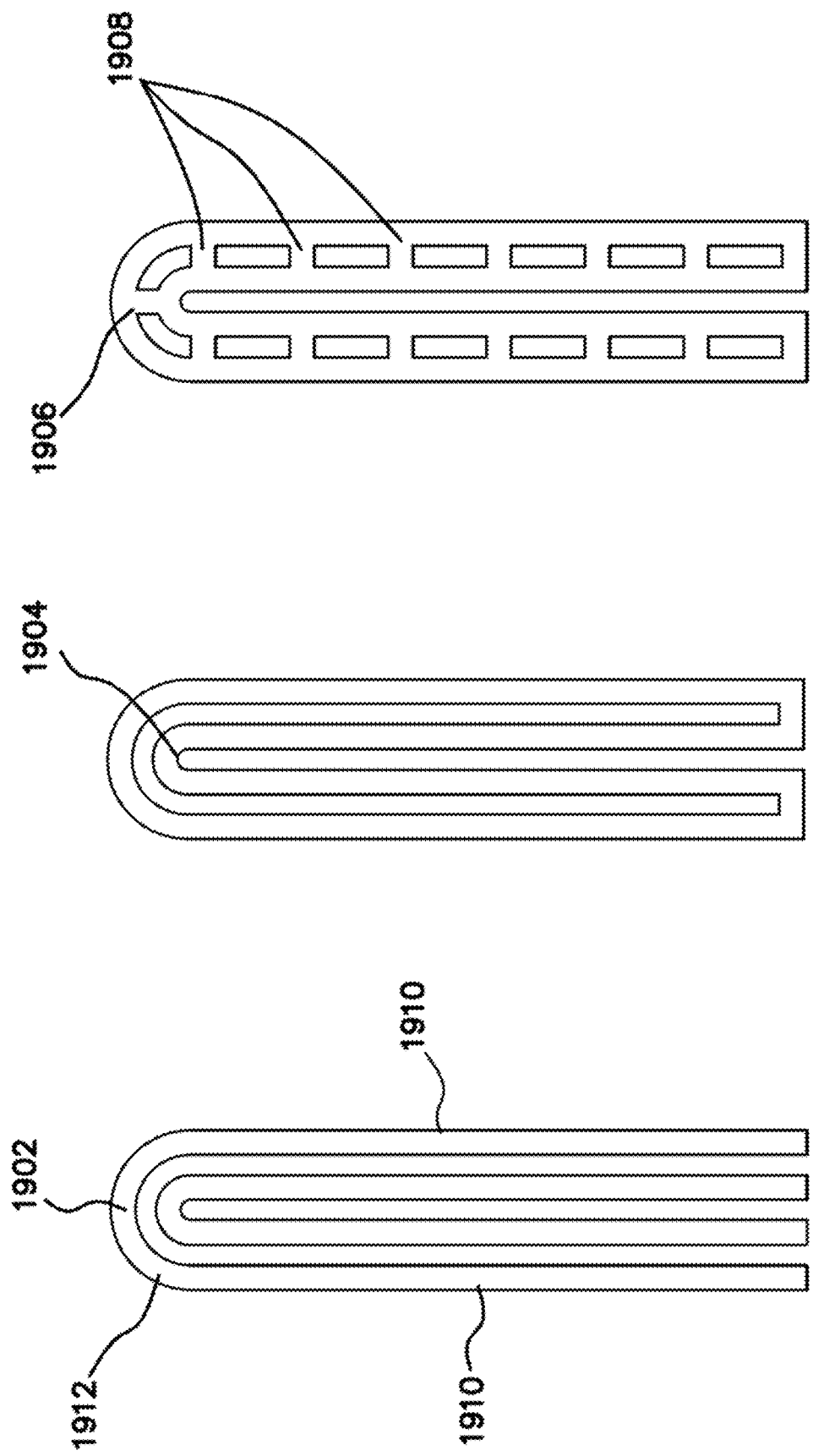
Figure 50:
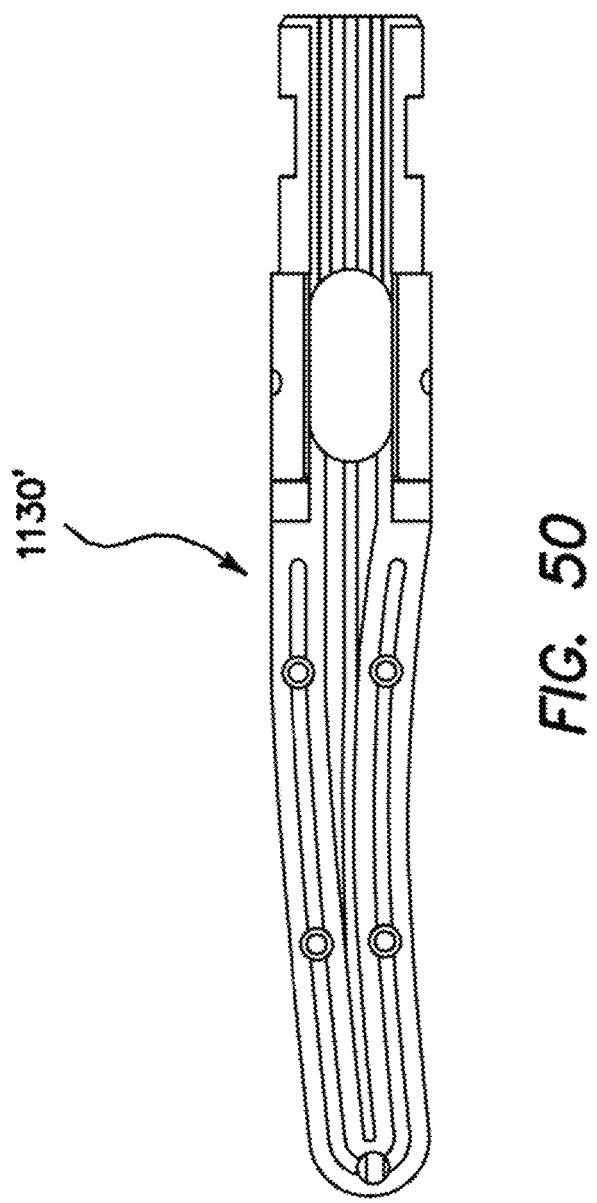
FIG. 50 is a top level view of a jaw assembly of a laparoscopic sealer/divider of FIG. 41A.

Turning now to some of the operational aspects of the electrosurgical instruments described herein, once a vessel 1030 or tissue bundle has been identified for sealing, the upper and lower jaws are placed around the tissue (see FIG. 46A). The actuation handle 1114 is squeezed moving the actuation handle 1114 proximally with respect to the actuation handle 1112 (see FIG. 46B). As the actuation handle 1114 moves proximally it pushes the pull block 1250 along the rails in the right and left handle frames. The pull block 1250 engages with the threaded nuts 1604 which are attached to the rear of the actuation tube 1122, causing the actuation tube 1122 to move proximally. Proximal movement of the actuation tube pivots the upper jaw 1132, coupled to the pull tube, towards the lower jaw, effectively clamping the tissue (see FIG. 46C). The force applied to the tissue by the upper jaw is translated through the pull tube and pull block 1250 to the actuation handle 1114. Once the preloaded force has been overcome, the actuation handle 1114 will begin to move the sliding pin 1206 distally (see FIG. 46D). When the preload on the trigger spring has been overcome, the actuation handle 1114 pivot point shifts from the sliding pin 1206 to the rear portion of the pull block 1250 where it contacts the actuation trigger. The sliding pin 1206 can advance distally because the preloaded force on the trigger spring 1208 has been overcome.

The continued manipulation of the actuation handle 1114 pivots the actuation handle 1114 to a location where the actuation handle 1114 engages with the latch mechanism 1260 in the right and left handle frames that maintains the trigger in the engaged position and prevents the trigger from returning to an opened position. When the engaged position is reached and nothing is present between the upper and lower jaws 1132, 1134, the trigger spring is extended to a distance that ensures that the force applied to the electrodes of the jaw assembly 1130 is near the lower end of the force range required for optimal vessel sealing. When a large, e.g., maximum, amount of tissue is placed in the jaws, the actuation handle 1114 extends the trigger spring 1208 a greater distance. However, the trigger spring 1208 ensures that the maximum amount of force applied does not exceed the maximum end of the force range used for optimal vessel sealing. From the engaged position, sealing radio frequency energy is applied to the tissue by depressing the power activation button. Once the tissue has been sealed, the actuation trigger can be reopened by continuing proximal advancement to a position that allows the actuation trigger's finger portion to disengage from the latch portions of the left and right handle frames. (See FIGS. 46A-46F))

The floating dual pivoting mechanism including a sliding pin 1206 and a pull block 1250 described above desirably provides a minimum force, optimal for sealing vessels and tissue, is maintained regardless of the amount of substance contained between the upper and lower jaws. This mechanism also reduces the risk that an extremely large amount of force is applied to the tissue. If too much force is applied to a vessel or tissue bundle, potential damage could occur. Thus, if a very small vessel or thin tissue bundle is clamped within the jaw, the instrument applies the minimum amount of force required to obtain a good tissue weld. The same is true with a very large vessel or tissue bundle. Since the travel of the jaw can vary greatly depending on tissue thickness, the force applied by the jaw is adjustable. It is desired that the instrument be self-adjusting and automatic (no action from the user). The floating dual pivot mechanism described below provides the self-adjustment, applying a specific range of force along the length of the electrode.

Once the actuation handle 1114 has been depressed to a predetermined force range for optimal vessel sealing, it will engage the matching latch of the right and left handle frames, locking the actuation trigger from moving further distally (See FIG. 46E). At this point the user can depress the activation button, applying the appropriate energy to the tissue for proper sealing.

Once the tissue has been sealed, the user can actuate the blade trigger 1402. When the blade trigger 1402 is moved proximally, the blade lever pivots, forcing the front and rear blade shafts and cutting blade 1400 to move distally. The cutting blade advances forward and divides the sealed portion of the tissue (see FIG. 46F). When the user releases the blade trigger 1402, the blade spring resets the cutting blade to its original position. When the blade trigger 1402 has been returned to its original or initial position the user can continue to squeeze the actuation handle 1114 to open the upper jaw. Continued proximal movement of the actuation handle 1114 will disengage the actuation handle 1114 from the latch mechanism 1260 of the right and left handle frames by biasing the extended arm portion 1262 of the actuation trigger upwards, over the end of the latch, to a position where the trigger can be released (see FIG. 46G).

The electrosurgical instrument is connectable to an electrosurgical generator specifically configured to apply the proper amount of energy to the tissue when the activation button is depressed, such as the electrosurgical generator described above. With reference to FIG. 47, the instrument is also connectable to an intermediate control unit 1800 in conjunction with an electrosurgical generator. The intermediate control unit 1800 can monitor the tissue sealing and ensure that the proper amount of sealing energy is applied to the tissue. The control unit 1800 in one aspect can have a set of cables configured to plug into most typical electrosurgical generators. The control unit also has a port for connecting the wiring harness 1500 plug from the instrument (see FIG. 47).

With continued reference to FIG. 47, in certain embodiments, the non-sterile power controller interfaces with the sterile vessel sealer/divider through a cord extending from the sealer/divider beyond the sterile field and plugged into the controller. In one aspect, the controller regulates and/or distributes power from a non-sterile reusable power supply to which the controller is attached or integrated. In some embodiments, the controller can be configured for a single use to maintain sterility of the surgical environment. In order to prevent reuse of the non-reusable controller, the cord of the electrosurgical tool, once plugged into the non-sterile controller cannot be removed. This connection permanently couples the sterile and non-sterile portions, preventing the user from being able to disconnect the controller for reuse in unintended surgical procedures or purposes. (see FIG. 47)

In grasping jaw assemblies such as the jaw assembly 1130 of the electrosurgical tool, the gripping force generated between the jaws can vary along the length of the jaws from a relative maximum Fmax near the proximal end to a relative minimum Fmin near the distal end. In some embodiments, the electrosurgical tool can be configured such that the forces are optimized along the length of the active electrode portions of the jaws, a predetermined force range for vessel sealing is maintained. A predetermined maximum amount of force utilized to obtain a proper vessel seal is desirably not exceeded at the proximal end of the active electrodes (closest to the pivot). In addition a gripping force at the distal most ends of the active electrodes is desirably greater than a predetermined minimum amount of force for optimal vessel sealing. Desirably, the gripping force generated at every point along the jaw assembly 1130 is within the range defined by the predetermined maximum force and the predetermined minimum force to achieve optimal sealing. (See FIG. 48A).

In some embodiments, the electrode width to form vessel seals is between about 0.25 mm and about 1.5 mm. In other embodiments, the electrode width is desirably between about 0.4 mm and about 1 mm. In other embodiments, the electrode width is preferably between about 0.6 mm and 0.8 mm. In some embodiments, the electrode width is approximately 0.75 mm. With an electrode of 0.75 mm, and the sufficient pressure for this type of electrode to achieve a vessel seal is approximately 3 pounds (see FIGS. 48B and 48C). However it can bee seen from FIG. 48C that a force range of approximately 0.4 pound to 2.3 kg on a 0.75 mm electrode can maintain burst pressures greater than 15 psi. In some embodiments, the jaw and electrode arrangement desirably can maintain a pressure of between 3 and 39 kg/cm^2, more desirably 10-30 kg/cm^2, and preferably approximately 23 kg/cm^2. Embodiments having different electrode widths can have different force ranges. In order to maximize sealing surface area while still maintaining the electrode configuration described above, in some embodiments, multiple rows of 0.75 mm electrodes may be provided (see FIG. 48D).

In some embodiments, electrode geometry on the conductive pads of the jaw assembly 1130 ensures that the sealing area completely encloses the distal portion of the blade cutting path. Single linear electrodes could cause vessel leakage when only a portion of a vessel is sealed. In one embodiment, the electrodes positioned on the jaw assembly 1130 comprise a single u-shaped electrode 1902 surface on each of the upper and lower jaws. Each u-shaped electrode can comprise generally parallel linear legs 1910 extending from a proximal end of the conductive pad of the jaw towards the distal end and a curved connector 1912 at the distal end extending from one leg to the opposite leg. Desirably, the u-shaped electrodes can completely encompass the distal end of the blade cutting path. In other embodiments, to provide a greater sealing area, two or more spaced u-shaped electrode surfaces on both the upper and lower jaws can be provided (see FIG. 49). In some embodiments, the electrodes 1904 can be connected at the distal ends to create a completely enclosed seal (see FIG. 49). In certain embodiments one or multiple bridge members 1908 between the u-shaped electrode 1906 surfaces can further ensure that the sealing area completely encloses the distal portion of the blade cutting path.

In some embodiments, for some surgical procedures the outer shape of the jaws 1130' can be curved such that the distal ends of the jaws are offset with respect to the longitudinal axis from the proximal ends of the jaws to improve visibility for a user such as a surgeon. In embodiments with curved jaws, the u-shaped electrodes can also be provided in a curved fashion while still maintaining proper electrode width and spacing (see FIG. 50).

Figure 51:
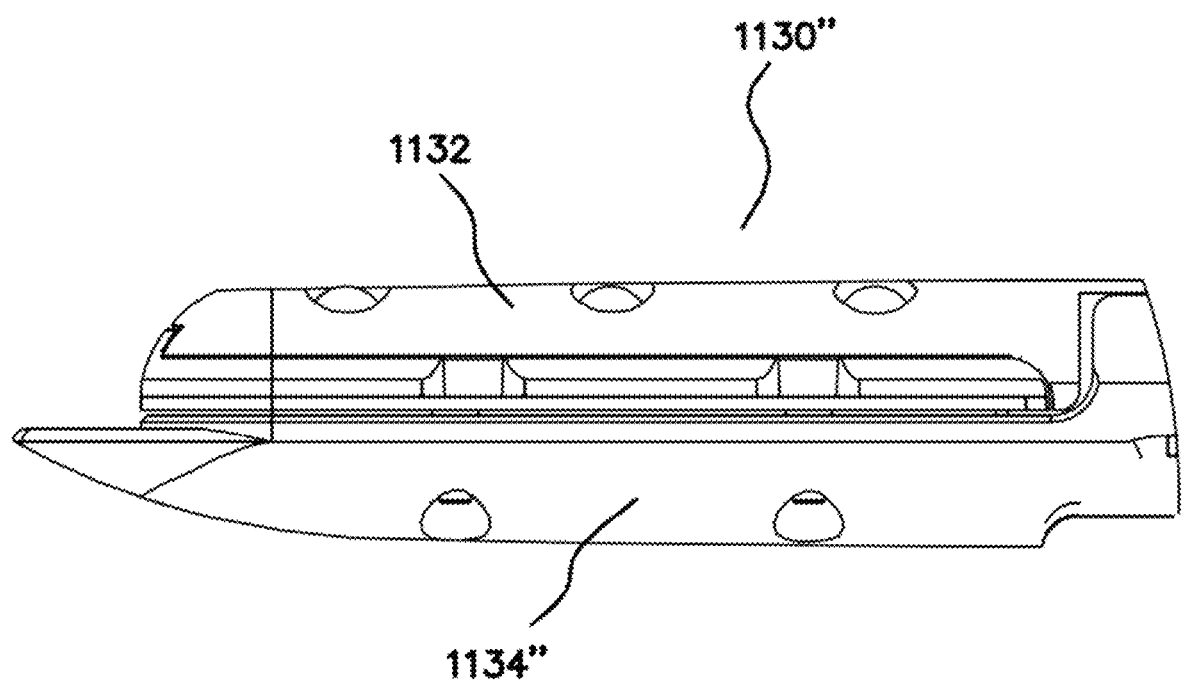
FIG. 51 is a side view of a jaw assembly of a laparoscopic sealer/divider of FIG. 41A.
Figures 1, 52:
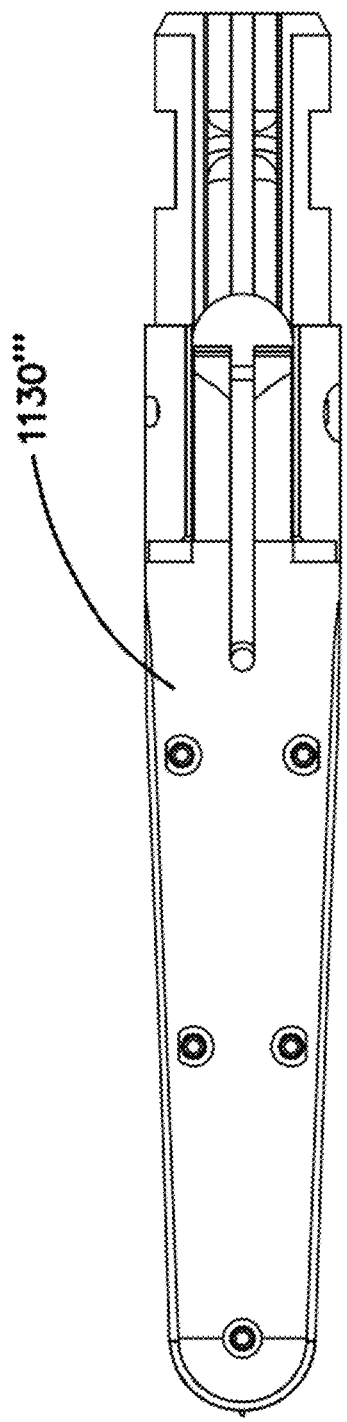
Figures 2, 52:
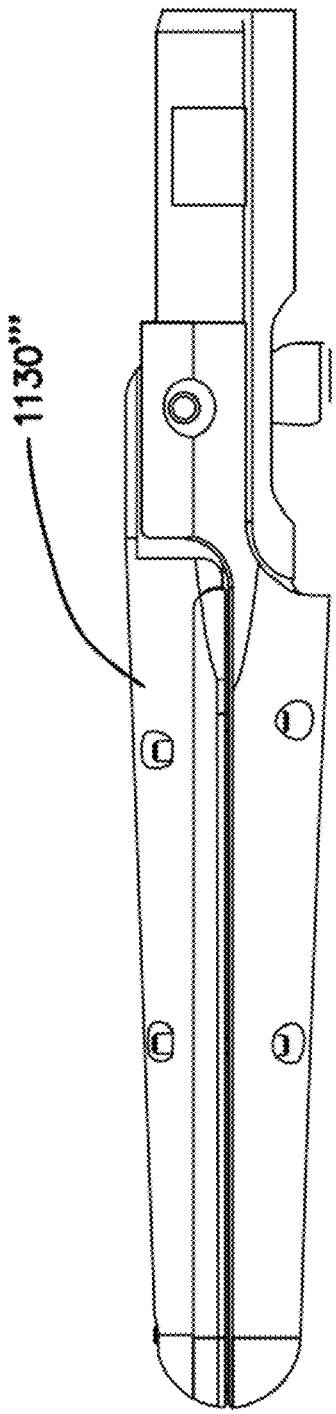

With reference to FIG. 51, in certain embodiments, the electrosurgical device can include a tissue dissector formed on the jaw assembly 1130". Advantageously, this integrated tissue dissector can facilitate dissection of non-vascular tissue either bluntly or electro-surgically, without having to exchange the vessel sealer/divider with another instrument. Thus, this multiple tool functionality can advantageously facilitate quicker surgical procedures. The reduced number of tool exchanges can be especially advantageous in laparoscopic procedures or procedures with relatively limited access as tool exchanges can be time consuming in these surgical environments.

With continued reference to FIG. 51, in some embodiments, one of the jaws of the jaw assembly 1130" can have an extended distal end distally beyond the distal end of the other jaw (see FIG. 51). In the illustrated embodiment, the lower jaw 1134" can have an extended distal end. Advantageously, in embodiments where the lower jaw 1134" is pivotally fixed to the elongate shaft, this extended arrangement can facilitate stability of the lower jaw during dissection. In other embodiments, the upper jaw 1132 can have an extended distal end, allowing the tissue dissector to be pivoted during the dissection operation by movement of the actuation handle 1114. In some embodiments, the extended distal end can be tapered in shape such that the distal end is relatively short and narrow compared to relatively more proximal portions of the jaw. Advantageously, this tapered shape allows the distal end to access tissue positioned in relatively confined environments while reducing the risk that adjacent tissue is contacted.

With reference to FIGS. 52A, 52B, In some embodiments, both jaws of the jaw assembly 1130''' are tapered laterally and/or in height along the length of the jaw's electrode portions, or at least part of the electrode portions. In these embodiments, the jaw assembly 1130''' has a low-profile distal end which can be used for tissue dissection. Advantageously, the low-profile distal end can also enhance access of the jaw assembly 1130''' to relatively confined surgical environments.

Figure 53A:
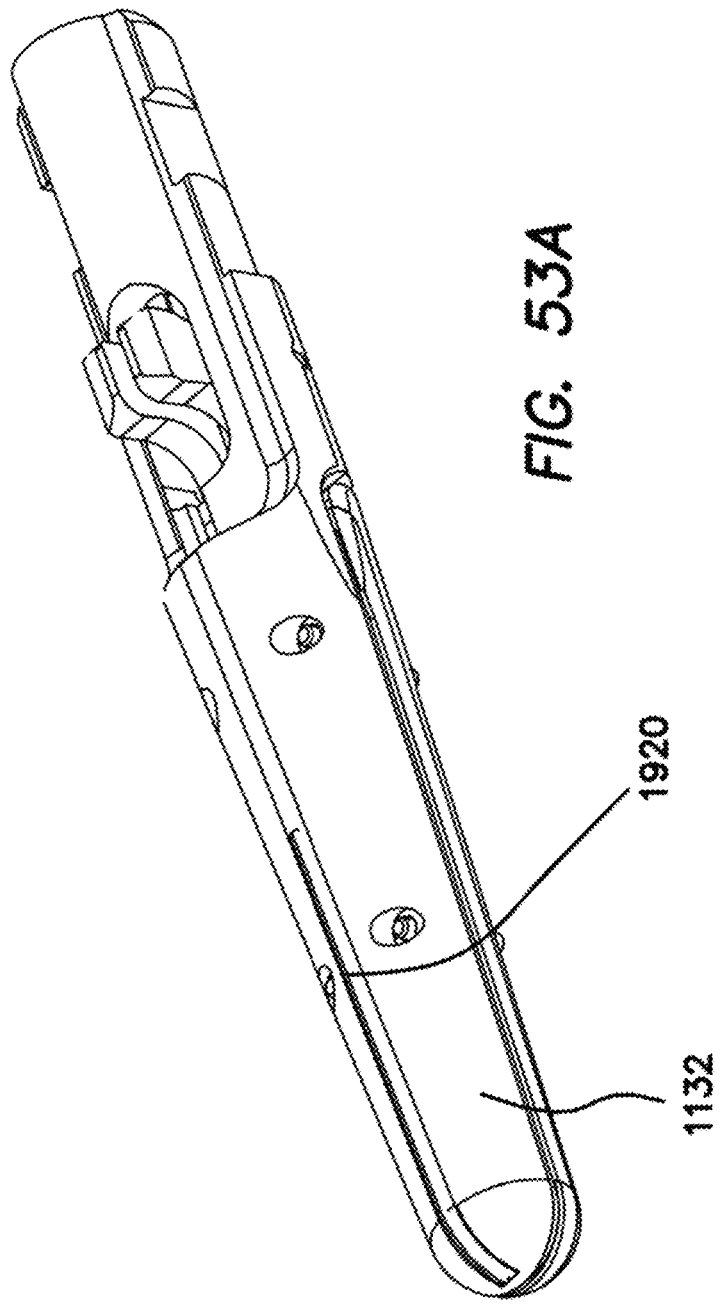
FIG. 53A is a perspective view of a jaw assembly of a laparoscopic sealer/divider of FIG. 51A.
Figure 53B:
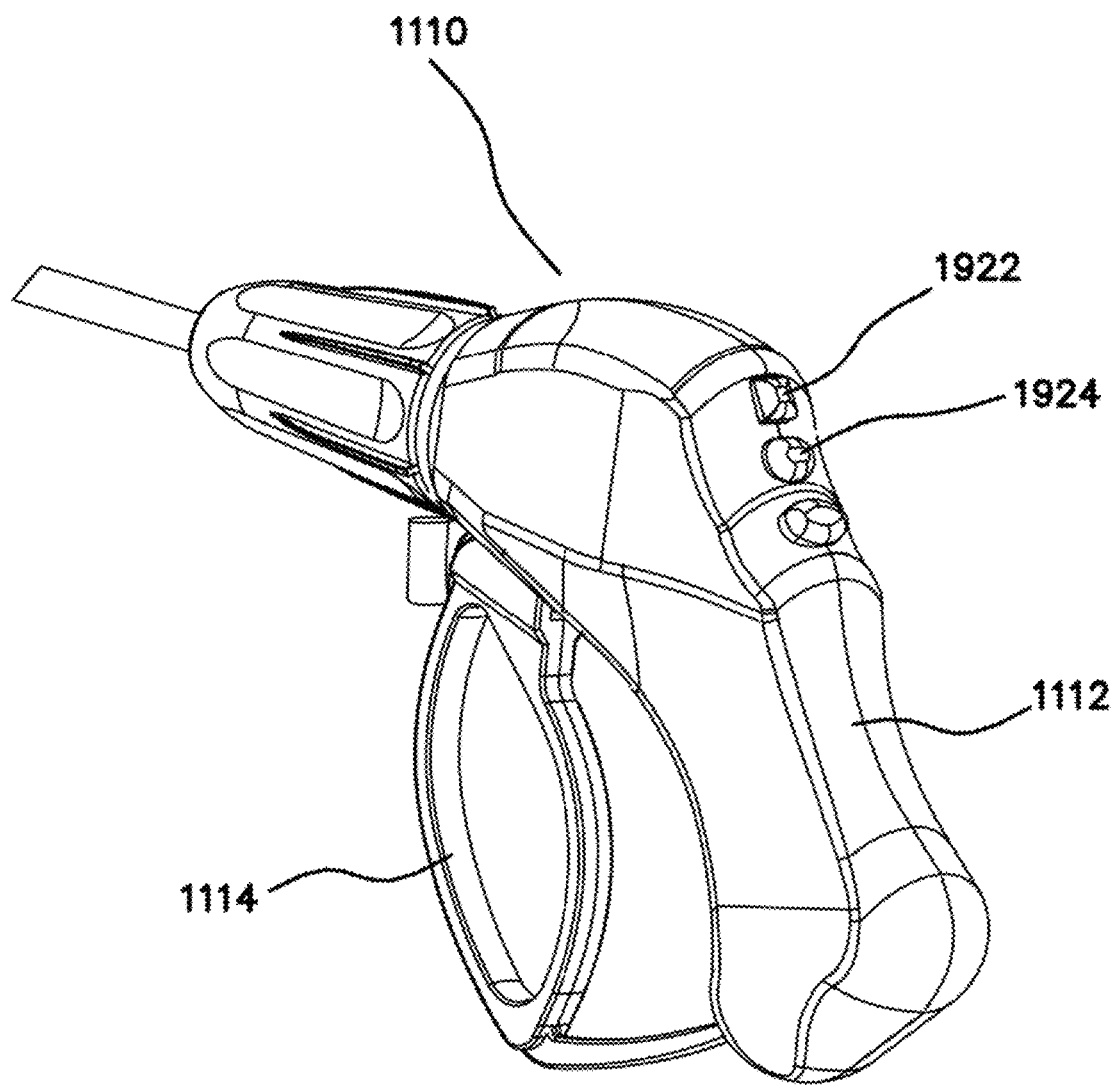
FIG. 53B is a perspective view of an actuator of a laparoscopic sealer/divider of FIG. 41A.

With reference to FIGS. 53A, 53B, in certain embodiments, a cutting/coagulating electrode can be disposed on an exterior surface of the jaw assembly 1130 to provide tissue dissection. In some embodiments, the cut/coagulation electrode is located on the jaw at, for example, the distal end on the outer surface of either the upper or lower jaw (see FIG. 53A). Desirably, the electrode 1920 can be electrically isolated or insulated from other components of the jaw assembly 1130, providing an active electrode for the bi-polar instrument. As such, an isolated wire can extend from the cut/coagulation electrode 1920 to the proximal end of the elongate shaft 1120 (similar to the isolated wire extending from the conductive pad on the upper jaw) to electrically couple the cut/coagulation electrode to the wiring harness 1500 of the electrosurgical tool in the handle assembly. In some embodiments, the isolated wire can extend within a protective sleeve within the outer cover tube of the elongate shaft. In other embodiments, the isolated wire can be integrally formed with a protective sheath. The isolated wire also in one aspect is coupled to a rotational connection, e.g., a rotational clip, similar to the isolated wire extending for the conductive pad.

With reference to FIG. 53B, the cut/coagulation electrode in one aspect can be selectively activated by at least one actuation button 1922, 1924 or switch on the handle assembly 1110. In some embodiments, the handle assembly can comprise a cut button 1922 to actuate the electrode with a tissue cutting electrosurgical signal and a coagulation button 1924 to actuate the electrode with a tissue coagulating electrosurgical signal. For example, in FIG. 53B, separate cut and coagulation buttons are illustrated on the actuator adjacent a tissue sealing button to actuate the electrodes on inner surfaces of the jaws. In other embodiments, a single, multifunction switch or button can actuate the cut/coagulation electrode in the desired configuration. In still other embodiments, the cut/coagulation electrode can be configured to receive only a cutting or only a coagulation electrosurgical signal, and a single corresponding actuation button or switch can be used to selectively actuate the electrode.

The vessel sealer/divider can use thin metallic tubes and small diameter machined rods for the internal elongated components used to actuate jaws such as the actuation tube and the blade actuation shaft. However, such components can be costly and in some embodiments, manufacturing and materials costs can be desirably reduced through the use of elongate injection molded plastic components. As discussed above with respect to the blade actuation shaft 1124, in some embodiments, costs and manufacturing difficulties can be reduced further through the use of an elongated shaft formed of two mating polymer shaft sections 124a, 1124b such as a proximal or rear shaft portion and a distal or front shaft portion. In some embodiments, the two shaft portions 1124a, 1124b can be connected by interlocks 1960, e.g., projections on one shaft section or component mating with corresponding slots on the other shaft section, to maintain concentricity and prevent unnecessary movement in their axial direction (see FIG. 54A-C). In other embodiments, other mating structures can be formed on the two mating shaft portions. For example, one of the shaft portions can be formed with one or more barbs thereon and the other shaft portion can be formed with a recess configured to receive and retain the barbs. In still other embodiments, the two mating shaft portions can be adhered with a chemical adhesive or epoxy, either in addition to, or in place of interlocks formed on the shaft portions.

With reference to FIGS. 55A and 55B, in certain embodiments, the elongate shaft 1120 of the electrosurgical tool can be configured such that the outer surface thereof does not translate proximally and distally during actuation of the jaw assembly 1130 by the actuation handle 1114. In other embodiments, moving the outer shaft component can be used to open and close the jaws and provide a proper clamping force without manipulating the handle assembly. However, moving the outer shaft component can also cause the vessel sealer/divider to move in relation to a trocar seal and thus potentially complicating a gas seal between the sealer/divider and the insufflated body cavity. As such, it can be desirable that the outer most shaft components remaining stationary throughout a surgical procedure. As such, in certain embodiments, the elongate shaft maintains the moving components (e.g., the pull tube and the blade actuation shaft) on the inside of a stationary outer cover tube (which may also con a dielectric coating or insulating sleeve). With continued reference to FIGS. 55A and 55B, as illustrated, the stationary outer cover tube is connected to the stationary portion of the jaws, while the pull tube is connected to the moving portion of the jaws (e.g., the upper jaw). Thus, as the jaw assembly 1130 is actuated from an open position (FIG. 55A) to a closed position (FIG. 55B), the pull tube translates longitudinally proximally while the outer cover sleeve remains stationary.

As discussed above with respect to the electrosurgical system, in certain embodiments the electrosurgical tool can comprise a memory such as a tool ID chip mounted on a small PCB. In some embodiments, the PCB can be disposed on or in the actuation handle 1112. In other embodiments, the PCB and chip can be integrated in the plug of the wiring harness. The PCB and chip can be molded with a tool-specific pattern. The tool ID chip and PCB can be electrically connected into the wiring harness and plug of the electrosurgical tool. A "spacer" between the plug and the tool ID chip, can allow the use of the same connector for all tools. In some embodiments, the spacer can have the same shape for all tools on the plug side, and a tool-specific pattern on the chip side such that during assembly there is a reduced risk that a PCB for one type of electrosurgical tool can be assembled into a different type of electrosurgical tool.

As discussed above with respect to the electrosurgical system, when the plug is inserted into the generator, the encrypted tool information stored in the memory is verified. General information (serial number of tool and generator) are exchanged, and the tool-specific software is uploaded into the generator. With completion of each tool use, tool-specific information (connections to generator, individual tool uses, errors, etc.) can be communicated, if needed, and stored in memory of the generator, the tool chip or both. In exemplary embodiment, the generator's memory is sized to hold data for about two months while the tool chip's memory can hold data for one surgical procedure.

As discussed above with respect to the electrosurgical system, in some embodiments, the electrosurgical fusion tool can be used in a system which monitors various operational parameters and determines a radiofrequency endpoint based on phase angle.

Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments of the present invention should be considered in all respects as illustrative and not restrictive.

Electrosurgical Dissection Tool

Laparoscopic surgical procedures typically require the dissection of connective or vascular tissue. Depending on factors such as tissue type, size, location and condition of the specific tissue, different tools and techniques can be used to perform a specific procedure. The choice of an individual tool can be based on functionality combined with a desire that the selected tool provide relatively little traumatic damage to the surrounding tissue. As an example, the dissection of connective tissue is usually performed by mechanical or electrosurgical cutting, whereas the dissection of vascular tissue typically relies on ligating techniques employing clips or staplers followed by a mechanical cut. Consequently, a typical laparoscopic procedure including dissection of both connective tissue and vascular tissue calls for multiple tools being consecutively exchanged through trocar access ports to the surgical site. This tool exchange increases both the cost and time of the surgical procedure. It is hence desirable to provide multi-functional tools that can greatly reduce the number of tool exchanges during laparoscopic procedures.

Figure 56:
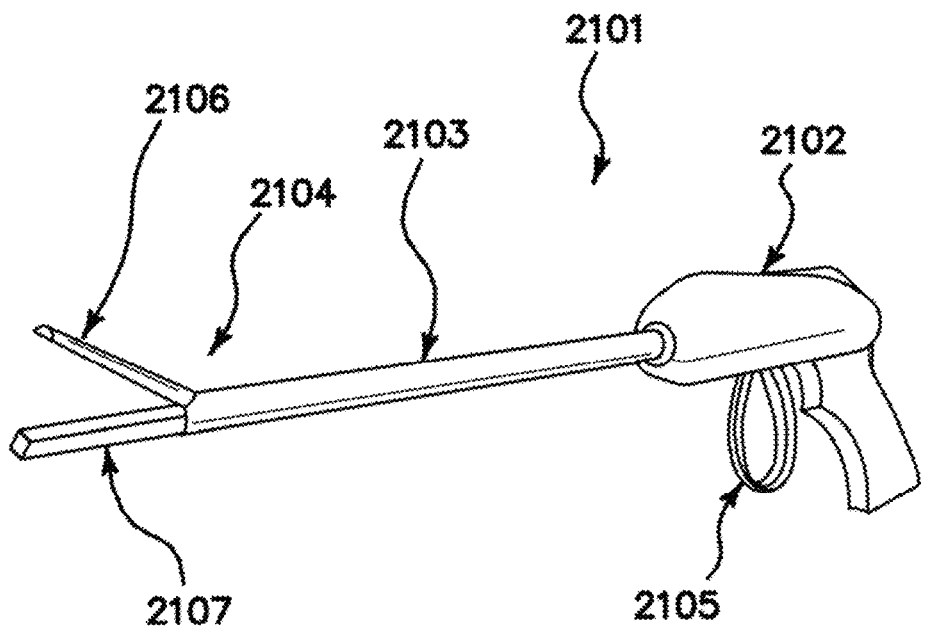
FIG. 56 is a perspective view of an embodiment of surgical tool for use in a laparoscopic surgical procedure.

Referring now to FIG. 56, in the illustrated embodiment, a bloodless tissue-dissecting tool 2101 comprises a proximal hand-piece 2102 that connects through a shaft 2103 to a distal end-piece 2104. Activation of the trigger 2105 on the hand-piece 2102 allows closing and opening of the jaw elements 2106, 2107 on the distal end-piece 2104 so that tissue can be clamped between the upper 2106 and lower 2107 jaw elements.

With continued reference to FIG. 56, in some embodiments, the tool 2101 can be configured to be electrically coupled to an electrosurgical generator. For example, in some embodiments, the tool 2101 can include an integrated power cord, or a socket or other connector adapted to receive a power cord. At least a portion of the tool can be selectively energized through actuation of a control or switch on the electrosurgical generator. For example, in some embodiments, the tool can be energized with a handswitch or a footswitch on or coupled to the electrosurgical generator.

Figure 57:
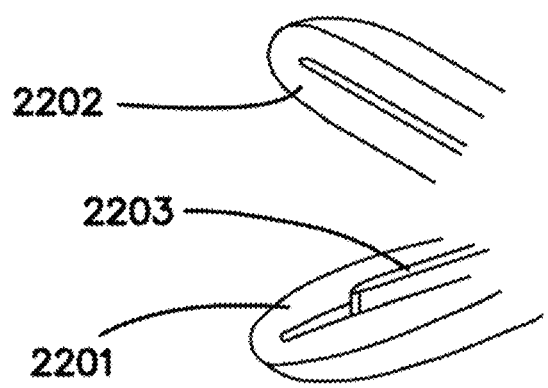
FIG. 57 is a perspective drawing of the distal end of an exemplary tissue fusion/cutting devices.

With reference to FIG. 57, an exemplary prior art electrosurgical device is illustrated. Electrosurgical tissue sealing devices that include a mechanical cutter can be used to first electrosurgically coagulate and then mechanically cut through a variety of tissue types. Certain harmonic tissue dividers can also be used to coagulate and/or to dissect a variety of tissue, ranging from connective to highly vascular tissue, such as organs.

As schematically depicted in FIG. 57, prior-art electrosurgical tissue dissectors include a lower jaw forming a first electrode 2201 and an upper jaw forming a second electrode 2202. In the prior art devices, the two jaw elements—or electrodes 2201, 2202—supply a relatively large amount of pressure to the tissue. High pressure with simultaneous application of electrical energy to the compressed tissue can be used to permanently occlude very large blood vessels by electrosurgical vessel fusion. After the electrical fusion process has been completed, the tissue can be separated by advancing a mechanical blade 2203.

Figure 58A:
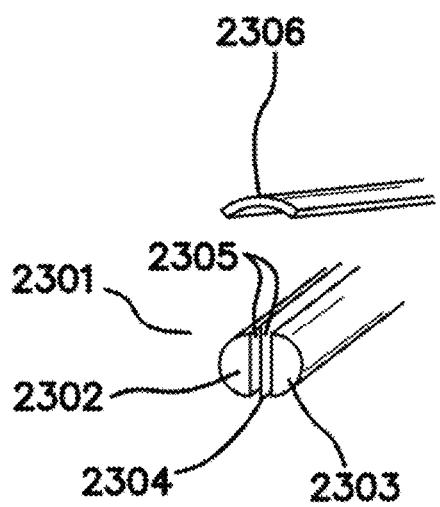
FIGS. 58A-D are schematic drawings of various embodiments of distal end configurations for an electrosurgical bloodless tissue dissection device.

In contrast to the prior art electrosurgical devices, with reference to FIG. 58*a*, one embodiment of an electrosurgical tool that can be configured in either an electrosurgical coagulation state or an electrosurgical cutting state is shown. In the illustrated embodiment, a lower jaw element 2301 comprises a first coagulating electrode 2302, a second coagulating electrode 2303, and an electrosurgical cutting electrode 2304. Each of the electrodes can be electrically isolated from each other by insulating members 2305. The upper jaw 2306 is not energized in this embodiment, but is merely used to press tissue against the lower jaw element 2301.

With the electrode arrangement illustrated in FIG. 58*a*, tissue that is in contact with the lower jaw element 2301 can be coagulated by electrically coupling each of the two coagulation electrodes 2302, 2303 with the corresponding outlet of a bipolar electrosurgical unit. Here, the two coagulation electrodes 2302 and 2303 can be supplied with electrical energy having opposite polarities. In some embodiments, it can be desirable that the supplied electrical energy has a potential difference of no more than 200V to reduce the risk of arcing and that electrode 2302 and 2303 have the same contact area with the tissue. The latter ensures the same electrosurgical effect for both electrodes.

With continued reference to FIG. 58*a*, after the two coagulation electrodes 2302, 2303 have achieved substantial hemostasis within the coagulated tissue volume, the tissue can be electrosurgically cut by applying energy to an electrosurgical cutting electrode 2304. During the electrosurgical cutting operation, the two coagulation electrodes 2302, 2303 can be electrically coupled to a corresponding outlet or outlets of a bipolar electrosurgical unit to function as return electrodes. Here, the potential difference between the cutting electrode 2304 and the two return electrodes 2302 and 2303 can desirably be between approximately 300-500V, while the two return electrodes can desirably be substantially equipotential.

With continued reference to FIG. 58*a*, in some embodiments, it can be desirable that the relative contact area of the electrodes with the tissue is much smaller for the cutting electrode 2304 than for the return electrodes 2302, 2303. For example, in some embodiments, desirably the cutting electrode can have a contact area that is between approximately 1% and 20% as large as a contact area of one of the return electrodes 2302, 2303. More desirably, the cutting electrode can have a contact area that is between about 5% and 10% as large as a contact area of one of the return electrodes 2302, 2303. In one embodiment, the cutting electrode can have a contact area that is approximately 10% as large as a contact area of one of the return electrodes 2302, 2303. This relative proportion between cutting area sizes lead to a relatively high current density (and hence high power density) in tissue close to the cutting electrode, which facilitates localized vaporization, or electrosurgical cutting of the tissue.

With continued reference to FIG. 58*a*, an additional aspect of the illustrated electrode arrangement is that the lower jaw 2301 can be used for both coagulation and cutting, regardless of whether the jaws are in an opened or closed position. This multiple functionality is advantageous when using the tool to spot-coagulate tissue, or to dissect tissue by configuring the tool in a cutting state and brushing the tool against the tissue.

Figure 58B:
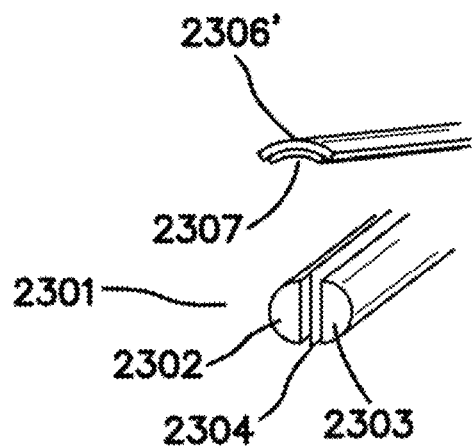

Another embodiment of electrode arrangement for a surgical tool is illustrated in FIG. 58*b*. In the illustrated embodiment, the upper jaw 2306' is not only used to press tissue against the lower jaw element 2301, but it also includes an upper electrode 2307 disposed thereon which can be supplied with electrical energy. Tissue can be coagulated by supplying the two lower coagulation electrodes 2302, 2303 with a first electrical polarity, and the upper electrode 2307 with a second, opposing polarity from a bipolar electrosurgical unit. Again, it is desirable that when configured for coagulation, the potential difference between the upper electrode 2307 and the two lower electrodes 2302, 2303 does not exceed 200V to reduce the risk of arcing to the tissue and that electrode 2307 has the same contact area with the tissue as the combined surface area of electrodes 2302 and 2303. The latter ensures the same electrosurgical effect for both electrode sides.

With continued reference to FIG. 58*b*, after hemostasis of the tissue between the upper electrode 2306' and the two lower electrodes 2302, 2303 has been substantially achieved, the tissue can be electrosurgically cut by supplying the electrosurgical cutting electrode 2304 with electrical energy. The upper coagulation electrode 2307 on the upper jaw 2306' can be configured as a return electrode by electrically coupling it with the corresponding outlet of a bipolar electrosurgical unit.

With continued reference to FIG. 58*b*, when the surgical tool is configured as a electrosurgical cutting device, desirably the potential difference between the cutting electrode 2304 and the return electrode 2307 is between approximately 300-500V. In some embodiments, it can be desirable that the contact area of the electrodes with the tissue is much smaller for the cutting electrode 2304 than with the return electrode 2307 on the upper jaw 2306'. For example, in some embodiments, desirably the cutting electrode can have a contact area that is between approximately 1% and 20% as large as a contact area of the return electrode 2307. More desirably, the cutting electrode can have a contact area that is between about 5% and 10% as large as a contact area of the return electrode 2307. In one embodiment, the cutting electrode can have a contact area that is approximately 10% as large as a contact area of the return electrode 2307. This relative sizing can lead to relatively high current density (and hence high power density) in the tissue close to the cutting electrode 2304, which facilitates localized vaporization, or electrosurgical cutting of the tissue. With the surgical tool distal end of FIG. 58*b* having electrodes 2302, 2303, 2304, 2307 as described above, only tissue between the two jaw elements can be coagulated and/or cut. Thus, unlike the embodiment of FIG. 58*a*, the tool illustrated in FIG. 58*b* is not configured to be used by employing the lower electrode only.

Figure 58C:
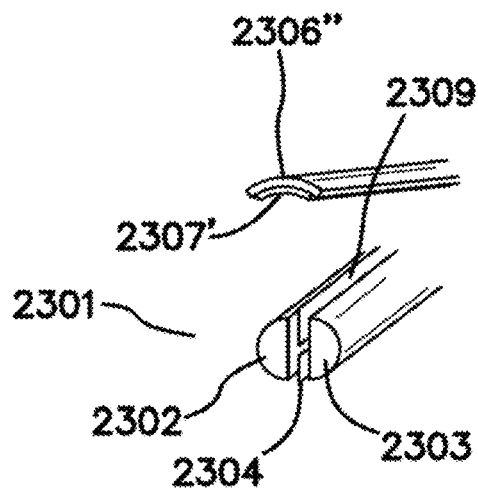

Another embodiment of electrode arrangement for a surgical tool is illustrated in FIG. 58*c*. In the illustrated embodiment, the upper jaw 2306" includes an upper electrode 2307', but also shows two cutting electrodes 2304 and 2309 that are sandwiched between two coagulation electrodes 2302 and 2303. In difference to the embodiment shown in FIG. 58*b*, both coagulation and cutting is distinguished for cases where the hand tool (and hence the jaw members) are fully opened or not fully opened. With a fully opened tool, tissue can be coagulated by applying the two lower coagulation electrodes 2302 and 2303 with opposing polarities, and will be cut by applying cutting electrode 2304 with the first and both electrodes 2302 and 2303 to the second polarity. In difference, a not fully opened tool will coagulate tissue by applying both lower coagulation electrodes 2302 and 2303 with one polarity and electrode 2307' to the opposing one, while cutting occurs between electrode 2309 and return electrode 2307'. Again, it is desirable that when configured for coagulation, the potential difference between the two lower electrodes 2302 and 2303 (tool fully open) or the upper electrode 2307' and the two lower electrodes 2302, 2303 (tool not fully open) does not exceed 200V to reduce the risk of arcing to the tissue.

The separation of cutting electrodes 2304 and 2309 facilitates cutting of tissue that is positioned within the upper and lower jaw elements (not fully opened), or cutting of tissue in contact with the bottom side of the tool. The separation prevents inadvertent cutting of tissue.

Figure 58D:
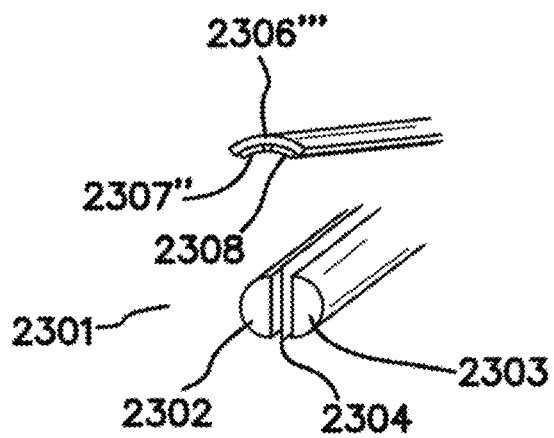

Another embodiment of electrode arrangement for a surgical tool is illustrated in FIG. 58*d* where the upper jaw 2306''' includes two separate electrodes 2307" and 2308. In this configuration, the upper jaw element 2306''' can be used to press tissue against the lower jaw element 2301, but can also supply electrical energy.

With continued reference to FIG. 58*d*, the electrodes 2302, 2303, 2307", 2308 can be selectively configured to a coagulation state. By supplying the coagulation electrodes 2302, 2303 on the lower jaw 2301 and the two coagulation electrodes 2307', 2308 on the upper jaw 2306''' with alternating polarities, tissue within the jaws can be coagulated. For example, in one possible coagulation state configuration, one coagulation electrode 2302 on the lower jaw 2301, and one coagulation electrode 2308 on the upper jaw 2306''' can be electrically coupled to a source of electrical energy having a first polarity. The other coagulation electrode 2303 on the lower jaw 2301, and the other coagulation electrode 2307" on the upper jaw 2306''' can be electrically coupled to a source of electrical energy having a second polarity generally opposite the first polarity. While this is an illustrative example, it is contemplated that other combinations of connections of the electrodes 2302, 2303, 2307", 2308 with electrical energy sources are possible to configure the tool in a coagulation state. It can be desirable that the contact area of the opposing coagulation electrode(s) are the same to provide the same electrosurgical effect for both electrode sides.

With continued reference to FIG. 58*d*, after homeostasis of the tissue between the upper electrodes 2307", 2308 and the two lower electrodes 2302, 2303 by application of electrical energy with the electrodes in the coagulation state, the tissue can be electrosurgically cut. The distal end of the surgical tool can be configured into a cutting state by supplying the electrosurgical cutting electrode 2304 with electrical energy. In various embodiments, one, some, or all of the other electrodes 2302, 2303, 2307", 2308 can be configured to function as return electrodes when the tool is in a cutting state by electrically coupling them with the corresponding outlet of a bipolar electrosurgical unit.

With continued reference to FIG. 58*d*, when the tool is configured in a cutting state, the potential difference between the cutting electrode and the return electrode is desirably between approximately 300-500V. Further, it can be desirable that the relative contact area of the electrodes with the tissue is much smaller for the cutting electrode 2304 than for any of the return electrodes 2302, 2303, 2307", 2308 or combinations thereof. For example, in some embodiments, desirably the cutting electrode 2304 can have a contact area that is between approximately 1% and 20% as large as a contact area of one of the return electrodes. More desirably, the cutting electrode can have a contact area that is between about 5% and 10% as large as a contact area of one of the return electrodes. In one embodiment, the cutting electrode can have a contact area that is approximately 10% as large as a contact area of one of the return electrodes. Just as with the embodiment illustrated and described with respect to FIG. 58*a*, the electrode arrangement illustrated in the embodiment of FIG. 58*d* can be used to spot-coagulate tissue, or to dissect the tissue when "brushing" the tool against it in a cutting mode.

The practicality of the tool configurations of FIGS. 58*a* through 58*d* can be further enhanced by selective activation and/or deactivation of the selected electrodes. In some embodiments, this selective activation and deactivation can be performed by operator-depressed electrical switches such as wired or wireless hand or foot operated switches, or switches positioned on the hand-piece. The electrosurgical unit will then address specific electrodes, depending on how far the jaws are opened and closed.

Figure 59A:
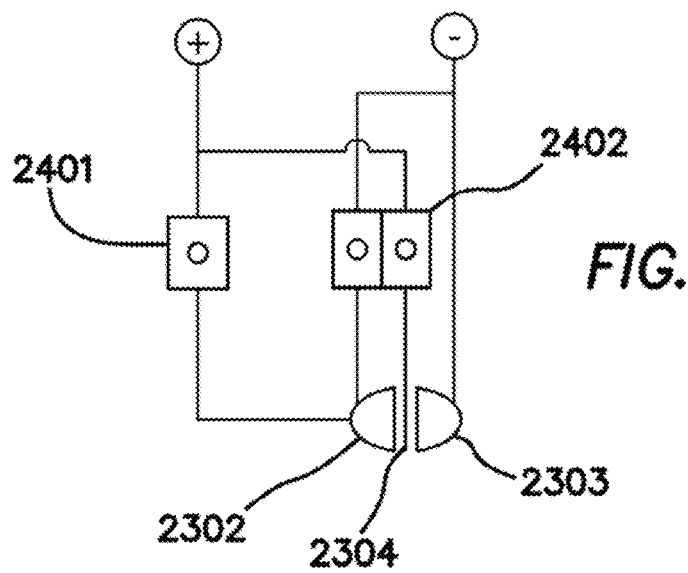
FIGS. 59A-C are schematic drawings of active electrode switching circuitries in the hand tools.

FIG. 59a illustrates a schematic circuit diagram for an electrode arrangement as given in FIG. 58a. Here, activation of a single-pole electrical switch 401 connects the outer coagulating electrodes 2302, 2303 to opposing polarities, while the center "cutting" electrode 2304 remains disengaged. This setting configures the electrodes in a coagulation state. Alternately, activation of a double-pole electrical switch 402 supplies the center "cutting" electrode 2304 with electrical energy having a first polarity, and the outer return electrodes 2302, 2303 with electrical energy having a second polarity generally opposing the first polarity. This setting configures the electrodes in a cutting state. As a result, the tool can be used for electrosurgical coagulation and/or cutting, and hence can perform the bloodless dissection of tissue.

Figure 59B:
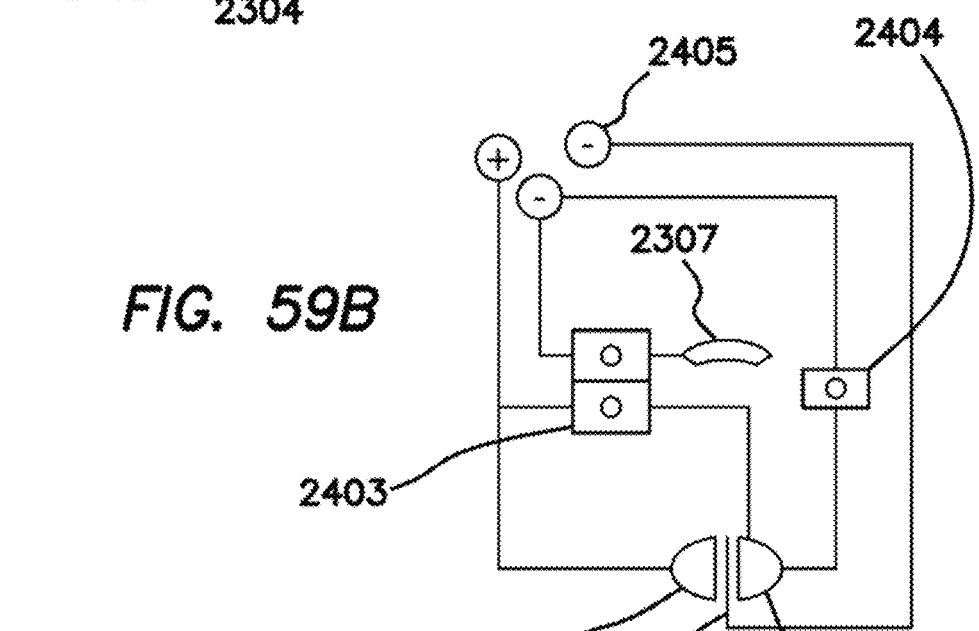

FIG. 59b illustrates a schematic power supply circuit that can be used for the electrode arrangement shown in FIG. 58b. In the illustrated embodiment, activation of a double-pole electrical switch 2403 connects the two outer coagulating electrodes 2302, 2303 on the lower jaw to a supply of electrical energy of a first polarity, and the coagulating electrode 2307 on the upper jaw to a supply of electrical energy of a second polarity substantially opposite the first polarity. With the switch 2403 in this position, the cutting electrode 2304 remains disengaged. This setting configures the electrodes of the surgical tool in a coagulation state. Alternately, activation of a single-pole electrical switch 2404 allows the lower jaw electrodes 2302, 2303 to be used for coagulation. The electrode on the upper jaw 2307 and the cutting electrode 2304 remain disengaged in this alternate coagulation configuration. To dissect tissue after it has been coagulated, a separate electrode outlet 2405 on an electrosurgical generator is used to address the cutting electrode 2304. Desirably, the cutting electrode is supplied with voltages of 300-500V with respect to the two return electrodes 2302, 2303 on the lower jaw.

Figure 59C:
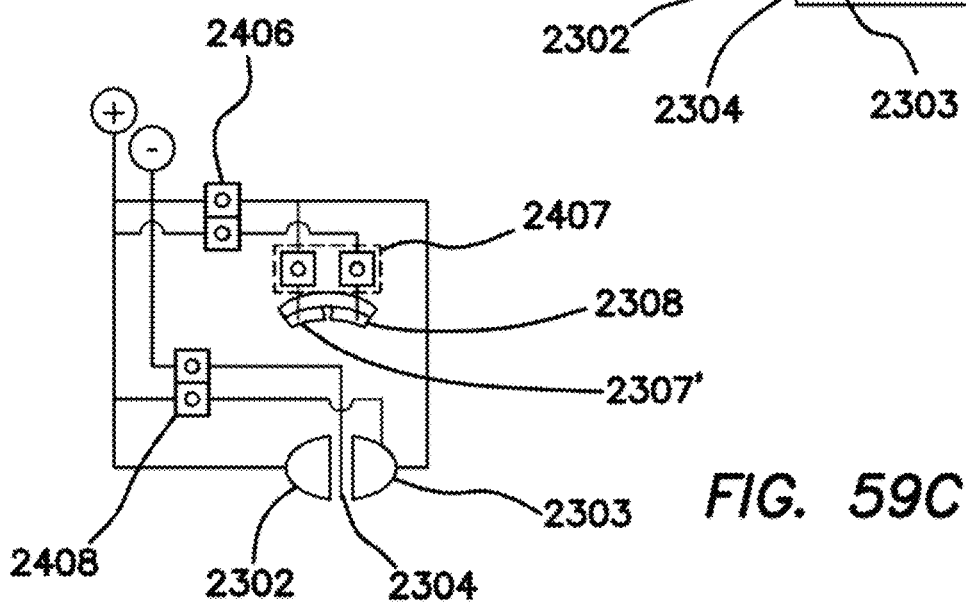

FIG. 59c illustrates a schematic power supply circuit that can be used to address the electrode arrangement of FIG. 58d. In the illustrated embodiment, activation of a double-pole electrical switch 2406 connects the two coagulating electrodes 2302, 2303, 2307", 2308 on both the lower and upper jaw to sources of electrical energy having opposing polarities. The cutting electrode 2304 remains disengaged. This setting can be used to configure the electrodes of a surgical tool in a coagulation state to coagulate tissue that is clamped between the upper and lower jaw element. Alternately, in other embodiments, a second coagulation double-pole switch 2407 can be implemented to separate the activation of the upper and lower jaws such that one or both jaws can be selectively actuated during a coagulation state. To utilize the lower jaw of the tool for electrosurgical cutting of coagulated tissue, activation of the cutting double-pole switch 2408 connects the cutting electrode 2304 to a source of electrical energy having a first polarity and the two return electrodes 2302, 2303 to a source of electrical energy having a second polarity substantially opposite the first polarity. The voltage supplied by the generator for this setting is desirably between approximately 300-500V to facilitate electrosurgical cutting. In the illustrated embodiment, the electrodes 2307", 2308 on the upper jaw element remain unaddressed during electrosurgical cutting.

As discussed in more detail above, the activation (or deactivation) of specific electrodes can configure the tool in a coagulation state or a cutting state. In certain embodiments, the selective activation and deactivation of specific electrodes can be facilitated by push-buttons, switches, or other electrical switching devices mounted on the hand-piece of the laparoscopic tool, or wired or wireless switches. In other embodiments, the selective activation and deactivation of specific electrodes can be facilitated by switches or other electrical switching devices that are incorporated into the handle mechanism of the hand-piece to switch at various positions of the jaw elements.

Regarding the circuit shown in FIG. 59a, referring to the tool shown in FIG. 58a, switching devices mounted on the hand-piece can be used to allow a user to selectively configure the electrodes on the tool. Switch 2401 can be a hand-activated switching device mounted on the hand-piece that can be selectively activated to configure the electrodes of the tool in a coagulation state. Switch 2402 can be a hand-activated switching device mounted on the hand-piece that can be selectively activated to configure the electrodes of the tool in a cutting state. In another embodiment, switches 2401, 2402 can be incorporated into the handle mechanism to such that the tool is automatically switched from a coagulation state to a cutting state at a predetermined position of the clamping members.

One benefit of switching the electrodes from a coagulation state to a cutting state at different positions of the jaw elements (e.g., open and nearly closed jaws) can be seen with respect to the embodiment of FIG. 59b. In certain embodiments, switches 2403 and 2404 can be incorporated within the handle of the surgical tool for self-switching based on the position of the trigger mechanism, rather than on the outside of the hand tool for hand-activation. In one embodiment, switch 2403 can be disengaged and switch 2404 engaged in a fully open jaw element position. Thus, with the jaw elements fully opened, the switches 2403, 2404 can be configured such that only the lower jaw element can be used for spot coagulation. In this embodiment when the trigger of the hand-piece is actuated to move the jaw elements closed from the fully opened jaw position, switch 2404 is disengaged and 2403 simultaneously engaged. Thus, with the jaw elements moved into a partially-closed configuration, the tool can be used to coagulate or cut tissue that is clamped between the upper and lower jaw element.

In the described embodiment, the electrode switches are automatically actuated as the jaw elements are closed. Although the described embodiment includes a switch point between a coagulation state and a cutting state upon commencement of closure from the jaws fully opened position, other embodiments can have different switching positions. For example, with this automatic switching, the switches 2403, 2404 can be configured such that the electrodes are activated and deactivated at any position in an opening or closing cycle. In other embodiments, a surgical tool can include the electrode configuration of FIG. 58b and the switching circuit of FIG. 59b with the switches 2403, 2404 configured for manual actuation, such as by positioning on the tool hand-piece.

Similarly, in certain embodiments, a surgical tool having the electrode configuration of FIG. 58d with the switching circuit of FIG. 59c can have the switches 2406, 2408 incorporated into the trigger mechanism for automatic switching between a coagulation state and a cutting state at certain jaw element positions. In certain embodiments, it can also be desirable to incorporate the second coagulation switch 2407 into the trigger mechanism of the hand-piece, disengaging the electrodes on the upper jaw element in predetermined jaw position such as a fully opened jaw position. This switching arrangement of the second coagulation switch 2407 allows for example to spot-coagulate tissue using the lower jaw element without inadvertently touching tissue with the electrodes on the upper jaw element. In other embodiments, it can be desirable for the second coagulation switch 2407 to be positioned on the hand-piece to be manually actuated by a user, allowing a user to selectively engage and disengage the electrodes on the upper jaw element. In other embodiments, all of the switches 2406, 2407, 2408 of the switching circuit of FIG. 59*c* can be positioned on the hand-piece of the surgical tool to be manually actuated by the user.

Figure 60:
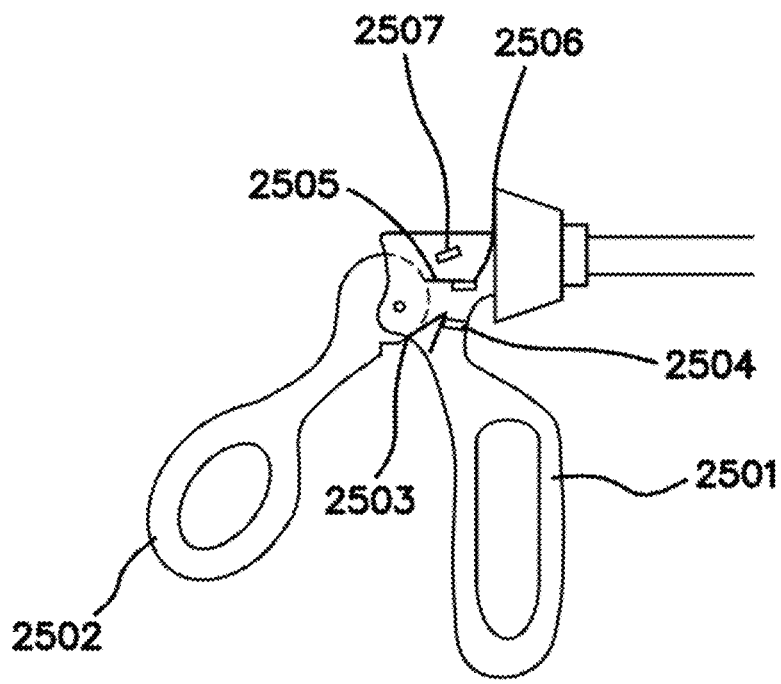
FIG. 60 is a schematic drawing of the inside of the hand-piece, illustrating the embodiment of active electrode switching mechanism based on the opening of the jaw elements.

With reference to FIG. 60, one configuration of tool switching is illustrated. In the illustrated embodiment, electrical contacts are incorporated both into the hand-piece 2501 and the trigger 2502. For example, as illustrated, the hand-piece 2501 includes a first electrical contact 2504, a second electrical contact 2506, and a third electrical contact 2507 positioned therein. In the illustrated embodiment, the trigger 2502 includes a first electrical contact 2503 and a second electrical contact 2505. All of the electrical contacts 2503, 2504, 2505, 2506, 2507 are positioned to engage and disengage one another at predetermined relative positions of the trigger 2502 and the hand-piece 2501.

With continued reference to FIG. 60, as shown, the first contact 2503 on the trigger 2502 engages the first contact 2504 on the hand-piece 2501 when the jaws are in a fully opened position, but the first contacts 2503, 2504 are disconnected when the trigger 2502 is moved from the open position to close the jaws. In the illustrated embodiment, with the jaws in the fully opened position, the second contact 2505 on the trigger 2502 engages the second contact 2506 on the hand-piece 2501. But, the second contacts 2505, 2506 are disconnected when the trigger 2502 is moved from the open position to close the jaws. As the jaws are closed further, the second contact 2505 on the trigger 2502 becomes engaged with the third contact 2507 on the hand-piece 2501, and the first contact 2503 on the trigger engages the second contact 2506 on the hand-piece 2501. This engagement allows switching of the polarity of the contacts 2507 as the hand-piece is closed further. As a result, and with reference to FIG. 58*b*, the switching mechanism in FIG. 60 allows for activation of the upper electrode 2307 and a lower coagulating electrode 2303 with opposing polarities in a fully open jaw position. With progressive tissue desiccation, the jaws start to close, and the upper electrode 2307 becomes electrically disengaged (by disconnecting contact 2503 and 2504 in FIG. 60), whereas the lower electrode 2303 is switched to the same polarity as the second electrode 2302 (by connecting contact 2505 from 2506 to contact 2507 in FIG. 60). In a separate step, the desiccated tissue between the upper and lower jaw elements can now be electrosurgically dissected.

Figure 61:
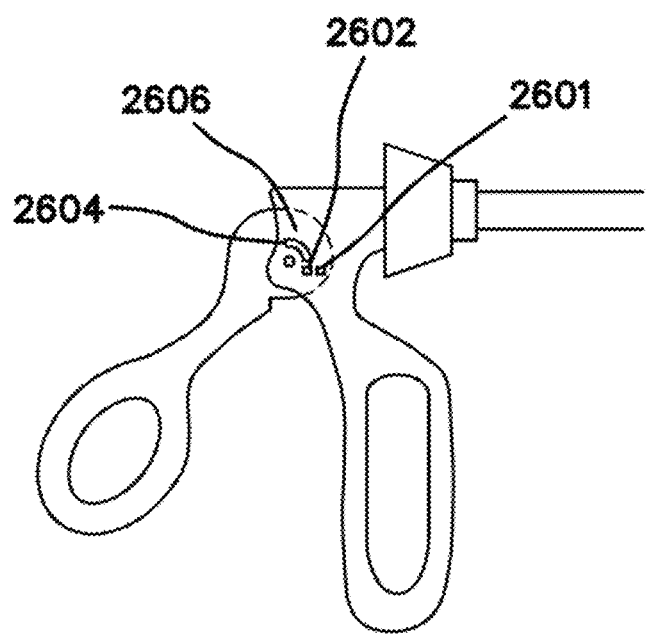
FIG. 61 depicts another embodiment of an active electrode switching mechanism, also based on the opening of the jaw elements.

With reference to FIG. 61, another embodiment of a switching mechanism is illustrated with the jaw members in a fully opened position. In the illustrated embodiment, concentric contact strips are disposed on the hand-piece and opposing contact pins are mounted on the trigger. In other embodiments, contact pins can be mounted on the hand-piece and contact strips positioned on the trigger. In the illustrated embodiment, trigger movement allows the pin contacts (which are connected to specific electrodes) to be supplied with electrical energy at certain tool positions. In some embodiments, the polarity of a single pin (i.e., the same electrode) might change as the jaws are opened or closed.

One contact strip and pin arrangement is illustrated in FIG. 61 for an electrode configuration of FIG. 3*b*. In the illustrated embodiment, pin 2601 is electrically coupled to the electrode 2307 (FIG. 58*b*) on the upper jaw member and is disengaged. As illustrated, pin 2602 is electrically coupled to one of the coagulating electrodes 2302, 2303 (FIG. 58*b*) on the lower jaw. As illustrated, pin 2602 is engaged as the trigger is moved from the "fully-open" position to a partially closed position. With further advancement of trigger, pin 2602 changes to the same polarity as the second coagulating electrode so that both can be used as return electrodes for cutting.

Figure 62:
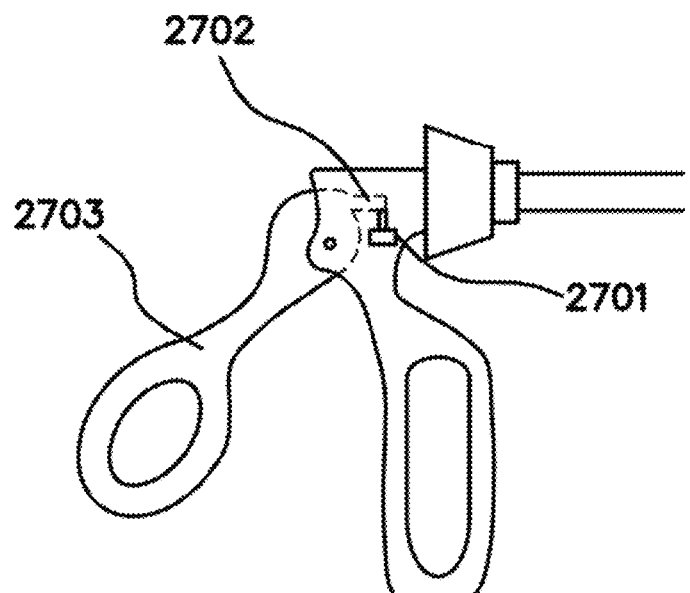
FIG. 62 depicts an embodiment of a passive switching mechanism, also based on the opening of the jaw elements.

While both FIG. 60 and FIG. 61 show active switching mechanisms in the hand tool (where active electrodes can be switched), which allows the tools to be used with "conventional" electrosurgical generators, FIG. 62 shows a configuration for passive switching. Here, a momentary switch 2701 is mounted in the handle and is closed by a trigger 2702 when lever 2703 is brought into the "fully open" position.

Figure 63:
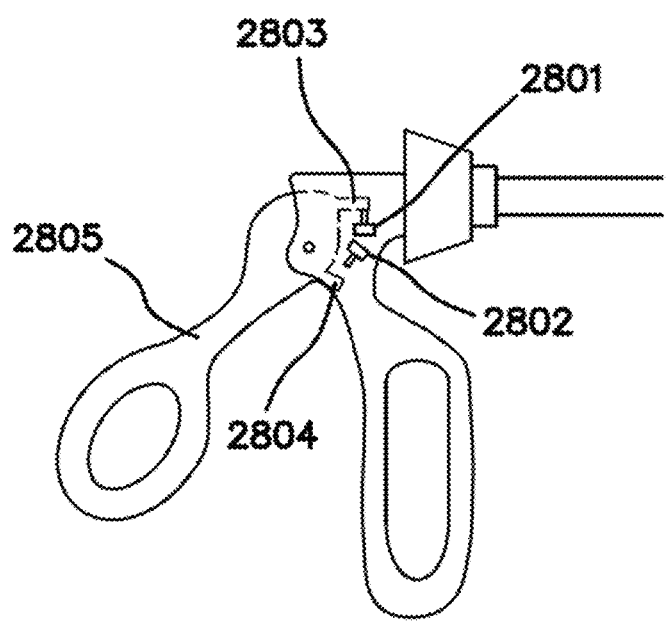
FIG. 63 depicts another embodiment of a passive switching mechanism, based on both the opening and closing of the jaw elements.

Similarly, FIG. 63 shows the incorporation of two momentary switches 2801 and 2802 that are closed by trigger 2803 and 2804 in the "tool fully open" and "tool fully closed" position, respectively. The closing of the momentary switches as shown in FIGS. 62 and 63 is then used for logic switching of multi-electrode generators, as described in the following.

Figure 64:
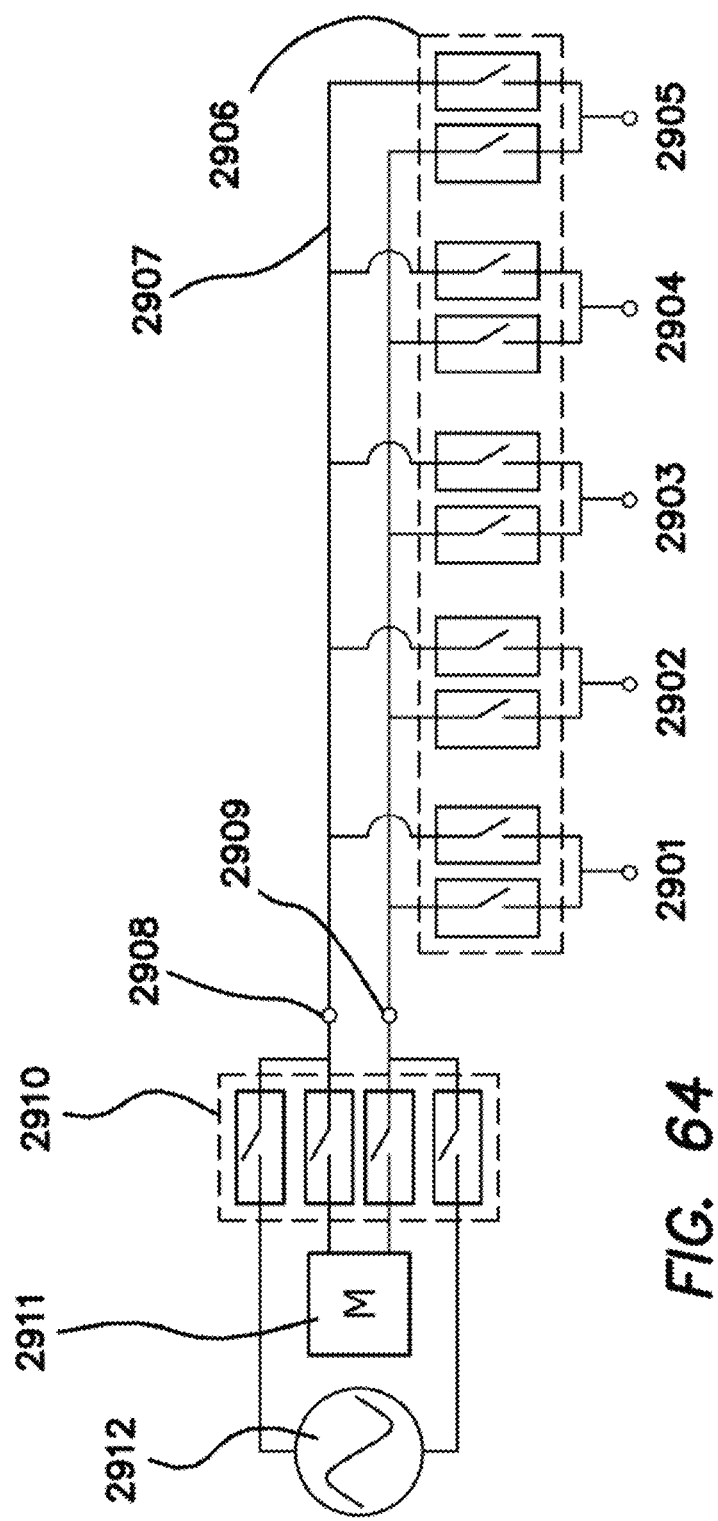
FIG. 64 depicts a schematic circuitry that connects five electrodes through relays to a bus bar which is relayed to a measurement circuit, or an electrosurgical power plant.

FIG. 64 shows a schematic of a multi-electrode switching power supply for directly connecting individual tool electrodes (such as all individual electrodes in FIGS. 58*a* through 58*d*) to an internal RF power source. Instead of switching two polarities of an external electrosurgical unit to different electrodes with active switches in the hand tools, this arrangement facilitates population of individually-connected electrodes with different polarities by switching within the power supply. Depending on the tool position, as determined by tool position switches shown in FIGS. 62 and 63, the electrodes can be populated differently as determined by pre-determined logic. As such, the five electrode connection points 2901 through 2905 are connected to a relay bank 2906 to a bus bar 2907. Through selected switching of all relays in the relay bank 2906, each outlet point 2901 through 2905 can be independently and/or concurrently connected to the plant connection points 2908 and 2909, respectively. The plant connection points 2908 and 2909 themselves can be connected through the relay bank 2910 to the two outlets of a tissue measurement circuit 2911, or a RF plant 2912.

Figure 65:
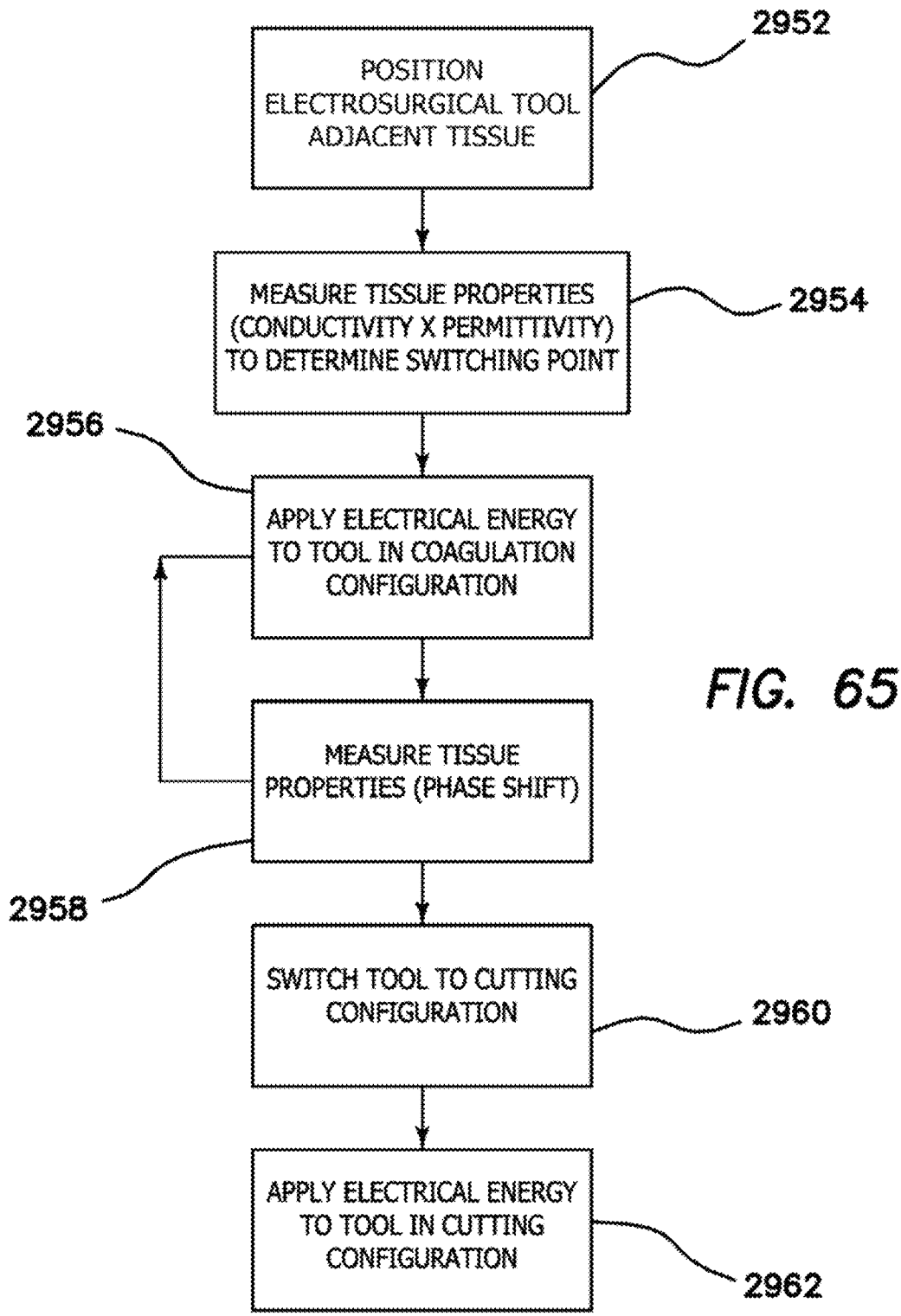
FIG. 65 schematically illustrates one embodiment of a method for substantially bloodless dissection of biological tissue.

With reference to FIG. 65, in certain embodiments, methods of using an electrosurgical tool for substantially bloodless tissue dissection are schematically illustrated. The illustrated method includes a positioning step 2952, a tissue assessment step 2954, an applying-electrical-energy-to-coagulate step 2956, a tissue measurement step 2958, a switching step 2960, and an applying-electrical-energy-to-cut step 2962. In the positioning step 2952 an electrosurgical tool having a plurality of electrodes being configurable in one of a coagulation configuration and a cutting configuration is positioned adjacent to tissue to be dissected. In certain embodiments, the electrosurgical tool comprises aspects of the electrosurgical tools discussed herein and illustrated in FIGS. 56 and 58-63.

In the tissue assessment step 2954, a measurement signal is applied to the tissue by the coagulation electrodes to determine a future trigger level to switch from coagulation to cutting. This determination can be achieved by measuring the product of conductivity and permittivity of the tissue, pointing to the desired electrical phase shift switching level for the respective tissue. For example, in some embodiments, desirable cutting switching levels occur at 10 degrees to 40 degrees. More desirably, the preferred switching level for blood vessels is between 10 to 30 degrees phase shift, while for highly vascular tissue (such as organs) it is rather between 20 to 40 degrees.

In the applying-electrical-energy-to-coagulate step 2956, electrical energy is applied to the electrosurgical tool in a coagulation configuration to achieve hemostasis in the tissue. In various embodiments discussed herein, electrode configurations for coagulation are provided. For example, applying electrical energy to the electrosurgical tool in the coagulation configuration can comprise supplying one of a plurality of electrodes with electrical energy having a first polarity and supplying another of the plurality of electrodes with electrical energy having a second polarity generally opposite the first polarity. Desirably, a potential difference between the electrode having the first polarity and the electrode having the second polarity is no more than approximately 200 V.

During the coagulation process of the tissue the phase shift between applied voltage and incurred current is measured concurrently in step 2958 to provide feedback of the coagulation status. Once the pre-determined switching level is reached, the process will proceed to the switching step 2960.

In the switching step 2960, as discussed above, some embodiments of electrosurgical tool can comprise a handle assembly including a switching mechanism. This switching mechanism can selectively configure the electrosurgical tool in either the coagulation configuration or the cutting configuration depending on a position of a trigger of the handle assembly. As discussed above, in some embodiments the switching mechanism can be configured such that with the electrosurgical tool in an open position, the electrodes are configured in the coagulation configuration. The switching mechanism can further be configured such that when the electrosurgical tool is moved towards a closed position, the electrodes are configured in the cutting configuration. In other embodiments, switching of the configuration of electrodes from the coagulation configuration to the cutting configuration can occur at different predetermined positions of the trigger of the handle assembly. In yet another embodiment, the switching can occur within a multi-electrode power supply as shown in FIG. 64.

In the applying-electrical-energy-to-cut step 2962, electrical energy is applied to the electrosurgical tool in a cutting configuration to dissect the tissue. In various embodiments discussed herein, electrode configurations for cutting are provided. For example, applying electrical energy to the electrosurgical tool in the cutting configuration can comprise supplying one of a plurality of electrodes with electrical energy and configuring another of the plurality of electrodes as a return electrode. Desirably, a potential difference between the cutting electrode and the return electrode is between approximately 300 V and approximately 500 V.

Electrosurgical Tissue Stapler

Historically, connecting or reconnecting living tissue has involved the use of suture, clips or staples. More recently, the use of electricity or heat has come to be used to complete the connection of living tissue or seal connected tissue against leakage or bleeding.

However, there remains a need to secure or connect portions of living tissue, especially conduits, without the use of staples, suture or clips.

An apparatus and method for permanently attaching or connecting living tissue comprising an electro-surgically generated electrical current that is delivered to tissue by a clamping jaw having features that increase current density at preferred locations are provided.

Referring to FIGS. 66-72 a surgical tissue fusing or welding instrument 3200 having an elongate body 3210, a proximal end 3230 comprising an operable handle 3235, and a distal end 3220 comprising a jaw assembly is provided. In some embodiments the jaw assembly can include fixed jaw 3280 and an operable jaw 3260 pivotable with respect to the fixed jaw 3280. In other embodiments, the jaw assembly can include two operable jaws. As discussed in further detail below, the tissue fusing or welding instrument 3200 can be configured to perform a stapling-like procedure, which can desirably be applied, for example in bariatric surgical procedures, or other procedures where staple-like closure of tissues is desirable.

Figure 66:
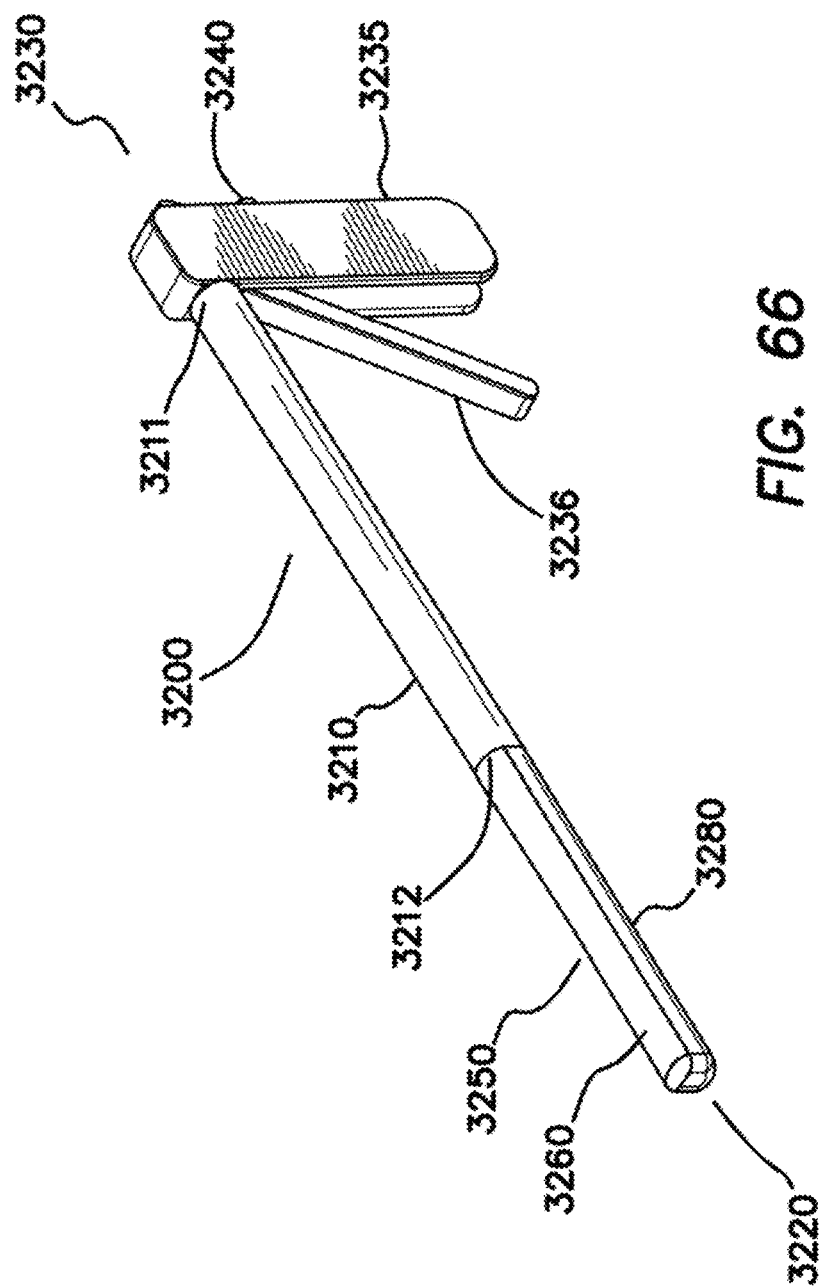
FIG. 66 is a perspective view of an electrosurgical instrument in a closed condition.
Figure 67:
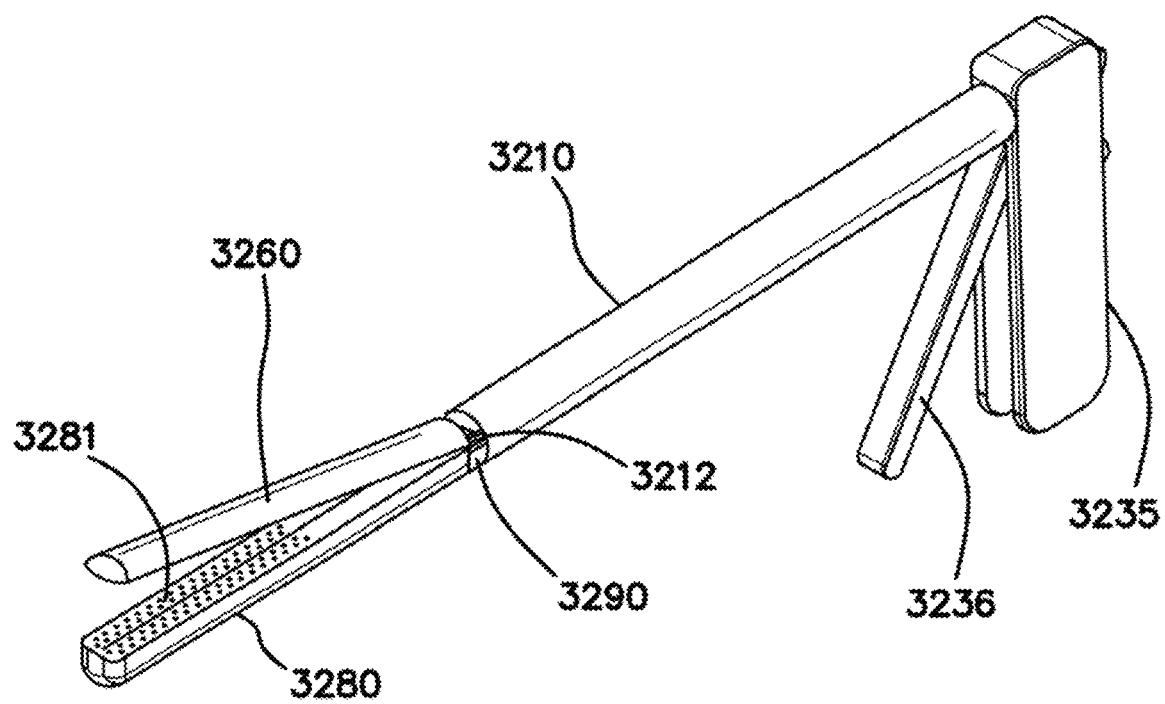
FIG. 67 is a perspective view of an electrosurgical instrument in an open condition.
Figure 68:
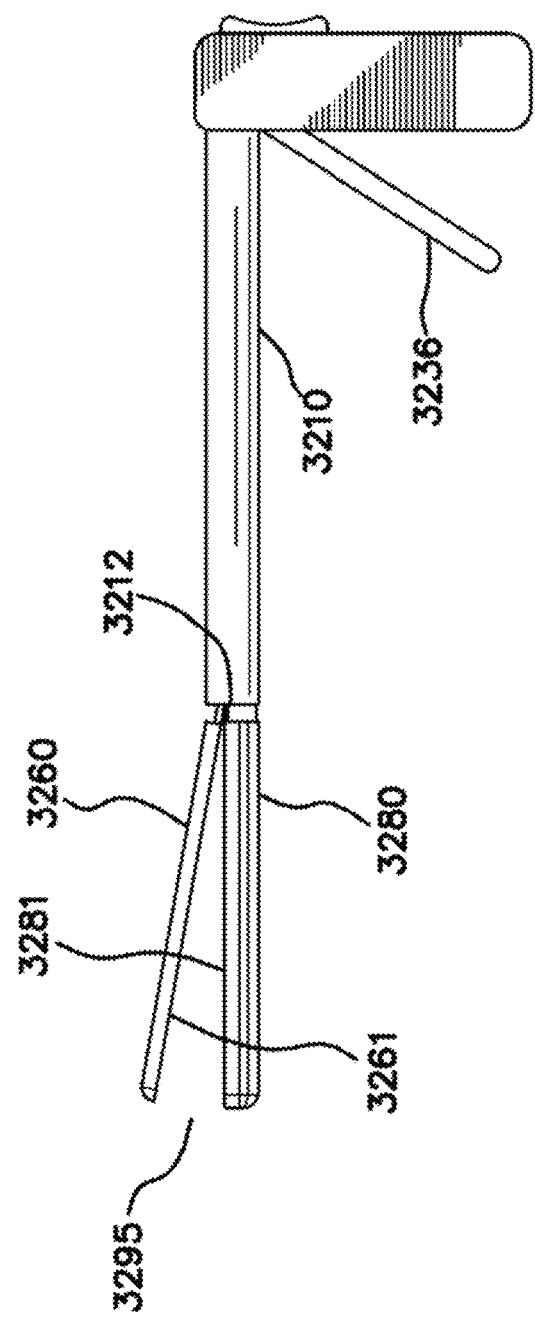
FIG. 68 is a side view of an electrosurgical instrument in an open condition.
Figure 69:
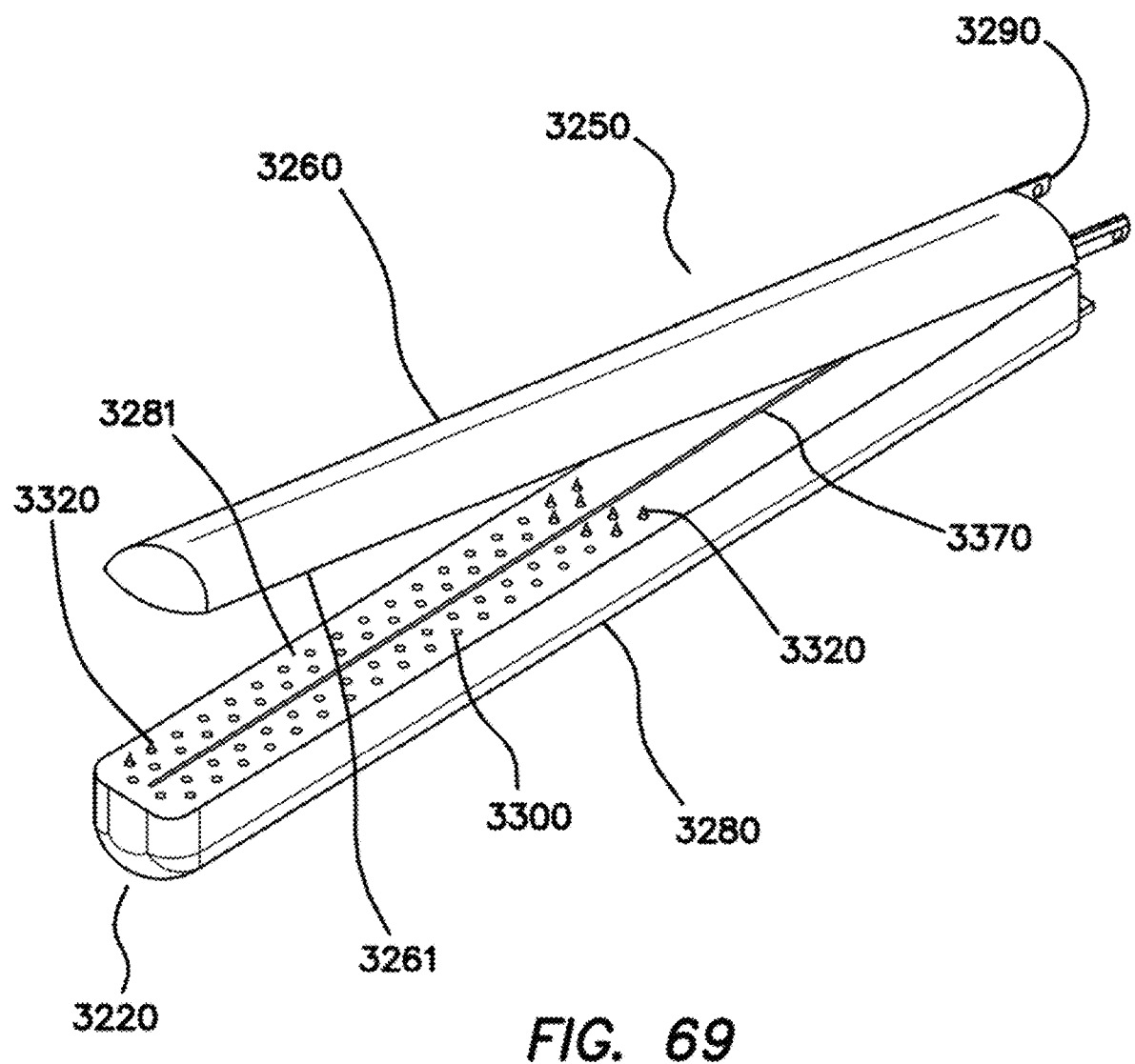
FIG. 69 is an enlarged perspective view of a clamping portion of an electrosurgical instrument in an open condition.
Figure 70:
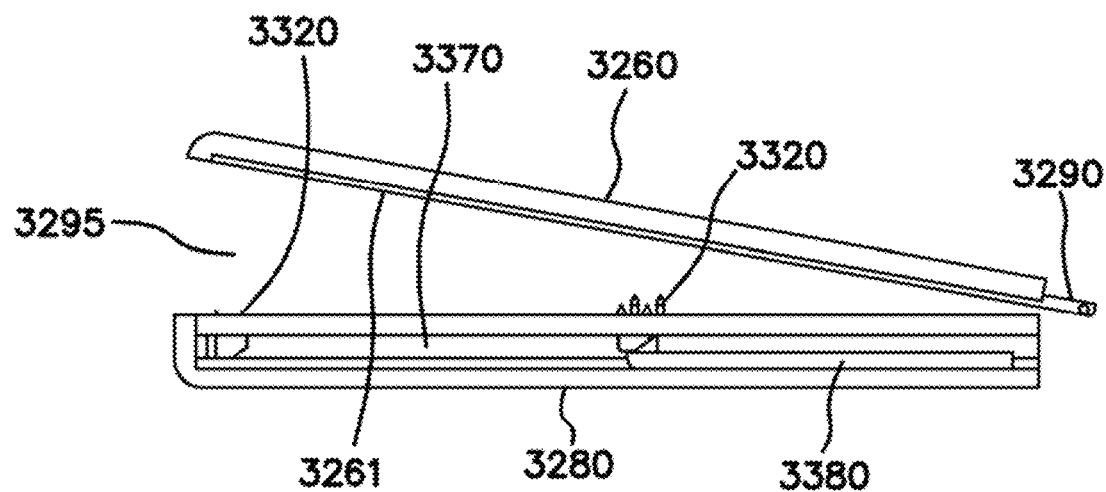
FIG. 70 is a side section view of an electrosurgical instrument in an open condition.
Figure 71:
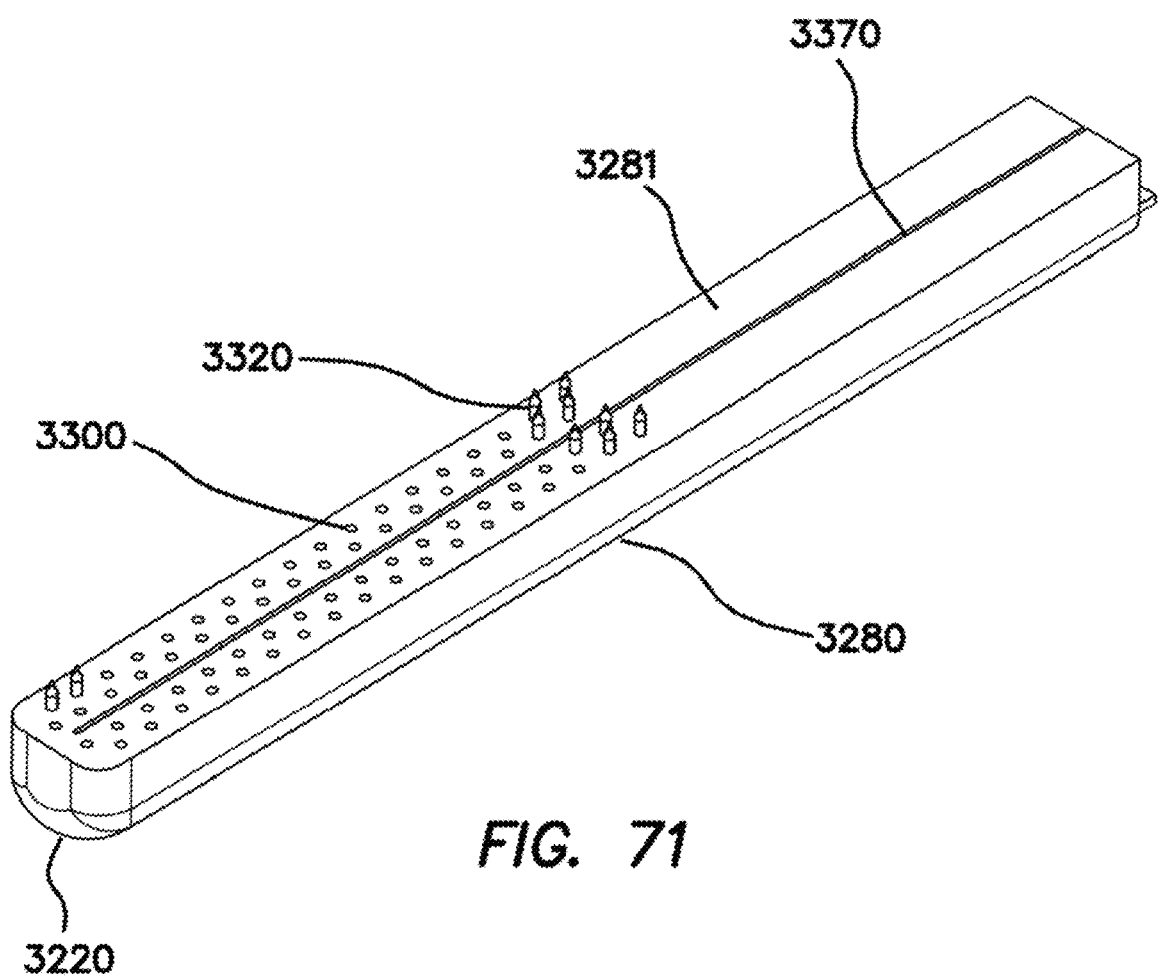
FIG. 71 is an enlarged perspective view of a clamping jaw portion with the top clamping jaw removed.
Figure 72:
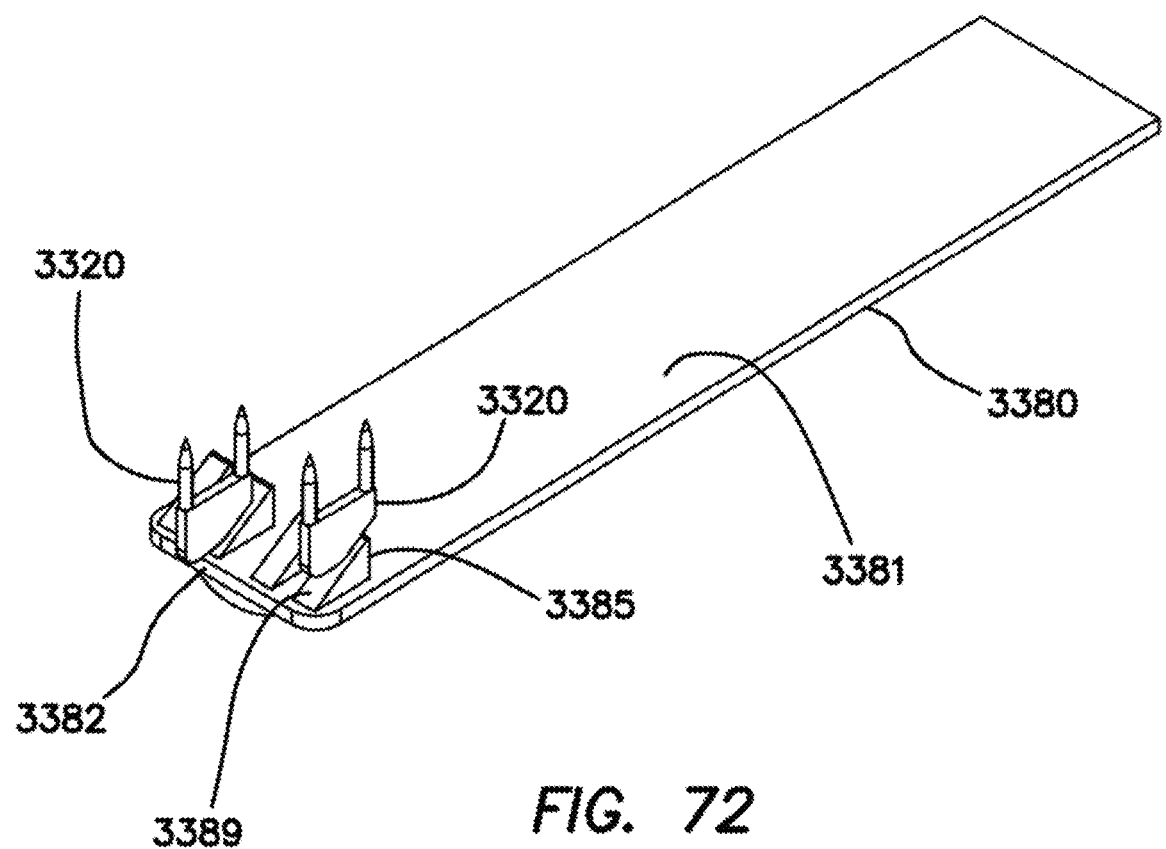
FIG. 72 is an enlarged perspective view of an actuator for advancing electrodes.
Figure 73:
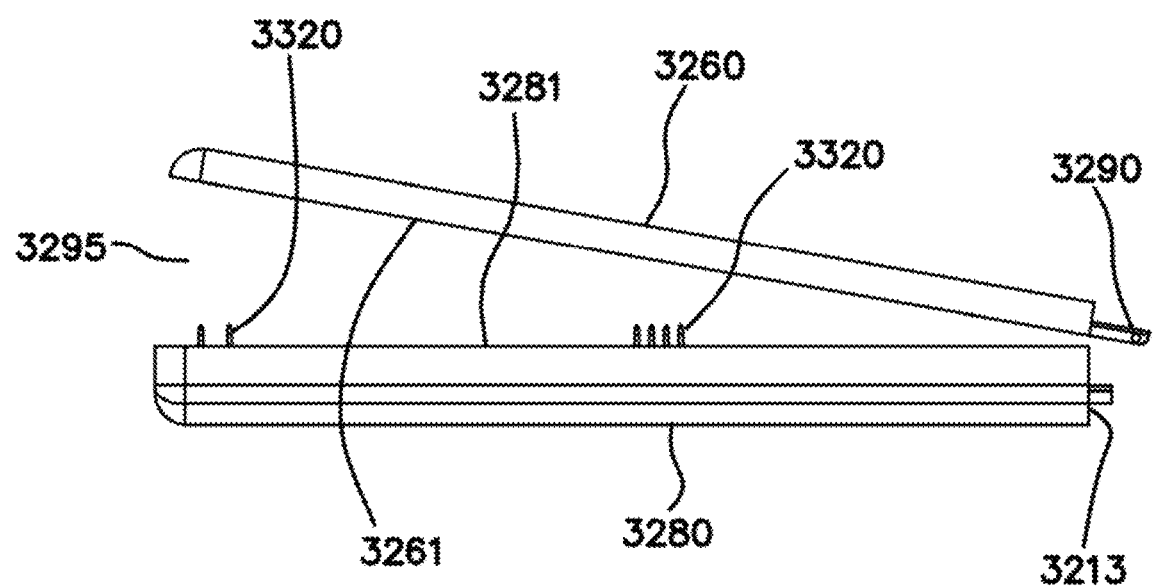
FIG. 73 is an enlarged side view of clamping jaws in an open condition with electrodes extended.
Figure 74:
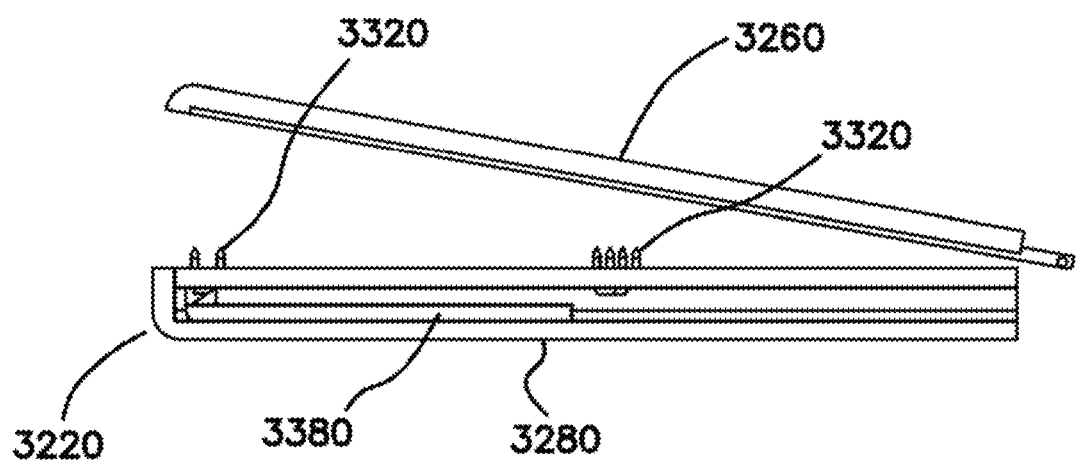
FIG. 74 is an enlarged side section view of clamping jaws in an open condition and having electrodes extended.

With reference to FIGS. 66-68, in certain embodiments, the elongate body 3210 can be sized and configured to be used through a surgical access port such as a trocar cannula for use in a laparoscopic procedure. For example, the elongate body can have an outer diameter corresponding to one of several standard sizes of trocar cannulae, or the elongate body can be sized for a non-standard application-specific access port. In other embodiments, the elongate body 3210 can be sized and configured for use in a portless surgical incision.

With continued reference to FIGS. 66-68, the proximal handle 3235 can be sized and configured to be usable by one hand of a user. The proximal handle 3235 can provide connecting features such as an electrical plug for connection to an electrosurgical surgical generator such as the electrosurgical generator discussed above with respect to the electrosurgical system. In some embodiments, the proximal handle 3235 can include an operating switch 3240. The operating switch 3240 can allow the user to electrically energize an active portion of the device 3200 selectively. The proximal handle can also include a movable lever 3236 operatively coupled to the jaw assembly to allow the user to grasp, hold and compress selected tissue between the distal jaw portions 3260, 3280. FIG. 66 illustrates the electrosurgical tool 3200 in a closed state with surfaces 3261, 3281 of the distal jaw portions 3260, 3280 proximate one another. FIGS. 67-68 illustrate the electrosurgical tool 3200 in an open state with surfaces 3261, 3281 of the distal jaw portions 3260, 3280 spaced apart from one another such that tissue can be received in a gap 3295 formed therebetween.

With reference to FIGS. 69-72, the jaw assembly 3250 of the electrosurgical tool 3200 can include a plurality of electrodes positioned thereon to simulate stapling action during application. In the illustrated embodiment, a plurality of electrodes 3320 is arranged in pairs in spaced rows within correspondingly spaced recesses 3300 in the first, fixed jaw 3280. The electrodes extend in four generally parallel columns extending longitudinally from a proximal end of the jaw assembly to a distal end of the jaw assembly. In other embodiments, it is contemplated that the number and arrangement of electrodes can be different from the illustrated embodiment. For example, in some embodiments, the first jaw 3280 can include spaced single electrodes, in other embodiments, the first jaw 3280 can include spaced rows of 3, 4, 5, 6, 7, or more than 7 electrodes. In still other embodiments, the first jaw 3280 can include geometric arrangements of electrodes such as, for example, electrodes in angled, curvilinear, or shaped rows, or electrodes can be randomly distributed in corresponding randomly distributed recesses in the first jaw 3280. For use in bipolar surgical procedures, it can be desirable that the electrodes are configured to be applied in pairs such that one pair member can be electrically coupled to an electrical energy source having a first polarity and the second member of each pair can be electrically coupled to an electrical energy source having a second polarity opposite the first polarity. In the illustrated embodiment, the electrodes 3320 are sized and configured to selectively extend and recede into the recesses 3300 to contact tissue positioned in the jaw assembly as further discussed below.

With continued reference to FIGS. 69-72, In the illustrated embodiment, the second jaw 3260 is pivotably coupled to the first jaw 3280. As illustrated, the movable second jaw 3260 is hingedly coupled to the first jaw 3280 at a proximal pivot point 3290. The second jaw 3260 can be operatively coupled to the movable lever 3236 such that the jaw assembly can be opened and closed by force supplied to the movable lever 3236.

With continued reference to FIGS. 69-72, the jaw assembly can further comprise a cutting element 3371 such as a slidable or movable cutting blade. In the illustrated embodiment, the first jaw 3280 comprises a linear slot 3370 that is sized and configured to hold the cutting element 3371. In operation, the cutting element is advanceable along the slot 3370 from a proximal position within the first jaw 3280 to a distal position within the first jaw 3280. In other embodiments, other cutting elements 3371 can be used in the electrosurgical tool. For example, some embodiments can have reciprocating mechanical cutting blades or radially advanceable cutting elements. Other embodiments of electrosurgical tool can include electrical cutting elements such as cutting electrodes.

With reference also to FIGS. 73-80 in certain embodiments, the electrodes 3320 can be urged upward or selectively extended by a distally moving actuation member such as a sled 3380 comprising a substantially flat elongate body 3381 and at least one cam or peak 3385 arranged to contact the electrodes 3320 at desired intervals. In some embodiments, the electrodes 3320 can be arranged in a staggered pattern. In other embodiments, the cams or peaks 3385 on the actuation member may be arranged in a staggered pattern to accomplish a sequential extension of the electrodes 3320. In still other embodiments, all of the plurality of electrodes 3320 can be selectively extended substantially concurrently, such as by movement of a plurality of cams or peaks on an actuation member.

With continued reference to FIGS. 73-80, in some embodiments, the electrosurgical tool is configured such that a sequential extension pattern includes a number of electrodes 3320 extended at any given moment or with any given force to desirably maximize the force supplied to the proximal lever 3236 and maximize the current density between the electrodes 3320 and the compressed tissue 3030. Advantageously, sequential extension and energizing of the electrodes 3320 can prevent excessive thermal damage to compressed tissue 3030 as would be the case if all electrodes 3320 were to be energized at the same time. In embodiments of electrosurgical tool including concurrent extension of the plurality of electrodes 3320, the electrodes can be sequentially energized to reduce the risk of thermal damage to tissue.

Figure 75:
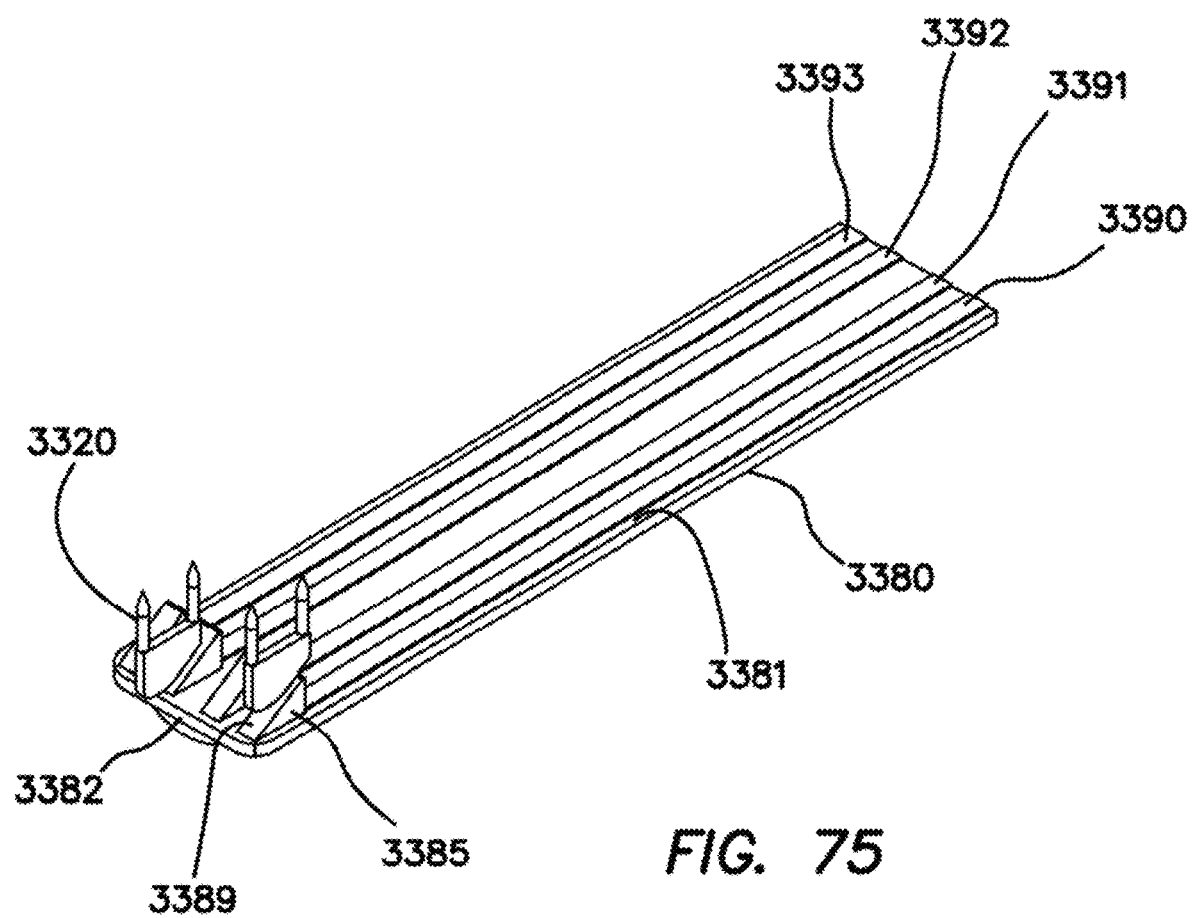
FIG. 75 is an enlarged perspective view of an actuator sled and associated electrical contacts.

With reference to FIG. 75, in certain embodiments, the electrodes 3320 can be electrically coupled to the electrosurgical tool through contacts disposed on the actuation member or sled 3380. In other embodiments, the electrodes can be electrically coupled to the electrosurgical tool through one or more wires extending longitudinally within the jaw assembly, a contact strip disposed on or in one of the jaws, or another electrical coupling. In the illustrated embodiment, electrical contact between the actuation member peaks 3385 and electrosurgical tool, which can be coupled to an electrical power source such as a generator can be provided by contact strips 3390, 3391, 3392, 3393 associated with the elongate flat portion 3381 of the movable actuator sled 3380. The sled 3380 can be configured to move and energize the electrodes in a sequence or rhythm. In various embodiments, the sled 3380 can be automatically or manually controlled.

As discussed further below, in some embodiments, the contact strips 3390, 3391, 3392, 3393 can be electrically energized such that the electrosurgical tool operates as a bipolar surgical tool. In the illustrated embodiment, which includes four longitudinally extending columns of electrodes 3320 (see, e.g., FIG. 71), one of the contact strips 3390, 3391, 3392, 3393 can electrically couple with one or more electrodes 3320 in a corresponding longitudinal column of electrodes. In other embodiments, other electrical contact arrangements are contemplated including more or fewer than four contact strips on the actuation member. For example, two contact strips can be relatively wide to each couple with two columns of electrodes in a four electrode column electrosurgical tool such as that illustrated in FIG. 71. In other embodiments, the electrosurgical tool can have more or fewer than four longitudinal columns of electrodes and can have a correspondingly more or fewer than four contact strips.

Figure 76:
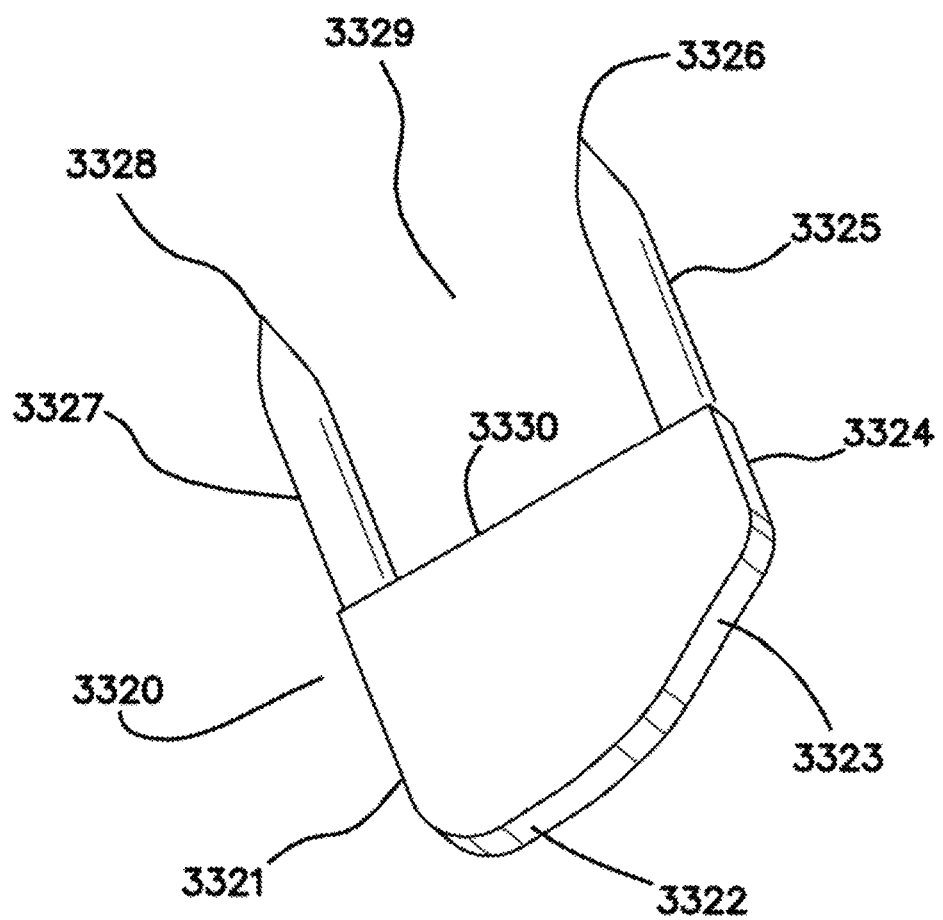
FIG. 76 is an enlarged perspective view of an electrode.

With reference to FIG. 76, the electrodes 3320 can be configured to be extended and retracted by the sliding actuation member peaks. In the illustrated embodiment, the electrodes 3320 comprise a flat body portion 3324 that is sized and configured to nest within recesses 3300 of the first jaw portion 3280 and maintain the electrode 3320 in a particular position depending on the relative position of the actuation member peak 3385. The flattened body 3324 can include a contacting surface 323 that is configured to elevate the electrode 3320 in response to the motion of an associated cam or contactor peak 3385. The flattened structural portion 3321 of the electrode 3320 transitions into a pair of pointed penetrating elements 3325, 3327 that extend through holes in the recesses 3300 of the first jaw 3280.

In operation, as the sled 3380 is advanced distally, the contacting surfaces 3323, 3322 of the electrodes 3320 and the cam surfaces 389 of the contactor peaks 3385 engage and extend the individual pairs of electrodes 3320 beyond the contacting face 3281 of the first jaw 3280. As the sled 3380 is advanced distally past a pair of electrodes 3320, the pair retracts into the first jaw 3280. Desirably, the electrodes 3320 are configured to be maintained within the jaw assembly after extension of the electrodes rather than be deposited in tissue once the electrosurgical tool is removed from a tissue site. As illustrated, the electrode pairs 3320 do not extend completely out of the first jaw 3280 as a contact surface 330 on the upper surface of the flattened structural portion 3321 interferes with the contacting face 3281 of the first jaw. While the illustrated embodiment illustrates paired electrodes 3320 with a connecting flattened structural portion 3321, in other embodiments, single electrodes 3320 can be maintained within the first jaw by a flared lower portion or flanged extensions that interfere with the contacting face 3281 of the first jaw.

Figure 77:
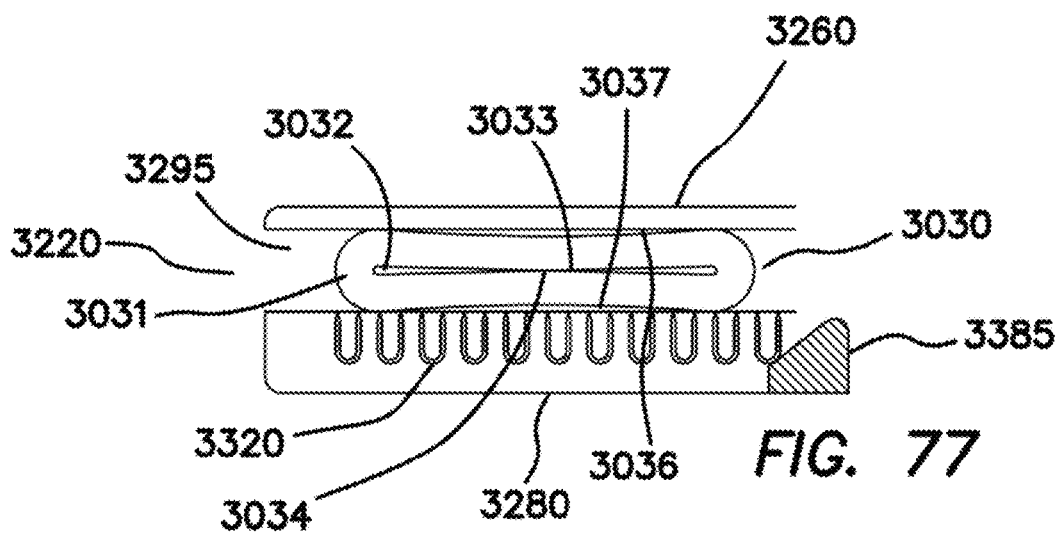
FIG. 77 illustrates a relationship between clamping jaws and tissue to be fused in a first, grasping condition.
Figure 78:
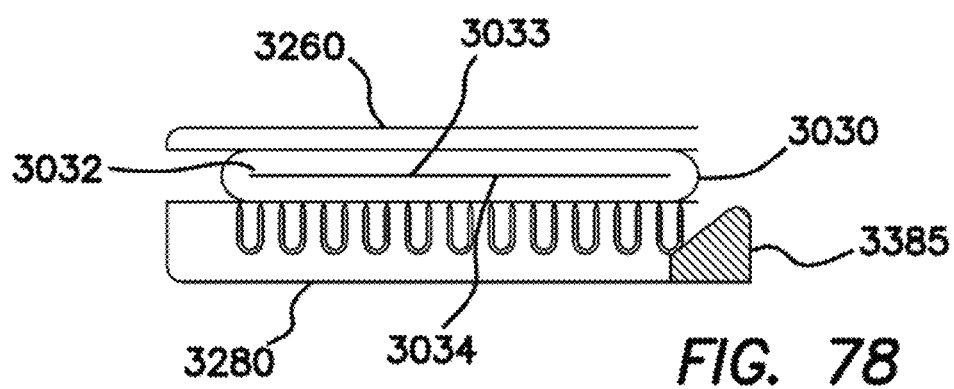
FIG. 78 illustrates a relationship between clamping jaws and tissue to be fused in a second, compressing condition.
Figure 79:
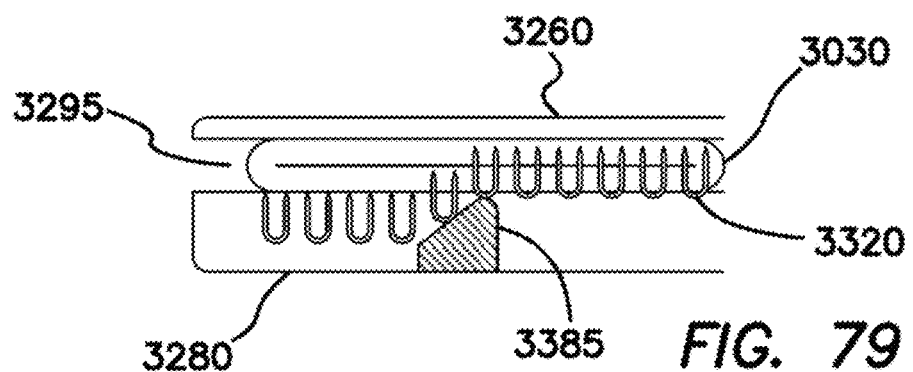
FIG. 79 illustrates a relationship between clamping jaws and tissue to be fused in a third, electrode-extending condition.
Figure 80:
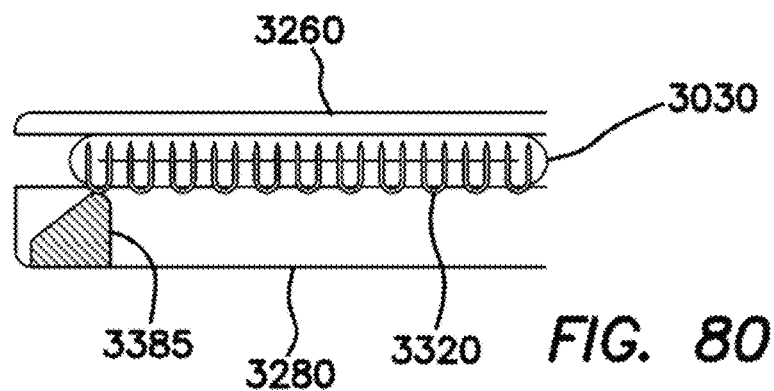
FIG. 80 illustrates a relationship between clamping jaws and tissue to be fused in a final, electrode-extending condition.

With reference to FIGS. 77-80, in certain embodiments, the movable lever 3236 is configured to actuate both the jaw assembly and moveable electrodes in a multi-step actuation process. In some embodiments, the movable lever 3236 can be operatively coupled to the jaw assembly such that a first action associated with a user grasping the movable proximal lever 3236 is that of the jaw assembly grasping selected tissue positioned therein, such as a body conduit or vessel 3030 (FIG. 77). Upon further movement of the movable lever 3236 by the user, the jaw assembly begins to compress the selected, grasped tissue 3030 (FIG. 78) as the movable jaw 3260 continues to pivot from the open state (FIG. 67) towards the closed state (FIG. 66). In the illustrated embodiments, the movable lever 3236 is operatively coupled to the plurality of electrodes 3320 in the jaw assembly such that upon advancement of the movable lever 3236, the plurality of paired-electrodes 3320 are sequentially advanced by the sled 3380 up from within the first jaw 3280 and toward the opposing face 261 of the movable, second jaw 3260 (FIGS. 79-80).

With reference to FIGS. 79 and 80, as the electrodes 3320 are sequentially advanced through the tissue 3030 compressed between the first jaw 3280 and the second jaw 3260, the electrodes 3320 are energized sequentially as they are extended by electrical coupling to the contacts 3390, 3391, 3392, 3393 on the sled 3380 (FIG. 75). This sequential energizing can create an exaggerated current density as the electrodes 3320 extend into the compressed tissue 3030. Once the electrodes 3320 have been extended and energized, they are sequentially disconnected from electrical contact with the corresponding electrical contacts on the sled 3380. The disconnected electrodes 3320 can then cool down in contact with the treated tissue 3030. In the illustrated embodiment, only the electrodes 3320 in direct contact with the sliding peaks 3385 of the actuation sled 3380 are energized. Once the contactor peaks 3385 have fully extended the electrodes 3320 and moved beyond any particular electrode or electrode pair, there is no longer a connection of the previous electrodes 3320 to a power supply to which the electrosurgical tool 3200 is coupled. In other embodiments, substantially all of the electrodes 3320 can be energized substantially concurrently by arrangement of electrical coupling to selectively provide energy to the electrodes 3320.

Figure 81:
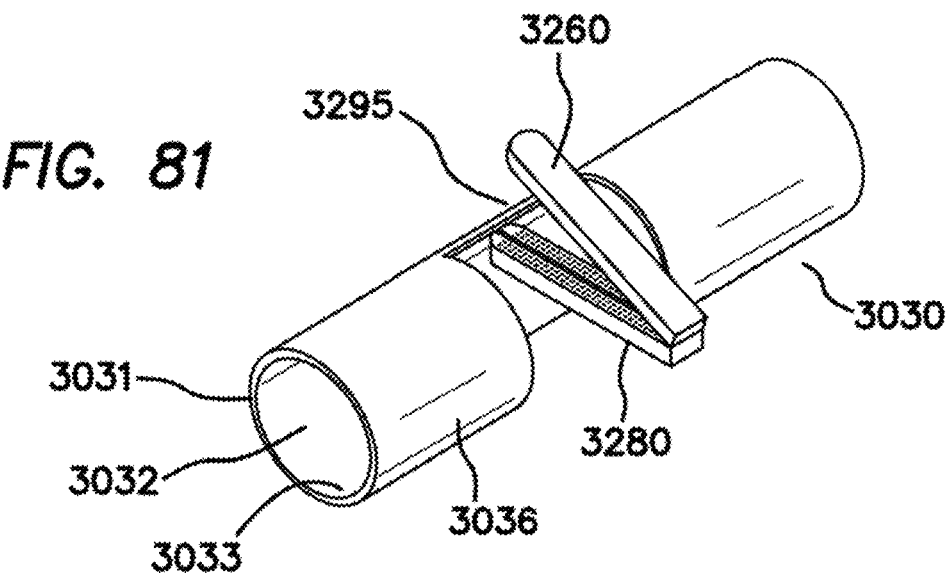
FIG. 81 is a perspective cut-out view of a body conduit showing an electrosurgical instrument moving into position to occlude a lumen of a conduit.
Figure 82:
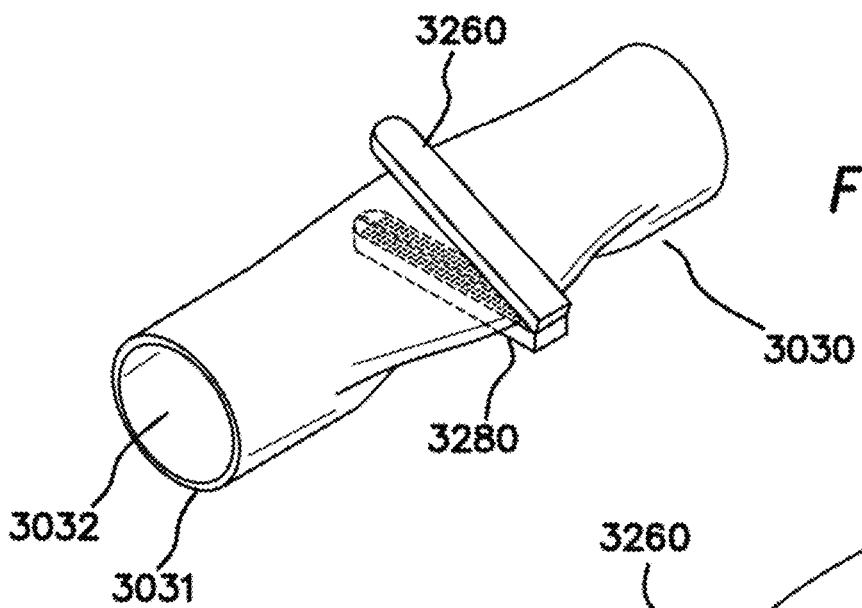
FIG. 82 is a perspective view of a body conduit showing an electrosurgical instrument in position to occlude a lumen of a conduit.
Figure 83:
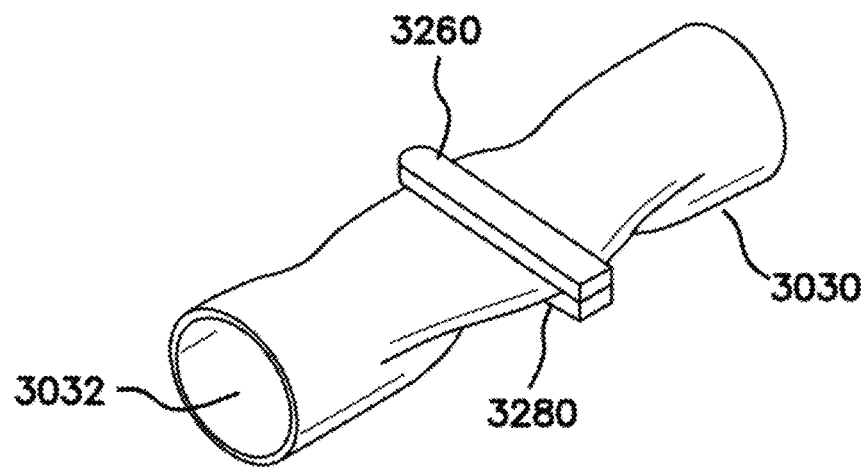
FIG. 83 is a perspective view of a body conduit showing an electrosurgical instrument occluding a lumen of a conduit.

Referring now to FIGS. 81-83, exemplary illustrations of a body conduit 3030 that may be closed, occluded, or sealed and subsequently separated are shown in accordance with certain embodiments of a jaw assembly of an electrosurgical tool 3200. In FIG. 81, the conduit 3030 is first selected and grasped. In FIGS. 82-83, the grasped tissue 3030 is fully compressed between distal jaws 3260, 3280. The movable lever 3236 associated with the proximal handle 3235 can be further actuated and the electrodes 3320 are sequentially energized and elevated into the compressed tissue 3030 (see, e.g., FIGS. 77-80). When the tissue 3030 is fully fused or welded in response to the energy supplied by the electrodes, a cutting element 3371 may be selectively advanced, as further discussed below with respect to FIGS. 98-100. The cutting element 3371 is sized and configured to cut the conduit or tissue 3030 between rows of electrode fusion leaving a plurality of fusion rows on each side of the cut. The electrodes 3320 are subsequently withdrawn from the selected tissue 3030 as the jaws 3260, 3280 are separated (see, e.g., FIGS. 77-80).

Figure 84:
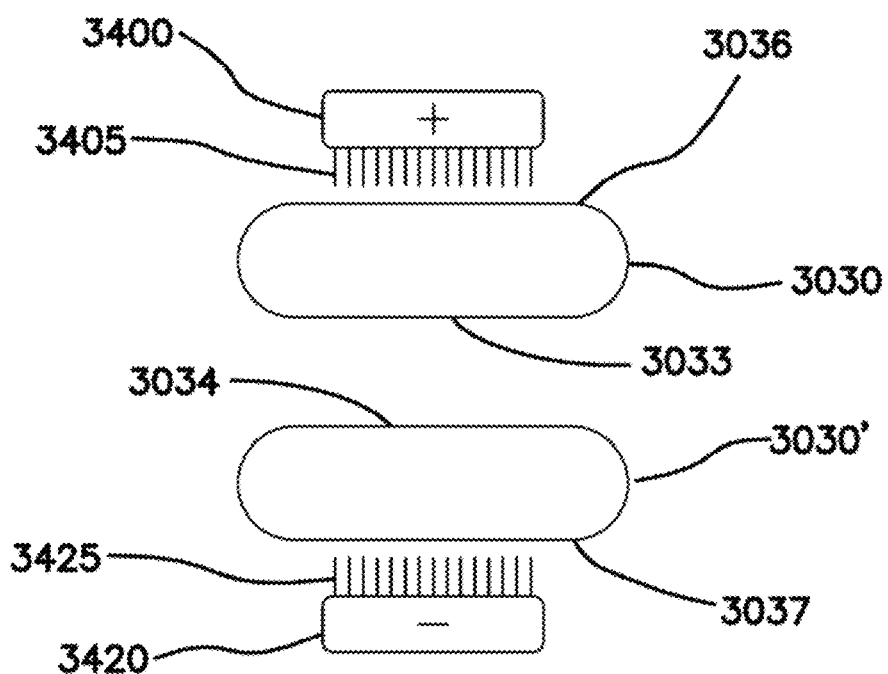
FIG. 84 is a schematic diagram illustrating current concentration through tissue in a first, non-contact condition.
Figure 85:
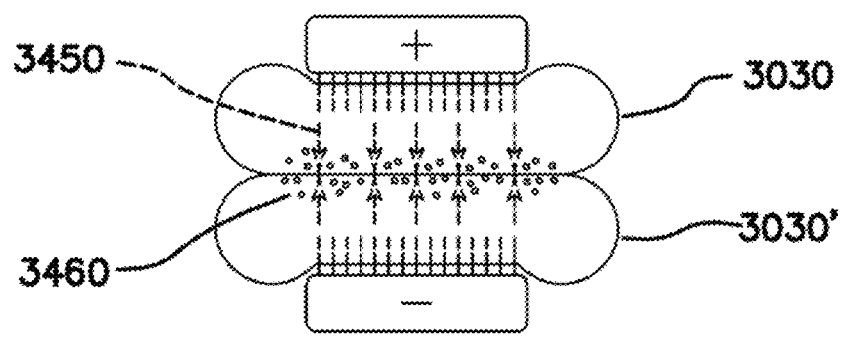
FIG. 85 is a schematic diagram illustrating current concentration through tissue in a full-contact condition.
Figure 86:
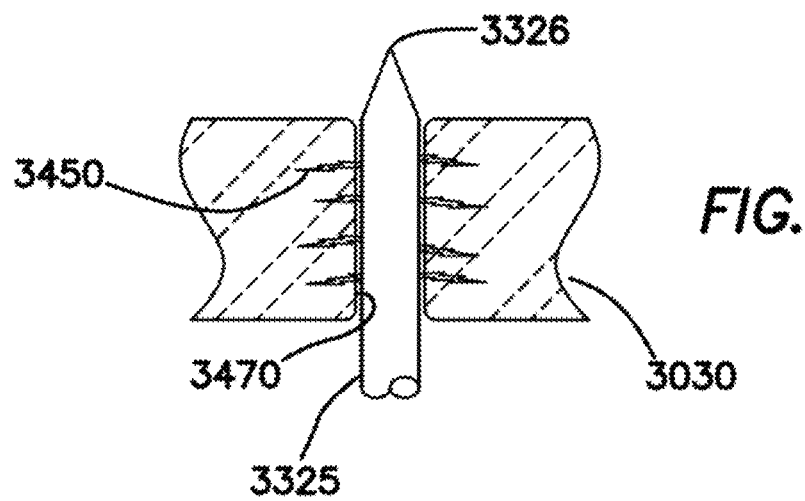
FIG. 86 illustrates electrosurgical energy radiation associated with penetrating electrodes.
Figure 87:
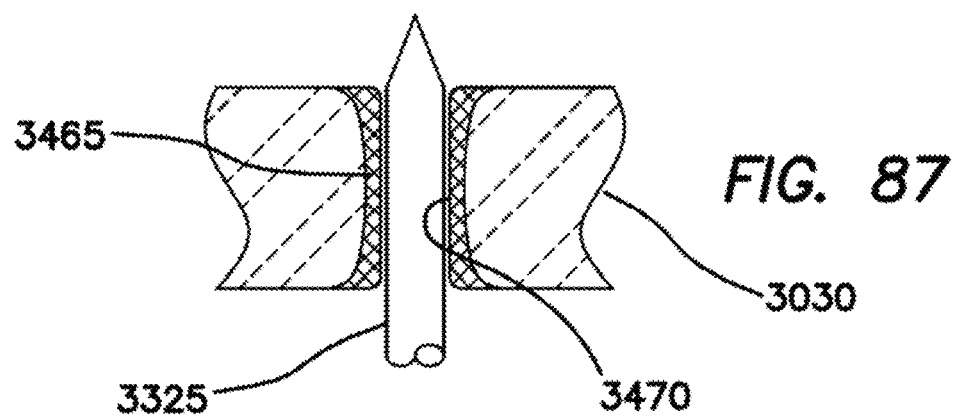
FIG. 87 illustrates a thermal zone associated with penetrating electrodes.
Figure 88:
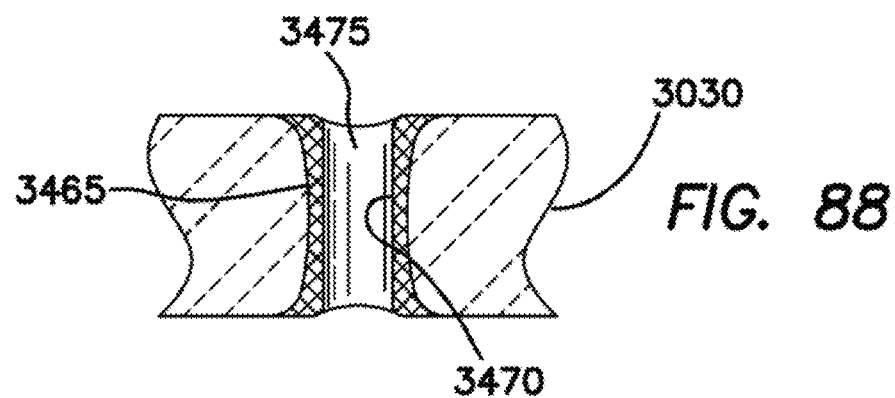
FIG. 88 illustrates a thermal zone associated with penetrating electrodes with the electrodes withdrawn.

With reference to FIGS. 84-85, certain aspects of a bipolar electrosurgical tissue fusion operation are illustrated. In previous bipolar surgical tools, electrical energy of a first polarity (+) can be provided to surface contact electrode pins 3405 on a first paddle 3400, and electrical energy of a second polarity (−) can be provided to electrode pins 3425 on a second paddle 3420. The paddles can be compressed over tissue such as a vessel having two portions 3030, 3030' such that the first paddle 3400 compresses an outer wall 3036 of the first portion 3030, and the second paddle 3420 compresses an outer wall 3037 of the second portion 3030'. In order for the two portions of tissue to be welded or fused together, the electrical energy must travel a relatively long distance between the pins 3405, 3425 to the interface between inner walls 3033, 3034 of the tissue portions 3030, 3030'. As the distance between pins increases in a bipolar electrosurgical instrument, the current density tends to decrease. Therefore, using such a device, it can be necessary to apply electrical energy over a fairly long duration, which can undesirably damage tissue 3030, 3030'.

With reference to FIGS. 86-91, advantageously, with an electrosurgical tool 3200, high current density of a short duration can produce effective seals/welds and with minimal or substantially no radiant thermal effects. Unlike conventional surface contact electrodes, an exemplary inserted electrode 3325 in the electrosurgical tool 3200 can provide a dense current path resulting in elevated thermal activity within the compressed tissue 3030. The margin of thermal damage concomitant to electrosurgical surface radiation is potentially noteworthy and as such the minimization or elimination of the margin of radiant thermal damage by inserting the electrodes 3325 such as, for example with sharpened or tapered tips 3326 to allow the electrodes 3325 to penetrate tissue to be fused. In other embodiments, the electrode 3325 can be otherwise configured to direct the current path in a manner that concentrates or focuses the energy at a particular location.

Figure 89:
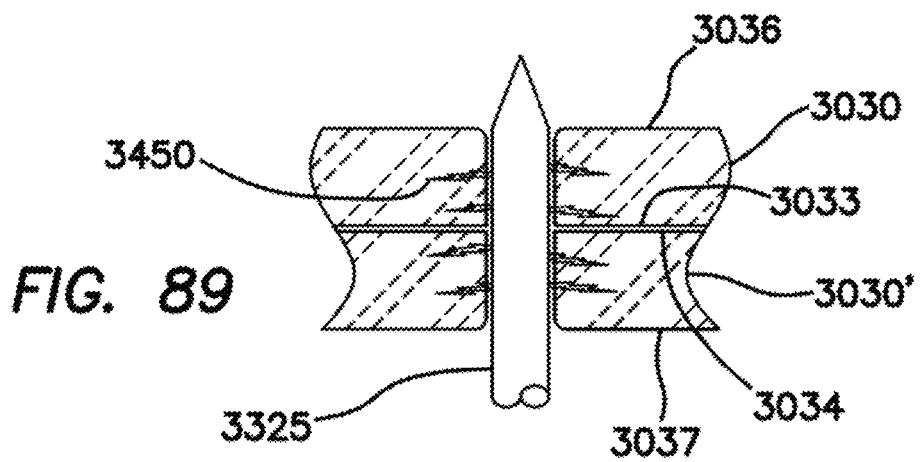
FIG. 89 illustrates electrosurgical energy radiation associated with penetrating electrodes within approximated tissue.
Figure 90:
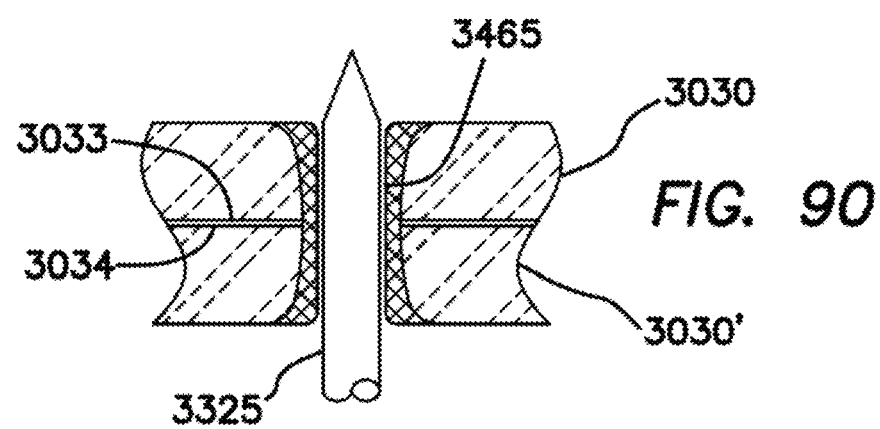
FIG. 90 illustrates a thermal zone associated with penetrating electrodes within approximated tissue.
Figure 91:
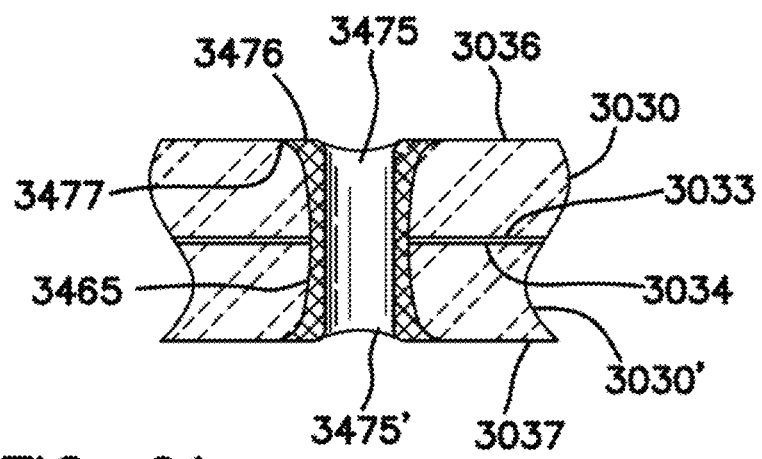
FIG. 91 illustrates a thermal zone associated with penetrating electrodes with electrodes withdrawn.

A section view of the activity associated with the electrodes 3325 may be seen in FIGS. 86-91 where a penetrating electrode element 3325 is inserted through or into a portion of compressed tissue 3030 through action of the tapered tip 3326 to create an interface surface 3470 within the tissue 3030. Energy from an energy source is supplied to the electrode 3325 and subsequently radiated into the adjacent tissue radially from the interface surface 3470. As the tissue is energized, it heats to a particular temperature at which it loses fluid content. The tissue 3030 then fuses at the cellular level in a manner that resembles cross-linking. The cross-linked collagen forms a continuous structure 3465 of denatured cells. When the electrode 3325 is removed, the denatured structure 3465 remains. As illustrated in FIGS. 89-91, the denatured structure 3465 may serve as a connecting structure 3475 between two portions of tissue 3030, 3030' such as two opposing walls 3033, 3034 of a compressed conduit 3030 that have been compressed to form a closure or occlusion. When fused with an electrosurgical tool 3200 described herein, the denatured structure 3475 generally extends through all tissue that has been compressed between the jaws 3260, 3280 of the electrosurgical tool 3200 and energized by the movable electrodes 3320. The denatured structure 3475 can resemble an "hourglass" shape where there is a wide first, insertion portion, a narrow mid portion and a wide exit portion.

Electro-surgery involves managing the timing and temperature of the procedure. Too little generated heat within the tissue prevents the tissue from properly fusing or welding and too much heat within the tissue may destroy it and result in complications. As such, the electrosurgical tool can be less sensitive to the variables within living tissue. The instrument may be coupled to feedback systems that measure or respond to conditions that develop within treated tissue. For instance, the electrosurgical tool may desiccate tissue during the heating phase so that resistance to electrical current develops. In some embodiments, that resistance may be measured or otherwise used to control the delivery of electrosurgical energy to the electrodes. In some embodiments, the phase changes between the initiation of the electrosurgical energy and any subsequent point during the delivery of the electrosurgical energy may be used to control the delivery. In other embodiments, a measurement of the temperature of the treated tissue can also be used to control the delivery.

Figure 92:
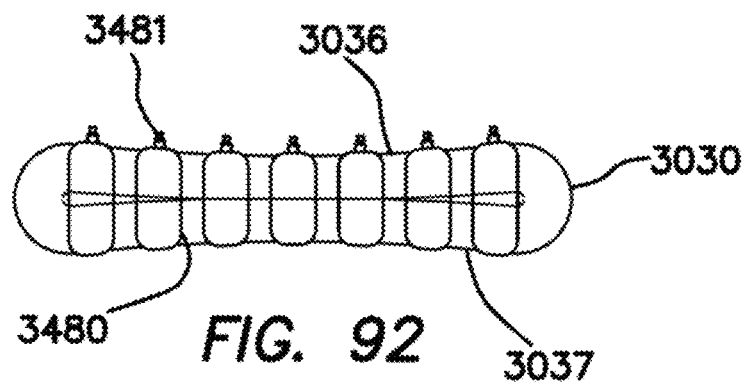
FIG. 92 is an end view of a conduit closed or occluded using a suturing technique.

A comparison between various methods of conduit occlusion may be appreciated in FIGS. 92-95. FIG. 92 illustrates a sutured conduit 3030. The sutured conduit 3030 comprises a plurality of individual or running sutures 3480 terminating in at least one knot 3481. The suturing process can require expertise, be time consuming, and may not always result in optimum occlusion. As a result the conduit 3030 may leak or ooze.

Figure 93:
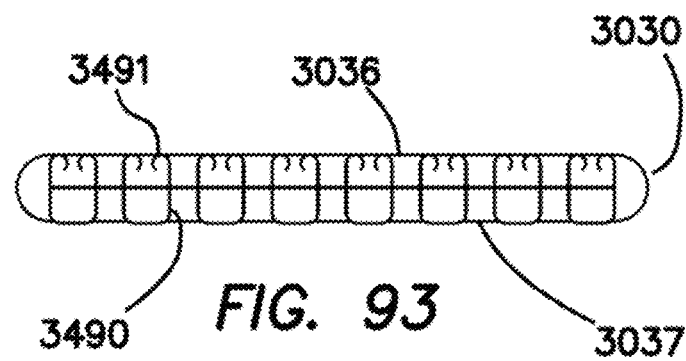
FIG. 93 is an end view of a conduit closed or occluded using a stapling technique.

FIG. 93 illustrates a stapled conduit 3030 in which a plurality of staples 3490 have been driven into the conduit 3030. The staples 3490 have folds 3491 to retain them in the conduit 3030 and apply occlusive forces to the conduit. Stapling using a surgical stapler, results in a more secure closure than suturing in many cases. However, even with stapling, suturing may be used to complete the closure since staples 3490 may not accommodate the wide variations in tissue thickness or texture. Several surgical procedures make use of stapling. In these cases, most of the staples 3490 remain within the surgical site. Generally, the staples 3490 are made from metal, such as titanium. It may be appreciated that a great deal of force is applied to the jaw portions of a stapling device to accomplish all the actions required to occlude the subject tissue 3030 and subsequently insert the staples 3490 and fold 3491 them appropriately. It should also be noted that the cartridges holding the staples 3490 are complex and expensive devices and hold only a single load of staples 3490. Therefore, there are generally several exchanges of stapling instruments during a typical surgical procedure. For example, during a surgical procedure involving the intestines, it is not uncommon to use, between three and ten cartridges of staples with each cartridge holding, up to thirty-six or more staples. The residual metal mass left behind is therefore significant. Moreover, if removal is desired, staples are not easily cut and, in addition, some of them may be dislodged during a cutting procedure. This may result in residual pieces of metal within a body cavity. In addition, electro-cautery is often used to completely seal a vessel or conduit 3030 that has been stapled.

Figure 94:
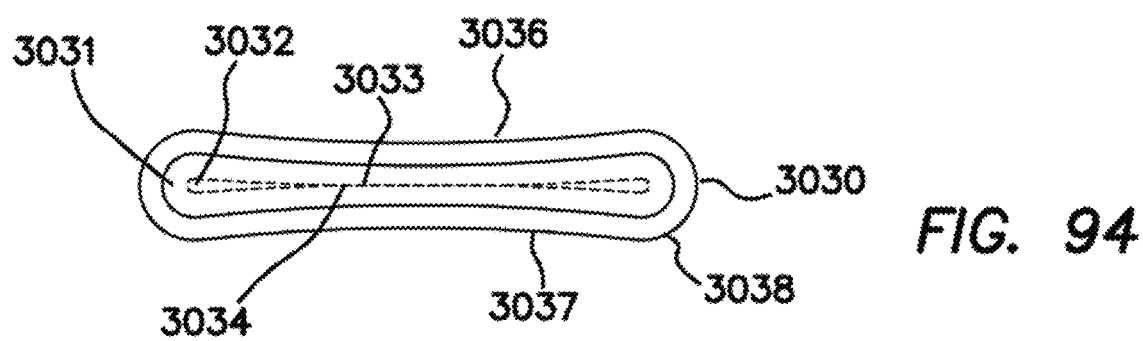
FIG. 94 is an end view of a conduit closed or occluded using a compressive fusion technique.

With reference to FIG. 94, compressive, external electrosurgical fusion such as applied by surface contact electrodes described above with respect to FIGS. 84 and 85 can be adequate for small vessels or conduits. However, as discussed above, there may be excessive radiant thermal damage associated with the use of these modalities, especially in larger conduits 3030. Thermal damage that eliminates the regeneration of residual tissue or prevents vascular re-perfusion or regeneration is undesirable in most cases. Accordingly, compressive, external electrosurgical fusion can be undesirable in relatively larger vessels or conduits where thermal damage can occur. Additionally, in some instances, compressive electrosurgical fusion can fail to provide sufficient compressive forces, resulting in non-occluded areas 3032 adjacent the conduit wall 3031. Both suturing and stapling accommodate regeneration when done properly in most cases. However, surgical stapling can often be responsible for necrosis of residual tissue since the delivery devices do not compensate well for variations in tissue thickness or texture.

As is apparent from the above discussion and FIG. 94, the electrosurgical tool 3200 described herein can fuse or weld in a manner that emulates the placement of a plurality of staples. The portions of tissue that have been treated resemble a connection made by staples. Moreover, with the electrosurgical tool 3200 described herein, unlike a stapler, the second, closing jaw does not have to be of sufficient strength to provide an anvil for the folding or bending of staple legs. Thus, the electrosurgical tool 3200 can be particularly advantageous in applications where the device may have to be operated through a small tubular access port.

Figure 95:
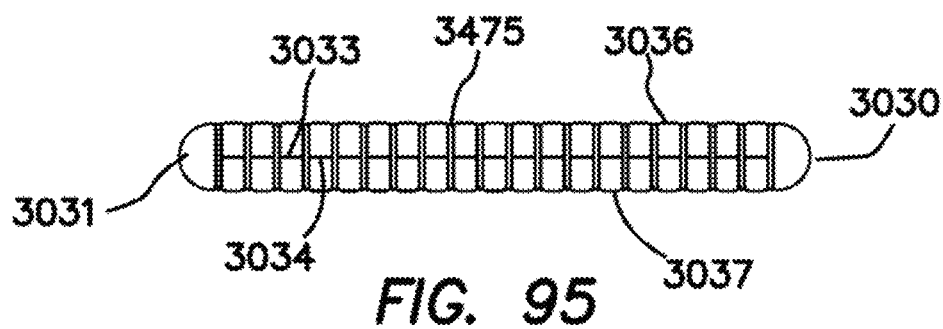
FIG. 95 is an end view of a conduit closed or occluded using a compressive fusion technique with inserted electrodes.

With reference to FIG. 95, compressing selected tissue and subsequently creating a plurality of denatured connecting structures 3475 for example with an electrosurgical tool 3200 as described herein provides a combination of occlusive security and minimal thermal radiation damage. Adequate vascular regeneration and minimization of necrosis of residual tissue are also provided. Accordingly, use of the electrosurgical tools 3200 described herein for conduit occlusion can desirably provide advantages of tissue suturing or stapling with reduction of the drawbacks of external contact electrosurgical fusion. Advantageously, sealing a conduit with an electrosurgical tool 3200 as described herein can also be accomplished relatively quickly and easily by a surgeon.

Figure 96:
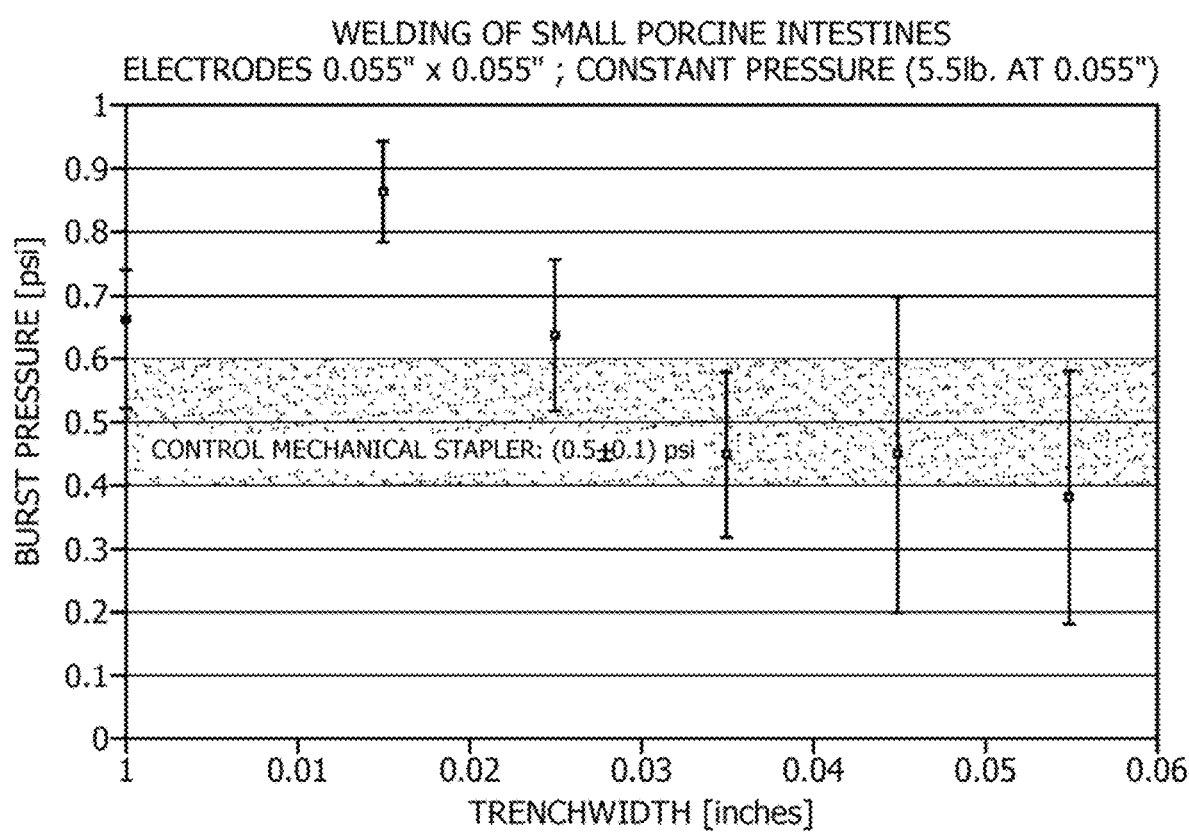
FIG. 96 is a graphical representation of exemplary burst pressure data of an occlusion using a compressive fusion technique with inserted electrodes
Figure 97:
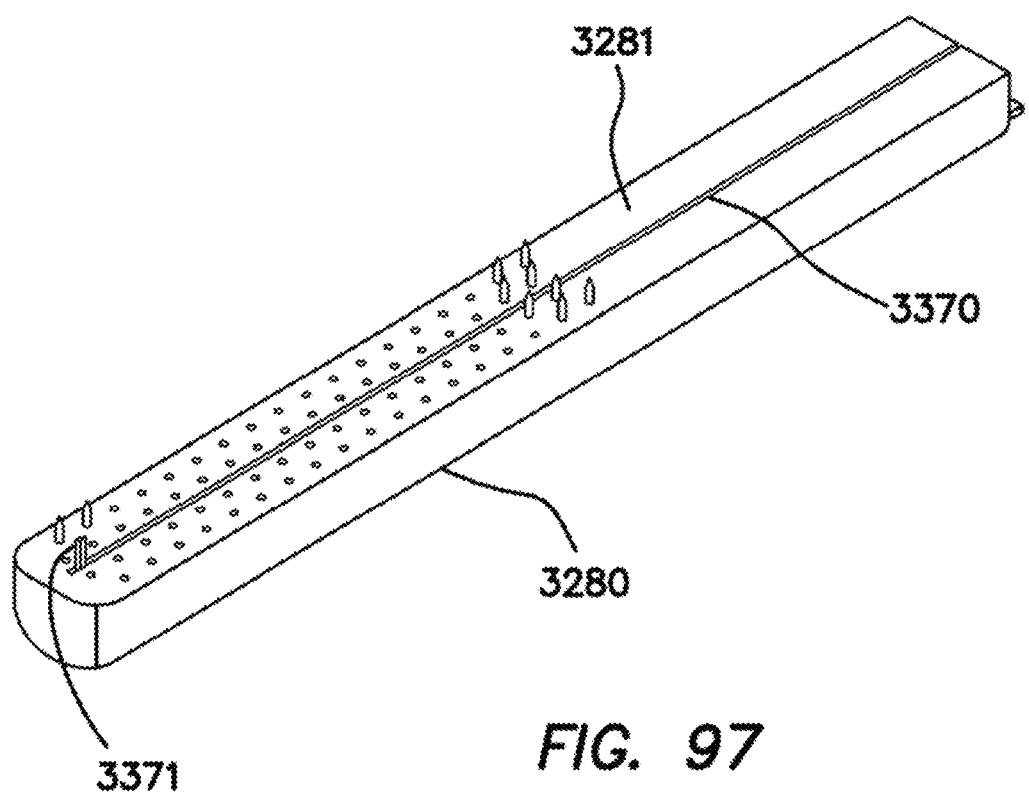
FIG. 97 is an enlarged perspective view of a clamping jaw showing an associated cutting element.
Figure 98:
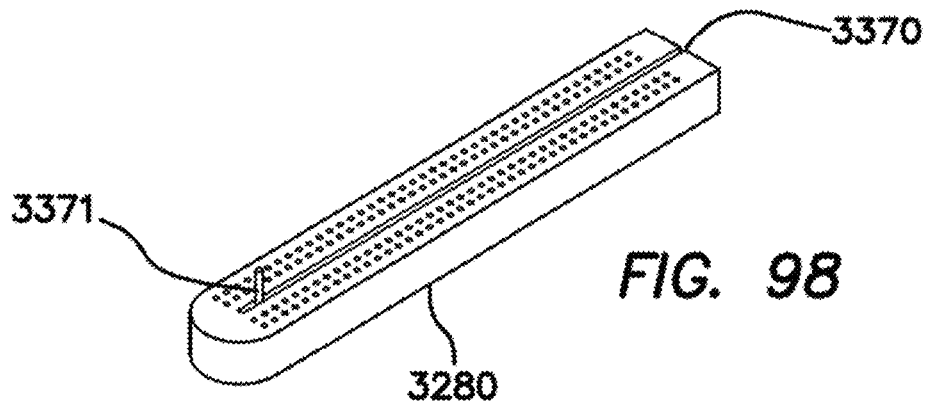
FIG. 98 is an enlarged perspective view of a clamping jaw showing an associated cutting element comprising an electrosurgical wire electrode.

With reference to FIG. 96, experimental data for sealing strength of various embodiments of electrosurgical tools is presented graphically. Various experiments were performed on porcine small intestinal tissue to demonstrate the strength of sealing of an electrosurgical tool 3200 as described herein. Using tools having trenchwidth (that is, spacing between adjacent electrodes) of between 0 and 0.055 inches, porcine intestinal tissue was sealed using the electrosurgical tool 3200 described herein and its burst pressure measured. As a control, it was initially established that a conventionally stapled section of intestinal tissue can withstand a burst pressure of 0.5+−0.1 pounds per square inch. Multiple tests were conducted at various trenchwidths, and a statistical range of the results was plotted in FIG. 96, with mean data for each trenchwidth appearing at a point designated in the range. As is apparent from FIG. 96, for relatively small trenchwidths, the electrosurgical tool 3200 can create an intenstinal tissue seal burst strength that outperforms conventional stapling. For relatively large trenchwidths, the electrosurgical tool 3200 can create an intenstinal tissue seal burst strength that performs similarly to, or marginally less than conventional stapling. Accordingly, the electrosurgical tools 3200 described herein offer similar or increased burst strength performance while being faster and easier to use and having other advantages discussed above.

Figure 99:
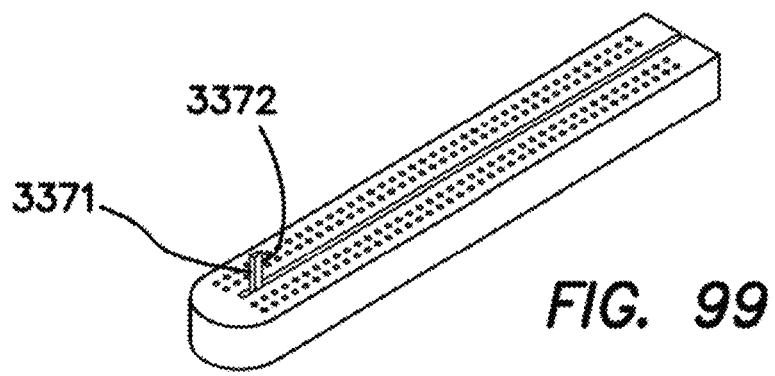
FIG. 99 is an enlarged perspective view of a clamping jaw showing an associated cutting element comprising an electrosurgical or mechanical wedge electrode-knife.
Figure 100:
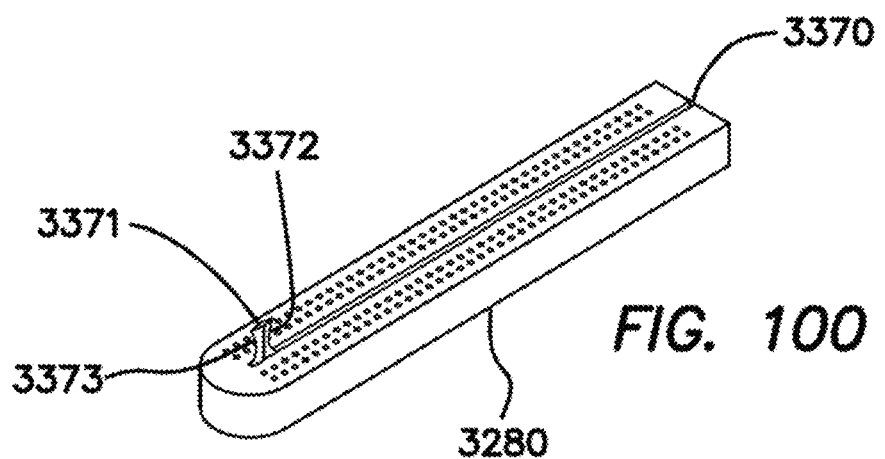
FIG. 100 is an enlarged perspective view of a clamping jaw showing an associated cutting element comprising an electrosurgical or mechanical double edge knife.

Referring to FIGS. 97-100, as discussed above, in some embodiments, the jaw assembly of the electrosurgical tool 3200 can include a cutting element 3371 such as a selectively operable cutting component. The cutting component can be selectively moved between a proximal location and a distal location to cut tissue compressed between the jaws of the jaw assembly. In various embodiments, the cutting element 3371 can be a sharp blade, hook, knife, or other cutting element that is sized and configured to cut between denatured structures 3475 in compressed tissue. As illustrated in FIG. 99, in some embodiments, the cutting element 3371 includes a sharpened edge 3372 on one of the proximal edge or the distal edge to allow cutting of tissue when the cutting element 3371 is moved in one direction towards the sharpened edge 3372. As illustrated in FIG. 100, in some embodiments, the cutting element 3371 includes a first sharpened edge 3372 and a second sharpened edge 373 on each of the proximal edge and the distal edge of the cutting element 3371 to allow cutting of tissue when the cutting element 3371 is moved either proximally or distally along the slot 3370 in the fixed jaw 3280.

While in illustrated embodiments, the cutting element is illustrated as a mechanical element, in other embodiments, the cutting element 3371 can comprise an energizable element or wire that can be selectively energized by a generator or power source. An electrosurgical cutting element 3371 can easily separate the compressed and fused tissue portion and can additionally provide fluid stasis or additional sealing of the lumen 3032 associated with the treated tissue 3030.

FIGS. 101-106 illustrate various configurations of current intensifying elements 3500, 3510, 3520, 3522, 3524, 3526, 3530, 3540, 3545, 3550 for use in an electrosurgical tool such as the electrosurgical tool 3200 described herein. The elements can be configured to focus or direct energy on or into a position within compressed tissue 3030. Thus, in various embodiments an electrosurgical tool can include a plurality of current intensifying elements in place of or in addition to a plurality of extendable electrodes as discussed above. Each of the various current intensifying elements can be desirable for certain surgical environments depending, among other considerations, on the depth of tissue penetration desired and the degree of energy intensification desired. In some embodiments, an electrosurgical tool can include a plurality of extendable electrodes as described above on one jaw of a jaw assembly and a plurality of current intensifying elements on the other jaw of the jaw assembly. In other embodiments, an electrosurgical tool can include a first plurality of current intensifying elements on one jaw of the jaw assembly and a second plurality of current intensifying elements on the other jaw of the jaw assembly.

Figure 101:
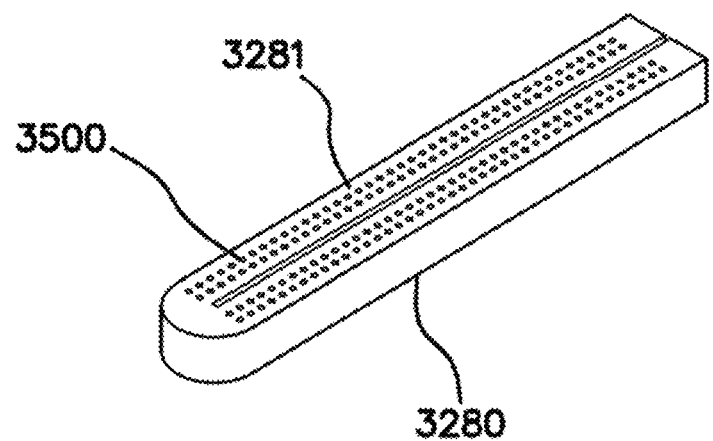
FIG. 101 is an enlarged perspective view of a clamping jaw showing a plurality of current intensifying elements comprising holes.
Figure 102:
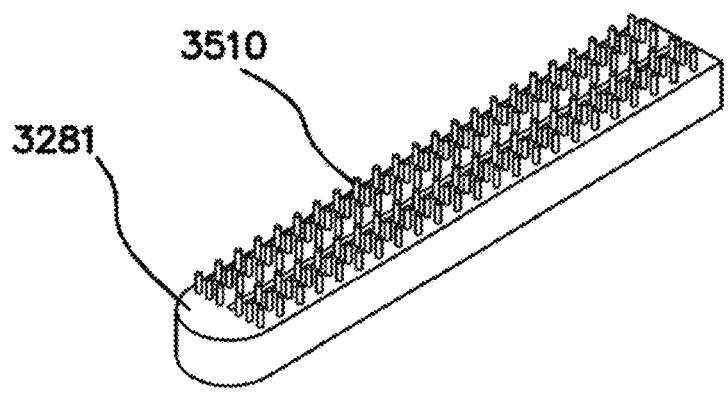
FIG. 102 is an enlarged perspective view of a clamping jaw showing a plurality of current intensifying elements comprising extended posts.
Figure 103A:
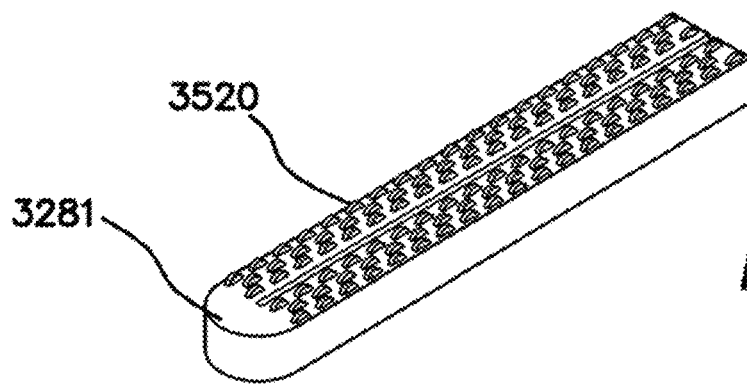
FIG. 103a is an enlarged perspective view of a clamping jaw showing a plurality of current intensifying elements comprising extended arcs.
Figure 105A:
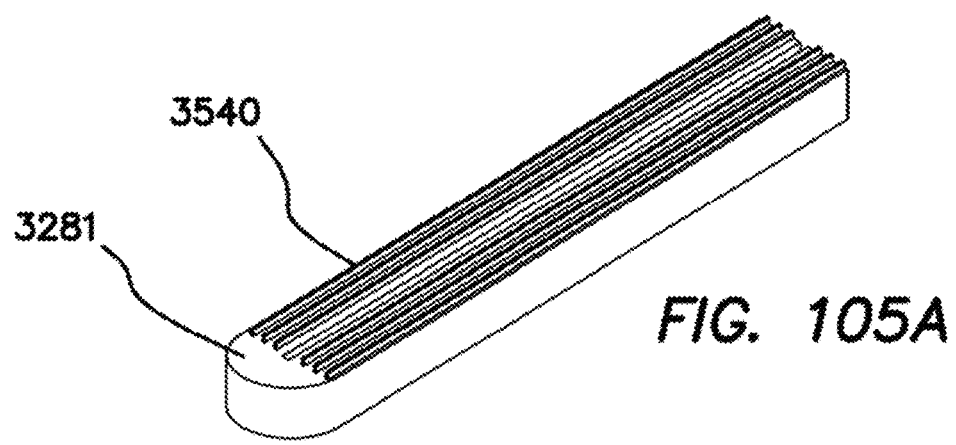
FIG. 105A is an enlarged perspective view of a clamping jaw showing a plurality of current intensifying elements comprising extended ridges.
Figure 106:
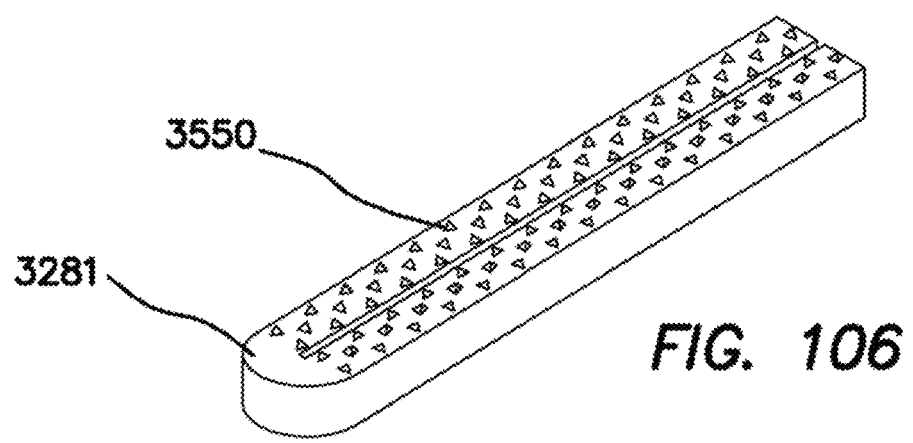
FIG. 106 is an enlarged perspective view of a clamping jaw showing a plurality of current intensifying elements comprising extended pyramids or cones.

In some embodiments, the elements can comprise holes 3500 that function as energy horns, as shown in FIG. 101. In other embodiments, the elements can additionally comprise rods 3510 or spikes that are stationary or movable, as depicted in FIG. 102. As an alternative, some applications may use a less intrusive configuration such as a plurality of subtle arcs or mounds 3520 (FIG. 103*a*). Some applications may favor a slightly more aggressive configuration comprising a plurality of raised squares 3522 (FIG. 103*b*), rods 3524 (FIG. 103*c*), "ball-and-cup"-like configurations 3526 (FIG. 103*d*), or rectangles 3530 (FIG. 104) where energy can be focused or concentrated at edges and corners. In other embodiments, the elements can comprise a plurality of elongate rows 3540 (FIG. 105*a*) or socket-and-spickets 3545 (FIG. 105*b*). In other embodiments, the elements can comprise a plurality of pyramids or cones 3550 (FIG. 106) or the like that are sized and configured to penetrate into the surface of tissue.

FIG. 107 illustrates a cross-sectional view of tissue that has been compressed and fused with an electrosurgical tool. As illustrated, the tissue 3030 is compressed within a square-patterned embodiment of the upper 3260 and lower jaw 3280 elements, and subjected to electrical RF current or thermal energy. This energy application can be accomplished by connecting both upper and lower jaw elements to a bipolar electrosurgical unit, or by encapsulating electrical (ohmic) heaters within each jaw element. Even though there can be some compression between "uncompressed" tissue areas, as well as some energy overspill into the "uncompressed" tissue area, the directly compressed and energized tissue areas will be the first areas to fuse together and can be the only ones to seal.

Figure 103B:
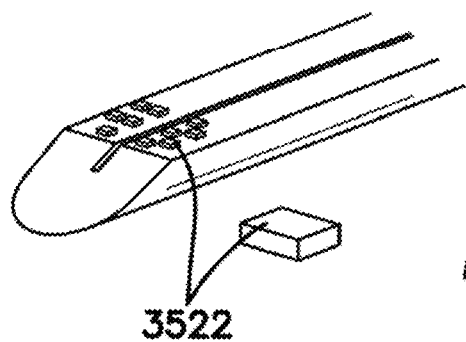
FIG. 103b is an enlarged perspective view of a clamping jaw showing a plurality of current intensifying elements comprising extended squares.
Figure 103C:
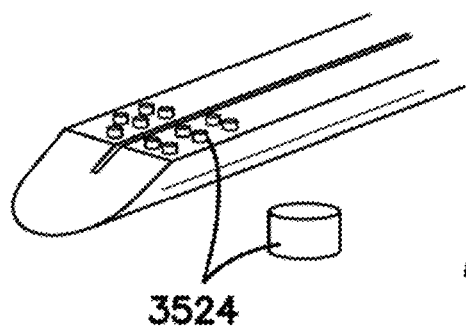
FIG. 103c is an enlarged perspective view of a clamping jaw showing a plurality of current intensifying elements comprising extended rods.
Figure 103D:
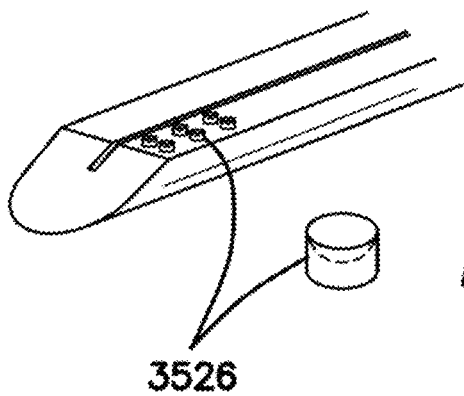
FIG. 103d is an enlarged perspective view of a clamping jaw showing a plurality of current intensifying elements comprising extended "ball-and-cups".
Figure 104:
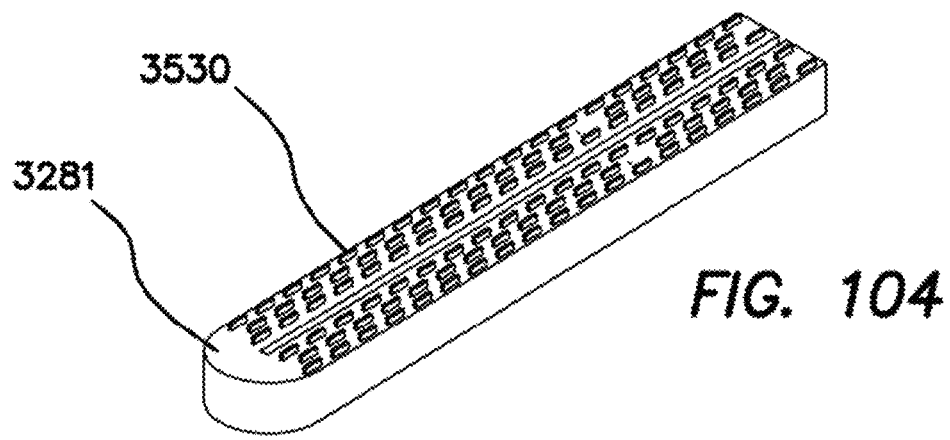
FIG. 104 is an enlarged perspective view of a clamping jaw showing a plurality of current intensifying elements comprising extended rectangles.

With reference to FIG. 108*a*, an example of the visual appearance of the obtained results on a fused and separated blood vessel 3030 is illustrated. As can be seen, each of the two sections of a sealed and cut vessel may include a pattern corresponding to the pattern of electrodes or current intensifying elements. For example, as shown in FIGS. 103*a-b*, the divided portions of the vessel are each sealed in a fluid tight manner by the respective double-rows of fused squares. The tissue between the fused squares, on the other hand, does not have to be fused, or even connected. For example, with reference to FIG. 108*b*, a cross-section along line 8-8 in FIG. 108*a* illustrates the fused and non-fused areas in the cut vessel. In this example, the fused and denatured (square) tissue elements are separated by tissue areas that have not been connected to opposing tissue areas.

FIG. 109*a* illustrates an exemplary sealed and cut tissue segment 3030, obtained by welding the tissue in two double-rows of round areas, and cutting the tissue between the two double rows. The divided portions of the tissue are each sealed in a fluid tight manner by the respective double-rows of fused circles. The tissue between the fused circles, on the other hand, does not have to be fused, or even connected. This is shown, for example, in FIG. 109*b*, which depicts a cross-section along line 9-9 in FIG. 109*a*. In this example, the fused and denatured (circular) tissue elements are separated by tissue areas that have not been connected (to opposing tissue areas).

With reference to FIG. 110, tissue 3030 within a jaw assembly 3250 of an electrosurgical tool having square patterned recesses is illustrated in cross-section. As illustrated, the tissue 3030 is compressed within the square pattern of the upper and lower jaw elements. In some embodiments of electrosurgical tool, energy can be supplied to the tissue by applying the upper electrode with ultrasonic energy, which can cause friction of the tissue with both upper and lower jaw element. The movement of the upper jaw element in FIG. 110 is indicated for illustrative purposes as parallel to the drawing plane, although the movement can also be provided in the transversal direction. Even though there will be some compression between "uncompressed" tissue areas into the "uncompressed" tissue area, also through heat conduction by the tissue, the directly compressed and energized tissue areas can be initially fused and can be the only areas to seal.

Referring to FIG. 111, tissue 3030 within a jaw assembly 3250 of an electrosurgical tool having square patterned recesses is illustrated in cross-section. Energy is then supplied to the tissue by irradiating it with UV and/or IR radiation, provided for example through fiber-optical cables within the square-patterned areas. Even though there will be some compression between "uncompressed" tissue areas, as well as some UV/IR energy overspill into the "uncompressed" tissue area, also through scattering, the directly compressed and energized tissue areas will be the first ones and can be the only ones to seal.

It is believed that UV (200 to 400 nanometers) is absorbed by proteins (and hemoglobin), leading to cleavage of chemical bonds within the proteins, while IR (>1 micrometer) is strongly absorbed by water, causing heating of the tissue. It has been demonstrated that the fusion of clamped arteries using incoherent UV within the spectral range of 300 to 500 nanometers, without substantial heating of the artery can be accomplished. The irradiation of the pressurized tissue with UV can cause collagens to bind each other through photochemical reactions, without desiccation or thermally-induced collagen degeneration.

In one aspect, the tissue is fused or welded in a manner that emulates the placement of a plurality of staples. The portions of tissue that have been treated resemble a connection made by staples. However, using the electrosurgical tool, a single grasping procedure can simulate the release of tens of staples, thus resulting in significant time savings over a similar procedure with a surgical stapler. When compared with a surgical stapler, advantageously, the second, closing jaw of the electrosurgical tool does not need to be of sufficient strength to provide an anvil for the folding or bending of staple legs. It may therefore favor laparoscopic applications where the device may have to be operated through a small tubular access port.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of the following claims.

The invention claimed is:

1. An electrosurgical system comprising:
    an electrosurgical generator arranged to output electrosurgical energy; and
    a bipolar electrosurgical tool removably coupled to the electrosurgical generator, the tool comprising:
        a stationary handle comprising a pull block and a plurality of threaded nuts contained within the pull block;
        an actuation handle coupled to the pull block;
        a blade trigger movably coupled to the stationary handle;
        a jaw assembly comprising an upper jaw having an inner surface, an outer surface, and an electrode disposed on the inner surface of the upper jaw and a lower jaw having an inner surface, an outer surface, an electrode disposed on the inner surface of the lower jaw, a blade channel, a cutting blade disposed within the blade channel, and a lower spacer extending lengthwise along the lower jaw and being disposed adjacent to the electrode and between the blade channel in the lower jaw and an outer periphery of the lower jaw, the lower spacer comprising a first protrusion next to and parallel with the blade channel and a second protrusion being disposed at a distal portion of the lower jaw aligned with and in front of the blade channel, the upper and lower jaws actuatable, by movement of the actuation handle, from an open configuration in which the inner surface of the upper jaw is spaced apart from the inner surface of the lower jaw to a closed configuration in which the inner surface of the upper jaw is proximate the inner surface of the lower jaw, arranged to contact tissue and apply the electrosurgical energy to the tissue from the electrosurgical generator; and
        a rotatable elongate shaft extending distally from the stationary handle and rotatable relative to the stationary handle, the rotatable elongate shaft having a proximal end and a distal end defining a central longitudinal axis therebetween, the jaw assembly pivotably connected and positioned at the distal end of the rotatable elongate shaft, the plurality of threaded nuts adjustable relative to each other providing length adjustment of the rotatable elongate shaft relative to the jaw assembly and the stationary handle, and the rotatable elongate shaft comprises a blade actuation shaft including a proximal shaft portion and a distal shaft portion, the cutting blade being connected to the distal shaft portion of the blade actuation shaft and the blade trigger being connected to the proximal shaft portion such that movement of the blade trigger moves the cutting blade longitudinally along the blade channel.

2. The electrosurgical system of claim 1 wherein the blade trigger is connected to a pivoting blade advancement link connected to the proximal shaft portion of the blade actuation shaft, the pivoting blade advancement link transferring and reversing a proximal motion of the blade trigger to the distal shaft portion of the blade actuation shaft coupled to the cutting blade.

3. The electrosurgical system of claim 2 further comprising a blade return spring connected to and biasing the blade advancement link proximally and biasing the cutting blade into a retracted position.

4. The electrosurgical system of claim 3 wherein the blade return spring biases the blade trigger distally and biases the cutting blade into the retracted position.

5. The electrosurgical system of claim 4 wherein the first protrusion and the second protrusion are equally sized and shaped to each other and the first protrusion having an orientation relative to the lower jaw different from an orientation of the second protrusion relative to the lower jaw.

6. The electrosurgical system of claim 5 wherein the lower spacer further comprises a third protrusion near a proximal most end of the lower jaw, the third protrusion having a size and shape different from the first and second protrusions and the electrode disposed on the inner surface of the upper jaw has a tissue contact area equal to a tissue contact area of the conductive pad of the electrode disposed on the inner surface of the lower jaw.

7. The electrosurgical system of claim 6 wherein the blade trigger is disposed between the rotatable elongate shaft and a bottom portion of the actuation handle and movable longitudinally relative to the stationary handle and the actuation handle, the actuation handle being pivotably movable relative to the stationary handle.

8. The electrosurgical system of claim 7 wherein the blade return spring extends longitudinally and is aligned with the central longitudinal axis and an actuation spring is coupled to an upper portion of the actuation handle and disposed above the blade return spring.

9. The electrosurgical system of claim 8 wherein the distal shaft portion of the blade actuation shaft comprises a cutting blade mount at its distal end, the cutting blade mount comprising at least one heat stake post arranged to engage with the cutting blade and the proximal shaft portion of the blade actuation shaft an interface node at its proximal end, the interface node comprising a spherical protrusion arranged to connect with the blade advancement link.

10. The electrosurgical system of claim 9 wherein the rotatable elongate shaft further comprises an actuation tube nested within an outer cover tube with the blade actuation shaft nested within the actuation tube, the actuation tube coupling the jaw assembly with the stationary handle, the stationary handle comprising a right handle frame and a left handle frame, a proximal portion of the rotatable elongate shaft being contained within the right and left handle frames such that proximal and distal movement of the jaw assembly with respect to the stationary handle is prevented while allowing for rotational movement of the rotatable elongate shaft.

11. The electrosurgical system of claim 10 further comprising a rotational hub connected to the proximal portion of the rotatable elongate shaft and the actuation handle comprises inwardly-extending flanges that interfere with proximal and distal movement of the rotational hub.

12. The electrosurgical system of claim 11 wherein the rotational hub further comprises at least one mating hub connected to the outer cover tube and a conductive sleeve attached to a proximal portion of the at least one mating hub.

13. The electrosurgical system of claim 12 wherein the conductive sleeve traps an exposed end of an isolated wire, the isolated wire extending from its entrapment point under the conductive sleeve through a slot in the actuation tube and then inside a protective sleeve, the protective sleeve and isolated wire extending distally inside the actuation tube towards the jaw assembly.

14. The electrosurgical system of claim 13 wherein the outer cover tube is connected to the lower jaw, the outer cover tube and the lower jaw is stationary, the upper jaw is movable from an open position to a closed position and is connected to the actuation tube, the actuation tube and the blade actuation shaft are translatable longitudinally while the outer cover tube remains stationary, and a threaded coupling is disposed on a distal end of the actuation tube with the plurality of threaded nuts connected thereto.

15. The electrosurgical system of claim 14 wherein the isolated wire extends through a hole in the upper jaw into a slot in a nonconductive portion of the upper jaw extending to a distal end of the nonconductive portion and then through the nonconductive portion to the conductive pad of the electrode of the upper jaw.

16. The electrosurgical system of claim 14 wherein the isolated wire connects to a wiring harness disposed within the stationary handle, the wiring harness connected within and exiting out the stationary handle to a plug including memory, the plug being removably connected to the electrosurgical generator.

17. The electrosurgical system of claim 16 further comprising a controller disposed between the electrosurgical generator and the bipolar electrosurgical tool, the plug removably connected to the controller removably connected to the electrosurgical generator.

18. The electrosurgical system of claim 16 wherein the electrosurgical generator further comprises an RF amplifier configured to apply an RF current, the RF current being greater than 5 Amps and less than 10 Amps.

19. The electrosurgical system of claim 16 wherein the stationary handle further comprises a rail formed in the stationary handle, the pull block slidably coupled to the rail of the stationary handle.

20. The electrosurgical system of claim 19 further comprising relay circuitry connected to the RF amplifier, the relay circuitry comprising a relay matrix configured to steer output voltage and current from the RF amplifier to one of a plurality of output ports of the electrosurgical generator.

* * * * *